US008017120B2

(12) United States Patent
Padhi et al.

(10) Patent No.: US 8,017,120 B2
(45) Date of Patent: Sep. 13, 2011

(54) METHOD FOR INHIBITING BONE RESORPTION

(75) Inventors: Ian Desmond Padhi, Newbury Park, CA (US); Graham Richard Jang, Santa Monica, CA (US)

(73) Assignee: Amgen Inc., Thousand Oaks, CA (US)

( * ) Notice: Subject to any disclaimer, the term of this patent is extended or adjusted under 35 U.S.C. 154(b) by 116 days.

(21) Appl. No.: 12/212,327

(22) Filed: Sep. 17, 2008

(65) Prior Publication Data
US 2009/0074763 A1   Mar. 19, 2009

Related U.S. Application Data

(60) Provisional application No. 60/973,024, filed on Sep. 17, 2007.

(51) Int. Cl.
*A61K 39/40* (2006.01)
*A61K 39/395* (2006.01)
(52) U.S. Cl. .................... 424/139.1; 424/141.1
(58) Field of Classification Search .............. None
See application file for complete search history.

(56) References Cited

U.S. PATENT DOCUMENTS

| 4,331,647 | A | 5/1982 | Goldenberg |
| 4,376,110 | A | 3/1983 | David et al. |
| 4,411,993 | A | 10/1983 | Gillis |
| 4,427,115 | A | 1/1984 | Laipply |
| 4,543,439 | A | 9/1985 | Frackelton, Jr. et al. |
| RE32,011 | E | 10/1985 | Zimmerman et al. |
| 4,837,440 | A | 6/1989 | Burtscher et al. |
| 4,902,614 | A | 2/1990 | Wakabayashi et al. |
| 5,070,108 | A | 12/1991 | Margolis |
| 5,145,684 | A | 9/1992 | Liversidge et al. |
| 5,223,409 | A | 6/1993 | Ladner et al. |
| 5,399,363 | A | 3/1995 | Liversidge et al. |
| 5,453,492 | A | 9/1995 | Butzow et al. |
| 5,466,468 | A | 11/1995 | Schneider et al. |
| 5,543,158 | A | 8/1996 | Gref et al. |
| 5,552,157 | A | 9/1996 | Yagi et al. |
| 5,565,213 | A | 10/1996 | Nakamori et al. |
| 5,567,434 | A | 10/1996 | Szoka, Jr. |
| 5,627,052 | A | 5/1997 | Schrader et al. |
| 5,641,515 | A | 6/1997 | Ramtoola et al. |
| 5,698,426 | A | 12/1997 | Huse |
| 5,738,868 | A | 4/1998 | Shinkarenko et al. |
| 5,780,263 | A | 7/1998 | Hastings et al. |
| 5,795,587 | A | 8/1998 | Gao et al. |
| 5,811,238 | A | 9/1998 | Stemmer et al. |
| 5,830,721 | A | 11/1998 | Stemmer et al. |
| 5,837,458 | A | 11/1998 | Minshull et al. |
| 5,877,397 | A | 3/1999 | Lonberg et al. |
| 6,054,561 | A | 4/2000 | Ring |
| 6,057,421 | A | 5/2000 | Muller et al. |
| 6,117,911 | A | 9/2000 | Grainger et al. |
| 6,133,426 | A | 10/2000 | Gonzalez et al. |
| 6,180,370 | B1 | 1/2001 | Queen et al. |
| 6,207,153 | B1 | 3/2001 | Dan et al. |
| 6,395,511 | B1 | 5/2002 | Brunkow et al. |
| 6,489,445 | B1 | 12/2002 | Brunkow et al. |
| 6,495,736 | B1 | 12/2002 | Brunkow et al. |
| 6,703,199 | B1 | 3/2004 | Koide |
| 6,803,453 | B1 | 10/2004 | Brunkow et al. |
| 6,806,055 | B2 | 10/2004 | Berman et al. |
| 6,815,201 | B2 | 11/2004 | Pinter |
| 6,818,748 | B2 | 11/2004 | Fulton et al. |
| 7,192,583 | B2 | 3/2007 | Brunkow et al. |
| 7,226,902 | B2 | 6/2007 | Winkler et al. |
| 7,332,276 | B2* | 2/2008 | Sutherland et al. ............ 435/6 |
| 7,578,999 | B2* | 8/2009 | Winkler et al. ........... 424/130.1 |
| 7,642,238 | B2 | 1/2010 | Shaughnessy et al. |
| 2003/0165410 | A1 | 9/2003 | Taylor |
| 2003/0186915 | A1 | 10/2003 | Pan et al. |
| 2003/0229041 | A1 | 12/2003 | Sutherland et al. |
| 2004/0009535 | A1 | 1/2004 | Brunkow et al. |
| 2004/0023356 | A1 | 2/2004 | Krumlauf et al. |
| 2004/0058321 | A1 | 3/2004 | Brunkow et al. |
| 2004/0141875 | A1 | 7/2004 | Doshi |

(Continued)

FOREIGN PATENT DOCUMENTS

DE          102 55 152        6/2004

(Continued)

OTHER PUBLICATIONS

Ominsky et al J of Bone Mineral Research, 2006, v.21, p. S44.*
Albertsen et al., A physical map and candidate genes in the BRCA1 region on chromosome 17q12-21. *Nature Genet.* 7:472-9 (1994).
Anonymous, Amgen presents denosumab and sclerostin antibody data at American Society for Bone and Mineral Research Annual Meeting. Amgen Media Press Release. <www.amgen.com/media/media_pr_detail.isp?releaseID=907028> (2006).
Anonymous, UCB on track. UCB News <http://hugin.info/133973/R/1176122/233395.pdf> (2007).
Bork et al., Go hunting in sequence databases by watch out for the traps. *Trends Genet.* 12: 4225-7 (1996).
Chan et al., A new paradigm in the treatment of osteoporosis: Wnt pathway proteins and their antagonists. *Curr. Opin. Invest. Drugs.* 8:293-8 (2007).

(Continued)

*Primary Examiner* — Michail Belyavskyi
(74) *Attorney, Agent, or Firm* — Marshall, Gerstein & Borun LLP

(57) ABSTRACT

The invention is directed to a method of inhibiting bone resorption. The method comprises administering to a human an amount of sclerostin inhibitor that reduces a bone resorption marker level for at least 2 weeks. The invention also provides a method of monitoring anti-sclerostin therapy comprising measuring one or more bone resorption marker levels, administering a sclerostin binding agent, then measuring the bone resorption marker levels. Also provided is a method of increasing bone mineral density; a method of ameliorating the effects of an osteoclast-related disorder; a method of treating a bone-related disorder by maintaining bone density; and a method of treating a bone-related disorder in a human suffering from or at risk of hypocalcemia or hypercalcemia, a human in which treatment with a parathyroid hormone or analog thereof is contraindicated, or a human in which treatment with a bisphosphonate is contraindicated.

10 Claims, 7 Drawing Sheets

U.S. PATENT DOCUMENTS

| | | | |
|---|---|---|---|
| 2004/0146888 | A1 | 7/2004 | Paszty et al. |
| 2004/0158045 | A1 | 8/2004 | Brunkow et al. |
| 2005/0014650 | A1 | 1/2005 | Seitz et al. |
| 2005/0106683 | A1 | 5/2005 | Winkler et al. |
| 2005/0238646 | A1 | 10/2005 | Ledbetter et al. |
| 2006/0233801 | A1* | 10/2006 | Brunkow et al. ......... 424/145.1 |
| 2007/0072797 | A1 | 3/2007 | Robinson et al. |
| 2007/0110747 | A1 | 5/2007 | Paszty et al. |
| 2007/0292444 | A1 | 12/2007 | Krumlauf et al. |
| 2008/0182788 | A1 | 7/2008 | Brunkow et al. |
| 2008/0234219 | A1 | 9/2008 | Brunkow et al. |
| 2009/0060924 | A1* | 3/2009 | Korytko et al. ......... 424/172.1 |
| 2009/0074763 | A1 | 3/2009 | Padhi et al. |

FOREIGN PATENT DOCUMENTS

| | | |
|---|---|---|
| FR | 2 838 379 | 10/2003 |
| JP | 4-141095 | 5/1992 |
| WO | WO-91/13152 | 9/1991 |
| WO | WO-92/02551 | 2/1992 |
| WO | WO-92/06693 | 4/1992 |
| WO | WO-95/30003 | 11/1995 |
| WO | WO-98/21335 | 5/1998 |
| WO | WO-99/03996 | 1/1999 |
| WO | WO-99/06554 | 2/1999 |
| WO | WO-99/15556 | 4/1999 |
| WO | WO-00/32773 | 6/2000 |
| WO | WO-00/75317 | 12/2000 |
| WO | WO-01/64885 | 9/2001 |
| WO | WO-01/92308 | 12/2001 |
| WO | WO-01/98491 | 12/2001 |
| WO | WO-02/24888 A2 | 3/2002 |
| WO | WO-03/050513 | 6/2003 |
| WO | WO-03/087763 | 10/2003 |
| WO | WO-03/106657 | 12/2003 |
| WO | WO-2004/082608 | 9/2004 |
| WO | WO-2005/003158 | 1/2005 |
| WO | WO-2005/014650 | 2/2005 |
| WO | WO-2006/102070 | 9/2006 |
| WO | WO 2006/119062 | 11/2006 |
| WO | WO-2006/119107 | 11/2006 |
| WO | WO-2008/061013 | 5/2008 |
| WO | WO-2008/063921 | 5/2008 |
| WO | WO-2008/092894 A1 | 8/2008 |
| WO | WO-2008/115732 | 9/2008 |
| WO | WO-2008/133722 | 11/2008 |
| WO | WO-2009/039175 | 3/2009 |
| WO | WO-2009/047356 A1 | 4/2009 |
| WO | WO-2009/056634 A2 | 5/2009 |

OTHER PUBLICATIONS

Colman, Effects of amino acid sequence changes on antibody-antigen interactions. Res. Immunol. 145: 33-6 (1994).

Delmas et al., The use of biochemical markers of bone turnover in osteoporosis. Osteoporosis International. Suppl. 6: S2-17 (2000).

Gazzerro et al., Potential drug targets within bone morphogenetic protein signaling pathways. Curr. Opin. Pharmacol. 7: 325-3 (2007).

Hillier et al., Generation and analysis of 280,000 human expressed sequence tags. Genome Res. 6: 807-28 (1996).

Kurahasi et al., Regions of genomic instability on 22q11 and 11 q23 as the etiology for the recurrent constitutional t (11;22). Hum. Molec. Genet. 9: 1665-70 (2000).

Leppert et al., Benign familial neonatal epilepsy with mutations in two potassium channel genes. Curr. Opin. Neurol. 12: 143-7 (1999).

Li et al., Sclerostin binds to LRP5/6 and antagonizes canonical Wnt signaling. J. Biol. Chem. 280: 19883-7 (2005).

Lowik et al., Wnt signaling is involved in the inhibitory action of sclerostin on BMP-stimulated bone formation. J. Musculoskeleton Neuronal Interact. 6: 357 (2006).

Malone et al., Bone anabolism achieved by reducing sclerostin bioavailability with an anti-sclerostin antibody. 37th International Sun Valley Workshop on Skeletal Tissue Biology. Aug. 5-8, 2007.

Nagaraja et al., X chromosome map at 75-kb STS resolution, revealing extremes of recombination and GC content. Genome Res. 7: 210-22 (1997).

OMIM #607625, Niemann-pick disease, type C2 (2007).

Padhi et al., Anti-sclerostin antibody increases markers of bone formation in healthy postmenopausal women. J. Bone Min. Res. 22: S37 (2007).

Padhi et al., OC35—Effects of anti-sclerostin monoclonal antibody in healthy postmenopausal women. Osteoporosis Int. 19: Suppl. 1: S19 (2008).

Pandey et al., Nucleotide sequence database: A gold mine for biologists. TIBS. 24: 276-80 (1999).

Patel et al., Current and potential future drug treatments for osteoporosis. Ann. Rheumatic Dis. 55: 700-14 (1996).

Piccolo et al., The head inducer Cerberus is a multifunctional antagonist of nodal, BMP and Wnt signals. Nature, 397: 707-10 (1999).

Poole et al., Sclerostin is a delayed secreted product of osteocytes that inhibit bone formation. FESEB J. 19: 1842-4 (2005).

Rawaldi et al., BMP-2 controls alkaline phosphatase expression and osteoblast mineralization by a Wnt autocrine loop. J. Bone Min. Res. 18: 1842-53 (2003).

Robinson et al., The sclerostin antibody project. Hum. Antibodies, 16: 36 (2007).

Staehling-Hampton et al., A 52-kb deletion in the SOST-MEOX1 intergenic region on 17g12-q21 is associated with van Buchem disease in the Dutch population. Am. J. Med. Gen. 110: 144-52 (2002).

van Bezooijen et al., Sclerostin is an osteocyte-expressed negative regulator of hone formation, but not a classical BMP antagonist. J. Exp. Med. 199: 805-14 (2004).

van Bezooijen et al., Wnt but Not BMP Signaling Is Involved in the Inhibitory Action of Sclerostin on BMP-Stimulated Bone Formation. J. Bone. Miner. Res. 22:19-28 (2007).

Winkler et al., Osteocyte control of bone formation via sclerostin, a novel BMP antagonist. EMBO J. 22: 6267-76 (2003).

Winkler et al., Sclerostin inhibition of Wnt-3a-induced C3H10T1/2 cell differentiation is indirect and mediated by bone morphogenetic proteins. J. Biol. Chem. 280: 2498-502 (2005).

Yanagita et al., USAG-1: A bone morphogenetic protein antagonist abundantly expressed in the kidney. Biochem. Res. Comm. 316:490-550 (2004).

Declaration of Dr. Martyn Robinson, submitted in Opposition to European Patent No. 1133558.

Declaration of Dr. Mary E. Brunkow, submitted in Opposition to European Patent No. 1133558.

Written submission of Eli Lilly & Company to European Patent Office, dated May 29, 2007, Opposition to European Patent No. 1133558.

Written submission of UCB S.A., Proprietor's Response to Opposition, dated Mar. 14, 2008, Opposition to European Patent No. 1133558.

European Patent Office Communication, dated Nov. 4, 2008, Opposition to European Patent No. 1133558.

Written submission—Observation by a Third Party According to Art.115 EPC, dated Nov. 25, 2008, Opposition to European Patent No. 1133558.

Expert Opinion from Dr. Catalina Lopez-Correa, dated Mar. 6, 2009, submitted in Opposition to European Patent No. 1133558.

Written Submission of Eli Lilly & Company, dated Mar. 9, 2009, Opposition to European Patent No. 1133558.

Written submission of UCB S.A., Proprietor's Preliminary Response to the Opponent's submission of Mar. 9, 2009, dated Mar. 20, 2009, Opposition to European Patent No. 1133558.

European Search Report, European Patent Office, EP 04 77 6553, dated Jan. 29, 2009.

International Search Report, European Patent Office, PCT/US1999/027990, dated Apr. 7, 2000.

Written Opinion of the International Searching Authority, European Patent Office, PCT/US1999/027990, dated Apr. 7, 2000.

International Preliminary Report on Patentability, PCT/US1999/027990, dated Mar. 16, 2001.

International Search Report, European Patent Office, PCT/US2004/018910, dated Mar. 30, 2005.

Written Opinion of International Searching Authority, European Patent Office, PCT/US2004/018910, dated Mar. 30, 2005.

International Preliminary Report on Patentability, PCT/US2004/018910, dated Dec. 19, 2005.

International Search Report, European Patent Office, PCT/US2004/018912, dated Mar. 29, 2005.
Written Opinion of the International Searching Authority, European Patent Office, PCT/US2004/018912, dated Mar. 29, 2005.
International Preliminary Report of Patentability, PCT/US2004/018912, dated Dec. 19, 2005.
International Search Report, European Patent Office, PCT/US2004/07565, dated Nov. 5, 2004.
Written Opinion of the International Searching Authority, PCT/US2004/07565, dated Nov. 5, 2004.
International Preliminary Report on Patentability, PCT/US2004/07565, dated Sep. 16, 2005.
International Search Report, European Patent Office, PCT/US2006/016345, dated Feb. 8, 2007.
Written Opinion of the International Searching Authority, European Patent Office, PCT/US2006/016345, dated Feb. 8, 2007.
International Preliminary Report on Patentability, PCT/US2006/016345, dated Nov. 6, 2007.
International Search Report, European Patent Office, PCT/US2006/016441, dated Nov. 8, 2006.
Written Opinion of the International Searching Authority, European Patent Office, PCT/US2006/016441, dated Nov. 8, 2007.
International Preliminary Report on Patentability, PCT/US2006/016441, dated Nov. 8, 2007.
International Search Report, European Patent Office, PCT/US2007/084276, dated Sep. 26, 2008.
Written Opinion of the International Searching Authority, European Patent Office, PCT/US2007/084276, dated Sep. 26, 2008.
International Preliminary Report of Patentability, PCT/US2007/084276, dated Sep. 26, 2008.
International Search Report, European Patent Office, PCT/US2007/084280, dated Jan. 27, 2009.
Written Opinion of the International Searching Authority, PCT/US2007/084280, dated Jan. 27, 2009.
International Preliminary Report on Patentability, European Patent Office, PCT/US2007/084280, dated May 12, 2009.
International Search Report, European Patent Office, PCT/US2008/086864, dated Mar. 20, 2009.
Written Opinion of International Searching Authority, European Patent Office, PCT/US2008/086864, dated Mar. 20, 2009.
International Search Report, European Patent Office, PCT/US2008/076679, dated Mar. 23, 2009.
Written Opinion of the International Searching Authority, PCT/US2008/076679, dated Mar. 23, 2009.
Eli Lilly Statement of Grounds of Appeal, Opposition to European Patent Application No. 1133558 B1, dated Sep. 28, 2009.
Declaration filed in connection with the European Patent EP 1133558 Opposition, Expert opinion of Prof. Dr. Thomas Muller, dated Sep. 23, 2009.
Winkler et al., Osteocyte control of bone formation via sclerostin, a novel BMP antagonist, *EMBO J.* 22(23): 6267-76 (2003).
van Bezooijen et al., SOST/sclerostin, an osteocyte-derived negative regulator of bone formation, *Cytokine Growth Factor Rev.*, 16: 319-27 (2005).
Li et al., Sclerostin binds to LRP5/6 and antagonizes canonical Wnt signaling, *J. Biol. Chem.* 280(20): 19883-7 (2005).
Declaration filed in connection with the European Patent EP 1133558 Opposition, Expert opinion of Dr. Walter Sebald, dated Sep. 24, 2009.
Kirsch et al., BMP-2 antagonists emerge from alterations in the low-affinity binding epitope for receptor BMPR-II, *EMBO J.* 19(13): 3314-24 (2000).
Heinecke et al., Receptor oligomerization and beyond: A case study in bone morphogenetic proteins, *BMC Biol.* 7: 59 (2009).
Declaration filed in connection with the European Patent EP 1133558 Opposition, Expert opinion of Prof. Dr. Edgar Wingender, dated Sep. 24, 2009.
Mayer et al., Differentiation of osteogenetic cells: Systems and regulators, *Z. Orthop.*, 130:276-84 (1992)—Abstract Only.
Blum et al., Study plan for German students in the summer of 1998, University Bioinformatik lecture announcement (1998).
Baxevanis (Ed.) et al., Bioinformatics: A practical guide to the analysis of genes and proteins, John Wiley & Sons, Inc. p. 234 (1998).

Bishop (Ed.), Guide to Human Genome Computing, Second Edition, Academic Press, Chapter 1: Introduction to human genome computer via the world wide web, pp. 1-14 (2003).
Declaration filed in connection with the European Patent EP 1133558 Opposition, Expert opinion of Dr. Auristela Freire de Paes Alves, Ph.D., dated Sep. 9, 2009.
Eli Lilly, Biacore experiment comparison results, Setup assay to measure BMP binding to captured SOST, referenced on p. 41 of reference C193 dated Sep. 28, 2009.
Alting-Mees et al., "Monoclonal Antibody Expression Libraries: A Rapid Alternative to Hybridomas," *Strategies in Molecular Biology*, 3:1-9 (1990).
Alves et al., "Sclerosteosis: A Marker of Dutch Ancestry?" *Rev. Bras. Genet.*, 4:825-834 (1982).
Angal et al., "A Single Amino Acid Substitution Abolishes the Heterogeneity of Chimeric Mouse/Human (IgG4) Antibody," *Mol. Immunol.*, 30(1):105-108 (1993).
Avsian-Kretcher et al., "Comparative Genomic Analysis of the Eight-Membered Ring Cystine Knot-Containing Bone Morphogenetic Protein Antagonists," *Mol. Endo.*, 18(1):1-12 (2004).
Babcook et al., "A Novel Strategy for Generating Monoclonal Antibodies from Single, Isolated Lymphocytes Producing Antibodies of Defined Specificities," *Proc. Natl. Acad. Sci. (USA)*, 93:7843-7848 (1996).
Baines et al., "Purification of Immunoglobulin G (IgG)," Methods in Molecular Biology, 10:79-104, The Humana Press, Inc. (1992).
Balemans et al., "Extracellular Regulation of BMP Signaling in Vertebrates: A Cocktail of Modulators," *Dev. Biol.*, 250:231-250 (2002).
Balemans et al., "Increased Bone Density in Sclerosteosis is due to the Deficiency of a Novel Secreted Protein (SOST)," *Hum. Mol. Genet.*, 10:537-543 (2001).
Balint et al., "Antibody Engineering by Parsimonious Mutagenesis," *Gene*, 137:109-188 (1993).
Beighton et al., "The Clinical Features of Sclerosteosis," *Annals of Internal Medicine*, 84:393-397 (1976).
Beighton et al., "The Syndromic Status of Sclerosteosis and van Buchem Disease," *Clinical Genetics*, 25:175-181 (1984).
Bendayan, M., "Possibilities of False Immunocytochemical Results Generated by the Use of Monoclonal Antibodies: The Example of the Anti-proinsulin Antibody," *J. Histochem. Cytochem.*, 43(9): 881-886 (1995).
Bendig, umanization of Rodent Monoclonal Antibodies by CDR Grafting, *Methods*, 8:83-93 (1995).
Berman et al., "The Protein Data Bank," *Acta. Cryst.*, 58(10:899-907 (2002).
Bird et al., "Single-Chain Antigen-Binding Proteins," *Science*, 242:423-426 (1988).
Birren et al., "Homo Sapiens chromosome 17, clone RP5-905N1," *EMBL Sequence Database*, AC003098.2 (2006).
Black et al., "A Somatic Cell Hybrid Map of the Long Arm of Human Chromosome 17, Containing the Familial Breast Cancer Locus (BRACI)," *Am. J. Hum. Genet.*, 52:702-710 (1993).
Boden et al., "Glucocorticoid-Induced Differentiation of Fetal Rat Calvarial Osteoblasts is Mediated by Bone Morphogenetic Protein-6," *Endocrinology*, 138(7):2820-2828 (1997).
Boerner et al., "Production of Antigen-Specific Human Monoclonal Antibodies from in Vitro-Primed Human Splenocytes," *J. Immunol.*, 147:86-95 (1991).
Bonaldo et al., "Normalization and Subtraction: Two Approaches to Facilitate Gene Discover," *Genome Res.*, 6(9):791 (1996).
Bondestam, "Ligands & Signaling Components of the Transforming Growth Factor, " Helsinki University Biomedical Dissertations (2002).
Bost et al., "Antibodies Against a Peptide Sequence Within the HIV Envelope Protein Crossreacts with Human Interleukin-2," *Immunological Investigations*, 17(6&7):577-586 (1988).
Bostrom et al., "Ligand & Signaling Components of the Transforming Growth Factor β Family," *J. Orth. Res.*, 13:357-367 (1995).
Bowie et al., "A Method to Identify Protein Sequences that Fold into a Known Three-Dimensional Structure," *Science*, 253:164-170 (1991).

Bowie et al., "Deciphering the Message in Protein Sequences: Tolerance to Amino Acid Substitutions," *Science* 247:1306-1310 (1990).
Bradley et al., "Modifying the Mouse: Design and Desire," *Bio/Technology*, 10:534-539 (1992).
Brenner et al., Curr. Op. Struct. Biol., 7(3):369-376 (1997).
Brown, T., "Hybridization Analysis of DNA Blots," 2.10.1-2.10.16 (2000).
Brown, T., "Hybridization Analysis of DNA Blots, " *Current Protocols in Protein Science*, 13:A.4H.1-A.4H.9 (1990).
Bruggemann et al., "Production of Human Antibody Repertoires in Transgenic Mice," *Curr. Opin. Biotechnol.*, 8:455-458 (1997).
Brunkow et al., "Bone Dysplasia Sclerosteosis Results from Loss of the SOST Gene Product, a Novel Cysteine Knot-Containing Protein," *Am. J. Hum. Genet.*, 68:577-589 (2001).
Burton et al., "Human Antibodies from Combinatorial Libraries," *Adv. Immunol.*, 57:191-280 (1994).
Byrne et al., "CD4+ CD45RBHi T Cell Transfer Induced Colitis in Mice is Accompanied by Osteopenia which is Treatable with Recombinant Human Osteoprotegerin," *Gut*, 54:78-86 (2005).
Campbell et al., "Totipotency or Multipotentiality of Cultured Cells: Applications and Progress," *Theriogenology*, 47:63-72 (1997).
Chandran et al.,"Recent Trends in Drug Delivery Systems: Liposomal Drug Delivery System—Preparation and Characterisation," *Indian J. Exp. Biol.*, 35(8):801-809 (1997).
Chou et al., "Empirical Predication of Protein Conformation," *Ann. Rev. Biochem.*, 47:251-276 (1979).
Chou et al., Adv. Enzymol. Relat. Areas Mol. Biol., 47:45-148 (1978).
Clark, "Antibody Humanization: A Case of the 'Emperor's New Clothes'?," *Immunology Today*, 21(8):397-402 (2000).
Coleman, "A Structural View of Immune Recognition by Antibodies," *Research in Immunology*, 145:33-36 (1994).
Collins, "Identifying Human Disease Genes by Positional Cloning," *The Harvey Lectures*, Series 86:149-164 (1992).
Collins, "Positional Cloning Moves from Perditional to Traditional," *Nature Genetics*, 9:347-350 (1995).
Cook et al., "Structural Basis for a Functional Antagonist in the Transforming Growth Factor β Superfamily," *Biological Chemistry* 280(48):40177-40186 (2005).
Cormier, "Markers of Bone Metabolism," *Curr. Opin. in Rheu.*, 7:243 (1995).
Couvreur et al., "Polyalkylcyanoacrylates as Colloidal Drug Carriers," *Crit. Rev. Ther. Drug Carrier Syst.*, 5(1):1-20 (1988).
Crameri et al., "DNA Shuffling of a Family of Genes from Diverse Species Accelerates Directed Evolution," *Nature*, 391:288-291 (1998).
Dall'Acqua et al., "Antibody Humanization by Framework Shuffling," *Methods*, 36(1):43-60 (2005).
Davies et al., "Affinity Improvement of Single Antibody VH Domains: Residues in all Three Hypervariable Regions Affect Antigen Binding," *Immunotechnology*, 2:169-179 (1996).
Durham et al., "Alterations in Insulin-Like Growth Factor (IGF)-Dependent IGF-Binding Protein-4 Proteolysis in Transformed Osteoblastic Cells," *Endocrinolgoy*, 136(4):1374-1380 (1995).
Ebara et al., "Mechanism for the Action of Bone Morphogenetic Proteins and Regulation of Their Activity," *Spine*, 27(165):S10-S15 (2002).
EMBL Accession No. AA393939.
EMBL Accession No. AC003098.
EMBL Accession No. A1113131.
Epstein et al., "Endocrine Function in Sclerosteosis," *S. Afr. Med. J.*, 55:1105-1110 (1979).
Frost et al., "On the Rat Model of Human Osteopenias and Osteoporoses," *Bone and Mineral*, 18:227-236 (1992).
Fujiwara et al., "Accession No. D79813," *EMBL Sequence Database* (1996).
Gazzerro et al., "Bone Morphogenetic Proteins Induce the Expression of Noggin, Which Limits Their Activity in Cultured Rat Osteoblasts," *J. Clin. Invest.*, 102(12):2106-2114 (1998).
Genbank Accession No. AA393768.
Genbank Accession No. AAB33865.
Genbank Accession No. BAA19765.
Genbank Accession No. CAA88759.

Genbank Accession No. D38082.
Genbank Accession No. D79813.
Genbank Accession No. D89675.
Genbank Accession No. NM_001203.
Genbank Accession No. NM_001204.
Genbank Accession No. NM_004329.
Genbank Accession No. NM_030849.
Genbank Accession No. NM_033346.
Genbank Accession No. NP_001194.
Genbank Accession No. S75359.
Genbank Accession No. U25110.
Genbank Accession No. Z48923.
Gencic et al., "Conservative Amino Acid Substitution in the Myelin Proteolipid Protein of Jimpy$^{msd}$ Mice," *The Journal of Neuroscience*, 10(1):117-124 (1990).
Geysen et al., "Cognitive Features of Continuous Antigenic Determinants," *Molecular Recognition* 1(1):32-41 (1988).
Gitelman et al., "Vgr-1/BMP-6 Induces Osteoblastic Differentiation of Pluripotential Mesenchymal Cells," *Cell Growth & Differentiation*, 6:827-836 (1995).
Glasky et al., "Stability of Specific Immunoglobulin Secretion by EBV-Transformed Lymphoblastoid Cells and Human-Murine Heterohybridomas," *Hybridoma*, 8:377-389 (1989).
Green et al., "Antigen-Specific Human Monoclonal Antibodies from Mice Engineered with Human Ig Heavy and Light Chain YACs," *Nature Genet.*, 7:13 (1994).
Greene et al., "Screening Recombinant DNA Libraries," *Current Protocols in Molecular Biology*, Ch. 6(1) (1990).
Gribskov et al., "Profile Analysis," *Meth. Enzym.*, 183:146-159 (1990).
Gribskov et al., "Profile Analysis: Detection of Distantly Related Proteins," *Proc. Nat. Acad. Sci.* (*USA*), 84(13):4355-4358 (1987).
Groeneveld et al., "Bone Morphogenetic Proteins in Human Bone Regeneration," *Eur. J. Endocrinol.*, 142:9-21 (2000).
Groppe et al., "Structural Basis of BMP Signalling Inhibition by the Cystine Knot Protein Noggin," *Nature*, 420:636-642 (2002).
Guinness-Hey, "Increased Trabecular Bone Mass in Rats Treated with Human Synthetic Parathyroid Hormone," *Metab. Bone Dis. Relat. Res.*, 5:177-181 (1984).
Harlow et al., "Antibodies: A Laboratory Manual, Cold Spring Harbor Laboratory, Cold Spring Harbor," 141-157 (1998).
Harris, "Processing of C-Terminal Lysine and Arginine Residues of Proteins Isolated from Mammalian Cell Culture," *Journal of Chromatography*, 705:129-134 (1995).
Hart et al., "Crystal Structure of the Human TβR2 Ectodomain-TGF-β3 Complex," *Nat. Struc. Biol.*, 9(3):203-208 (2002).
Hay et al., "ATCC Cell Line and Hybridomas," American Type Culture Collection, 8th Ed., pp. 149, 258, 428 (1994).
Hill et al., "Multiple Extracellular Signals Promote Osteoblast Survival and Apoptosis," *Endocrinology*, 138(9):3849-3858 (1997).
Hillier et al., "WashU-Merck EST Project 1997," *EMBL Sequence Database*, AA393768.1 (1997).
Hillier et al., "WashU-Merck EST Project 1997," *EMBL Sequence Datatbase*, AA393939.1 (1997).
Hock et al., "Perspective: Osteoblast Apoptosis and Bone Turnover," *J. Bone Miner. Res.*, 16(6):975-984 (2001).
Hoffman et al., "BMP Signaling Pathways in Cartilage and Bone Formation," *Critical Review in Eukaryotic Gene Expression*, 11(1-3):23-45 (2001).
Hollinger et al., "Engineered Antibody Fragments and the Rise of Single Domains," *Nature Biotech.*, 23(9):1126-1136 (2005).
Holm et al., "Protein Folds and Families: Sequence and Structure Alignments," *Nucl. Acid Res.*, 27(1):244-247 (1999).
Holt, et al., "Domain antibodies: proteins for therapy," *Trends in Biotech.*, 21(11):484-490 (2003).
Hoogenboom et al., "By-Passing Immunisation: Human Antibodies from Synthetic Repertoires of Germline $V_H$ Gene Segmens Rearranged in Vitro," *J. Molec. Biol.*, 227:381-388 (1992).
Hsu et al., "The Xenopus Dorsalizing Factor Gremlin Indentified a Novel Family of Secreted Proteins that Antagonize BMP Activities," *Molecular Cell*, 1:673-683 (1998).

Huse et al., "Generation of a Large Combinatorial Library of the Immunoglobulin Repertoire in Phage Lambda," *Science*, 246:1275-1281 (1989).

Hwang et al., "Use of Human Germline Genes in a CDR Homoloy-Based Approach to Antibody Humanization," *Methods*, 36(1):35-42 (2005).

Lemura et al., "Direct Binding of Follistatin to a Complex of Bone-Morphogenetic Protein and its Receptor Inhibits Ventral and Epidermal Cell Fates in Early Xenopus Embryo," *Proc. Natl. Acad. Sci. USA*, 95:9337-9342 (1998).

Innis et al., "Evolutionary Trace Analysis of TGF-B and Related Growth Factors: Implications for Stie-Directed Mutagenesis," *Protein Engineering*, 13(12):839-847 (2000).

Jakobovits et al., "Production of Antigen-Specific Human Antibodies from Mice Engineered with Human Heavy and Light Chain YACs$^a$," *Ann. N. Y. Acad. Sci.*, 764:525-535 (1995).

Jee et al., "Overview: Animal Models of Osteopenia and Osteoporosis," *J. Musculoskel. Neuron. Interact.*, 1:193-207 (2001).

Jilka et al., "Increased Bone Formation by Prevention of Osteoblast Apoptosis with Parathyroid Hormone," *J. Clin. Invest.*, 104:439-446 (1999).

Jones, "Progress in Protein Structure Predication," *Curr. Opin. Struct. Biol.*, 7(3):377-387 (1997).

Kabat et al., "Sequences of Proteins of Immunological Interest," U.S. Department of Health and Human Services, NIH, USA (1987) (Table of Contents).

Kalu, The Ovariectomized Rat Model of Postmenopausal Bone Loss, *Bone and Mineral*, 15:175-192 (1991).

Kang et al., "Linkage of Recognition and Replication Functions by Assembling Combinatorial Antibody Fab Libraries Along Phage Surfaces," *Proc. Natl. Acad. Sci. (USA)*, 88:4363-4366 (1991).

Katagiri et al., "The Non-Osteogenic Mouse Pluripotent Cell Line, C3H10T1/2, is Induced to Differentiate into Osteoblastic Cells by Recombinant Human Bone Morphogenetic Protein-2," *Biochem. Biophys. Res. Comm.*, 172(1):295-299 (1990).

Kawabata et al., "Signal Transduction by Bone Morphogenetic Proteins," *Cytokine and Growth Factor Reviews*, 9(1):49-61 (1998).

Keller et al., "Molecular recognition of BMP-2 and BMP receptor IA," *Nature Structural & Molecular Biolody* 11(5):481-488 (2004).

Khalil, TGF-β: From Latent to Active, *Microbes and Infection*, 1(15):1255-1263 (1999).

Khosla et al., "Concise Review for Primary-Care Physicians. Treatment Options for Osteoporosis," *Mayo Clin. Pro.*, 70:978-982 (1995).

Kohler et al., "Continuous Cultures of Fused Cells Secreting Antibody of Predefined Specificity," *Nature*, 256:495 (1975).

Koli et al., "Latency, Activation, and Binding Proteins of TGF-β," *Microscopy Res. Tech.*, 52:354-362 (2001).

Koreth et al., "Microsatellites and PCR Genomic Analysis," *J. Pathology*, 178:239-248 (1996).

Kramer et al., "The Gapped Duplex DNA Approach to Oligonucleotide-Directed Mutation Construction," *Nucleic Acids Res.*, 12:9441 (1984).

Kunkel et al., "Rapid and Efficient Site-Specific Mutagenesis without Phenoypic Selection," *Methods in Enzymol.*, 154:367-382 (1987).

Kunkel, "Rapid and Efficient Site-Specific Mutagenesis without Phenotypic Selection," *Proc. Natl. Acad. Sci. (USA)*, 82:488-492 (1985).

Kusu et al., "Sclerostin is a Novel Secreted Osteoclast-Dervied Bone Morphogenetic Protein Antagonist with Unique Ligand Specificity," *J. Biol. Chem.*, 278:24113-24117 (2003).

Lasic, "Novel Applications of Liposomes," *Trends Biotechnol.*, 16(7):307-321 (1998).

Latham, "The Biochemical and Cellular Characterization of Sclerostin, The Causative Gene for Sclerosteosis,"*Calcified Tissue International*, 70(4):244 (2002).

Lian et al., "Bone Formation: Osteoblast Lineage Cells, Growth Factors, Matrix Proteins, and the Mineralization Process," *Primer on the Metabolic Bone Diseases and Disorders of Mineral Metabolism*, 4th Edition, 14-29 (1999).

Liu et al., "Human Type II Receptor for Bone Morphogenic Proteins (BMPs): Extension of the Two-Kinase Receptor Model to the BMPs," *Molecular and Cellular Biology*, 15(7):3479-3486 (1995).

Lonberg et al., "Antigen-Specific Human Antibodies from Mice Comprising Four Distinct Genetic Modifications," *Nature*, 368:856 (1994).

Low et al., "Mimicking Somatic Hypermutation: Affinity Maturation of Antibodies Displayed on Bacteriophage using a Bacterial Mutator Strain," *J. Mol. Biol.*, 250:350-368 (1996).

Margalit, "Liposome-Mediated Drug Targeting in Topical and Regional Therapies," *Crit. Rev. Ther. Drug Carrier Syst.*, 12(2-3):233-261 (1995).

Marks et al., "By-Passing Immunization: Building High Affinity Human Antibodies by Chain Shuffling," *Bio/Technology*, 10:779-783 (1992).

Miyazono et al., "Divergence and Convergence of TGFβ/BMP Signaling," *J. Cell. Physiol.*, 187:265-276 (2001).

Miyazono et al., "TGF-β Signaling by Smad Proteins," *Adv. Immunology*, 75:115-157 (2000).

Mori et al., Á Novel Amino Acid Substitution at the Receptor-Binding Site on the Hemagglutinin of H3N2 Influenza A Viruses Isolated From 6 Cases With Acute Encephalopathy During the 1997-1998 Season in Tokyo, *Arch. Virol.*, 144: 147-155 (1999).

Moult, "The Current State of the Art in Protein Structure Predicion," *Curr. Opin. Biotech.*, 7(4):422-427 (1996).

Mullins et al., "Perspectives Series: Molecular Medicine in Genetically Engineered Animals; Transgenesis in the Rat and Larger Mammals," *J. Clin. Invest.*, 97(7):1557-1560 (1996).

Nakase et al., "Transient and Localized Expression of Bone Morphogenetic Protein 4 Messenger RNA During Fracture Healing," *J. Bone Miner. Res.*, 9(5):651-659 (1994).

Nelson, "Positional Cloning Reaches Maturity," *Current Opinion in Genetics and Development*, 5:298-303 (1995).

Nickel et al., "The Crystal Structure of the BMP-2:BMPR-1A Complex and the Generation of BMP-2 Antagonists," *J. of Bone and Joint Surgery*, 83-A:S1-7-S1-14 (2001).

Nicolas et al., "An Age-Related Decrease in the Concentration of Insulin-Like Growth Factor Binding protein-5 in Human Cortical Bone," *Calcif. Tissue Int.*, 57:206-212 (1995).

Nifuji et al., "Coordinated Expression of Noggin and Bone Morphogenetic Proteins (BMPs) During Early Skeletogenesi and Induction of Noggin Expression by BMP-7," *J. Bone Miner. Res.*, 14(12):2057-2066 (1999).

Nisonoff et al., "Separation of Univalent Fragments from the Bivalent Rabbit Antidody Molecule by Reduction of Disulfide Bonds," *Arch. Biochem. Biophys.*, 89:230-244 (1960).

Nygren et al., "Scaffolds for Engineering Novel Binding Sites in Proteins," *Curr. Opin. Struct. Biol.*, 7:463-469 (1997).

Oelgeschlager et al., "The Evolutionarily Conserved BMP-Binding Protein Twisted Gastrulation Promotes BMP Signalling," *Nature*, 105:757-763 (2000).

Ominsky, et al., "Sclerostin Monoclonal Antibody Treatment Increases Bone Strength in Aged Osteopenic Ovariectomozed Rats", Abstract.

Oreffo et al., "Human Bone Marrow Osteoprogenitors Express Estrogen Receptor-Alpha and Bone Morphogenetic Proteins 2 and 4 mRNA During Osteoblastic Differentiation," *J. Cell. Biochem.*, 75:382-392 (1999).

Oshima et al., "TGF-β Receoptor Type II Deficiency Results in Defects of Yolk Sac Hematopoiesis and Vasculogenesis," *Developmental Biology*, 179:297-302 (1996).

Padlan et al., "Structure of an antibody-antigen complex; Crystal structure of the HyHEL-10 Feb-lysozyme complex," *Proc. Natl. Acad. Sci. USA*, 86:5938-5942 (1989).

Patten et al., "Applications of DNA Shuffling to Pharmaceuticals and Vaccines," *Curr. Opin. Biotechnol.*, 8:724-733 (1997).

Piek et al., "Specificity, Diversity, and Regulation of TGF-β Superfamily Signaling," *FASEB J.*, 13:2105-2124 (1999).

Pietromonaco et al., "Protein Kinase C-0 Phosphorylation of Moesin in the Actin-Binding Sequence," *J. Biol. Chem.*, 273:7594-7603 (1998).

Pignatti et al., "Tracking Disease Genes by Reverse Genetics," *J. Psychiar. Res.*, 26(4):287-298 (1992).

Pittenger et al., "Multilineage Potential of Adult Human Mesenchymal Stem Cells," *Science*, 284:143-147 (1999).

Pluckthun et al., "Expression of Functional Anitbody Fv and Fab Fragments in *Escherichia coli*," *Methods Enzymol.*, 178:497-515 (1989).

Pockwinse et al., "Expression of Cell Growth and Bone Specific Genes at Single Cell Resolution During Development of Bone Tissue-Like Organization in Primary Osteoblast Cultures," *Journal of Cellular Biochemistry*, 49:310-323 (1992).

Porter, "The Hydrolysis of Rabbit γ-Globulin and Antibodies with Crystalline Papain," *Biochem. J.*, 73:119-126 (1959).

Quintanar-Guerrero et al., "Preparation Techniques and Mechanisms of Formation of Biodegradable Nanoparticles from Preformed Polymers," *Drug Dev. Ind. Pharm.*, 24(12):1113-1128 (1998).

Reddi, "Interplay Between Bone Morphogenetic Proteins and Cognate Binding Proteins in Bone and Cartilage Development: Noggin, Chordin and DAN,"*Arthritis Res.*, 3(1):1-5 (2000).

Riggs, "Overview of Osteoporosis," *West J. Med.*, 154:63-77 (1991).

Rosenzweig et al., "Cloning and characterization of a human type II receptor for bone morphogenetic proteins," *Proc. Natl. Acad. Sci, USA*, 92:7632-7636 (1995).

Rudikoff, et al., "Single Amino Acid Substitution Altering Antigen-binding Specificity," *Proc. Natl. Acad. Sci. USA*, 79:1979-1983 (1982).

Sali et al., "Comparative Protein Modeling by Satisfaction of Spatial Restraints," *J. Mol. Biol.*, 234:779-815 (1993).

Sambrook et al., "Synthetic Oligonucleotide Probes," *Molecular Cloning—A Laboratory Manual*, Ch.11:11.1-11.19 and 11.58-11.61 (1989).

Sanger et al., "DNA Sequencing with Chain-Terminating Inhibitors," *PNAS*, 74:5463-5467 (1997).

Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. (USA)*, 86:5728-5732 (1989).

Scatchard et al., "The Attractions of Proteins for Small Molecules and Ions," *Ann. N.Y. Acad. Sci.*, 51:660-672 (1949).

Scheufler et al., "Crystal Structure of Human Bone Morphogenetic Protein-2 at 2.7 A Resolution," *J. Mol. Biol.*, 287(1):103-115 (1999).

Schlebusch et al., "Production of a Single-Chain Fragment of the Murine Anti-Idiotypic Antibody ACA125 as Phage-Displayed and Soluble Antibody by Recombinant Phage Antibody Technique," *Hybridoma*, 16:47-52 (1997).

Schlunegger et al., "Refined Crystal Structure of Human Transforming Growth Factor β2 at 1.95 A Resolution," *J. Mol. Biol.*, 231:445-458 (1993).

Schmitt et al., "Bone Morphogenetic Proteins: An Update on Basic Biology and Clinical Relevance," *Journal of Orthopaedic Research*, 17:269-278 (1999).

Serra et al., "Expression of a Truncated, Kinase-Defective TGF-β Type II Receeptor in Mouse Skeletal Tissue Promotes Terminal Chondrocyte Differentiation and Osteoarthritis," *J. Cell Biol.*, 139(2):541-552 (1997).

Sigmund, "Viewpoint: Are Studies in Genetically Altered Mice Out of Control?" *Arterioscler. Thromb. Vasc. Biol.*, 20:1425-1429 (2000).

Sippl et al., "Threading Thrills and Threats," *Structure*, 4(1):15-19 (1996).

Sivakumar et al., "New Insights into Extracellular Matrix Assembly and Reorganization from Dynamic Imaging of Extracellular Matrix Proteins in Living Osteoblasts," *J. Cell. Sci.*, 119(7):1350-1360 (2006).

Smith et al., "Glucocorticoids Inhibit Development Stage-Specific Osteoblast Cell Cycle," *J. Biol. Chem.*, 275:19992-20001 (2000).

Smith, "TGF β Inhibitors, New and Unexpected Requirements in Vertebrate Development," *TIG*, 15(1):3-5 (1999).

Sudo et al., "In Vitro Differentiation and Calcification in a New Clonal Osteogenic Cell Line Derived from Newborn Mouse Calvaria," *J. Cell Biol.*, 96:191-198 (1983).

Sutherland et al., "Sclerostin Promotes the Apoptosis of Human Osteoblastic Cells: A Novel Regulation of Bone Formation," *Bone*, 35:828-835 (2004).

Suzawa et al., "Extracellular Matrix-Associated Bone Morphogenetic Proteins are Essential for Differentiation of Murine Osteoblastic Cells in Vitro," *Endocrinology*, 140:2125-2133 (1999).

Takakura, "Drug Delivery Systems in Gene Therapy," *Nippon Rinsho*, 56(3):691-695 (1998) (Abstract Only).

Takeda, K., Expression of serine/threonine kinase receptors during ectopic bone formation induced by bone morphogenetic protein (BMP), *Kokubyo Gakkai Zasshi*, 61(4):512-26 (1994).

Tam et al., "TGF-β Receptor Expression on Human Keratinocytes: A 150 kDa GPI-Anchored TGF-β1 Binding Protein Forms a Heteromeric Complex with Type I and Type II Receptors," *J. Cellular Biochem.*, 70:573-586 (1998).

Taylor et al., "Human Immunoglobulin Transgenes Undergo Rearrangement, Somatic Mutation and Class Switching in Mice That Lack Endogenous IgM," *Int. Immun.*, 6:579 (1994).

The Merck Manual-Second Home Edition, Ch. 61:1-3 (2005).

Thompson et al., "Affinity Maturation of a High-Affinity Human Monoclonal Antibody Against the Third Hypervariable Loop of Human Immunodeficiency Virus: Use of Phage Display to Improve Affinity and Broaden Strain Reactivity," *J. Mol. Biol.*, 256:77-88 (1996).

Thornton et al., "Prediction of Progress at Last," *Nature*, 354:105-106 (1991).

Van Hul et al., "Van Buchem Disease (Hyperostosis Corticalis Generalisata) Maps to Chromosome 17q12-a21," *Am. J. Hum. Genet.*, 2:391-399 (1998).

von Bubnoff et al., "Intracellular BMP Signaling Regulation in Vertebrates: Pathway or Network?" *Dev. Biol.*, 239:1-14 (2001).

Wall, "Transgenic Livestock: Progress and Prospects for the Future," *Theriogenology*, 45:57-68 (1996).

Wang, "Bone Morphogenetic Proteins (BMPs): Therapeutic Potential in Healing Bony Defects," *TIBTECH*, 11:379-383 (1993).

Warmington et al., "Sclerostin Antagonism in Adult Rodents, via Monoclonal Antibody Mediated Blockade, Increases Bone Mineral Density and Implicates Sclerostia as a Key Regulator of Bone Mass During Adulthood," *J. Bone Min. Res.*, 19:S56-S57 (2004).

Winter et al., "Making Antibodies by Phase Display Technology," *Annu. Rev. Immunol.*, 12:433-455 (1994).

Wolff et al., "Monoclonal Antibody Homodimers: Enhanced Antitumor Activity in Nude Mice," *Cancer Res.*, 53:2560-2565 (1993).

Yang et al., "CDR Walking Mutagenesis for the Affinity Maturation of a Potent Human Anti-HIV-1 Antibody into the Picomolar Range," *J. Mol. Biol.*, 254:392-403 (1995).

Zambaux et al., "Influence of Experimental Parameters on the Characteristics of Poly(Lactic Acid) Nanoparticles Prepared by a Double Emulsion Method," *J. Controlled Release*, 50(1-3):31-40 (1998).

Zhang et al., "Humanization of an Anti-Human TNF-α Antibody by Variable Region Resurfacing with the Aid of Molecular Modeling," *Molecular Immunology*, 42(12):1445-1451 (2005).

Zimmerman et al., "The Spemann Organizer Signal Noggin Binds and Inactives Bone Morphogenetic Protein 4," *Cell*, 86:599-606 (1996).

zur Muhlen et al., "Solid Lipid Nanoparticles (SLN) for Controlled Drug Delivery—Drug Release and Release Mechanism," *Eur. J. Pharm. Biopharm.*, 45(2):149-155 (1998).

Notice of Opposition to European Patent No. 1 133 558 dated May 29, 2007.

Li et al., Treatment with an anti-sclerostin antibody directly stimulates bone formation in a dose-dependent manner in ovariectomized rats with established osteopenia. *J. Bone Min. Res.* 22(Suppl. S1): S65 (2007).

Niu et al., Sclerostin inhibition leads to increased periosteal and endocortical bone formation as well as decreased cortical porosity in aged ovariectomized rats. *J. Bone Min. Res.* 22(Suppl. S1): S65 (2007).

* cited by examiner

Dose Related Increase Observed in Osteocalcin Following Single-dose SC Administration of Scl-Mab to Healthy Postmenopausal Women Large Anabolic Window Following Single SC Doses of 5 & 10 mg/kg Scl-Mab to Healthy Postmenopausal Women Single Doses of Scl-Mab Resulted in an Increase in BMD in Healthy Postmenopausal Women

METHOD FOR INHIBITING BONE RESORPTION

CROSS-REFERENCE TO RELATED APPLICATIONS AND INCORPORATION BY REFERENCE

This application claims priority to U.S. Provisional Patent Application No. 60/973,024, filed Sep. 17, 2007.

The following applications are hereby incorporated by reference in their entirety: U.S. patent application Ser. No. 11/410,540, filed Apr. 25, 2006, which claims priority to U.S. Provisional Patent Application No. 60/792,645, filed Apr. 17, 2006, U.S. Provisional Patent Application No. 60/782,244, filed Mar. 13, 2006, U.S. Provisional Patent Application No. 60/776,847, filed Feb. 24, 2006, and U.S. Provisional Patent Application No. 60/677,583, filed May 3, 2005; and U.S. patent application Ser. No. 11/411,003, filed Apr. 25, 2006, which claims priority to U.S. Provisional Patent Application No. 60/792,645, filed Apr. 17, 2006, U.S. Provisional Patent Application No. 60/782,244, filed Mar. 13, 2006, and U.S. Provisional Patent Application No. 60/776,847, filed Feb. 24, 2006.

TECHNICAL FIELD OF THE INVENTION

The invention generally relates to methods of using sclerostin binding agents to modulate bone density.

BACKGROUND OF THE INVENTION

Loss of bone mineral content can be caused by a wide variety of conditions and may result in significant medical problems. For example, osteoporosis is a debilitating disease in humans and is characterized by marked decreases in skeletal bone mass and mineral density, structural deterioration of bone, including degradation of bone microarchitecture and corresponding increases in bone fragility (i.e., decreases in bone strength), and susceptibility to fracture in afflicted individuals. Osteoporosis in humans is generally preceded by clinical osteopenia, a condition found in approximately 25 million people in the United States. Another 7-8 million patients in the United States have been diagnosed with clinical osteoporosis. The frequency of osteoporosis in the human population increases with age. Among Caucasians, osteoporosis is predominant in women who, in the United States, comprise 80% of the osteoporosis patient pool. The increased fragility and susceptibility to fracture of skeletal bone in the aged is aggravated by the greater risk of accidental falls in this population. Fractured hips, wrists, and vertebrae are among the most common injuries associated with osteoporosis. Hip fractures in particular are extremely uncomfortable and expensive for the patient, and for women, correlate with high rates of mortality and morbidity.

SUMMARY OF THE INVENTION

The invention is directed to methods of using a sclerostin inhibitor for inhibiting bone resorption in humans. The method comprises administering to a human an amount of sclerostin inhibitor that is effective to reduce the level of a marker of bone resorption and optionally increase the level of a marker of bone formation. In some embodiments, bone resorption is inhibited and bone formation is increased for at least about 7 days, 2 weeks, 3 weeks, 4 weeks, 1 month, 5 weeks, 6 weeks, 7 weeks, 8 weeks, 2 months, 3 months or longer. In related embodiments, the invention provides a method of increasing bone mineral density or treating a bone-related disorder. The invention further provides a method of ameliorating the effects of an osteoclast-related disorder. The method comprises administering to a human a sclerostin inhibitor that reduces the level of a marker of bone resorption compared to bone marker levels absent treatment. The sclerostin inhibitor also increases the level of a marker of bone formation by at least about 10% compared to bone marker levels absent treatment. The sclerostin inhibitor can be administered via a single dose or in multiple doses. For example, the sclerostin inhibitor can be administered in a short-term therapy regimen to, e.g., increase bone formation, and/or can be administered long-term to prevent loss of bone mineral density in a maintenance therapeutic regimen.

In any of the methods disclosed herein, the level of one or more markers of bone resorption is reduced by at least about 5%, 10%, 15%, 20%, 30%, 40%, 50% or more for at least 2 weeks, 3 weeks, 30 days, 1 month, 6 weeks, 2 months or longer, compared to pre-treatment levels or normal levels for that patient population. By way of non-limiting example, the level of the marker of bone resorption by 3 weeks after treatment is decreased by, e.g., at least about 20% compared to pre-treatment levels or normal levels for that patient population. In any of the preceding methods, the level of the marker of bone formation is increased by at least about 10%, about 20%, about 30%, about 40%, about 50%, about 60%, about 70%, about 80%, about 90%, about 100% or more for at least about 2 weeks, 3 weeks, 30 days, 1 month, 6 weeks, 2 months or longer, compared to pre-treatment levels or normal levels for that patient population. By way of non-limiting example, the level of the marker of bone formation by 3 weeks after treatment is increased by, e.g., at least about 20% compared to pre-treatment levels or normal levels for that patient population. In one exemplary embodiment, the marker of bone resorption is serum level of C-telopeptide of type I collagen (CTX). In other exemplary embodiments, the marker of bone formation is bone-specific alkaline phosphatase (BSAP), osteocalcin (OstCa), and/or N-terminal extension of procollagen type 1 (P1NP).

The invention also provides a method of treating a bone-related disorder, wherein the method comprises administering to a human one or more amounts of a sclerostin inhibitor effective to increase bone mineral density for the total body (e.g., head, trunk, arms, and legs) or at the hip (e.g., total hip and/or femoral neck), spine (e.g., lumbar spine), wrist, finger, shin bone and/or heel by about 1%, about 2%, about 3%, about 4%, about 5%, about 6%, about 8%, about 10%, about 12%, about 15%, about 18%, about 20%, about 25%, or 30% or more. In some embodiments, the bone mineral density of the human before treatment is characteristic of osteoporosis or osteopenia, and one or more doses of sclerostin inhibitor are administered in an amount and for a time effective to improve bone mineral density such that the bone mineral density is no longer characteristic of osteoporosis and/or osteopenia. For example, one or more doses may be administered for an initial time period to increase bone mineral density to within 2.5, or one, standard deviations of the density normal for a young adult (i.e., a T-score≧−2.5 or a T-score≧−1, as defined below). In exemplary embodiments, the initial time period is about 3 months or less, 6 months or less, 9 months or less, 1 year or less, 18 months or less, or longer. The method may further comprise subsequently administering one or more amounts of a sclerostin inhibitor effective to maintain bone mineral density, optionally for a maintenance time period of at least about 6 months, 1 year, 2 years or longer (e.g., over the life-time of the subject).

The invention further provides a method of treating a bone-related disorder in a human by administering one or more doses between about 0.1 to about 20 mg/kg, or about 0.1 to about 12 mg/kg, or about 0.5 to about 12 mg/kg, or about 1 to about 10 mg/kg, or about 1 to about 8 mg/kg, or about 2 to about 8 mg/kg, or about 3 to about 8 mg/kg. In some embodiments, doses may be administered at an interval of about once 2 weeks or longer, once every month or longer, or once every 2 months or longer, or once every 3 months or longer, or once every 4 months or longer, or once every 5 months or longer, or once every 6 months or longer, or once every 9 months or longer, or once every year or longer. The sclerostin inhibitor may be used in the preparation of a medicament for administration using any of the dosing and timing regimens described herein. Optionally, the sclerostin inhibitor is presented in a container, such as a single dose or multidose vial, containing a dose of sclerostin inhibitor for administration (e.g., about 70 to about 450 mg of sclerostin inhibitor). In one exemplary embodiment, a vial may contain about 70 mg or 75 mg of sclerostin inhibitor, e.g. anti-sclerostin antibody, and would be suitable for administering a single dose of about 1 mg/kg. In other embodiments, a vial may contain about 140 mg or 150 mg; or about 210 mg or 220 mg or 250 mg; or about 280 mg or 290 mg or 300 mg; or about 350 mg or 360 mg; or about 420 mg or 430 mg or 440 mg or 450 mg of sclerostin inhibitor, e.g., anti-sclerostin antibody.

Additionally, the invention provides a method of treating a bone-related disorder in a human suffering from or at risk of hypocalcemia or hypercalcemia, a human in which treatment with a parathyroid hormone or analog thereof is contraindicated, or a human in which treatment with a bisphosphonate is contraindicated. The method comprises administering to the human an amount of a sclerostin inhibitor effective to increase the level of a marker of bone formation and/or reduce the level of a marker of bone resorption, without resulting in hypocalcemia or hypercalcemia (e.g., clinically-significant hypocalcemia or hypercalcemia).

The invention also provides a method of monitoring anti-sclerostin therapy, i.e., the physiological response to a sclerostin inhibitor. The method comprises the steps of administering one or more doses of a sclerostin inhibitor, and detecting the level of one or more markers of bone resorption, wherein a reduction of at least about 5%, about 10%, about 15%, about 20%, about 30%, about 40%, about 50% or more in the level of a marker of bone resorption, compared to pre-treatment levels or normal levels for that patient population, is indicative of effective treatment. The method optionally further comprises the step of detecting the level of one or more markers of bone formation, wherein an increase of at least about 10%, about 20%, about 30%, about 40%, about 50%, about 60%, about 70%, about 80%, about 90%, or about 100% in the level of a marker of bone formation, compared to pre-treatment levels or normal levels for that patient population, is indicative of effective treatment. In certain embodiments, the increase in bone formation marker levels is about 20%. The method may further comprise the step of adjusting the dose of a sclerostin inhibitor to a different amount, e.g., higher if the change in bone resorption and/or bone formation is less than desired, or lower if the change in bone resorption and/or bone formation is more than desired.

In a different aspect, the invention provides selected sclerostin inhibitors that reduce the level of a marker of bone resorption by at least about 5%, about 10%, about 15%, about 20%, about 30%, about 40%, about 50% or more and increase the level of a marker of bone formation by at least about 10%, about 20%, about 30%, about 40%, about 50%, about 60%, about 70%, about 80%, about 90%, about 100%, or more, for at least about 1 week, about 2 weeks, about 1 month, about 6 weeks, about 2 months, about 10 weeks, or about 3 months. In a related aspect, the invention provides a method of selecting such sclerostin inhibitors by administering a candidate sclerostin inhibitor to an animal and selecting a candidate sclerostin inhibitor that changes the level of a marker of bone resorption and/or formation to the desired extent.

In any of the preceding methods or embodiments of the invention, the sclerostin inhibitor may be a sclerostin binding agent. The use of sclerostin binding agents disclosed in U.S. Patent Publication No. 20070110747, e.g., in any of the methods disclosed herein or for preparation of medicaments for administration according to any of the methods disclosed herein, is specifically contemplated. In this regard, the invention includes use of a sclerostin binding agent in preparation of a medicament for inhibiting bone resorption in an amount from about 1 mg/kg to about 10 mg/kg, wherein the amount is effective to reduce serum level of C-telopeptide of type I collagen (CTX) by at least 20%, compared to pre-treatment or normal levels, by 3 weeks after treatment begins. The invention also includes use of a sclerostin binding agent in preparation of a medicament for increasing bone mineral density in an amount from about 1 mg/kg to about 10 mg/kg, wherein the amount is effective to (a) reduce serum level of CTX by at least 20% compared to pre-treatment or normal levels, by 3 weeks after treatment begins, and (b) increase serum level of a bone formation marker selected from the group consisting of serum level of bone-specific alkaline phosphatase (BSAP), serum level of amino-terminal extension of peptide of procollagen type 1 (PINP), and serum level of osteocalcin (OstCa), by at least 20%, compared to pre-treatment or normal levels, by 3 weeks after treatment begins.

The invention further includes use of a sclerostin binding agent in preparation of a medicament for treating a bone-related disorder in an amount from about 1 mg/kg to about 10 mg/kg for a first period of time, wherein the amount is effective to increase bone mineral density at the hip, spine, wrist, finger, shin bone and/or heel by at least about 3%, followed by an amount of from about 1 mg/kg to about 10 mg/kg for a second period of time effective to maintain bone mineral density. Use of a sclerostin binding agent in preparation of a medicament for treating a bone-related disorder in a human suffering from or at risk of hypocalcemia or hypercalcemia in an amount from about 1 mg/kg to about 10 mg/kg, also is contemplated, as well as use of a sclerostin binding agent in preparation of a medicament for treating a bone-related disorder in (a) a human in which treatment with a parathyroid hormone or analog thereof is contraindicated or (b) a human in which treatment with bisphosphonate is contraindicated.

The invention also includes containers comprising anti-sclerostin antibody or fragment thereof. In one embodiment, the container comprises anti-sclerostin antibody or fragment thereof and instructions for administering the antibody or fragment thereof in an amount effective to (a) reduce serum level of C-telopeptide of type I collagen (CTX) by at least 20%, compared to pre-treatment or normal levels, by 3 weeks after treatment begins, and (b) increase serum level bone-specific alkaline phosphatase (BSAP), serum level of amino-terminal extension of peptide of procollagen type 1 (PINP), or serum level of osteocalcin (OstCa) by at least 20%, compared to pre-treatment or normal levels, by 3 weeks after treatment begins. Alternatively or in addition, the container comprises an amount of anti-sclerostin antibody from about 70 mg to about 450 mg. The invention further provides a container comprising anti-sclerostin antibody or fragment thereof and instructions for administering the antibody or fragment thereof for treating a bone-related disorder in an amount from about 1 mg/kg to about 10 mg/kg every two or four weeks. In addition, the invention provides a container comprising anti-sclerostin antibody or fragment thereof and instructions for administering the antibody or fragment thereof for treating a bone-related disorder in an amount from about 1 mg/kg to about 10 mg/kg for a period of about 3 months.

DETAILED DESCRIPTION OF THE INVENTION

Figure 1:
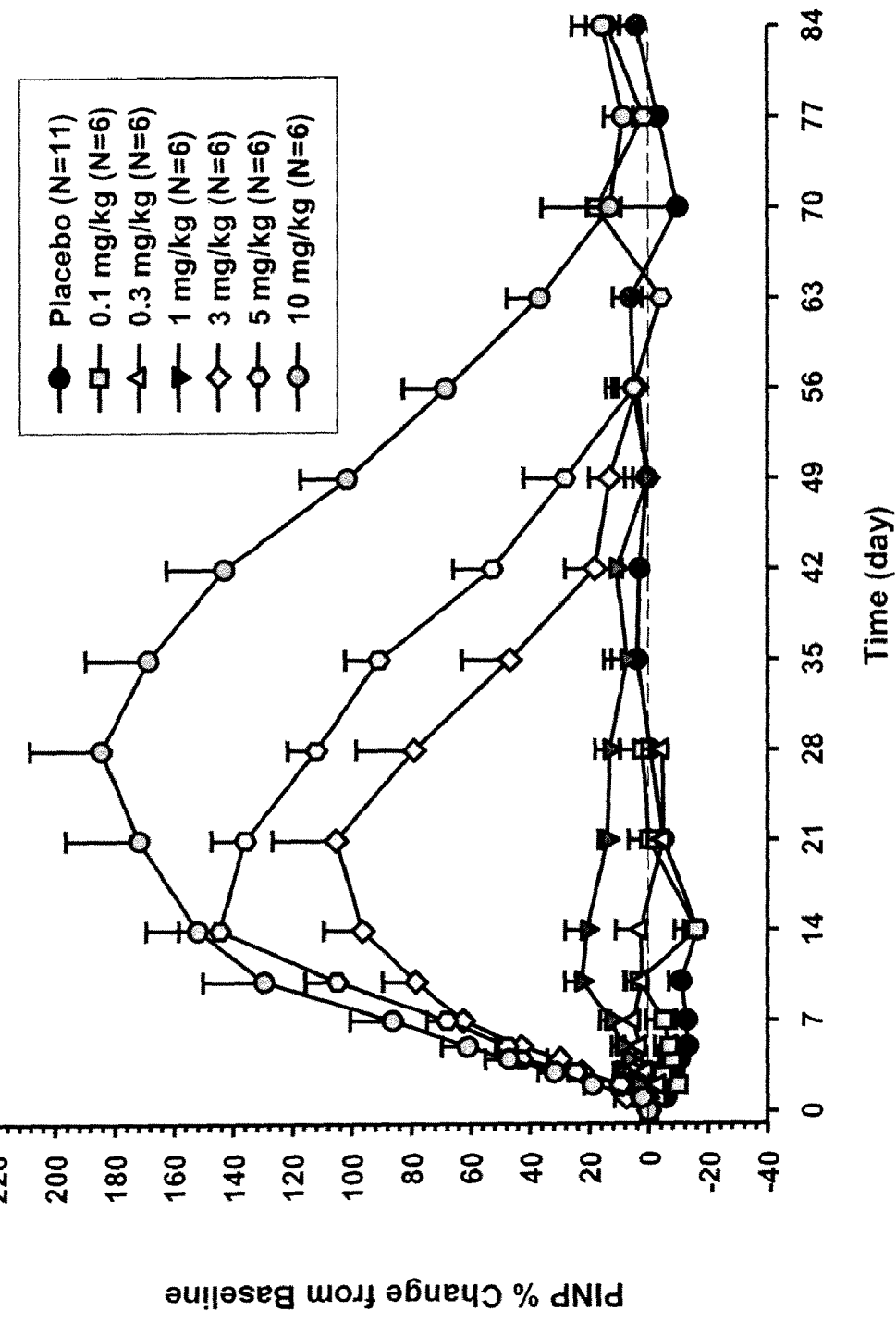
FIG. 1 is a graph of percent change of N-terminal extension of procollagen type 1 (P1NP) levels compared to baseline and placebo P1NP levels versus time (day) post-administration of various single doses of a sclerostin binding agent in healthy, postmenopausal women.

The invention is predicated, at least in part, on the surprising discovery that blocking or inhibiting the biological activity of human sclerostin triggers multiple physiological responses linked to increased bone mineral density (BMD), including significant inhibition of bone resorption. Most currently available therapies only inhibit bone resorption without increasing bone formation. Some currently available therapies for disorders associated with reduced BMD only increase bone formation without significantly reducing bone resorption. For example, when bone formation is triggered by some current drugs, bone resorption may also increase (albeit potentially at a lower rate than before therapy). In contrast, agents that interfere with sclerostin activity both enhance bone formation and reduce bone resorption. In other words, sclerostin inhibitors "uncouple" bone formation and bone resorption to more effectively build bone. The materials and methods of the invention are superior to existing therapies whose therapeutic efficacy is limited and which are accompanied by potentially serious adverse side effects.

In this regard, the invention provides a method of inhibiting bone resorption, e.g., bone resorption mediated by osteoclasts, bone cells that dissolve bone mineral matrices. The invention further provides a method of ameliorating the effects of an osteoclast-related disorder, i.e., a disorder caused by abnormally increased osteoclast activity that, in some embodiments, manifests as abnormally high bone resorption. The inventive method comprises administering to a human an amount of sclerostin binding agent that reduces the level of a marker of bone resorption and, optionally, increases the level of a marker of bone formation.

Activity of a sclerostin inhibitor, e.g., a sclerostin binding agent, (further described below) may be measured in a variety of ways. Sclerostin binding agent-mediated increases in bone mineral content or bone density may be measured using single- and dual-energy X-ray absorptometry, ultrasound, computed tomography, radiography, and magnetic resonance imaging. The amount of bone mass may also be calculated from body weights or by using other methods (see Guinness-Hey, *Metab. Bone Dis. Relat. Res.*, 5:177-181 (1984)). Animals and particular animal models are used in the art for testing the effect of the pharmaceutical compositions and methods on, for example, parameters of bone loss, bone resorption, bone formation, bone strength, or bone mineralization that mimic conditions of human disease such as osteoporosis and osteopenia. Examples of such models include the ovariectomized rat model (Kalu, *Bone and Mineral*, 15:175-192 (1991); Frost and Jee, *Bone and Mineral*, 18:227-236 (1992); and Jee and Yao, *J. Musculoskel. Neuron. Interact.*, 1:193-207 (2001)). The methods for measuring sclerostin binding agent activity described herein also may be used to determine the efficacy of other sclerostin inhibitors.

In humans, bone mineral density can be determined clinically using dual x-ray absorptiometry (DXA) of, for example, the hip and spine. Other techniques include quantitative computed tomography (QCT), ultrasonography, single-energy x-ray absorptiometry (SXA), and radiographic absorptiometry. Common central skeletal sites for measurement include the spine and hip; peripheral sites include the forearm, finger, wrist and heel. Except for ultrasonography, the American Medical Association notes that BMD techniques typically involve the use of x-rays and are based on the principle that attenuation of the radiation depends on thickness and composition of the tissues in the radiation path. All techniques involve the comparison of results to a normative database.

Alternatively, a physiological response to one or more sclerostin binding agents can be gauged by monitoring bone marker levels. Bone markers are products created during the bone remodeling process and are released by bone, osteoblasts, and/or osteoclasts. Fluctuations in bone resorption and/or bone formation "marker" levels imply changes in bone remodeling/modeling. The International Osteoporosis Foundation (IOF) recommends using bone markers to monitor bone density therapies (see, e.g., Delmas et al., *Osteoporos Int.*, Suppl. 6:S2-17 (2000), incorporated herein by reference). Markers indicative of bone resorption (or osteoclast activity) include, for example, C-telopeptide (e.g., C-terminal telopeptide of type 1 collagen (CTX) or serum cross-linked C-telopeptide), N-telopeptide (N-terminal telopeptide of type 1 collagen (NTX)), deoxypyridinoline (DPD), pyridinoline, urinary hydroxyproline, galactosyl hydroxylysine, and tartrate-resistant acid phosphatase (e.g., serum tartrate-resistant acid phosphatase isoform 5b). Bone formation/mineralization markers include, but are not limited to, bone-specific alkaline phosphatase (BSAP), peptides released from N- and C-terminal extension of type I procollagen (P1NP, PICP), and osteocalcin (OstCa). Several kits are commercially-available to detect and quantify markers in clinical samples, such as urine and blood.

Upon administration, the sclerostin binding agent preferably reduces the level of one or more markers of bone resorption, such as the serum level of C-telopeptide of type I collagen (CTX). Accordingly, the invention further provides a method of monitoring anti-sclerostin therapy, i.e., the physiological response to a sclerostin binding agent or other sclerostin inhibitor. The method comprises administering a sclerostin binding agent, then measuring the level of one or more markers of bone resorption. In addition, the method can comprise measuring the level of one or more markers of bone formation before administration of a sclerostin binding agent. The level of bone resorption marker during and/or after treatment with the sclerostin binding agent may be compared to a pre-treatment level, or alternatively may be compared to a standard range typical of that patient population. One of ordinary skill in the art can readily determine a suitable standard range by testing a representative number of patients of like age, gender, disease level, and/or other characteristics of the patient population. The level of bone resorption marker can be reduced by at least about 5% (e.g., about 10%, about 20%, or about 30%) by a single dose of sclerostin binding agent. In some embodiments, the dose of sclerostin binding agent reduces the level of bone resorption marker at least about 40% (e.g., about 50%, about 60%, or about 70%) compared to the level of the bone resorption marker prior to administering the sclerostin binding agent. In addition, the bone resorption marker level may be reduced for at least about 3 days (e.g., about 7 days, about 2 weeks, about 3 weeks, about 1 month, about 5 weeks, about 6 weeks, about 7 weeks, about 2 months, about 9 weeks, about 10 weeks, about 11 weeks, or about 3 months) after administration of a single dose of the sclerostin binding agent.

In addition to decreasing the level of bone resorption markers, the amount of sclerostin binding agent administered to a patient also can increase the level of one or more markers of bone formation, such as the serum level of BSAP, the serum level of P1NP, and/or the serum level of OstCa. A single dose of sclerostin binding agent can increase the level of a bone formation marker by, for example, at least about 5% (e.g., about 10%, about 20%, or about 30%). In some embodiments, the dose of sclerostin binding agent elevates the level of a bone formation marker at least about 40% (e.g., about 50%, about 60%, or about 70%). In other embodiments, the dose of sclerostin binding agent increases the level of one or more bone formation markers by at least about 75% (e.g., about 80%, about 90%, about 100%, or about 110%). In yet other embodiments, the dose of sclerostin binding agent increases the level of a bone formation marker by at least about 120% (e.g., about 130%, about 140%, about 150%, about 160% or about 170%). In alternative embodiments, the sclerostin binding agent increases the level of bone formation marker by least about 180% (e.g., about 190% or about 200%). Bone formation marker levels ideally remain elevated (compared to bone formation marker levels pre-treatment or to a standard range typical of that patient population) for at least about 3 days (e.g., about 7 days, about 2 weeks, about 3 weeks, about 1 month, about 5 weeks, about 6 weeks, about 7 weeks, about 2 months, about 9 weeks, about 10 weeks, about 11 weeks, or about 3 months) after administration of a single dose of the sclerostin binding agent.

The invention also provides a method of increasing bone mineral density (BMD), wherein an amount of sclerostin binding agent that (a) reduces the level of a marker of bone resorption and (b) increases the level of a marker of bone formation is administered to a human. BMD generally correlates with skeletal fragility and osteoporosis. Typically, BMD is can be measured "total body" (e.g., head, trunk, arms, and legs) or at the hip (e.g., total hip and/or femoral neck), spine (e.g., lumbar spine), wrist, finger, shin bone and/or heel. In osteoporosis diagnosis, a patient's BMD is compared to the peak density of a 30-year old healthy adult (i.e., a "young adult"), creating the so-called "T-score." A patient's BMD also may be compared to an "age-matched" bone density (see, e.g., World Health Organization Scientific Group on the Prevention and Management of Osteoporosis, "Prevention and management of osteoporosis: report of a WHO scientific group." *WHO Technical Report Series;* 921, Geneva, Switzerland (2000)). The difference between a patient's BMD and that of a healthy, young adult is conventionally referred to in terms of the multiple of a "standard deviation," which typically equals about 10% to about 12% decrease in bone density. The World Health Organization proposed four diagnostic categories based on BMD T-scores. A BMD value within 1 standard deviation of the young adult reference mean (T-score≧−1) is "normal." Low bone mass (osteopenia) is indicated by a BMD value more than 1 standard deviation below the young adult mean, but less than 2 standard deviations (T-score<−1 and >−2.5). A T-score of more than 2.5 standard deviations below the norm supports a diagnosis of osteoporosis. If a patient additionally suffers from one or more fragility fractures, the patient qualifies as having severe osteoporosis.

The sclerostin inhibitor, e.g., a sclerostin binding agent, may be administered to a patient to improve bone mineral density regardless of the patient's T-score. The sclerostin binding agent may be administered at a dose and for a time period effective to increase BMD in the patient by at least about 1% (about 2%, about 3%, about 4%, about 5%, or about 6%). In some embodiments, BMD is increased by at least about 8% (e.g., at least about 10%, about 12%, about 15%, or about 18%). In other embodiments, BMD is increased by the sclerostin binding agent at least about 20% (e.g., at least about 22%, about 25%, or about 28%) at the hip, spine, wrist, finger, shin bone, and/or heel. In yet other embodiments, BMD is increased at least about 30% (e.g., at least about 32%, about 35%, about 38%, or about 40%). In other words, the BMD can be increased to the range of about 1 to about 2.5 standard deviations (preferably a range of about 0 to about 1 standard deviations) below the normal BMD of a healthy young adult.

Alterations in bone remodeling can lead to fluctuations in mineral concentrations throughout the body. Bone is one of the principal regulators of calcium levels in the bloodstream. Osteoclast-mediated bone resorption releases stored calcium into the systemic circulation, while osteoblast-mediated bone formation removes calcium from circulation to incorporate into bone tissue. In normal bone remodeling, these processes cycle to maintain healthy, strong bone and maintain free calcium levels at about 8.5 mg/dL to about 10.5 mg/dL (e.g., about 2.2 mmol/L to about 2.6 mmol/L). Bone disorders, other illnesses, and even certain therapies can disrupt systemic calcium levels with dire consequences. Hypercalcemia is associated with high levels of calcium in the blood (e.g., greater than 12 mg/dL or 3 mmol/L). Extraordinarily high calcium levels leads to, for example, fatigue, confusion, constipation, decreased appetite, frequent urination, heart problems, and bone pain. Hypocalcemia is an electrolyte imbalance indicated by an abnormally low level of calcium in the blood (e.g., less than about 9 mg/dL or 2.2 mmol/L). Calcium levels of <7.5 mg/dL (<1.87 mmol/L) or less are considered severe hypocalcemia and may be accompanied by clinical symptoms.

Common symptoms of hypocalcemia include nerve and muscle spasms and cramps, numbness, tingling in the extremities, confusion, and heart irregularities. Extreme variations in system calcium can lead to coma and death.

Several ailments and pharmaceutical therapies alter system calcium levels. Hypercalcemia and hypocalcemia can result from, for example, chronic kidney disease, renal failure, primary or secondary hyperparathyroidism, pseudohyperparathyroidism, hypoparathyroidism, pseudohypoparathyroidism, magnesium depletion, alcoholism, bisphosphonate therapy, severe hypermagnesemia, vitamin D deficiency, hyperphosphatemia, acute pancreatitis, hungry bone syndrome, chelation, osteoblastic metastases, sepsis, surgery, chemotherapy, neoplasia syndrome, familial hypocalciuric hypercalcemia, sarcoidosis, tuberculosis, berylliosis, histoplasmosis, Candidiasis, Coccidioidomycosis, histiocytosis X, Hodgkin's or Non-Hodgkin's lymphoma, Crohn's disease, Wegener's granulomatosis, leukemia, pneumonia, silicone-induced granulomas, immobilization, or drug therapy, such as administration of thiazide diuretics, lithium, estrogens, fluorides, glucose, and insulin. In addition, serum calcium fluctuations are a side effect of many existing bone-related therapies, such as bisphosphonate and parathyroid hormone therapy. Because of the potentially life-threatening consequences of calcium imbalance, patients susceptible to hypocalcemia or hypercalcemia may need to forego certain therapy options.

Remarkably, sclerostin inhibitors, e.g., sclerostin binding agents, have been shown to promote bone formation and inhibit (or slow) bone resorption with minimal fluctuations in systemic calcium levels (e.g., calcium levels fluctuate 10% or less from baseline serum calcium levels). Accordingly, the materials and method of the invention are particularly advantageous in treating patients that are susceptible or sensitive to unstable calcium levels. The amount of sclerostin binding agent administered to a human in the context of this aspect of the invention is an amount that does not result in hypocalcemia or hypercalcemia (e.g., clinically-significant hypocalcemia or hypercalcemia). In addition, the invention provides a method of treating a bone-related disorder in a human suffering from or at risk of hypocalcemia or hypercalcemia or a human in which treatment with bisphosphonate, a parathyroid hormone, or parathyroid hormone analog is contraindicated. The method comprises administering to the human an amount of a sclerostin binding agent effective to increase the level of a marker of bone formation, such as serum levels of BSAP, P1NP, and/or OstCa and/or reduce the level of a marker of bone resorption, such as CTX.

The inventive method is useful for treating or preventing bone-related disorders, such as bone-related disorders associated with abnormal osteoblast or osteoclast activity. Indeed, the sclerostin inhibitor (e.g., sclerostin binding agent) can be administered to a human suffering from a bone related disorder selected from the group consisting of achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, pyogenic osteomyelitis, periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthe's Disease, adolescent idiopathic scoliosis, infantile onset multi-system inflammatory disease, Winchester Syndrome, Menkes Disease, Wilson's Disease, ischemic bone disease (such as Legg-Calve-Perthes disease and regional migratory osteoporosis), anemic states, conditions caused by steroids, glucocorticoid-induced bone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, chemotherapy-associated bone loss, tumor-induced bone loss, cancer-related bone loss, hormone ablative bone loss, multiple myeloma, drug-induced bone loss, anorexia nervosa, disease-associated facial bone loss, disease-associated cranial bone loss, disease-associated bone loss of the jaw, disease-associated bone loss of the skull, bone loss associated with aging, facial bone loss associated with aging, cranial bone loss associated with aging, jaw bone loss associated with aging, skull bone loss associated with aging, and bone loss associated with space travel.

The inventive method need not cure the patient of the disorder or completely protect against the onset of a bone-related disorder to achieve a beneficial biological response. The method may be used prophylactically, meaning to protect, in whole or in part, against a bone-related disorder or symptom thereof. The method also may be used therapeutically to ameliorate, in whole or in part, a bone-related disorder or symptom thereof, or to protect, in whole or in part, against further progression of a bone-related disorder or symptom thereof. Indeed, the materials and methods of the invention are particularly useful for increasing bone mineral density and maintaining the increased BMD over a period of time. In this regard, the invention provides a method of treating a bone-related disorder, which method comprises (a) administering one or more amounts of a sclerostin binding agent effective to increase BMD measured for the total body (e.g., head, trunk, arms, and legs) or at the hip (e.g., total hip and/or femoral neck), spine (e.g., lumbar spine), wrist, finger, shin bone and/or heel by about 1%, about 2%, about 3%, about 6%, about 8%, about 10%, about 12%, about 15%, about 18%, about 20%, about 25%, or 30% or more. One or more administrations of a pharmaceutical composition comprising the sclerostin binding agent may be carried out over a therapeutic period of, for example, about 1 month to about 12 months (e.g., about 2 months, about 3 months, about 4 months, about 5 months, about 6 months, about 7 months, about 8 months, about 9 months, about 10 months, or about 11 months). The method further includes (b) subsequently administering one or more amounts of a sclerostin binding agent effective to maintain bone mineral density. By "maintain bone mineral density" is meant that the increased BMD resulting from step (a) does not fall more than about 1% to about 5% over the course of step (b) (e.g., about 6 months, about 9 months about 1 year, about 18 months, about 2 years, or over the course of the patient's life). It will be appreciated that a patient can require alternate treatment phases for increasing bone density and maintaining bone density.

The sclerostin binding agent is preferably administered to a patient in a physiologically-acceptable (e.g., pharmaceutical) composition, which can include carriers, excipients, or diluents. It will be appreciated that the sclerostin binding agents described herein may be used in the preparation of a medicament for administration using any of the dosage and timing regimens disclosed herein. Pharmaceutical compositions and methods of treatment are disclosed in U.S. Patent Publication No. 20050106683, which is incorporated by reference herein. "Physiologically-acceptable" refers to molecular entities and compositions that do not produce an allergic or similar untoward reaction when administered to a human. In addition, the composition administered to a subject may contain more than one sclerostin inhibitor (e.g., a sclerostin binding agent and a synthetic chemical sclerostin inhibitor) or a sclerostin inhibitor in combination with one or more therapeutics having different mechanisms of action.

The development of suitable dosing and treatment regimens for using the particular compositions described herein in a variety of treatment regimens, including e.g., subcutaneous, oral, parenteral, intravenous, intranasal, and intramuscular administration and formulation, is well known in the art and discussed in U.S. Patent Publication No. 20070110747. For example, in certain circumstances, it will be desirable to deliver a pharmaceutical composition comprising a sclerostin binding agent subcutaneously, parenterally, intravenously, intramuscularly, or even intraperitoneally. Such approaches are well known to the skilled artisan, some of which are further described, for example, in U.S. Pat. Nos. 5,543,158; 5,641,515; and 5,399,363. Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. For example, one dose may be dissolved in 1 ml of isotonic NaCl solution and either added to 1000 ml of hypodermoclysis fluid or injected at the proposed site of infusion (see, for example, Remington's Pharmaceutical Sciences, 15th ed., Mack Pub. Co., Easton, Pa., pp. 1035-1038 and 1570-1580). Some variation in dosage and frequency of administration may occur depending on the condition of the subject being treated; age, height, weight, and overall health of the patient; and the existence of any side effects. In addition, a pharmaceutical composition comprising a sclerostin binding agent may be placed within containers (e.g., vials), along with packaging material that provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) that may be necessary to reconstitute the pharmaceutical composition.

The sclerostin binding agent is administered in an amount that reduces the level of a bone resorption marker and/or increases the level of a bone formation marker and/or increases bone density. The dose of sclerostin binding agent administered may range from about 0.5 mg/kg to about 20 mg/kg (e.g., 12 mg/kg) of body weight. For example, the dose of sclerostin binding agent may range from about 1 mg/kg to about 10 mg/kg (e.g., about 2 mg/kg or about 9 mg/kg), about 1 mg/kg to about 3 mg/kg, or about 3 mg/kg to about 8 mg/kg (e.g., about 4 mg/kg, 5 mg/kg, 6 mg/kg, or 7 mg/kg).

In addition, it may be advantageous to administer multiple doses of a sclerostin binding agent or space out the administration of doses, depending on the therapeutic regimen selected for a particular patient. The sclerostin binding agent can be administered periodically over a time period of one year or less (e.g., 9 months or less, 6 months or less, or 3 months or less). In this regard, the sclerostin binding agent can be administered to the human once every about 7 days, or 2 weeks, or 3 weeks, or 1 month, or 5 weeks, or 6 weeks, or 7 weeks, or 2 months, or 9 weeks, or 10 weeks, or 11 weeks, or 3 months, or 13 weeks, or 14 weeks, or 15 weeks, or 4 months, or 17 weeks, or 18 weeks, or 19 weeks, or 5 months, or 21 weeks, or 22 weeks, or 23 weeks, or 6 months, or 12 months.

The inventive method comprises administering an amount of a "sclerostin inhibitor." As used herein, the term "sclerostin inhibitor" means any molecule that inhibits the biological activity of sclerostin on bone, as measured by changes to bone mineralization, bone density, effect on osteoblasts and/or osteoclasts, markers of bone formation, markers of bone resorption, markers of osteoblast activity, and/or markers of osteoclast activity. Such inhibitors may act by binding to sclerostin or its receptor or binding partner. Inhibitors in this category include "sclerostin binding agents," such as, e.g., antibodies or peptide-based molecules. "Sclerostin inhibitors" also refers to small organic chemical compounds, optionally of less than about 1000 Daltons in molecular weight that bind sclerostin and inhibit its activity. Inhibitors may alternatively act by inhibiting expression of sclerostin. Inhibitors in this category include polynucleotides or oligonucleotides that bind to sclerostin DNA or mRNA and inhibit sclerostin expression, including an antisense oligonucleotide, inhibitory RNA, DNA enzyme, ribozyme, an aptamer or pharmaceutically acceptable salts thereof that inhibit the expression of sclerostin.

A "sclerostin binding agent" specifically binds to sclerostin or portions thereof to block or impair binding of human sclerostin to one or more ligands. Sclerostin, the product of the SOST gene, is absent in sclerosteosis, a skeletal disease characterized by bone overgrowth and strong dense bones (Brunkow et al., *Am. J. Hum. Genet.*, 68:577-589 (2001); Balemans et al., *Hum. Mol. Genet.*, 10:537-543 (2001)). The amino acid sequence of human sclerostin is reported by Brunkow et al. and is disclosed in U.S. Patent Publication No. 20070110747 as SEQ ID NO: 1 (which patent publication is incorporated in its entirety for its description of sclerostin binding agents and Sequence Listing). Recombinant human sclerostin/SOST is commercially available from R&D Systems (Minneapolis, Minn., USA; 2006 Catalog #1406-ST-025). Additionally, recombinant mouse sclerostin/SOST is commercially available from R&D Systems (Minneapolis, Minn., USA; 2006 Catalog #1589-ST-025). Research grade sclerostin-binding monoclonal antibodies are commercially available from R&D Systems (Minneapolis, Minn., USA; mouse monoclonal: 2006 Catalog # MAB1406; rat monoclonal: 2006 Catalog # MAB1589). U.S. Pat. Nos. 6,395,511 and 6,803,453, and U.S. Patent Publication Nos. 20040009535 and 20050106683 refer to anti-sclerostin antibodies generally. Examples of sclerostin binding agents suitable for use in the context of the invention also are described in U.S. Patent Publication Nos. 20070110747 and 20070072797, which are hereby incorporated by reference. Additional information regarding materials and methods for generating sclerostin binding agents can be found in U.S. Patent Publication No. 20040158045.

The sclerostin binding agent of the invention preferably is an antibody. The term "antibody" refers to an intact antibody, or a binding fragment thereof. An antibody may comprise a complete antibody molecule (including polyclonal, monoclonal, chimeric, humanized, or human versions having full length heavy and/or light chains), or comprise an antigen binding fragment thereof. Antibody fragments include $F(ab')_2$, Fab, Fab', Fv, Fc, and Fd fragments, and can be incorporated into single domain antibodies, single-chain antibodies, maxibodies, minibodies, intrabodies, diabodies, triabodies, tetrabodies, v-NAR and bis-scFv (see, e.g., Hollinger and Hudson, *Nature Biotechnology,* 23(9):1126-1136 (2005)). Antibody polypeptides, including fibronectin polypeptide monobodies, also are disclosed in U.S. Pat. No. 6,703,199. Other antibody polypeptides are disclosed in U.S. Patent Publication No. 20050238646. Anti-sclerostin antibodies may bind to sclerostin of SEQ ID NO: 1, or a naturally occurring variant thereof, with an affinity of less than or equal to $1\times10^{-7}$M, less than or equal to $1\times10^{-8}$M, less than or equal to $1\times10^{-9}$M, less than or equal to $1\times10^{-10}$M, less than or equal to $1\times10^{-11}$M, or less than or equal to $1\times10^{-12}$ M. Affinity may be determined by an affinity ELISA assay. In certain embodiments, affinity may be determined by a BIAcore assay. In certain embodiments, affinity may be determined by a kinetic method. In certain embodiments, affinity may be determined by an equilibrium/solution method.

An antibody fragment may be any synthetic or genetically engineered protein. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker (scFv proteins).

Another form of an antibody fragment is a peptide comprising one or more complementarity determining regions (CDRs) of an antibody. CDRs (also termed "minimal recognition units" or "hypervariable region") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., *Methods: A Companion to Methods in Enzymology,* 2:106 (1991); Courtenay-Luck, "Genetic Manipulation of Monoclonal Antibodies," in *Monoclonal Antibodies Production, Engineering and Clinical Application*, Ritter et al. (eds.), page 166, Cambridge University Press (1995); and Ward et al., "Genetic Manipulation and Expression of Antibodies," in *Monoclonal Antibodies: Principles and Applications*, Birch et al., (eds.), page 137, Wiley-Liss, Inc. (1995)).

In one embodiment of the invention, the sclerostin binding agent cross-blocks the binding of at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24 (all of which are described in U.S. Patent Publication No. 20070110747) to sclerostin. Alternatively or in addition, the sclerostin binding agent is cross-blocked from binding to sclerostin by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24 (all of which are described in U.S. Patent Publication No. 20070110747). The terms "cross-block," "cross-blocked," and "cross-blocking" are used interchangeably herein to mean the ability of an antibody or other binding agent to interfere with the binding of other antibodies or binding agents to sclerostin. The extent to which an antibody or other binding agent is able to interfere with the binding of another to sclerostin, and therefore whether it can be said to cross-block, can be determined using competition binding assays. In some aspects of the invention, a cross-blocking antibody or fragment thereof reduces sclerostin binding of a reference antibody between about 40% and about 100%, such as about 60% and about 100%, specifically between 70% and 100%, and more specifically between 80% and 100%. A particularly suitable quantitative assay for detecting cross-blocking uses a Biacore machine which measures the extent of interactions using surface plasmon resonance technology. Another suitable quantitative cross-blocking assay uses an ELISA-based approach to measure competition between antibodies or other binding agents in terms of their binding to sclerostin.

Suitable sclerostin binding agents include antibodies and portions thereof described in U.S. Patent Publication No. 20070110747, such as one or more of CDR-H1, CDR-H2, CDR-H3, CDR-L1, CDR-L2 and CDR-L3 as specifically disclosed therein. At least one of the regions of CDR-H1, CDR-H2, CDR-H3, CDR-L1, CDR-L2, and CDR-L3 may have at least one amino acid substitution, provided that the binding agent retains the binding specificity of the non-substituted CDR. The non-CDR portion of the binding agent may be a non-protein molecule, wherein the binding agent cross-blocks the binding of an antibody disclosed herein to sclerostin and/or neutralizes sclerostin. The non-CDR portion of the binding agent may be a non-protein molecule in which the binding agent exhibits a similar binding pattern to human sclerostin peptides in a human sclerostin peptide epitope competition binding assay as that exhibited by at least one of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24 (all of which are described in U.S. Patent Publication No. 20070110747), and/or neutralizes sclerostin. The non-CDR portion of the binding agent may be composed of amino acids, wherein the binding agent is a recombinant binding protein or a synthetic peptide, and the recombinant binding protein cross-blocks the binding of an antibody to sclerostin and/or neutralizes sclerostin. The non-CDR portion of the binding agent may be composed of amino acids, wherein the binding agent is a recombinant binding protein, and the recombinant binding protein exhibits a similar binding pattern to human sclerostin peptides in the human sclerostin peptide epitope competition binding assay (described in U.S. Patent Publication No. 20070110747) as that exhibited by at least one of the antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, and Ab-24 (described in U.S. Patent Publication No. 20070110747), and/or neutralizes sclerostin. Preferably, the sclerostin binding agent is Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23, or Ab-24 of U.S. Patent Publication No. 20070110747.

In addition, the sclerostin binding agent can comprise at least one CDR sequence having at least 75% identity (e.g., 100% identity) to a CDR selected from SEQ ID NOs: 39, 40, 41, 42, 43, 44, 45, 46, 47, 48, 49, 50, 51, 52, 53, 54, 55, 56, 57, 58, 59, 60, 61, 62, 78, 79, 80, 81, 99, 100, 101, 102, 103, 104, 105, 106, 107, 108, 109, 110, 111, 112, 113, 114, 115, 116, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 351, 352, 353, 358, 359, and 360 disclosed in U.S. Patent Publication No. 20070110747. Preferably, the sclerostin binding agent comprises at least one CDR sequence having at least 75% identity to a CDR selected from SEQ ID NOs: 245, 246, 247, 78, 79, 80, 269, 270, 271, 239, 240, and 24, all of which is described in U.S. Patent Publication No. 20070110747. As described in U.S. Patent Publication No. 20070110747, the sclerostin binding agent can comprise: a) CDR sequences of SEQ ID NOs:54, 55, and 56 and CDR sequences of SEQ ID NOs:51, 52, and 53; b) CDR sequences of SEQ ID NOs:60, 61, and 62 and CDR sequences of SEQ ID NOs:57, 58, and 59; c) CDR sequences of SEQ ID NOs:48, 49, and 50 and CDR sequences of SEQ ID NOs:45, 46, and 47; d) CDR sequences of SEQ ID NOs:42, 43, and 44 and CDR sequences of SEQ ID NOs:39, 40, and 41; e) CDR sequences of SEQ ID NOs:275, 276, and 277 and CDR sequences of SEQ ID NOs:287, 288, and 289; f) CDR sequences of SEQ ID NOs:278, 279, and 280 and CDR sequences of SEQ ID NOs:290, 291, and 292; g) CDR sequences of SEQ ID NOs:78, 79, and 80 and CDR sequences of SEQ ID NOs: 245, 246, and 247; h) CDR sequences of SEQ ID NOs:81, 99, and 100 and CDR sequences of SEQ ID NOs:248, 249, and 250; i) CDR sequences of SEQ ID NOs: 101, 102, and 103 and CDR sequences of SEQ ID NOs:251, 252, and 253; j) CDR sequences of SEQ ID NOs:104, 105, and 106 and CDR sequences of SEQ ID NOs:254, 255, and 256; k) CDR sequences of SEQ ID NOs:107, 108, and 109 and CDR sequences of SEQ ID NOs:257, 258, and 259; l) CDR sequences of SEQ ID NOs:110, 111, and 112 and CDR sequences of SEQ ID NOs:260, 261, and 262; m) CDR sequences of SEQ ID NOs:281, 282, and 283 and CDR sequences of SEQ ID NOs:293, 294, and 295; n) CDR sequences of SEQ ID NOs:113, 114, and 115 and CDR sequences of SEQ ID NOs:263, 264, and 265; o) CDR sequences of SEQ ID NOs:284, 285, and 286 and CDR sequences of SEQ ID NOs:296, 297, and 298; p) CDR sequences of SEQ ID NOs:116, 237, and 238 and CDR sequences of SEQ ID NOs:266, 267, and 268; q) CDR sequences of SEQ ID NOs:239, 240, and 241 and CDR sequences of SEQ ID NOs:269, 270, and 271; r) CDR sequences of SEQ ID NOs:242, 243, and 244 and CDR sequences of SEQ ID NOs:272, 273, and 274; or s) CDR sequences of SEQ ID NOs:351, 352, and 353 and CDR sequences of SEQ ID NOs:358, 359, and 360.

The sclerostin binding agent also can comprise at least one CDR sequence having at least 75% identity to a CDR selected from CDR-H1, CDR-H2, CDR-H3, CDR-L1, CDR-L2, and CDR-L3 wherein CDR-H1 has the sequence given in SEQ ID NO: 245 or SEQ ID NO: 269, CDR-H2 has the sequence given in SEQ ID NO: 246 or SEQ ID NO: 270, CDR-H3 has the sequence given in SEQ ID NO: 247 or SEQ ID NO: 271, CDR-L1 has the sequence given in SEQ ID NO: 78 or SEQ ID NO: 239, CDR-L2 has the sequence given in SEQ ID NO: 79 or SEQ ID NO: 240 and CDR-L3 has the sequence given in SEQ ID NO: 80 or SEQ ID NO 241, all of which is described in U.S. Patent Publication No. 20070110747.

Alternatively, the sclerostin binding agent can have a heavy chain comprising CDR's H1, H2, and H3 and comprising a polypeptide having the sequence provided in SEQ ID NO: 137 or a variant thereof in which said CDR's are at least 75% identical to SEQ ID NO: 245, 246, and 247, respectively, and a light chain comprising CDR's L1, L2 and L3 and comprising a polypeptide having the sequence provided in SEQ ID NO: 133 or a variant thereof in which said CDR's are at least 75% identical to SEQ ID NO: 78, 79, and 80, respectively (as described in U.S. Patent Publication No. 20070110747).

The sclerostin binding agent may have a heavy chain comprising CDR's H1, H2, and H3 and comprising a polypeptide having the sequence provided in SEQ ID NO: 145 or 392 or a variant thereof in which said CDR's are at least 75% identical to SEQ ID NO: 245, 246, and 247, respectively, and a light chain comprising CDR's L1, L2, and L3 and comprising a polypeptide having the sequence provided in SEQ ID NO: 141 or a variant thereof in which said CDR's are at least 75% identical to SEQ ID NO: 78, 79, and 80, respectively (as described in U.S. Patent Publication No. 20070110747).

The sclerostin binding agent may have a heavy chain comprising CDR's H1, H2, and H3 and comprising a polypeptide having the sequence provided in SEQ ID NO: 335 or a variant thereof in which said CDR's are at least 75% identical to SEQ ID NO: 269, 270, and 271, respectively, and a light chain comprising CDR's L1, L2, and L3 and comprising a polypeptide having the sequence provided in SEQ ID NO: 334 or a variant thereof in which said CDR's are at least 75% identical to SEQ ID NO: 239, 240, and 241, respectively (as described in U.S. Patent Publication No. 20070110747).

Alternatively, the sclerostin binding agent has a heavy chain comprising CDR's H1, H2, and H3 and comprising a polypeptide having the sequence provided in SEQ ID NO: 331 or a variant thereof in which said CDR's are at least 75% identical to SEQ ID NO: 269, 270, and 271, respectively, and a light chain comprising CDR's L1, L2, and L3 and comprising a polypeptide having the sequence provided in SEQ ID NO: 330 or a variant thereof in which said CDR's are at least 75% identical to SEQ ID NO: 239, 240, and 241, respectively (as described in U.S. Patent Publication No. 20070110747).

The sclerostin binding agent may have a heavy chain comprising CDR's H1, H2, and H3 and comprising a polypeptide having the sequence provided in SEQ ID NO: 345 or 396 or a variant thereof in which said CDR's are at least 75% identical to SEQ ID NO: 269, 270, and 271, respectively, and a light chain comprising CDR's L1, L2, and L3 and comprising a polypeptide having the sequence provided in SEQ ID NO: 341 or a variant thereof in which said CDR's are at least 75% identical to SEQ ID NO: 239, 240, and 241, respectively (as described in U.S. Patent Publication No. 20070110747).

Alternatively, the sclerostin binding agent has a heavy chain comprising a polypeptide having the sequence provided in SEQ ID NO: 137, and a light chain comprising a polypeptide having the sequence provided in SEQ ID NO: 133; or a heavy chain comprising a polypeptide having the sequence provided in SEQ ID NO: 145 or 392, and a light chain comprising a polypeptide having the sequence provided in SEQ ID NO: 141; or a heavy chain comprising a polypeptide having the sequence provided in SEQ ID NO: 335, and a light chain comprising a polypeptide having the sequence provided in SEQ ID NO: 334; or a heavy chain comprising a polypeptide having the sequence provided in SEQ ID NO: 331, and a light chain comprising a polypeptide having the sequence provided in SEQ ID NO: 330; or a heavy chain comprising a polypeptide having the sequence provided in SEQ ID NO: 345 or 396, and a light chain comprising a polypeptide having the sequence provided in SEQ ID NO: 341 (as described in U.S. Patent Publication No. 20070110747).

Sclerostin binding agents for use in the inventive method preferably modulate sclerostin function in the cell-based assay described in U.S. Patent Publication No. 20070110747 and/or the in vivo assay described in U.S. Patent Publication No. 20070110747 and/or bind to one or more of the epitopes described in U.S. Patent Publication No. 20070110747 and/or cross-block the binding of one of the antibodies described in U.S. Patent Publication No. 20070110747 and/or are cross-blocked from binding sclerostin by one of the antibodies described in U.S. Patent Publication No. 20070110747.

Alternatively, the inventive method can comprise administering a sclerostin inhibitor other than a sclerostin binding agent described herein. Such agents can act directly or indirectly on SOST or sclerostin. Sclerostin inhibitors contemplated for use in the inventive method include those described in U.S. Patent Publication No. 20030229041 (the entire disclosure of which is hereby incorporated by reference, with particular emphasis upon the description of sclerostin inhibitors). For example, agents useful for modulating SOST expression and sclerostin activity include, but are not limited to, steroids (such as those corresponding to Formula 1 of U.S. Patent Publication No. 20030229041), alkaloids, terpenoids, peptoids, and synthetic chemicals. In some embodiments, the SOST antagonist or agonist can bind to a glucocorticoid receptor. For example, dexamethasone tends to abolish the stimulatory effect of BMP-4 and BMP-6 on SOST expression. Other chemical entities including glucocorticoid analogs, bile salts (such as those corresponding to Formula 3 of U.S. Patent Publication No. 20030229041), and prostaglandins (such as those corresponding to Formula 2 of U.S. Patent Publication No. 20030229041) also modulate the effects of bone morphogenetic proteins on SOST expression, and are contemplated for use in the inventive method.

The sclerostin inhibitor may also be other small molecule therapeutics that act directly or indirectly on SOST or sclerostin to decrease the level of at least one bone resorptive marker and/or increase the level of at least one bone formation marker in vivo. The term "small molecule" includes a compound or molecular complex, either synthetic, naturally derived, or partially synthetic, and which preferably has a molecular weight of less than 5,000 Daltons (e.g., between about 100 and 1,500 Daltons). Agents can be obtained using any of the numerous approaches in combinatorial library methods known in the art, including spatially addressable parallel solid phase or solution phase libraries, synthetic library methods requiring deconvolution, the "one-bead one-compound" library method, and synthetic library methods using affinity chromatography selection (see, e.g., Lam, *Anti-cancer Drug Des.*, 12:145 (1997) and U.S. Pat. Nos. 5,738, 996; 5,807,683; and 7,261,892). Methods of developing and screening sclerostin inhibitors are further described in U.S. Patent Publication No. 20030229041, the discussion of which is hereby incorporated by reference.

Sclerostin expression inhibitors that may be used according to the methods of the invention include inhibitor oligonucleotides or polynucleotides, including pharmaceutically acceptable salts thereof, e.g., sodium salts. Nonlimiting examples include: antisense oligonucleotides (Eckstein, *Antisense Nucleic Acid Drug Dev.*, 10: 117-121 (2000); Crooke, *Methods Enzymol.*, 313: 3-45 (2000); Guvakova et al., *J. Biol. Chem.*, 270: 2620-2627 (1995); Manoharan, *Biochim. Biophys. Acta*, 1489: 117-130 (1999); Baker et al., *J. Biol. Chem.*, 272: 11994-12000 (1997); Kurreck, *Eur. J. Biochem.*, 270: 1628-1644 (2003); Sierakowska et al., *Proc. Natl. Acad. Sci. USA*, 93: 12840-12844 (1996); Marwick, *J. Am. Med. Assoc.*, 280: 871 (1998); Tomita and Morishita, *Curr. Pharm. Des.*, 10: 797-803 (2004); Gleave and Monia, *Nat. Rev. Cancer*, 5: 468-479 (2005) and Patil, *AAPS J.*, 7: E61-E77 (2005)), triplex oligonucleotides (Francois et al., *Nucleic Acids Res.*, 16: 11431-11440 (1988) and Moser and Dervan, *Science*, 238: 645-650 (1987)), ribozymes/deoxyribozymes (DNAzymes) (Kruger et al., *Tetrahymena. Cell*, 31: 147-157 (1982); Uhlenbeck, *Nature*, 328: 596-600 (1987); Sigurdsson and Eckstein, *Trends Biotechnol.*, 13: 286-289 (1995); Kumar et al., *Gene Ther.*, 12: 1486-1493 (2005); Breaker and Joyce, *Chem. Biol.*, 1: 223-229 (1994); Khachigian, *Curr. Pharm. Biotechnol.*, 5: 337-339 (2004); Khachigian, *Biochem. Pharmacol.*, 68: 1023-1025 (2004) and Trulzsch and Wood, *J. Neurochem.*, 88: 257-265 (2004)), small-interfering RNAs/RNAi (Fire et al., *Nature*, 391: 806-811 (1998); Montgomery et al., *Proc. Natl. Acad. Sci. U.S.A.*, 95: 15502-15507 (1998); Cullen, *Nat. Immunol.*, 3: 597-599 (2002); Hannon, *Nature*, 418: 244-251 (2002); Bernstein et al., *Nature*, 409: 363-366 (2001); Nykanen et al., *Cell*, 107: 309-321 (2001); Gilmore et al., *J. Drug Target.*, 12: 315-340 (2004); Reynolds et al., *Nat. Biotechnol.*, 22: 326-330 (2004); Soutschek et al., *Nature*, 432173-178 (2004); Ralph et al., *Nat. Med.*, 11: 429-433 (2005); Xia et al., *Nat. Med.*, 10816-820 (2004) and Miller et al., *Nucleic Acids Res.*, 32: 661-668 (2004)), aptamers (Ellington and Szostak, *Nature*, 346: 818-822 (1990); Doudna et al., *Proc. Natl. Acad. Sci. U.S.A.*, 92: 2355-2359 (1995); Tuerk and Gold, *Science*, 249: 505-510 (1990); White et al., *Mol. Ther.*, 4: 567-573 (2001); Rusconi et al., *Nature*, 419: 90-94 (2002); Nimjee et al., *Mol. Ther.*, 14: 408-415 (2006); Gragoudas et al., *N. Engl. J. Med.*, 351: 3805-2816 (2004); Vinores, *Curr. Opin. Mol. Ther.*, 5673-679 (2003) and Kourlas and Schiller et al., *Clin. Ther.*, 28: 36-44 (2006)) or decoy oligonucleotides (Morishita et al., *Proc. Natl. Acad. Sci. U.S.A.*, 92: 5855-5859 (1995); Alexander et al., *J. Am. Med. Assoc.*, 294: 2446-2454 (2005); Mann and Dzau, *J. Clin. Invest.*, 106: 1071-1075 (2000) and Nimjee et al., *Annu. Rev. Med.*, 56: 555-583 (2005)). The foregoing documents are hereby incorporated by reference in their entirety herein, with particular emphasis on those sections of the documents relating to methods of designing, making and using inhibitory oligonucleotides. Commercial providers such as Ambion Inc. (Austin, Tex.), Darmacon Inc. (Lafayette, Colo.), InvivoGen (San Diego, Calif.), and Molecular Research Laboratories, LLC (Herndon, Va.) generate custom siRNA molecules. In addition, commercial kits are available to produce custom siRNA molecules, such as SILENCER™ siRNA Construction Kit (Ambion Inc., Austin, Tex.) or psiRNA System (InvivoGen, San Diego, Calif.).

Inhibitory oligonucleotides which are stable, have a high resistance to nucleases, possess suitable pharmacokinetics to allow them to traffic to target tissue site at non-toxic doses, and have the ability to cross through plasma membranes are contemplated for use as a therapeutic. Inhibitory oligonucleotides may be complementary to the coding portion of a target gene, 3' or 5' untranslated regions, or intronic sequences in a gene, or alternatively coding or intron sequences in the target mRNA. Intron sequences are generally less conserved and thus may provide greater specificity. In one embodiment, the inhibitory oligonucleotide inhibits expression of a gene product of one species but not its homologue in another species; in other embodiments, the inhibitory oligonucleotide inhibits expression of a gene in two species, e.g. human and primate, or human and murine.

The constitutive expression of antisense oligonucleotides in cells has been shown to inhibit gene expression, possibly via the blockage of translation or prevention of splicing. In certain embodiments, the inhibitory oligonucleotide is capable of hybridizing to at least 8, 9, 10, 11, or 12 consecutive bases of the sclerostin gene or mRNA (or the reverse strand thereof) under moderate or high stringency conditions. Suitable inhibitory oligonucleotides may be single stranded and contain a segment, e.g. at least 12, 15 or 18 bases in length, that is sufficiently complementary to, and specific for, an mRNA or DNA molecule such that it hybridizes to the mRNA or DNA molecule and inhibits transcription, splicing or translation. Generally complementarity over a length of less than 30 bases is more than sufficient.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short nucleic acids (e.g., 10 to 50 nucleotides) and at least about 60° C. for longer nucleic acids (e.g., greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C., and a wash in 0.5× to 1×SSC at 55° C. to 60° C. Exemplary high stringency conditions include hybridization in 50% formamide, 1 M NaCl, 1% SDS at 37° C., and a wash in 0.1×SSC at 60° C. to 65° C. Duration of hybridization is generally less than about 24 hours, usually about 4 hours to about 12 hours.

In some cases, depending on the length of the complementary region, one, two or more mismatches may be tolerated without affecting inhibitory function. In certain embodiments, the inhibitory oligonucleotide is an antisense oligonucleotide, an inhibitory RNA (including siRNA or RNAi, or shRNA), a DNA enzyme, a ribozyme (optionally a hammerhead ribozyme), an aptamer, or pharmaceutically acceptable salts thereof. In one embodiment, the oligonucleotide is complementary to at least 10 bases of the nucleotide sequence encoding SEQ ID NO: 1 of U.S. Patent Publication No. 20040158045. In one embodiment, the oligonucleotide targets the nucleotides located in the vicinity of the 3' untranslated region of the sclerostin mRNA.

The specific sequence utilized in design of the oligonucleotides may be any contiguous sequence of nucleotides contained within the expressed gene message of the target. Factors that govern a target site for the inhibitory oligonucleotide sequence include the length of the oligonucleotide, binding affinity, and accessibility of the target sequence. Sequences may be screened in vitro for potency of their inhibitory activity by measuring inhibition of target protein translation and target related phenotype, e.g., inhibition of cell proliferation in cells in culture. In general it is known that most regions of the RNA (5' and 3' untranslated regions, AUG initiation, coding, splice junctions and introns) can be targeted using antisense oligonucleotides. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference in its entirety.

Phosphorothioate antisense oligonucleotides may be used. Modifications of the phosphodiester linkage as well as of the heterocycle or the sugar may provide an increase in efficiency. Phophorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

Most mRNAs have been shown to contain a number of secondary and tertiary structures. Secondary structural elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure. A number of researchers have measured the binding energies of a large number of RNA duplex structures and have derived a set of rules which can be used to predict the secondary structure of RNA (see, e.g., Jaeger et al., *Proc. Natl. Acad. Sci. USA*, 86:7706 (1989); and Turner et al., *Annu. Rev. Biophys. Biophys. Chem.* 17:167 (1988)). The rules are useful in identification of RNA structural elements and, in particular, for identifying single stranded RNA regions which may represent segments of the mRNA to target for siRNA, ribozyme, or antisense technologies.

Short interfering (si) RNA technology (also known as RNAi) generally involves degradation of an mRNA of a particular sequence induced by double-stranded RNA (dsRNA) that is homologous to that sequence, thereby "interfering" with expression of the corresponding gene. Any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of as few as 21 to 22 base pairs in length. Accordingly, siRNA may be affected by introduction or expression of relatively short homologous dsRNAs. Exemplary siRNAs have sense and antisense strands of about 21 nucleotides that form approximately 19 nucleotides of double stranded RNA with overhangs of two nucleotides at each 3' end. Indeed the use of relatively short homologous dsRNAs may have certain advantages.

Mammalian cells have at least two pathways that are affected by double-stranded RNA (dsRNA). In the sequence-specific siRNA pathway, the initiating dsRNA is first broken into short interfering RNAs, as described above. Short interfering RNAs are thought to provide the sequence information that allows a specific messenger RNA to be targeted for degradation. In contrast, the nonspecific pathway is triggered by dsRNA of any sequence, as long as it is at least about 30 base pairs in length.

The nonspecific effects occur because dsRNA activates two enzymes: PKR, which in its active form phosphorylates the translation initiation factor eIF2 to shut down all protein synthesis, and 2', 5' oligoadenylate synthetase (2', 5'-AS), which synthesizes a molecule that activates RNase L, a nonspecific enzyme that targets all mRNAs. The nonspecific pathway may represent a host response to stress or viral infection, and, in general, the effects of the nonspecific pathway are preferably minimized. Significantly, longer dsRNAs appear to be required to induce the nonspecific pathway and, accordingly, dsRNAs shorter than about 30 bases pairs are contemplated to effect gene repression by RNAi (see Hunter et al., *J. Biol. Chem.,* 250: 409-17 (1975); Manche et al., *Mol. Cell. Biol.* 12: 5239-48 (1992); Minks et al., *J. Biol. Chem.,* 254: 10180-3 (1979); and Elbashir et al., *Nature,* 411: 494-8 (2001)).

siRNA has proven to be an effective means of decreasing gene expression in a variety of cell types. siRNA typically decreases expression of a gene to lower levels than that achieved using antisense techniques, and frequently eliminates expression entirely (see Bass, *Nature,* 411: 428-9 (2001)). In mammalian cells, siRNAs are effective at concentrations that are several orders of magnitude below the concentrations typically used in antisense experiments (Elbashir et al., *Nature,* 411:494-8 (2001)).

The double stranded oligonucleotides used to effect RNAi are preferably less than 30 base pairs in length, for example, about 25, 24, 23, 22, 21, 20, 19, 18, or 17 base pairs or less in length, and contain a segment sufficiently complementary to the target mRNA to allow hybridization to the target mRNA. Optionally the dsRNA oligonucleotides may include 3' overhang ends. Exemplary 2-nucleotide 3' overhangs may be composed of ribonucleotide residues of any type and may even be composed of 2'-deoxythymidine residues, which lowers the cost of RNA synthesis and may enhance nuclease resistance of siRNAs in the cell culture medium and within transfected cells (see Elbashi et al., supra). Exemplary dsRNAs may be synthesized chemically or produced in vitro or in vivo using appropriate expression vectors (see, e.g., Elbashir et al., *Genes Dev.,* 15:188-200 (2001)). Longer RNAs may be transcribed from promoters, such as T7 RNA polymerase promoters, known in the art.

Longer dsRNAs of 50, 75, 100, or even 500 base pairs or more also may be utilized in certain embodiments of the invention. Exemplary concentrations of dsRNAs for effecting RNAi are about 0.05 nM, 0.1 nM, 0.5 nM, 1.0 nM, 1.5 nM, 25 nM, or 100 nM, although other concentrations may be utilized depending upon the nature of the cells treated, the gene target and other factors readily discernable to the skilled artisan.

Further compositions, methods and applications of siRNA technology are provided in U.S. Pat. Nos. 6,278,039; 5,723, 750; and 5,244,805, which are incorporated herein by reference in its entirety.

Compared to siRNA, shRNA offers advantages in silencing longevity and delivery options. See, e.g., Hannon et al., *Nature,* 431:371-378 (2004) for review. Vectors that produce shRNAs, which are processed intracellularly into short duplex RNAs having siRNA-like properties have been reported (Brummelkamp et al., *Science,* 296: 550-553 (2000); Paddison et al., *Genes Dev.,* 16: 948-958 (2002)). Such vectors provide a renewable source of a gene-silencing reagent that can mediate persistent gene silencing after stable integration of the vector into the host-cell genome. Furthermore, the core silencing 'hairpin' cassette can be readily inserted into retroviral, lentiviral, or adenoviral vectors, facilitating delivery of shRNAs into a broad range of cell types (Brummelkamp et al., *Cancer Cell,* 2:243-247 (2002); Dirac et al., *J. Biol. Chem.,* 278:11731-11734 (2003); Michiels et al., *Nat. Biotechnol.,* 20:1154-1157 (2002); Stegmeie et al., *Proc. Natl. Acad. Sci. USA,* 102:13212-13217 (2005); Khvorova et al., *Cell,* 115:209-216 (2003)) in any of the innumerable ways that have been devised for delivery of DNA constructs that allow ectopic mRNA expression.

A hairpin can be organized in either a left-handed hairpin (i.e., 5'-antisense-loop-sense-3') or a right-handed hairpin (i.e., 5'-sense-loop-antisense-3'). The siRNA may also contain overhangs at either the 5' or 3' end of either the sense strand or the antisense strand, depending upon the organization of the hairpin. Preferably, if there are any overhangs, they are on the 3' end of the hairpin and comprise between 1 to 6 bases. The overhangs can be unmodified, or can contain one or more specificity or stabilizing modifications, such as a halogen or O-alkyl modification of the 2' position, or internucleotide modifications such as phosphorothioate, phosphorodithioate, or methylphosphonate modifications. The overhangs can be ribonucleic acid, deoxyribonucleic acid, or a combination of ribonucleic acid and deoxyribonucleic acid.

Additionally, a hairpin can further comprise a phosphate group on the 5'-most nucleotide. The phosphorylation of the 5'-most nucleotide refers to the presence of one or more phosphate groups attached to the 5' carbon of the sugar moiety of the 5'-terminal nucleotide. Preferably, there is only one phosphate group on the 5' end of the region that will form the antisense strand following Dicer processing. In one exemplary embodiment, a right-handed hairpin can include a 5' end (i.e., the free 5' end of the sense region) that does not have a 5' phosphate group, or can have the 5' carbon of the free 5'-most nucleotide of the sense region being modified in such a way that prevents phosphorylation. This can be achieved by a variety of methods including, but not limited to, addition of a phosphorylation blocking group (e.g., a 5'-O-alkyl group), or elimination of the 5'-OH functional group (e.g., the 5'-most nucleotide is a 5'-deoxy nucleotide). In cases where the hairpin is a left-handed hairpin, preferably the 5' carbon position of the 5'-most nucleotide is phosphorylated.

Hairpins that have stem lengths longer than 26 base pairs can be processed by Dicer such that some portions are not part of the resulting siRNA that facilitates mRNA degradation. Accordingly the first region, which may comprise sense nucleotides, and the second region, which may comprise antisense nucleotides, may also contain a stretch of nucleotides that are complementary (or at least substantially complementary to each other), but are or are not the same as or complementary to the target mRNA. While the stem of the shRNA can be composed of complementary or partially complementary antisense and sense strands exclusive of overhangs, the shRNA can also include the following: (1) the portion of the molecule that is distal to the eventual Dicer cut site contains a region that is substantially complementary/homologous to the target mRNA; and (2) the region of the stem that is proximal to the Dicer cut site (i.e., the region adjacent to the loop) is unrelated or only partially related (e.g., complementary/homologous) to the target mRNA. The nucleotide content of this second region can be chosen based on a number of parameters including but not limited to thermodynamic traits or profiles.

Modified shRNAs can retain the modifications in the post-Dicer processed duplex. In exemplary embodiments, in cases in which the hairpin is a right handed hairpin (e.g., 5'-S-loop-AS-3') containing 2-6 nucleotide overhangs on the 3' end of the molecule, 2'-O-methyl modifications can be added to nucleotides at position 2, positions 1 and 2, or positions 1, 2, and 3 at the 5' end of the hairpin. Also, Dicer processing of hairpins with this configuration can retain the 5' end of the sense strand intact, thus preserving the pattern of chemical modification in the post-Dicer processed duplex. Presence of a 3' overhang in this configuration can be particularly advantageous since blunt ended molecules containing the prescribed modification pattern can be further processed by Dicer in such a way that the nucleotides carrying the 2' modifications are removed. In cases where the 3' overhang is present/retained, the resulting duplex carrying the sense-modified nucleotides can have highly favorable traits with respect to silencing specificity and functionality. Examples of exemplary modification patterns are described in detail in U.S. Patent Publication No. 20050223427 and International Patent Publication Nos. WO 2004/090105 and WO 2005/078094, the disclosures of each of which are incorporated by reference herein in their entirety.

shRNA may comprise sequences that were selected at random, or according to any rational design selection procedure. For example, rational design algorithms are described in International Patent Publication No. WO 2004/045543 and U.S. Patent Publication No. 20050255487, the disclosures of which are incorporated herein by reference in their entireties. Additionally, it may be desirable to select sequences in whole or in part based on average internal stability profiles ("AISPs") or regional internal stability profiles ("RISPs") that may facilitate access or processing by cellular machinery.

Ribozymes are enzymatic RNA molecules capable of catalyzing specific cleavage of mRNA, thus preventing translation. (For a review, see Rossi, Current Biology, 4:469-471 (1994)). The mechanism of ribozyme action involves sequence specific hybridization of the ribozyme molecule to complementary target RNA, followed by an endonucleolytic cleavage event. The ribozyme molecules preferably include (1) one or more sequences complementary to a target mRNA, and (2) the well known catalytic sequence responsible for mRNA cleavage or a functionally equivalent sequence (see, e.g., U.S. Pat. No. 5,093,246, which is incorporated herein by reference in its entirety).

While ribozymes that cleave mRNA at site-specific recognition sequences can be used to destroy target mRNAs, hammerhead ribozymes may alternatively be used. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art and is described more fully in Haseloff and Gerlach, Nature, 334:585-591 (1988); and International Patent Publication. No. WO 89/05852, the contents of which are incorporated herein by reference in its entirety.

Gene targeting ribozymes may contain a hybridizing region complementary to two regions of a target mRNA, each of which is at least 5, 6, 7, 8, 9, 10, 11, 12, 13, 14, 15, 16, 17, 18, 19, or 20 contiguous nucleotides (but which need not both be the same length).

Hammerhead ribozyme sequences can be embedded in a stable RNA such as a transfer RNA (tRNA) to increase cleavage efficiency in vivo (Perriman et al., Proc. Natl. Acad. Sci. USA, 92:6175-79 (1995); de Feyter and Gaudron, Methods in Molecular Biology, Vol. 74, Chapter 43, "Expressing Ribozymes in Plants," Turner, P. C. (ed.), Humana Press Inc., Totowa, N.J.). In particular, RNA polymerase III-mediated expression of tRNA fusion ribozymes are well known in the art (see Kawasaki et al., Nature, 393:284-9 (1998); Kuwabara et al., Nature Biotechnol., 16:961-5 (1998); and Kuwabara et al., Mol. Cell, 2:617-27 (1998); Koseki et al., J. Virol., 73:1868-77 (1999); Kuwabara et al., Proc. Natl. Acad. Sci. USA, 96:1886-91 (1999); Tanabe et al., Nature, 406:473-4 (2000)). There are typically a number of potential hammerhead ribozyme cleavage sites within a given target cDNA sequence. Preferably the ribozyme is engineered so that the cleavage recognition site is located near the 5' end of the target mRNA- to increase efficiency and minimize the intracellular accumulation of non-functional mRNA transcripts. Furthermore, the use of any cleavage recognition site located in the target sequence encoding different portions of the target mRNA would allow the selective targeting of one or the other target genes.

Ribozymes for use in the inventive method also include RNA endoribonucleases ("Cech-type ribozymes") such as the one which occurs naturally in Tetrahymena thermophila (known as the IVS, or L-19 IVS RNA) and which has been extensively described in Zaug et al., Science, 224:574-578 (1984); Zaug, et al., Science, 231:470-475 (1986); Zaug et al., Nature, 324:429-433 (1986); International Patent Publication No. WO 88/04300; and Been et al., Cell, 47:207-216 (1986)). The Cech-type ribozymes have an eight base pair active site which hybridizes to a target RNA sequence whereafter cleavage of the target RNA takes place. In one embodiment, the inventive method employs those Cech-type ribozymes which target eight base-pair active site sequences that are present in a target gene or nucleic acid sequence.

Ribozymes can be composed of modified oligonucleotides (e.g., for improved stability, targeting, etc.) and can be chemically synthesized or produced through an expression vector. Because ribozymes, unlike antisense molecules, are catalytic, a lower intracellular concentration is required for efficiency. Additionally, in certain embodiments, a ribozyme may be designed by first identifying a sequence portion sufficient to cause effective knockdown by RNAi. Portions of the same sequence may then be incorporated into a ribozyme.

Alternatively, target gene expression can be reduced by targeting deoxyribonucleotide sequences complementary to the regulatory region of the gene (i.e., the promoter and/or enhancers) to form triple helical structures that prevent transcription of the gene in target cells in the body. (See generally Helene, C., Anticancer Drug Des., 6:569-84 (1991); Helene et al., Ann. N.Y. Acad. Sci., 660:27-36 (1992); and Maher, L. J., Bioassays, 14:807-15 (1992)).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the target sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Alternatively, DNA enzymes may be used to inhibit expression of target gene, such as the sclerostin gene. DNA enzymes incorporate some of the mechanistic features of both antisense and ribozyme technologies. DNA enzymes are designed so that they recognize a particular target nucleic acid sequence, much like an antisense oligonucleotide. They are, however, also catalytic and specifically cleave the target nucleic acid.

DNA enzymes include two basic types identified by Santoro and Joyce (see, for example, U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions.

Preferably, the unique or substantially unique sequence is a G/C rich segment of approximately 18 to 22 nucleotides. High G/C content helps insure a stronger interaction between the DNA enzyme and the target sequence. The specific antisense recognition sequence that will target the enzyme to the message may be divided between the two arms of the DNA enzyme.

Methods of making and administering DNA enzymes can be found, for example, in U.S. Pat. No. 6,110,462. Additionally, one of skill in the art will recognize that, like antisense oligonucleotide, DNA enzymes can be optionally modified to improve stability and improve resistance to degradation.

Inhibitory oligonucleotides can be administered directly or delivered to cells by transformation or transfection via a vector, including viral vectors or plasmids, into which has been placed DNA encoding the inhibitory oligonucleotide with the appropriate regulatory sequences, including a promoter, to result in expression of the inhibitory oligonucleotide in the desired cell. Known methods include standard transient transfection, stable transfection and delivery using viruses ranging from retroviruses to adenoviruses. Delivery of nucleic acid inhibitors by replicating or replication-deficient vectors is contemplated. Expression can also be driven by either constitutive or inducible promoter systems (Paddison et al., *Methods Mol. Biol.*, 265:85-100 (2004)). In other embodiments, expression may be under the control of tissue or development-specific promoters.

For example, vectors may be introduced by transfection using carrier compositions such as Lipofectamine 2000 (Life Technologies) or Oligofectamine (Life Technologies). Transfection efficiency may be checked using fluorescence microscopy for mammalian cell lines after co-transfection of hGFP-encoding pAD3 (Kehlenback et al., *J. Cell Biol.*, 141:863-74 (1998)).

The delivery route will be the one that provides the best inhibitory effect as measured according to the criteria described above. Delivery mediated by cationic liposomes, delivery by retroviral vectors and direct delivery are efficient.

The effectiveness of the inhibitory oligonucleotide may be assessed by any of a number of assays, including reverse transcriptase polymerase chain reaction or Northern blot analysis to determine the level of existing human sclerostin mRNA, or Western blot analysis using antibodies which recognize the human sclerostin protein, after sufficient time for turnover of the endogenous pool after new protein synthesis is repressed.

The invention is further described in the following example. The example serves only to illustrate the invention and are not intended to limit the scope of the invention in any way.

EXAMPLE

This example describes in vivo studies wherein a sclerostin binding agent reduced the level of a marker of bone resorption and increased the level of one or more markers of bone formation.

A single-center, randomized, double-blind, placebo-controlled, ascending single-dose study in healthy men and postmenopausal women was conducted. Approximately 72 subjects enrolled in one of six dose cohorts. For cohorts 1, 2, 3a, 4, 5 and 6a, eight healthy postmenopausal women were randomized to receive a sclerostin binding agent or placebo via subcutaneous injection in a 3:1 ratio at dose levels of 0.1 mg/kg, 0.3 mg/kg, 1 mg/kg, 3 mg/kg, 5 mg/kg, or 10 mg/kg, respectively. In cohorts 3b and 6b, 8 healthy males received the sclerostin binding agent or a placebo intravenously and subcutaneously in a 3:3:1:1 ratio (sclerostin binding agent intravenously:sclerostin binding agent subcutaneously:placebo intravenously:placebo subcutaneously) at a dose level of 1 mg/kg or 10 mg/kg (reduced to 5 mg/kg), respectively. For cohorts 3c and 6c, four healthy postmenopausal women were randomized to receive the sclerostin binding agent or placebo intravenously in a 3:1 ratio at a dose level of 1 mg/kg or 10 mg/kg (reduced to 5 mg/kg), respectively.

The anti-sclerostin therapy was monitored by measuring the levels of bone resorption markers and bone formation markers prior to administration, then at least every week for 12 weeks post-administration. P1NP and BSAP levels were monitored following a single-dose subcutaneous administration of sclerostin binding agent in healthy, postmenopausal women (see FIGS. 1 and 2). Subjects dosed at 0.1 mg/kg and 0.3 mg/kg enjoyed the least elevation of P1NP or BSAP levels (e.g., levels increased less than 20%).

Figure 2:
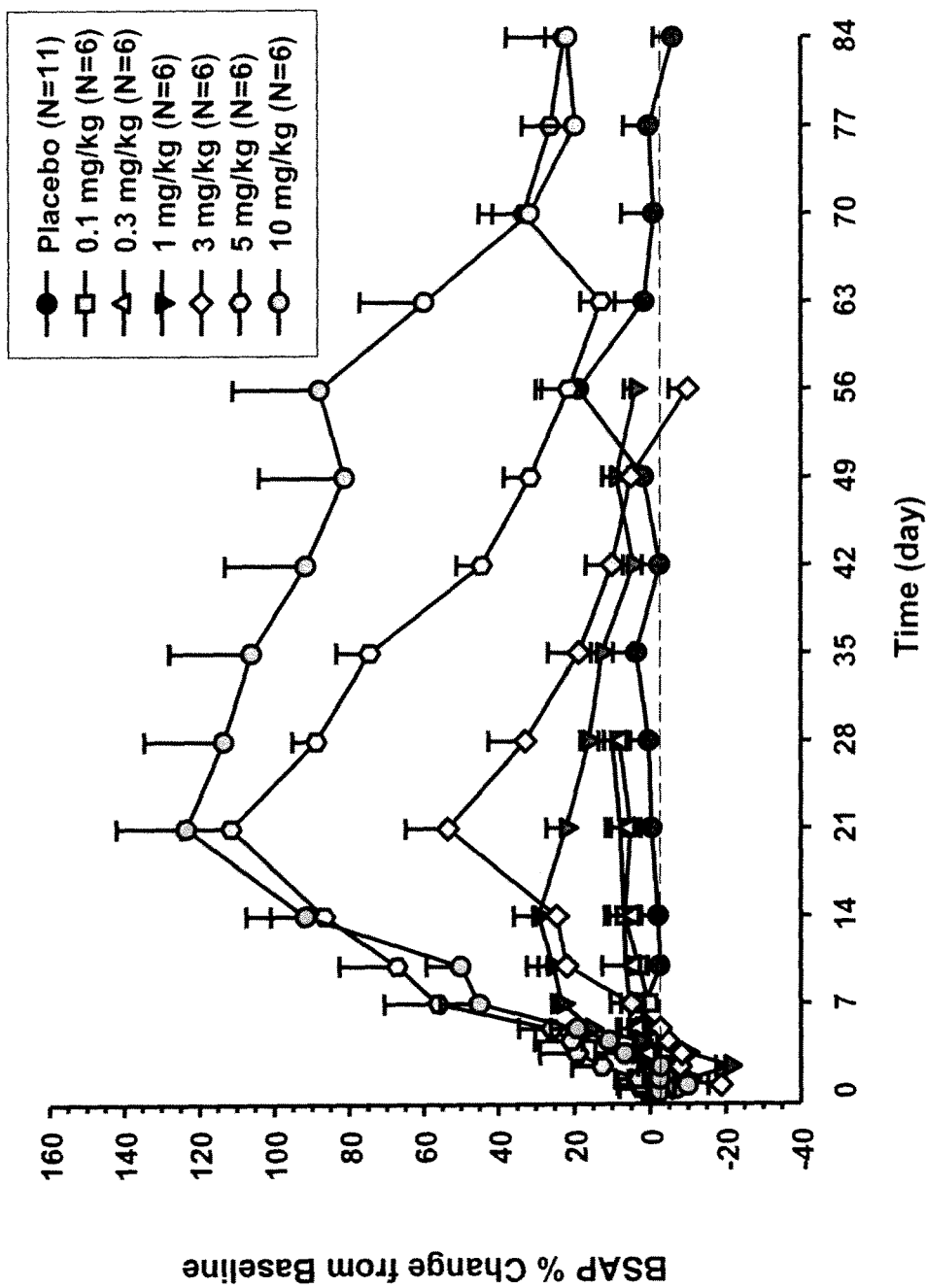
FIG. 2 is a graph of percent change of bone-specific alkaline phosphatase (BSAP) levels compared to baseline and placebo BSAP levels versus time (day) post-administration of various single doses of a sclerostin binding agent in healthy, postmenopausal women.

P1NP levels in subjects given 1 mg/kg increased approximately 20% by Day 10 and gradually tapered off to baseline around Day 56, while BSAP levels peaked at Day 14 at about 30% above baseline. P1NP and BSAP levels in subjects given 3 mg/kg peaked at Day 21 at approximately 100% (P1NP) and 60% (BSAP) increase from baseline, and returned to baseline about Day 56. In subjects administered 5 mg/kg, the level of P1NP rose to about 140% above baseline at Day 14 post-administration, and remained elevated at Day 77. In other words, the level of P1NP increased about 140% by two weeks post-treatment. BSAP rose to about 115% above baseline and remained elevated at Day 84. Similarly, administration of 10 mg/kg triggered a 180% increase in P1NP levels at about Day 28. P1NP levels remained elevated throughout the monitoring period. Subjects administered 10 mg/kg demonstrated a peak increase of BSAP levels at Day 21 (125% baseline for 3 weeks post-administration), which also remained elevated at Day 84. The results of the study are illustrated in FIGS. 1 and 2.

Figure 3:
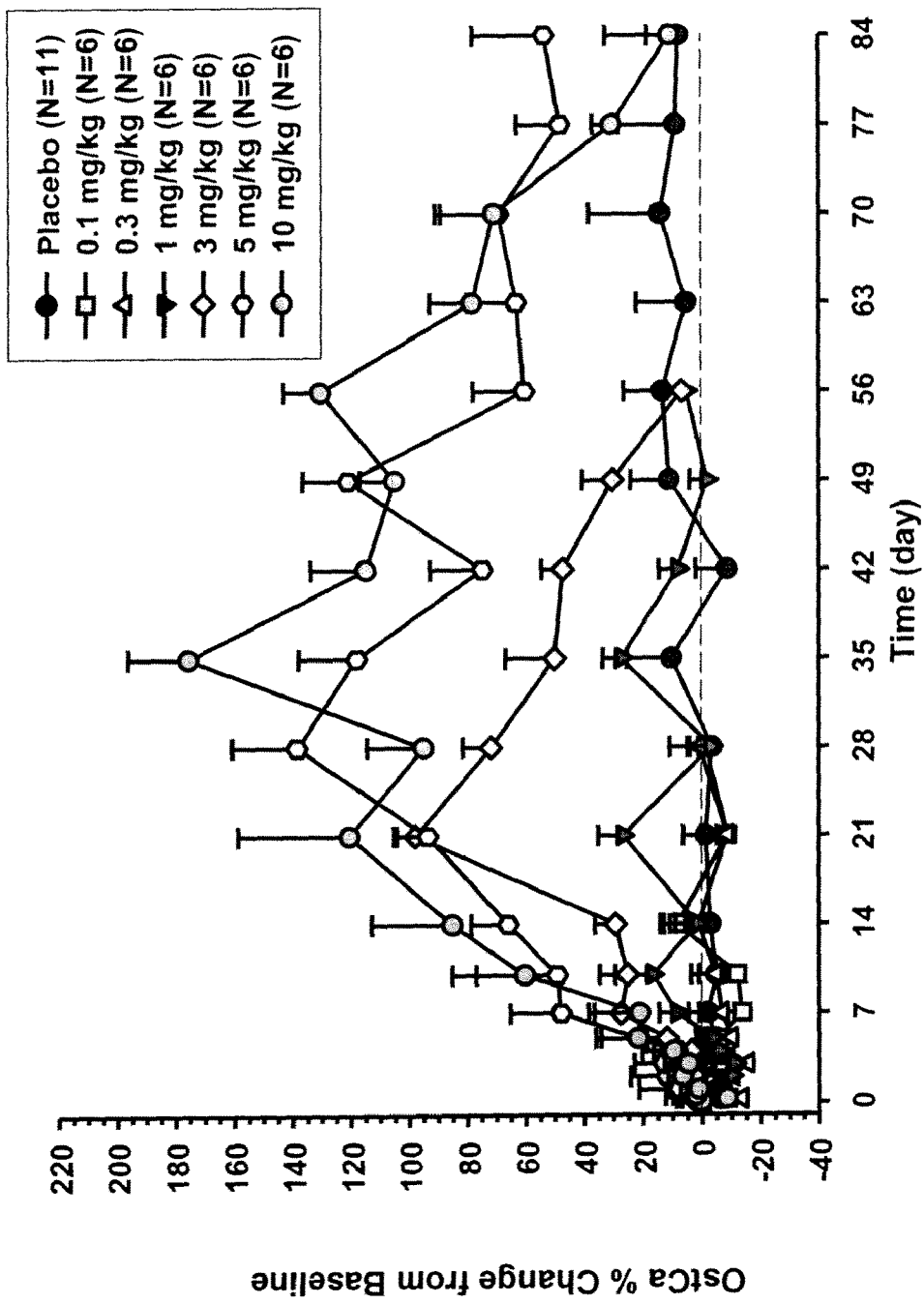
FIG. 3 is a graph of percent change of osteocalcin levels compared to baseline and placebo osteocalcin levels versus time (day) post-administration of various single doses of a sclerostin binding agent in healthy, postmenopausal women.

Osteocalcin also was monitored following a single-dose, subcutaneous administration of sclerostin binding agent in healthy, postmenopausal women (see FIG. 3). Subjects given less than 1 mg/kg experienced little elevation of Osteocalcin. Osteocalcin levels fluctuated in patients administered 1 mg/kg, peaking at about 30% above baseline at Days 21 and 35. Osteocalcin levels peaked at about 100% above baseline at Day 21 in subjects administered 3 mg/kg, and levels remained elevated until about Day 56. Likewise, administration of 5 mg/kg sclerostin binding agent resulted in a 140% increase in osteocalcin levels at day 28, which levels remained at Day 84. Subjects dosed at 10 mg/kg demonstrated a peak osteocalcin level of about 180% above baseline at Day 35. Osteocalcin levels remained elevated above baseline until at least about Day 77.

Figure 4:
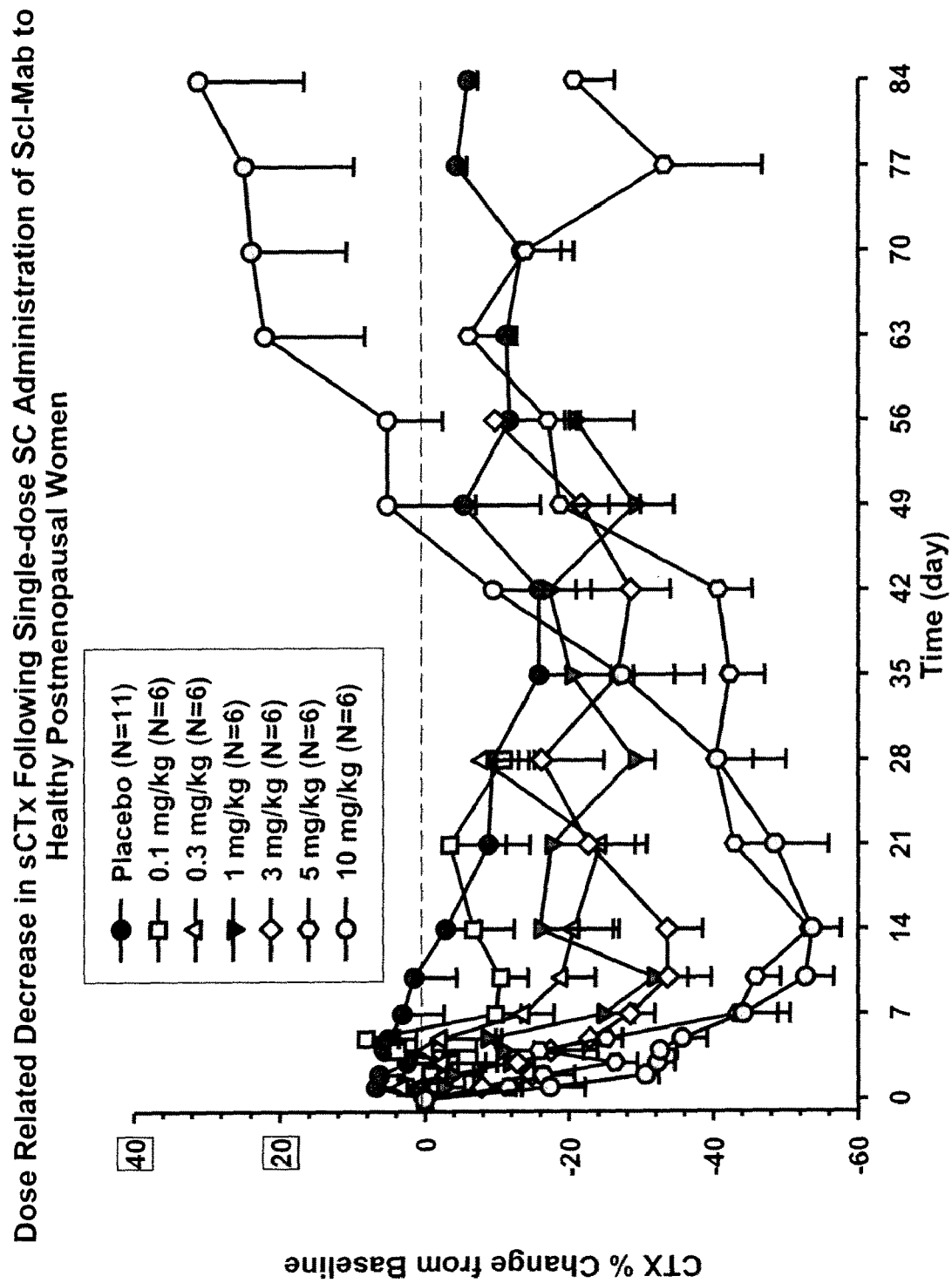
FIG. 4 is a graph of percent change of serum C-terminal telopeptide of type 1 collagen (CTX) levels compared to baseline and placebo serum CTX levels versus time (day) post-administration of various single doses of a sclerostin binding agent in healthy, postmenopausal women.
Figure 5:
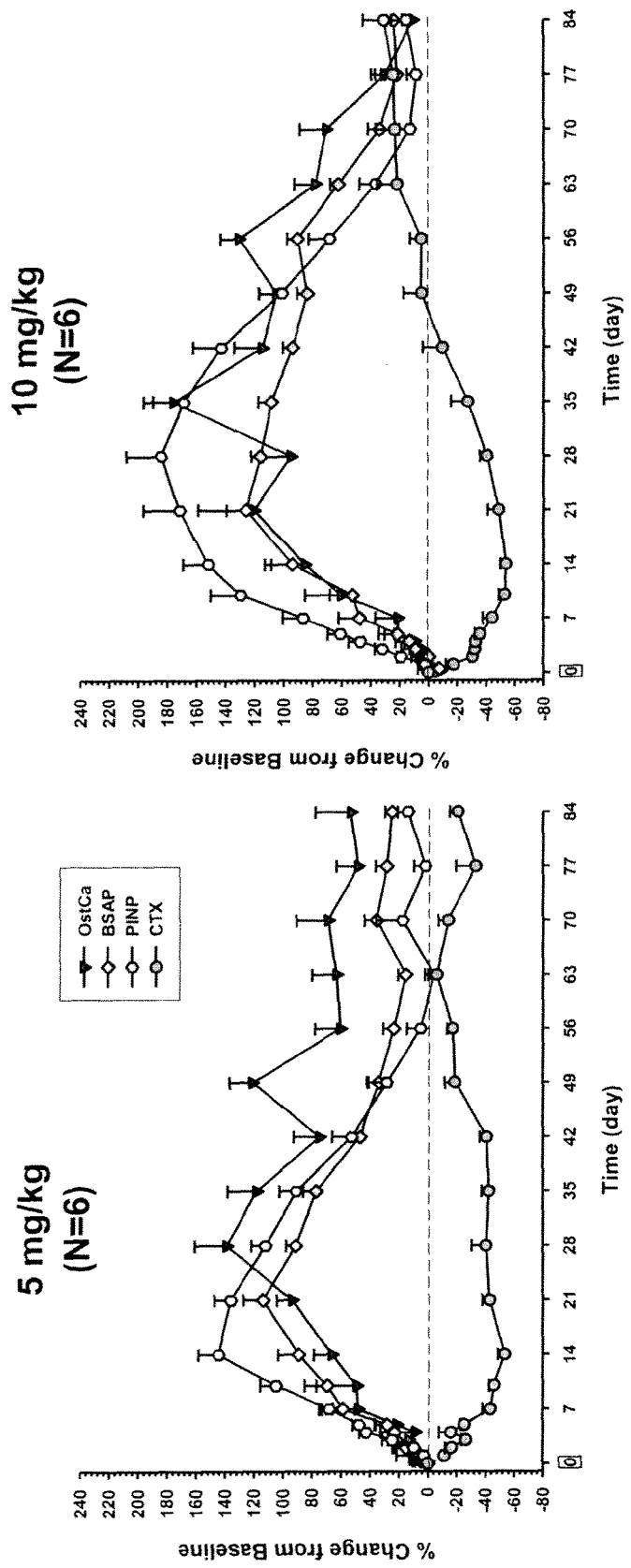
FIG. 5 are graphs of percent change of osteocalcin, BSAP, P1NP, and CTX levels compared to baseline and placebo levels versus time (day) post-administration of a single dose of 5 mg/kg or 10 mg/kg of sclerostin binding agent in healthy, postmenopausal women.

Levels of the bone resorptive marker sCTx also were monitored (see FIG. 4). Subjects administered placebo and 0.1 mg/kg demonstrated modest decreases in sCTx levels (e.g., less than 20%). Administration of 0.3 mg/kg of sclerostin binding agent reduced sCTx levels by about 20% by Day 21 (i.e., sCTX levels were reduced about 20% by two weeks after treatment). Levels fluctuated in subjects dosed at 1 mg/kg but reached about 30% below baseline at Days 10, 28, and 49. Levels in subjects administered 3 mg/kg, 5 mg/kg, and 10 mg/kg fell lowest at Day 14 to about 35%, 55%, and 55% below baseline, respectively, and levels remained below baseline when monitored thereafter. A comparison of the levels of all monitored biomarkers is provided in FIG. 5.

Figure 6:
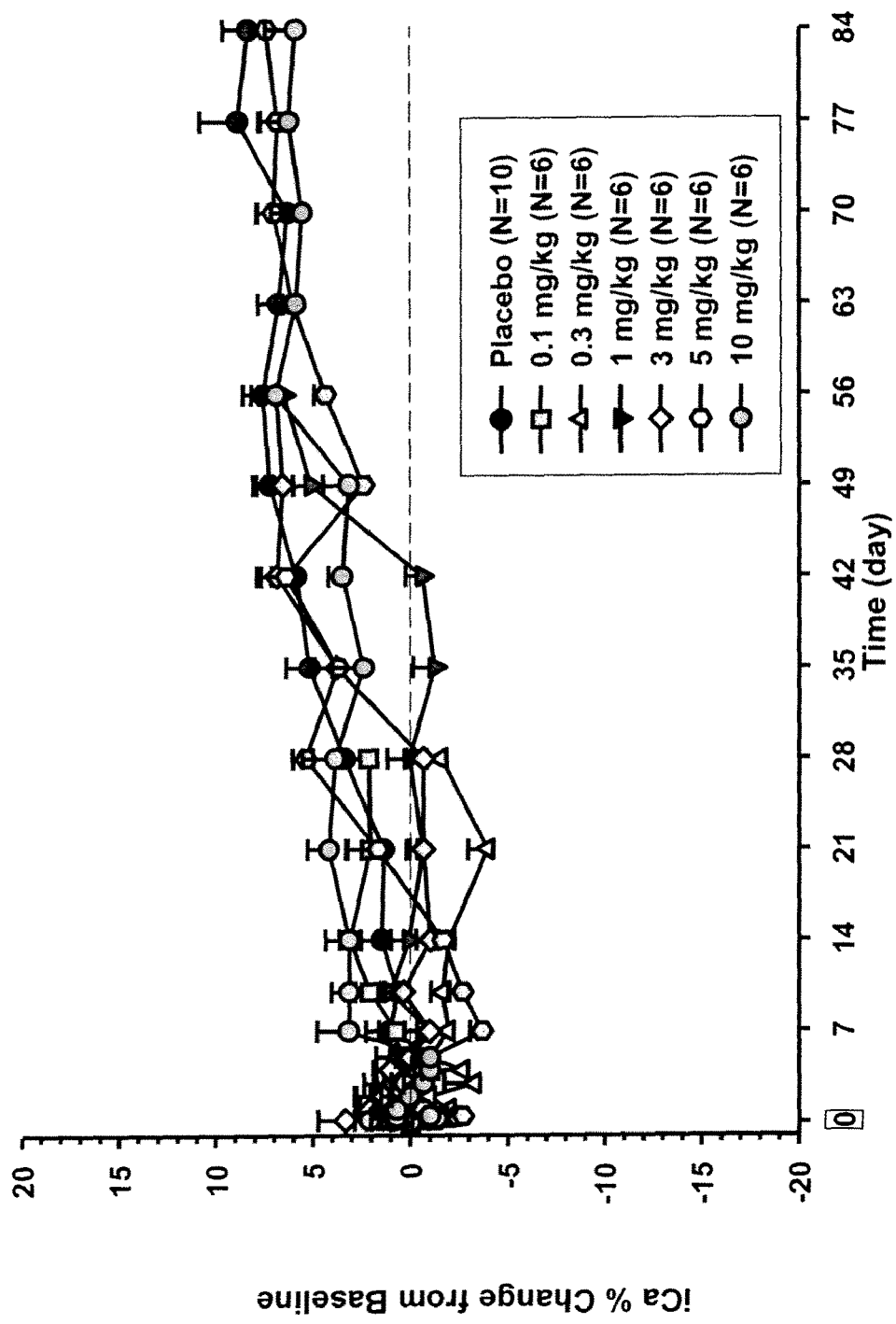
FIG. 6 is a graph of percent change of serum calcium levels compared to baseline and placebo serum calcium levels versus time (day) post-administration of various single doses of a sclerostin binding agent in healthy, postmenopausal women.

Serum ionized calcium levels were monitored following a single, subcutaneous dose of sclerostin binding agent in healthy, postmenopausal women (see FIG. 6). Remarkably, ionized calcium levels did not fluctuate dramatically at any dosage. Indeed, all subjects (including those receiving placebo) experienced a modest transient decrease in serum ionized calcium of approximately 5% during the monitoring period.

Figure 7:
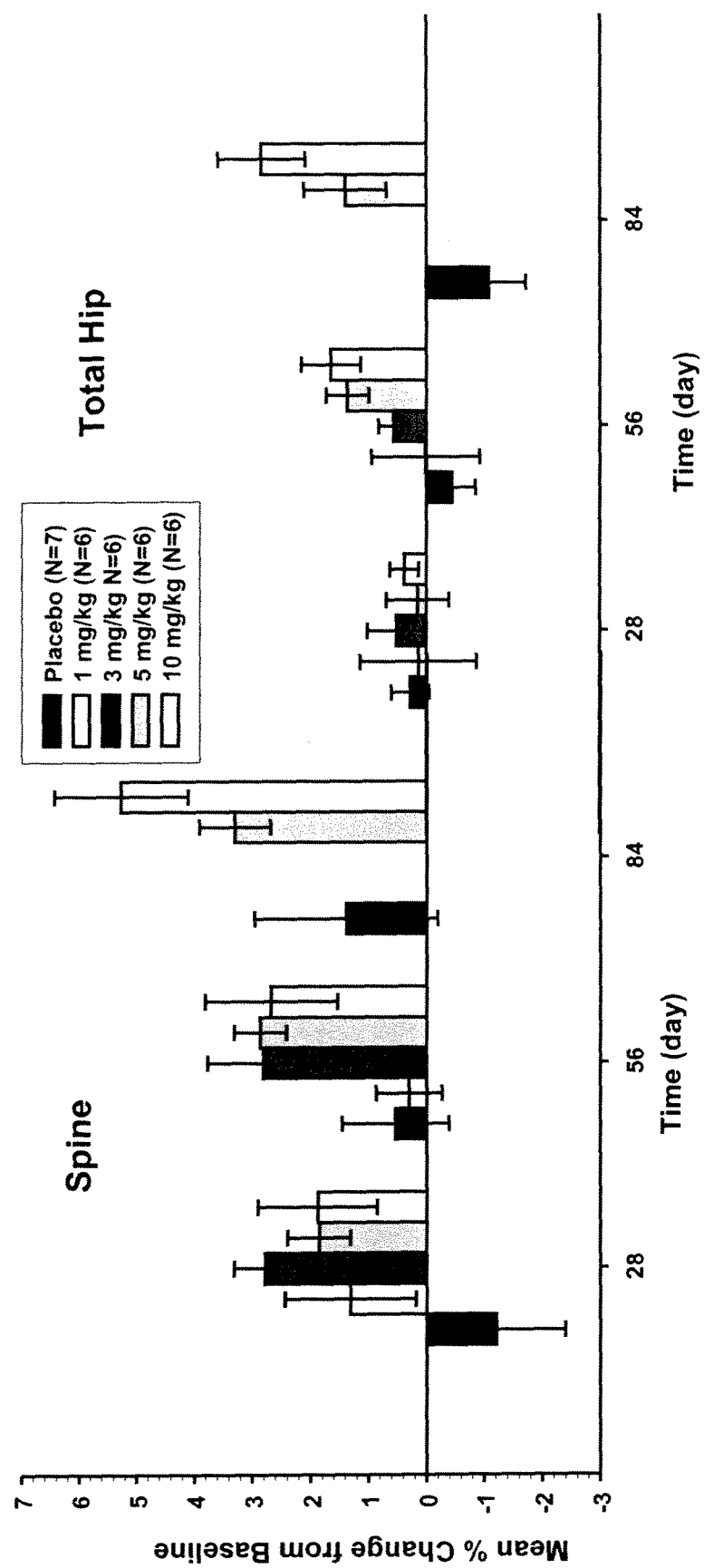
FIG. 7 are graphs of percent change of bone mineral density compared to baseline and placebo versus time (day) post-administration of various single doses of sclerostin binding agent in healthy, postmenopausal women.

Finally, bone mineral density was measured in the spine and hip of healthy, postmenopausal women receiving 1 mg/kg, 3 mg/kg, 5 mg/kg, or 10 mg/kg sclerostin binding agent (see FIG. 7). Significant increases in BMD were observed in the spine, for example, at Days 28, 56, and 84, particularly in patients receiving 5 mg/kg and 10 mg/kg. BMD in the hip increased less than that of the spine, but BMD was elevated at Day 56 in patients administered 3 mg/kg, 5 mg/kg, and 10 mg/kg. BMD was further elevated at Day 84 in patients dosed at 5 mg/kg and 10 mg/kg.

This example illustrates the ability of the inventive method to reduce levels of a marker of bone resorption, elevate levels of markers of bone formation, and increase bone mineral density without dramatic alterations in serum calcium. The therapeutic effect of a single dose of sclerostin binding agent is long-lived, with increased bone formation marker levels and decreased bone resorptive marker levels continuing to be observed at 84 days (12 weeks) post treatment. Furthermore, data described herein suggests that the therapeutic efficacy of the invention have significant advantages compared to other treatments by "uncoupling" bone formation and bone resorption to maximize bone formation and mineralization in vivo.

All of the references cited herein, including patents, patent applications, literature publications, and the like, are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. A method for administering an anti-sclerostin antibody to a human in need thereof, the method comprising administering to said human from about 1 mg/kg to about 3 mg/kg of an anti-sclerostin antibody that (a) demonstrates a binding affinity for sclerostin of SEQ ID NO: 1 of less than or equal to $1 \times 10^{-7}$ M and (b) comprises a CDR-H1 of SEQ ID NO:245, a CDR-H2 of SEQ ID NO:246, a CDR-H3 of SEQ ID NO:247, a CDR-L1 of SEQ NO:78, a CDR-L2 of SEQ ID NO:79 and a CDR-L3 of SEQ ID NO:80.

2. The method of claim 1, wherein the anti-sclerostin antibody is administered at about 2 mg/kg.

3. The method of claim 1, wherein the anti-sclerostin antibody is administered once every two weeks.

4. The method of claim 1, wherein the anti-sclerostin antibody is administered once per month.

5. The method of claim 2, wherein the anti-sclerostin antibody is administered once every two weeks.

6. The method of claim 2, wherein the anti-sclerostin antibody is administered once per month.

7. The method of any one of claims 1-6 wherein the human is a post-menopausal woman.

8. The method of any one of claims 1-6 wherein the human is suffering from osteoporosis.

9. The method of any one of claims 1-6 wherein the human is suffering from a bone-related disorder selected from the group consisting of achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, pyogenic osteomyelitis, periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthes' Disease, adolescent idiopathic scoliosis, infantile onset multi-system inflammatory disease, Winchester Syndrome, Menkes Disease, Wilson's Disease, ischemic bone disease (such as Legg-Calve-Perthes disease, regional migratory osteoporosis), anemic states, conditions caused by steroids, glucocorticoid-induced hone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, chemotherapy associated hone loss, tumor induced hone loss, cancer-related bone loss, hormone ablative bone loss, multiple myeloma, drug-induced bone loss, anorexia nervosa, disease associated facial hone loss, disease associated cranial bone loss, disease associated bone loss of the jaw, disease associated bone loss of the skull, bone loss associated with aging, facial bone loss associated with aging, cranial bone loss associated with aging, jaw bone loss associated with aging, skull bone loss associated with aging, and bone loss associated with space travel.

10. The method of any one of claims 1-6, wherein the antibody is a human antibody, a humanized antibody, a monoclonal antibody, or a chimeric antibody.

* * * * *

UNITED STATES PATENT AND TRADEMARK OFFICE
CERTIFICATE OF CORRECTION

PATENT NO. : 8,017,120 B2  
APPLICATION NO. : 12/212327  
DATED : September 13, 2011  
INVENTOR(S) : Ian D. Padhi et al.

Page 1 of 1

It is certified that error appears in the above-identified patent and that said Letters Patent is hereby corrected as shown below:

In the Specification:

At Column 21, line 39, "discernable" should be -- discernible --.

In the Claims:

At Column 395, line 6, "hone" should be -- bone --.

At Column 396, line 3, "hone" should be -- bone --.

At Column 396, line 4, "hone" should be -- bone --.

At Column 396, line 6, "hone" should be -- bone --.

Signed and Sealed this  
Twelfth Day of November, 2013

Teresa Stanek Rea  
*Deputy Director of the United States Patent and Trademark Office*

SEQUENCE LISTING

```
<160> NUMBER OF SEQ ID NOS: 396

<210> SEQ ID NO 1
<211> LENGTH: 190
<212> TYPE: PRT
<213> ORGANISM: Homo sapiens

<400> SEQUENCE: 1

Gln Gly Trp Gln Ala Phe Lys Asn Asp Ala Thr Glu Ile Ile Pro Glu
1               5                   10                  15

Leu Gly Glu Tyr Pro Glu Pro Pro Glu Leu Glu Asn Asn Lys Thr
            20                  25                  30

Met Asn Arg Ala Glu Asn Gly Gly Arg Pro Pro His His Pro Phe Glu
        35                  40                  45

Thr Lys Asp Val Ser Glu Tyr Ser Cys Arg Glu Leu His Phe Thr Arg
    50                  55                  60

Tyr Val Thr Asp Gly Pro Cys Arg Ser Ala Lys Pro Val Thr Glu Leu
65                  70                  75                  80

Val Cys Ser Gly Gln Cys Gly Pro Ala Arg Leu Leu Pro Asn Ala Ile
                85                  90                  95

Gly Arg Gly Lys Trp Trp Arg Pro Ser Gly Pro Asp Phe Arg Cys Ile
            100                 105                 110

Pro Asp Arg Tyr Arg Ala Gln Arg Val Gln Leu Leu Cys Pro Gly Gly
        115                 120                 125

Glu Ala Pro Arg Ala Arg Lys Val Arg Leu Val Ala Ser Cys Lys Cys
    130                 135                 140

Lys Arg Leu Thr Arg Phe His Asn Gln Ser Glu Leu Lys Asp Phe Gly
145                 150                 155                 160

Thr Glu Ala Ala Arg Pro Gln Lys Gly Arg Lys Pro Arg Pro Arg Ala
                165                 170                 175

Arg Ser Ala Lys Ala Asn Gln Ala Glu Leu Glu Asn Ala Tyr
            180                 185                 190
```

```
<210> SEQ ID NO 2
<211> LENGTH: 14
<212> TYPE: PRT
<213> ORGANISM: Homo sapiens

<400> SEQUENCE: 2

Asp Val Ser Glu Tyr Ser Cys Arg Glu Leu His Phe Thr Arg
1               5                   10

<210> SEQ ID NO 3
<211> LENGTH: 16
<212> TYPE: PRT
<213> ORGANISM: Homo sapiens

<400> SEQUENCE: 3

Ser Ala Lys Pro Val Thr Glu Leu Val Cys Ser Gly Gln Cys Gly Pro
1               5                   10                  15

<210> SEQ ID NO 4
<211> LENGTH: 16
<212> TYPE: PRT
<213> ORGANISM: Homo sapiens

<400> SEQUENCE: 4

Trp Trp Arg Pro Ser Gly Pro Asp Phe Arg Cys Ile Pro Asp Arg Tyr
1               5                   10                  15

<210> SEQ ID NO 5
<211> LENGTH: 12
<212> TYPE: PRT
<213> ORGANISM: Homo sapiens

<400> SEQUENCE: 5

Leu Val Ala Ser Cys Lys Cys Lys Arg Leu Thr Arg
1               5                   10

<210> SEQ ID NO 6
<211> LENGTH: 26
<212> TYPE: PRT
<213> ORGANISM: Homo sapiens

<400> SEQUENCE: 6

Cys Gly Pro Ala Arg Leu Leu Pro Asn Ala Ile Gly Arg Gly Lys Trp
1               5                   10                  15

Trp Arg Pro Ser Gly Pro Asp Phe Arg Cys
            20                  25

<210> SEQ ID NO 7
<211> LENGTH: 214
<212> TYPE: PRT
<213> ORGANISM: Mus musculus

<400> SEQUENCE: 7

Asp Val Gln Met Ile Gln Ser Pro Ser Ser Leu Ser Ala Ser Leu Gly
1               5                   10                  15

Asp Ile Val Thr Met Thr Cys Gln Ala Ser Gln Gly Thr Ser Ile Asn
            20                  25                  30

Leu Asn Trp Phe Gln Gln Lys Pro Gly Lys Ala Pro Lys Leu Leu Ile
        35                  40                  45

Tyr Gly Ser Ser Asn Leu Glu Asp Gly Val Pro Ser Arg Phe Ser Gly
    50                  55                  60

Ser Arg Tyr Gly Thr Asp Phe Thr Leu Thr Ile Ser Ser Leu Glu Asp
65                  70                  75                  80
```

```
Glu Asp Leu Ala Thr Tyr Phe Cys Leu Gln His Ser Tyr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
        210

<210> SEQ ID NO 8
<211> LENGTH: 645
<212> TYPE: DNA
<213> ORGANISM: Mus musculus

<400> SEQUENCE: 8
gatgtccaga tgattcagtc tccatcctcc ctgtctgcat ctttgggaga catagtcacc    60
atgacttgcc aggcaagtca gggcactagc attaatttaa actggtttca gcaaaaacca   120
gggaaggctc ctaagctcct gatctatggt tcaagcaact ggaagatggg gtcccatca    180 aggttcagtg gcagtagata tggacagat ttcactctca ccatcagcag cctggaggat    240
gaagatctgg caactyattt ctgtctacaa catagttatc tcccgtacac gttcggaggg   300
gggaccaagc tggaaataaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag caccctcacg   540
ttgaccaagg acgagtatga acgacataac agctatacct gtgaggccac tcacaagaca   600
tcaacttcac ccattgtcaa gagcttcaac aggaatgagt gttag                   645

<210> SEQ ID NO 9
<211> LENGTH: 236
<212> TYPE: PRT
<213> ORGANISM: Mus musculus

<400> SEQUENCE: 9

Met Asn Thr Arg Ala Pro Ala Glu Phe Leu Gly Phe Leu Leu Leu Trp
1               5                   10                  15

Phe Leu Gly Ala Arg Cys Asp Val Gln Met Ile Gln Ser Pro Ser Ser
            20                  25                  30

Leu Ser Ala Ser Leu Gly Asp Ile Val Thr Met Thr Cys Gln Ala Ser
        35                  40                  45

Gln Gly Thr Ser Ile Asn Leu Asn Trp Phe Gln Gln Lys Pro Gly Lys
    50                  55                  60

Ala Pro Lys Leu Leu Ile Tyr Gly Ser Ser Asn Leu Glu Asp Gly Val
65                  70                  75                  80
```

```
Pro Ser Arg Phe Ser Gly Ser Arg Tyr Gly Thr Asp Phe Thr Leu Thr
                85                  90                  95
Ile Ser Ser Leu Glu Asp Glu Asp Leu Ala Thr Tyr Phe Cys Leu Gln
               100                 105                 110
His Ser Tyr Leu Pro Tyr Thr Phe Gly Gly Gly Thr Lys Leu Glu Ile
               115                 120                 125
Lys Arg Ala Asp Ala Ala Pro Thr Val Ser Ile Phe Pro Pro Ser Ser
           130                 135                 140
Glu Gln Leu Thr Ser Gly Gly Ala Ser Val Val Cys Phe Leu Asn Asn
145                 150                 155                 160
Phe Tyr Pro Lys Asp Ile Asn Val Lys Trp Lys Ile Asp Gly Ser Glu
                165                 170                 175
Arg Gln Asn Gly Val Leu Asn Ser Trp Thr Asp Gln Asp Ser Lys Asp
            180                 185                 190
Ser Thr Tyr Ser Met Ser Ser Thr Leu Thr Leu Thr Lys Asp Glu Tyr
                195                 200                 205
Glu Arg His Asn Ser Tyr Thr Cys Glu Ala Thr His Lys Thr Ser Thr
            210                 215                 220
Ser Pro Ile Val Lys Ser Phe Asn Arg Asn Glu Cys
225                 230                 235

<210> SEQ ID NO 10
<211> LENGTH: 711
<212> TYPE: DNA
<213> ORGANISM: Mus musculus

<400> SEQUENCE: 10
atgaacacga gggcccctgc tgagttcctt gggttcctgt tgctctggtt tttaggtgcc        60
agatgtgatg tccagatgat tcagtctcca tcctccctgt ctgcatcttt gggagacata       120
gtcaccatga cttgccaggc aagtcagggc actagcatta atttaaactg gtttcagcaa       180
aaaccaggga aggctcctaa gctcctgatc tatggttcaa gcaacttgga agatggggtc       240
ccatcaaggt tcagtggcag tagatatggg acagatttca ctctcaccat cagcagcctg       300
gaggatgaag atctggcaac ttatttctgt ctacaacata gttatctccc gtacacgttc       360
ggagggggga ccaagctgga aataaaacgg gctgatgctg caccaactgt atccatcttc       420
ccaccatcca gtgagcagtt aacatctgga ggtgcctcag tcgtgtgctt cttgaacaac       480
ttctacccca agacatcaa tgtcaagtgg aagattgatg gcagtgaacg acaaaatggc       540
gtcctgaaca gttggactga tcaggacagc aaagacagca cctacagcat gagcagcacc       600
ctcacgttga ccaaggacga gtatgaacga cataacagct atacctgtga ggccactcac       660
aagacatcaa cttcacccat tgtcaagagc ttcaacagga atgagtgtta g               711

<210> SEQ ID NO 11
<211> LENGTH: 443
<212> TYPE: PRT
<213> ORGANISM: Mus musculus

<400> SEQUENCE: 11

Glu Val Gln Leu Gln Gln Ser Gly Pro Glu Leu Val Thr Pro Gly Ala
1               5                  10                  15
Ser Val Lys Ile Ser Cys Lys Ala Ser Gly Tyr Thr Phe Thr Asp His
                20                  25                  30
Tyr Met Ser Trp Val Lys Gln Ser His Gly Lys Ser Leu Glu Trp Ile
            35                  40                  45
Gly Asp Ile Asn Pro Tyr Ser Gly Glu Thr Thr Tyr Asn Gln Lys Phe
```

```
                 50                  55                  60
Lys Gly Thr Ala Thr Leu Thr Val Asp Lys Ser Ser Ile Ala Tyr
 65                  70                  75                  80

Met Glu Ile Arg Gly Leu Thr Ser Glu Asp Ser Ala Val Tyr Tyr Cys
                 85                  90                  95

Ala Arg Asp Asp Tyr Asp Ala Ser Pro Phe Ala Tyr Trp Gly Gln Gly
                100                 105                 110

Thr Leu Val Thr Val Ser Ala Ala Lys Thr Thr Pro Pro Ser Val Tyr
                115                 120                 125

Pro Leu Ala Pro Gly Ser Ala Ala Gln Thr Asn Ser Met Val Thr Leu
            130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys Gly Cys Lys
210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
                260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
            290                 295                 300

Met His Gln Asp Trp Leu Asn Gly Lys Glu Phe Lys Cys Arg Val Asn
305                 310                 315                 320

Ser Pro Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Ile Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
                420                 425                 430

Thr Glu Lys Ser Leu Ser His Ser Pro Gly Lys
            435                 440

<210> SEQ ID NO 12
<211> LENGTH: 1332
<212> TYPE: DNA
<213> ORGANISM: Mus musculus
```

```
<400> SEQUENCE: 12
gaggtccagc tgcaacagtc tggacctgaa ctggtgacgc ctggggcttc agtgaagata    60
tcttgtaagg cttctggata cacattcact gaccactaca tgagctgggt gaagcagagt   120
catgaaaaaa gccttgagtg gattggagat attaatccct attctggtga aactacctac   180
aaccagaagt tcaagggcac ggccacattg actgtagaca gtcttccag  tatagcctac   240
atggagatcc gcggcctgac atctgaggac tctgcagtct attactgtgc aagagatgat   300
tacgacgcct ctccgtttgc ttactggggc caagggactc tggtcactgt ctctgcagcc   360
aaaacgacac cccatctgt  ctatccactg gcccctggat ctgctgccca aactaactcc   420
atggtgaccc tgggatgcct ggtcaagggc tatttccctg agccagtgac agtgacctgg   480
aactctggat ccctgtccag cggtgtgcac accttcccag ctgtcctgca gtctgacctc   540
tacactctga gcagctcagt gactgtcccc tccagcacct ggcccagcga ccgtcacc    600
tgcaacgttg cccacccggc cagcagcacc aaggtggaca gaaaaattgt gcccagggat   660
tgtggttgta agccttgcat atgtacagtc ccagaagtat catctgtctt catcttcccc   720
ccaaagccca aggatgtgct caccattact ctgactccta aggtcacgtg tgttgtggta   780
gacatcagca aggatgatcc cgaggtccag ttcagctggt ttgtagatga tgtggaggtg   840
cacacagctc agacgcaacc ccgggaggag cagttcaaca gcactttccg ctcagtcagt   900
gaacttccca tcatgcacca ggactggctc aatggcaagg agttcaaatg cagggtcaac   960
agtccagctt tccctgcccc catcgagaaa accatctcca aaaccaaagg cagaccgaag  1020
gctccacagg tgtacaccat tccacctccc aaggagcaga tggccaagga taaagtcagt  1080
ctgacctgca tgataacaga cttcttccct gaagacatta ctgtggagtg cagtggaat   1140
gggcagccag cggagaacta caagaacact cagcccatca tggacacaga tggctcttac  1200
ttcatctaca gcaagctcaa tgtgcagaag agcaactggg aggcaggaaa tactttcacc  1260
tgctctgtgt tacatgaggg cctgcacaac caccatactg agaagagcct ctcccactct  1320
cctggtaaat ga                                                       1332

<210> SEQ ID NO 13
<211> LENGTH: 462
<212> TYPE: PRT
<213> ORGANISM: Mus musculus

<400> SEQUENCE: 13

Met Arg Cys Arg Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Thr
            20                  25                  30

Pro Gly Ala Ser Val Lys Ile Ser Cys Lys Ala Ser Gly Tyr Thr Phe
        35                  40                  45

Thr Asp His Tyr Met Ser Trp Val Lys Gln Ser His Gly Lys Ser Leu
    50                  55                  60

Glu Trp Ile Gly Asp Ile Asn Pro Tyr Ser Gly Glu Thr Thr Tyr Asn
65                  70                  75                  80

Gln Lys Phe Lys Gly Thr Ala Thr Leu Thr Val Asp Lys Ser Ser Ser
                85                  90                  95

Ile Ala Tyr Met Glu Ile Arg Gly Leu Thr Ser Glu Asp Ser Ala Val
            100                 105                 110

Tyr Tyr Cys Ala Arg Asp Asp Tyr Asp Ala Ser Pro Phe Ala Tyr Trp
        115                 120                 125
```

```
Gly Gln Gly Thr Leu Val Thr Val Ser Ala Ala Lys Thr Pro Pro
            130                 135                 140
Ser Val Tyr Pro Leu Ala Pro Gly Ser Ala Ala Gln Thr Asn Ser Met
145                 150                 155                 160
Val Thr Leu Gly Cys Leu Val Lys Gly Tyr Phe Pro Glu Pro Val Thr
                165                 170                 175
Val Thr Trp Asn Ser Gly Ser Leu Ser Ser Gly Val His Thr Phe Pro
            180                 185                 190
Ala Val Leu Gln Ser Asp Leu Tyr Thr Leu Ser Ser Ser Val Thr Val
        195                 200                 205
Pro Ser Ser Thr Trp Pro Ser Glu Thr Val Thr Cys Asn Val Ala His
210                 215                 220
Pro Ala Ser Ser Thr Lys Val Asp Lys Lys Ile Val Pro Arg Asp Cys
225                 230                 235                 240
Gly Cys Lys Pro Cys Ile Cys Thr Val Pro Glu Val Ser Ser Val Phe
                245                 250                 255
Ile Phe Pro Pro Lys Pro Lys Asp Val Leu Thr Ile Thr Leu Thr Pro
            260                 265                 270
Lys Val Thr Cys Val Val Val Asp Ile Ser Lys Asp Asp Pro Glu Val
        275                 280                 285
Gln Phe Ser Trp Phe Val Asp Asp Val Glu Val His Thr Ala Gln Thr
290                 295                 300
Gln Pro Arg Glu Glu Gln Phe Asn Ser Thr Phe Arg Ser Val Ser Glu
305                 310                 315                 320
Leu Pro Ile Met His Gln Asp Trp Leu Asn Gly Lys Glu Phe Lys Cys
                325                 330                 335
Arg Val Asn Ser Pro Ala Phe Pro Ala Pro Ile Glu Lys Thr Ile Ser
            340                 345                 350
Lys Thr Lys Gly Arg Pro Lys Ala Pro Gln Val Tyr Thr Ile Pro Pro
        355                 360                 365
Pro Lys Glu Gln Met Ala Lys Asp Lys Val Ser Leu Thr Cys Met Ile
370                 375                 380
Thr Asp Phe Phe Pro Glu Asp Ile Thr Val Glu Trp Gln Trp Asn Gly
385                 390                 395                 400
Gln Pro Ala Glu Asn Tyr Lys Asn Thr Gln Pro Ile Met Asp Thr Asp
                405                 410                 415
Gly Ser Tyr Phe Ile Tyr Ser Lys Leu Asn Val Gln Lys Ser Asn Trp
            420                 425                 430
Glu Ala Gly Asn Thr Phe Thr Cys Ser Val Leu His Glu Gly Leu His
        435                 440                 445
Asn His His Thr Glu Lys Ser Leu Ser His Ser Pro Gly Lys
450                 455                 460

<210> SEQ ID NO 14
<211> LENGTH: 1389
<212> TYPE: DNA
<213> ORGANISM: Mus musculus

<400> SEQUENCE: 14
atgagatgca ggtggatctt tctctttctc ctgtcaggaa ctgcaggtgt cctctctgag      60
gtccagctgc aacagtctgg acctgaactg gtgacgcctg ggcttcagt gaagatatct     120 tgtaaggctt ctggatacac attcactgac cactacatga ctgggtgaa gcagagtcat     180 ggaaaaagcc ttgagtggat tgagatatt aatccctatt ctggtgaaac tacctacaac     240
cagaagttca gggcacggc cacattgact gtagacaagt cttccagtat agcctacatg     300
```

```
gagatccgcg gcctgacatc tgaggactct gcagtctatt actgtgcaag agatgattac    360
gacgcctctc cgtttgctta ctggggccaa gggactctgg tcactgtctc tgcagccaaa    420
acgacacccc catctgtcta tccactggcc cctggatctg ctgcccaaac taactccatg    480
gtgaccctgg gatgcctggt caagggctat ttccctgagc cagtgacagt gacctggaac    540
tctggatccc tgtccagcgg tgtgcacacc ttcccagctg tcctgcagtc tgacctctac    600
actctgagca gctcagtgac tgtcccctcc agcacctggc ccagcgagac cgtcacctgc    660
aacgttgccc acccggccag cagcaccaag gtggacaaga aaattgtgcc cagggattgt    720
ggttgtaagc cttgcatatg tacagtccca gaagtatcat ctgtcttcat cttcccccca    780
aagcccaagg atgtgctcac cattactctg actcctaagg tcacgtgtgt tgtggtagac    840
atcagcaagg atgatcccga ggtccagttc agctggtttg tagatgatgt ggaggtgcac    900
acagctcaga cgcaaccccg ggaggagcag ttcaacagca cttTccgctc agtcagtgaa    960
cttcccatca tgcaccagga ctggctcaat ggcaaggagt tcaaatgcag ggtcaacagt    1020
ccagcttTcc ctgcccccat cgagaaaacc atctccaaaa ccaaaggcag accgaaggct    1080
ccacaggtgt acaccattcc acctcccaag gagcagatgg ccaaggataa agtcagtctg    1140
acctgcatga taacagactt cttccctgaa gacattactg tggagtggca gtggaatggg    1200
cagccagcgg agaactacaa gaacactcag cccatcatgg acacagatgg ctcttacttc    1260
atctacagca agctcaatgt gcagaagagc aactgggagg caggaaatac tttcacctgc    1320
tctgtgttac atgagggcct gcacaaccac catactgaga agagcctctc ccactctcct    1380
ggtaaatga    1389
```

<210> SEQ ID NO 15
<211> LENGTH: 218
<212> TYPE: PRT
<213> ORGANISM: Mus musculus

<400> SEQUENCE: 15

```
Asp Ile Val Leu Thr Gln Ser Pro Ala Ser Leu Thr Val Ser Leu Gly
  1               5                  10                  15

Leu Arg Ala Thr Ile Ser Cys Lys Ala Ser Gln Ser Val Asp Tyr Asp
             20                  25                  30

Gly Asp Ser Tyr Met Asn Trp Tyr Gln Gln Lys Pro Gly Gln Pro Pro
         35                  40                  45

Lys Leu Leu Ile Tyr Ala Ala Ser Asn Leu Glu Ser Gly Ile Pro Ala
     50                  55                  60

Arg Phe Ser Gly Asn Gly Ser Gly Thr Asp Phe Thr Leu Asn Ile His
 65                  70                  75                  80

Pro Val Glu Glu Glu Asp Ala Val Thr Tyr Tyr Cys Gln Gln Ser Asn
                 85                  90                  95

Glu Asp Pro Trp Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175
```

```
Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
            195                 200                 205

Ile Val Lys Ser Phe Asn Arg Asn Glu Cys
            210                 215

<210> SEQ ID NO 16
<211> LENGTH: 657
<212> TYPE: DNA
<213> ORGANISM: Mus musculus

<400> SEQUENCE: 16
gacattgtgc tgacccaatc tccagcttct tgactgtgt ctctaggcct gagggccacc      60
atctcctgca aggccagcca agtgttgat tatgatggtg atagttatat gaactggtac     120
cagcagaaac caggacagcc acccaaactc ctcatctatg ctgcatccaa tctagaatct    180
gggatcccag ccaggtttag tggcaatggg tctgggacag acttcaccct caacatccat    240
cctgtggagg aggaggatgc tgtaacctat tactgtcaac aaagtaatga ggatccgtgg    300
acgttcggtg gaggcaccaa gctggaaatc aaacgggctg atgctgcacc aactgtatcc    360
atcttcccac catccagtga gcagttaaca tctggaggtg cctcagtcgt gtgcttcttg    420
aacaacttct accccaaaga catcaatgtc aagtggaaga ttgatggcag tgaacgacaa    480
aatggcgtcc tgaacagttg gactgatcag gacagcaaag acagcaccta cagcatgagc    540
agcaccctca cgttgaccaa ggacgagtat aacgcacata cagctatac ctgtgaggcc     600 actcacaaga catcaacttc acccattgtc aagagcttca caggaatga gtgttag        657

<210> SEQ ID NO 17
<211> LENGTH: 238
<212> TYPE: PRT
<213> ORGANISM: Mus musculus

<400> SEQUENCE: 17

Met Glu Thr Asp Thr Ile Leu Leu Trp Val Leu Leu Trp Val Pro
1                5                  10                  15

Gly Ser Thr Gly Asp Ile Val Leu Thr Gln Ser Pro Ala Ser Leu Thr
            20                  25                  30

Val Ser Leu Gly Leu Arg Ala Thr Ile Ser Cys Lys Ala Ser Gln Ser
            35                  40                  45

Val Asp Tyr Asp Gly Asp Ser Tyr Met Asn Trp Tyr Gln Gln Lys Pro
        50                  55                  60

Gly Gln Pro Pro Lys Leu Leu Ile Tyr Ala Ala Ser Asn Leu Glu Ser
65                  70                  75                  80

Gly Ile Pro Ala Arg Phe Ser Gly Asn Gly Ser Gly Thr Asp Phe Thr
                85                  90                  95

Leu Asn Ile His Pro Val Glu Glu Asp Ala Val Thr Tyr Tyr Cys
            100                 105                 110

Gln Gln Ser Asn Glu Asp Pro Trp Thr Phe Gly Gly Gly Thr Lys Leu
            115                 120                 125

Glu Ile Lys Arg Ala Asp Ala Ala Pro Thr Val Ser Ile Phe Pro Pro
        130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175
```

-continued

```
Ser Glu Arg Gln Asn Gly Val Leu Asn Ser Trp Thr Asp Gln Asp Ser
            180                 185                 190
Lys Asp Ser Thr Tyr Ser Met Ser Ser Thr Leu Thr Leu Thr Lys Asp
        195                 200                 205
Glu Tyr Glu Arg His Asn Ser Tyr Thr Cys Ala Thr His Lys Thr
    210                 215                 220
Ser Thr Ser Pro Ile Val Lys Ser Phe Asn Arg Asn Glu Cys
225                 230                 235
```

<210> SEQ ID NO 18
<211> LENGTH: 717
<212> TYPE: DNA
<213> ORGANISM: Mus musculus

<400> SEQUENCE: 18

```
atggagacag acacaatcct gctatgggtg ctgctgctct gggttccagg ctccactggt     60
gacattgtgc tgacccaatc tccagcttct ttgactgtgt ctctaggcct gagggccacc    120
atctcctgca aggccagcca agtgttgat tatgatggtg atagttatat gaactggtac     180
cagcagaaac aggacagcc acccaaactc ctcatctatg ctgcatccaa tctagaatct    240
gggatcccag ccaggtttag tggcaatggg tctgggacag acttcaccct caacatccat    300
cctgtggagg aggaggatgc tgtaacctat tactgtcaac aaagtaatga ggatccgtgg    360
acgttcggtg aggcaccaa gctggaaatc aaacggctg atgctgcacc aactgtatcc    420
atcttcccac catccagtga gcagttaaca tctggaggtg cctcagtcgt gtgcttcttg    480
aacaacttct accccaaaga catcaatgtc aagtggaaga ttgatggcag tgaacgacaa    540
aatggcgtcc tgaacagttg gactgatcag acagcaaag acagcaccta cagcatgagc    600
agcaccctca cgttgaccaa ggacgagtat gaacgacata cagctatac ctgtgaggcc    660
actcacaaga catcaacttc acccattgtc aagagcttca caggaatga gtgttag       717
```

<210> SEQ ID NO 19
<211> LENGTH: 449
<212> TYPE: PRT
<213> ORGANISM: Mus musculus

<400> SEQUENCE: 19

```
Glu Val Gln Leu Gln Gln Ser Gly Pro Glu Leu Val Lys Pro Gly Thr
1               5                   10                  15
Ser Val Lys Met Ser Cys Lys Ala Ser Gly Tyr Thr Phe Thr Asp Cys
            20                  25                  30
Tyr Met Asn Trp Val Lys Gln Ser His Gly Lys Ser Leu Glu Trp Ile
        35                  40                  45
Gly Asp Ile Asn Pro Phe Asn Gly Gly Thr Thr Tyr Asn Gln Lys Phe
    50                  55                  60
Lys Gly Lys Ala Thr Leu Thr Val Asp Lys Ser Ser Ser Thr Ala Tyr
65                  70                  75                  80
Met Gln Leu Asn Ser Leu Thr Ser Asp Ser Ala Val Tyr Tyr Cys
                85                  90                  95
Ala Arg Ser His Tyr Tyr Phe Asp Gly Arg Val Pro Trp Asp Ala Met
            100                 105                 110
Asp Tyr Trp Gly Gln Gly Thr Ser Val Thr Val Ser Ser Ala Lys Thr
        115                 120                 125
Thr Pro Pro Ser Val Tyr Pro Leu Ala Pro Gly Ser Ala Ala Gln Thr
    130                 135                 140
Asn Ser Met Val Thr Leu Gly Cys Leu Val Lys Gly Tyr Phe Pro Glu
```

```
           145                 150                 155                 160
       Pro Val Thr Val Thr Trp Asn Ser Gly Ser Leu Ser Ser Gly Val His
                       165                 170                 175

Thr Phe Pro Ala Val Leu Gln Ser Asp Leu Tyr Thr Leu Ser Ser Ser
                   180                 185                 190

Val Thr Val Pro Ser Ser Thr Trp Pro Ser Glu Thr Val Thr Cys Asn
                   195                 200                 205

Val Ala His Pro Ala Ser Ser Thr Lys Val Asp Lys Lys Ile Val Pro
           210                 215                 220

Arg Asp Cys Gly Cys Lys Pro Cys Ile Cys Thr Val Pro Glu Val Ser
       225                 230                 235                 240

Ser Val Phe Ile Phe Pro Pro Lys Pro Lys Asp Val Leu Thr Ile Thr
                       245                 250                 255

Leu Thr Pro Lys Val Thr Cys Val Val Val Asp Ile Ser Lys Asp Asp
                   260                 265                 270

Pro Glu Val Gln Phe Ser Trp Phe Val Asp Asp Val Glu Val His Thr
                   275                 280                 285

Ala Gln Thr Gln Pro Arg Glu Glu Gln Phe Asn Ser Thr Phe Arg Ser
           290                 295                 300

Val Ser Glu Leu Pro Ile Met His Gln Asp Trp Leu Asn Gly Lys Glu
       305                 310                 315                 320

Phe Lys Cys Arg Val Asn Ser Ala Ala Phe Pro Ala Pro Ile Glu Lys
                       325                 330                 335

Thr Ile Ser Lys Thr Lys Gly Arg Pro Lys Ala Pro Gln Val Tyr Thr
                   340                 345                 350

Ile Pro Pro Pro Lys Glu Gln Met Ala Lys Asp Lys Val Ser Leu Thr
                   355                 360                 365

Cys Met Ile Thr Asp Phe Phe Pro Glu Asp Ile Thr Val Glu Trp Gln
           370                 375                 380

Trp Asn Gly Gln Pro Ala Glu Asn Tyr Lys Asn Thr Gln Pro Ile Met
       385                 390                 395                 400

Asp Thr Asp Gly Ser Tyr Phe Ile Tyr Ser Lys Leu Asn Val Gln Lys
                       405                 410                 415

Ser Asn Trp Glu Ala Gly Asn Thr Phe Thr Cys Ser Val Leu His Glu
                   420                 425                 430

Gly Leu His Asn His His Thr Glu Lys Ser Leu Ser His Ser Pro Gly
           435                 440                 445

Lys

<210> SEQ ID NO 20
<211> LENGTH: 1350
<212> TYPE: DNA
<213> ORGANISM: Mus musculus

<400> SEQUENCE: 20
gaggtccagc tgcaacaatc tggacctgag ctggtgaagc tgggacttca gtgaagatg      60 tcctgtaagg cttctggata cacattcact gactgctaca tgaactgggt gaagcagagc    120
catgggaaga gccttgaatg gattggagat attaatcctt caacggtgg tactacctac     180 aaccagaagt tcaagggcaa ggccacattg actgtagaca atcctccag cacagcctac    240 atgcagctca acagcctgac atctgacgac tctgcagtct attactgtgc aagatcccat    300
tattacttcg atggtagagt cccttgggat gctatggact actggggtca aggaacctca    360
gtcaccgtct cctcagccaa aacgacaccc ccatctgtct atccactggc ccctggatct    420
```

```
gctgcccaaa ctaactccat ggtgaccctg ggatgcctgg tcaagggcta tttccctgag    480
ccagtgacag tgacctggaa ctctggatcc ctgtccagcg tgtgcacac cttcccagct    540 gtcctgcagt ctgacctcta cactctgagc agctcagtga ctgtcccctc agcacctgg    600 cccagcgaga ccgtcacctg caacgttgcc caccgggcca gcagcaccaa ggtggacaag    660
aaaattgtgc ccagggattg tggttgtaag ccttgcatat gtacagtccc agaagtatca    720
tctgtcttca tcttccccc aaagcccaag gatgtgctca ccattactct gactcctaag    780
gtcacgtgtg ttgtggtaga catcagcaag gatgatcccg aggtccagtt cagctggttt    840
gtagatgatg tggaggtgca cacagctcag acgcaacccc gggaggagca gttcaacagc    900
actttccgct cagtcagtga acttcccatc atgcaccagg actggctcaa tggcaaggag    960
ttcaaatgca gggtcaacag tgcagctttc cctgccccca tcgagaaaac catctccaaa   1020
accaaaggca gaccgaaggc tccacaggtg tacaccattc cacctcccaa ggagcagatg   1080
gccaaggata aagtcagtct gacctgcatg ataacagact tcttccctga agacattact   1140
gtggagtggc agtggaatgg gcagccagcg gagaactaca agaacactca gcccatcatg   1200
gacacagatg gctcttactt catctacagc aagctcaatg tgcagaagag caactgggag   1260
gcaggaaata ctttcacctg ctctgtgtta catgagggcc tgcacaacca ccatactgag   1320
aagagcctct cccactctcc tggtaaatga                                     1350

<210> SEQ ID NO 21
<211> LENGTH: 468
<212> TYPE: PRT
<213> ORGANISM: Mus musculus

<400> SEQUENCE: 21

Met Gly Trp Asn Trp Ile Phe Leu Phe Leu Leu Ser Gly Thr Ala Gly
1               5                   10                  15

Val Tyr Ser Glu Val Gln Leu Gln Gln Ser Gly Pro Glu Leu Val Lys
            20                  25                  30

Pro Gly Thr Ser Val Lys Met Ser Cys Lys Ala Ser Gly Tyr Thr Phe
        35                  40                  45

Thr Asp Cys Tyr Met Asn Trp Val Lys Gln Ser His Gly Lys Ser Leu
    50                  55                  60

Glu Trp Ile Gly Asp Ile Asn Pro Phe Asn Gly Thr Thr Tyr Asn
65                  70                  75                  80

Gln Lys Phe Lys Gly Lys Ala Thr Leu Thr Val Asp Lys Ser Ser Ser
                85                  90                  95

Thr Ala Tyr Met Gln Leu Asn Ser Leu Thr Ser Asp Asp Ser Ala Val
            100                 105                 110

Tyr Tyr Cys Ala Arg Ser His Tyr Tyr Phe Asp Gly Arg Val Pro Trp
        115                 120                 125

Asp Ala Met Asp Tyr Trp Gly Gln Gly Thr Ser Val Thr Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
```

```
              210                 215                 220
Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
            245                 250                 255

Glu Val Ser Ser Val Phe Ile Phe Pro Pro Lys Pro Lys Asp Val Leu
        260                 265                 270

Thr Ile Thr Leu Thr Pro Lys Val Thr Cys Val Val Val Asp Ile Ser
    275                 280                 285

Lys Asp Asp Pro Glu Val Gln Phe Ser Trp Phe Val Asp Asp Val Glu
290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
            325                 330                 335

Gly Lys Glu Phe Lys Cys Arg Val Asn Ser Ala Ala Phe Pro Ala Pro
        340                 345                 350

Ile Glu Lys Thr Ile Ser Lys Thr Lys Gly Arg Pro Lys Ala Pro Gln
    355                 360                 365

Val Tyr Thr Ile Pro Pro Pro Lys Glu Gln Met Ala Lys Asp Lys Val
370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
            405                 410                 415

Pro Ile Met Asp Thr Asp Gly Ser Tyr Phe Ile Tyr Ser Lys Leu Asn
        420                 425                 430

Val Gln Lys Ser Asn Trp Glu Ala Gly Asn Thr Phe Thr Cys Ser Val
    435                 440                 445

Leu His Glu Gly Leu His Asn His His Thr Glu Lys Ser Leu Ser His
450                 455                 460

Ser Pro Gly Lys
465

<210> SEQ ID NO 22
<211> LENGTH: 1407
<212> TYPE: DNA
<213> ORGANISM: Mus musculus

<400> SEQUENCE: 22
atgggatgga actggatctt tctcttcctc ttgtcaggaa ctgcaggtgt ctactctgag      60
gtccagctgc aacaatctgg acctgagctg gtgaagcctg gacttcagt gaagatgtcc     120 tgtaaggctt ctggatacac attcactgac tgctacatga actgggtgaa gcagagccat     180
gggaagagcc ttgaatggat tggagatatt aatcctttca acgtggtac tacctacaac     240 cagaagttca agggcaaggc cacattgact gtagacaaat cctccagcac agcctacatg     300
cagctcaaca gcctgacatc tgacgactct gcagtctatt actgtgcaag atcccattat     360
tacttcgatg gtagagtccc ttgggatgct atggactact ggggtcaagg aacctcagtc     420
accgtctcct cagccaaaac gacaccccca tctgtctatc cactggcccc tggatctgct     480
gcccaaacta actccatggt gaccctggga tgcctggtca agggctattt ccctgagcca     540
gtgacagtga cctggaactc tggatccctg tccagcggtg tgcacacctt cccagctgtc     600
ctgcagtctg acctctacac tctgagcagc tcagtgactg tcccctccag cacctggccc     660
```

```
agcgagaccg tcacctgcaa cgttgcccac ccggccagca gcaccaaggt ggacaagaaa    720
attgtgccca gggattgtgg ttgtaagcct tgcatatgta cagtcccaga agtatcatct    780
gtcttcatct tccccccaaa gcccaaggat gtgctcacca ttactctgac tcctaaggtc    840
acgtgtgttg tggtagacat cagcaaggat gatcccgagg tccagttcag ctggtttgta    900
gatgatgtgg aggtgcacac agctcagacg caaccccggg aggagcagtt caacagcact    960
ttccgctcag tcagtgaact tcccatcatg caccaggact ggctcaatgg caaggagttc   1020
aaatgcaggg tcaacagtgc agctttccct gcccccatcg agaaaaccat ctccaaaacc   1080
aaaggcagac cgaaggctcc acaggtgtac accattccac ctcccaagga gcagatggcc   1140
aaggataaag tcagtctgac ctgcatgata acagacttct ccctgaagaa cattactgtg   1200
gagtggcagt ggaatgggca gccagcggag aactacaaga acactcagcc catcatggac   1260
acagatggct cttacttcat ctacagcaag ctcaatgtgc agaagagcaa ctgggaggca   1320
ggaaatactt tcacctgctc tgtgttacat gagggcctgc acaaccacca tactgagaag   1380
agcctctccc actctcctgg taaatga                                       1407
```

<210> SEQ ID NO 23
<211> LENGTH: 217
<212> TYPE: PRT
<213> ORGANISM: Rabbit-Mouse Chimera

<400> SEQUENCE: 23

```
Ala Gln Val Leu Thr Gln Thr Pro Ala Ser Val Ser Ala Ala Val Gly
1               5                   10                  15

Gly Thr Val Thr Ile Asn Cys Gln Ser Ser Gln Ser Val Tyr Asp Asn
            20                  25                  30

Asn Trp Leu Ala Trp Phe Gln Gln Lys Pro Gly Gln Pro Pro Lys Leu
        35                  40                  45

Leu Ile Tyr Asp Ala Ser Asp Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Ala Asp Ala Ala Thr Tyr Tyr Cys Gln Gly Ala Tyr Asn Asp
                85                  90                  95

Val Ile Tyr Ala Phe Gly Gly Gly Thr Glu Val Val Lys Arg Thr
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215
```

<210> SEQ ID NO 24
<211> LENGTH: 654
<212> TYPE: DNA

<213> ORGANISM: Rabbit-Mouse Chimera

<400> SEQUENCE: 24

```
gcgcaagtgc tgacccagac tccagcctcc gtgtctgcag ctgtgggagg cacagtcacc     60
atcaattgcc agtccagtca gagtgtttat gataacaact ggttagcctg gtttcagcag    120
aaaccagggc agcctcccaa gctcctgatt tatgatgcat ccgatctggc atctggggtc    180
ccatcgcggt tcagtggcag tggatctggg acacagttca ctctcaccat cagcggcgtg    240
cagtgtgccg atgctgccac ttactactgt caaggcgctt ataatgatgt tatttatgct    300
ttcggcggag ggaccgaggt ggtggtcaaa cgtacggatg ctgcaccaac tgtatccatc    360
ttcccaccat ccagtgagca gttaacatct ggaggtgcct cagtcgtgtg cttcttgaac    420
aacttctacc ccaaagacat caatgtcaag tggaagattg atggcagtga acgacaaaat    480
ggcgtcctga acagttggac tgatcaggac agcaaagaca gcacctacag catgagcagc    540
accctcacgt tgaccaagga cgagtatgaa cgacataaca gctatacctg tgaggccact    600
cacaagacat caacttcacc cattgtcaag agcttcaaca ggaatgagtg ttag          654
```

<210> SEQ ID NO 25
<211> LENGTH: 239
<212> TYPE: PRT
<213> ORGANISM: Rabbit-Mouse Chimera

<400> SEQUENCE: 25

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ala Ser
                20                  25                  30

Val Ser Ala Ala Val Gly Gly Thr Val Thr Ile Asn Cys Gln Ser Ser
            35                  40                  45

Gln Ser Val Tyr Asp Asn Asn Trp Leu Ala Trp Phe Gln Gln Lys Pro
        50                  55                  60

Gly Gln Pro Pro Lys Leu Leu Ile Tyr Asp Ala Ser Asp Leu Ala Ser
65                  70                  75                  80

Gly Val Pro Ser Arg Phe Ser Gly Ser Gly Ser Gly Thr Gln Phe Thr
                85                  90                  95

Leu Thr Ile Ser Gly Val Gln Cys Ala Asp Ala Ala Thr Tyr Tyr Cys
            100                 105                 110

Gln Gly Ala Tyr Asn Asp Val Ile Tyr Ala Phe Gly Gly Gly Thr Glu
        115                 120                 125

Val Val Val Lys Arg Thr Asp Ala Ala Pro Thr Val Ser Ile Phe Pro
130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235
```

```
<210> SEQ ID NO 26
<211> LENGTH: 720
<212> TYPE: DNA
<213> ORGANISM: Rabbit-Mouse Chimera

<400> SEQUENCE: 26
atggacacga gggcccccac tcagctgctg gggctcctgc tgctctggct cccaggtgcc      60
acatttgcgc aagtgctgac ccagactcca gcctccgtgt ctgcagctgt gggaggcaca     120
gtcaccatca attgccagtc cagtcagagt gtttatgata caactggtt agcctggttt      180 cagcagaaac cagggcagcc tcccaagctc ctgatttatg atgcatccga tctggcatct     240
ggggtcccat cgcggttcag tggcagtgga tctgggacac agttcactct caccatcagc     300
ggcgtgcagt gtgccgatgc tgccacttac tactgtcaag gcgcttataa tgatgttatt     360
tatgctttcg gcggagggac cgaggtggtg gtcaaacgta cggatgctgc accaactgta     420
tccatcttcc caccatccag tgagcagtta acatctggag gtgcctcagt cgtgtgcttc     480
ttgaacaact ctacccccaa agacatcaat gtcaagtgga gattgatgg cagtgaacga     540 caaaatggcg tcctgaacag ttggactgat caggacagca agacagcac ctacagcatg     600 agcagcaccc tcacgttgac caaggacgag tatgaacgca taacagcta tacctgtgag     660 gccactcaca agacatcaac ttcacccatt gtcaagagct tcaacaggaa tgagtgttag     720

<210> SEQ ID NO 27
<211> LENGTH: 433
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody

<400> SEQUENCE: 27

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Trp
            20                  25                  30

Met Asn Trp Val Arg Gln Ala Pro Gly Glu Gly Leu Glu Trp Ile Gly
        35                  40                  45

Thr Ile Asp Ser Gly Gly Arg Thr Asp Tyr Ala Ser Trp Ala Lys Gly
    50                  55                  60

Arg Phe Thr Ile Ser Arg Thr Ser Thr Thr Met Asp Leu Lys Met Thr
65                  70                  75                  80

Ser Leu Thr Thr Gly Asp Thr Ala Arg Tyr Phe Cys Ala Arg Asn Trp
                85                  90                  95

Asn Leu Trp Gly Gln Gly Thr Leu Val Thr Val Ser Ser Ala Ser Thr
            100                 105                 110

Lys Gly Pro Ser Val Tyr Pro Leu Ala Pro Gly Ser Ala Ala Gln Thr
        115                 120                 125

Asn Ser Met Val Thr Leu Gly Cys Leu Val Lys Gly Tyr Phe Pro Glu
    130                 135                 140

Pro Val Thr Val Thr Trp Asn Ser Gly Ser Leu Ser Ser Gly Val His
145                 150                 155                 160

Thr Phe Pro Ala Val Leu Gln Ser Asp Leu Tyr Thr Leu Ser Ser Ser
                165                 170                 175

Val Thr Val Pro Ser Ser Thr Trp Pro Ser Glu Thr Val Thr Cys Asn
            180                 185                 190
```

```
Val Ala His Pro Ala Ser Ser Thr Lys Val Asp Lys Lys Ile Val Pro
    195                 200                 205

Arg Asp Cys Gly Cys Lys Pro Cys Ile Cys Thr Val Pro Glu Val Ser
210                 215                 220

Ser Val Phe Ile Phe Pro Pro Lys Pro Lys Asp Val Leu Thr Ile Thr
225                 230                 235                 240

Leu Thr Pro Lys Val Thr Cys Val Val Val Asp Ile Ser Lys Asp Asp
                245                 250                 255

Pro Glu Val Gln Phe Ser Trp Phe Val Asp Asp Val Glu Val His Thr
            260                 265                 270

Ala Gln Thr Gln Pro Arg Glu Glu Gln Phe Asn Ser Thr Phe Arg Ser
        275                 280                 285

Val Ser Glu Leu Pro Ile Met His Gln Asp Trp Leu Asn Gly Lys Glu
    290                 295                 300

Phe Lys Cys Arg Val Asn Ser Ala Ala Phe Pro Ala Pro Ile Glu Lys
305                 310                 315                 320

Thr Ile Ser Lys Thr Lys Gly Arg Pro Lys Ala Pro Gln Val Tyr Thr
                325                 330                 335

Ile Pro Pro Pro Lys Glu Gln Met Ala Lys Asp Lys Val Ser Leu Thr
            340                 345                 350

Cys Met Ile Thr Asp Phe Phe Pro Glu Asp Ile Thr Val Glu Trp Gln
        355                 360                 365

Trp Asn Gly Gln Pro Ala Glu Asn Tyr Lys Asn Thr Gln Pro Ile Met
    370                 375                 380

Asn Thr Asn Gly Ser Tyr Phe Val Tyr Ser Lys Leu Asn Val Gln Lys
385                 390                 395                 400

Ser Asn Trp Glu Ala Gly Asn Thr Phe Thr Cys Ser Val Leu His Glu
                405                 410                 415

Gly Leu His Asn His His Thr Glu Lys Ser Leu Ser His Ser Pro Gly
            420                 425                 430

Lys

<210> SEQ ID NO 28
<211> LENGTH: 1302
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody

<400> SEQUENCE: 28
cagtcgctgg aggagtccgg gggtcgcctg gtcacgcctg gacacccct gacactcacc      60 tgcacagcct ctggattctc cctcagtagt tattggatga actgggtccg ccaggctcca     120
ggggaggggc tggaatggat cggaaccatt gattctggtg gtaggacgga ctacgcgagc     180
tgggcaaaag gccgattcac catctccaga acctcgacta cgatggatct gaaaatgacc     240
agtctgacga ccgggacac ggcccgttat ttctgtgcca gaaattggaa cttgtggggc     300
caaggcaccc tcgtcaccgt ctcgagcgct tctacaaagg gcccatctgt ctatccactg     360
gcccctggat ctgctgccca aactaactcc atggtgaccc tgggatgcct ggtcaagggc     420
tatttccctg agccagtgac agtgacctgg aactctggat ccctgtccag cggtgtgcac     480
accttcccag ctgtcctgca gtctgacctc tacactctga gcagtcagt gactgtcccc     540 tccagcacct ggcccagcga gaccgtcacc tgcaacgttg cccaccccggc cagcagcacc     600
```

-continued

```
aaggtggaca agaaaattgt gcccagggat tgtggttgta agccttgcat atgtacagtc      660
ccagaagtat catctgtctt catcttcccc ccaaagccca aggatgtgct caccattact      720
ctgactccta aggtcacgtg tgttgtggta gacatcagca aggatgatcc cgaggtccag      780
ttcagctggt ttgtagatga tgtggaggtg cacacagctc agacgcaacc ccgggaggag      840
cagttcaaca gcactttccg ctcagtcagt gaacttccca tcatgcacca ggactggctc      900
aatggcaagg agttcaaatg cagggtcaac agtgcagctt ccctgccccc catcgagaaa      960
accatctcca aaccaaagg cagaccgaag gctccacagg tgtacaccat tccacctccc     1020
aaggagcaga tggccaagga taaagtcagt ctgacctgca tgataacaga cttcttccct     1080
gaagacatta ctgtggagtg gcagtggaat gggcagccag cggagaacta caagaacact     1140
cagcccatca tggacacaga tggctcttac ttcgtctaca gcaagctcaa tgtgcagaag     1200
agcaactggg aggcaggaaa tactttcacc tgctctgtgt tacatgaggg cctgcacaac     1260
caccatactg agaagagcct ctcccactct cctggtaaat ga                       1302
```

<210> SEQ ID NO 29
<211> LENGTH: 452
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody

<400> SEQUENCE: 29

```
Met Glu Thr Gly Leu Arg Trp Leu Leu Leu Val Ala Val Leu Lys Gly
1               5                   10                  15

Val His Cys Gln Ser Leu Glu Glu Ser Gly Gly Arg Leu Val Thr Pro
                20                  25                  30

Gly Thr Pro Leu Thr Leu Thr Cys Thr Ala Ser Gly Phe Ser Leu Ser
            35                  40                  45

Ser Tyr Trp Met Asn Trp Val Arg Gln Ala Pro Gly Glu Gly Leu Glu
        50                  55                  60

Trp Ile Gly Thr Ile Asp Ser Gly Gly Arg Thr Asp Tyr Ala Ser Trp
65                  70                  75                  80

Ala Lys Gly Arg Phe Thr Ile Ser Arg Thr Ser Thr Thr Met Asp Leu
                85                  90                  95

Lys Met Thr Ser Leu Thr Thr Gly Asp Thr Ala Arg Tyr Phe Cys Ala
            100                 105                 110

Arg Asn Trp Asn Leu Trp Gly Gln Gly Thr Leu Val Thr Val Ser Ser
        115                 120                 125

Ala Ser Thr Lys Gly Pro Ser Val Tyr Pro Leu Ala Pro Gly Ser Ala
    130                 135                 140

Ala Gln Thr Asn Ser Met Val Thr Leu Gly Cys Leu Val Lys Gly Tyr
145                 150                 155                 160

Phe Pro Glu Pro Val Thr Val Thr Trp Asn Ser Gly Ser Leu Ser Ser
                165                 170                 175

Gly Val His Thr Phe Pro Ala Val Leu Gln Ser Asp Leu Tyr Thr Leu
            180                 185                 190

Ser Ser Ser Val Thr Val Pro Ser Ser Thr Trp Pro Ser Glu Thr Val
        195                 200                 205

Thr Cys Asn Val Ala His Pro Ala Ser Ser Thr Lys Val Asp Lys Lys
    210                 215                 220

Ile Val Pro Arg Asp Cys Gly Cys Lys Pro Cys Ile Cys Thr Val Pro
```

```
            225                 230                 235                 240
Glu Val Ser Ser Val Phe Ile Phe Pro Pro Lys Pro Lys Asp Val Leu
                245                 250                 255

Thr Ile Thr Leu Thr Pro Lys Val Thr Cys Val Val Val Asp Ile Ser
            260                 265                 270

Lys Asp Asp Pro Glu Val Gln Phe Ser Trp Phe Val Asp Asp Val Glu
        275                 280                 285

Val His Thr Ala Gln Thr Gln Pro Arg Glu Glu Gln Phe Asn Ser Thr
    290                 295                 300

Phe Arg Ser Val Ser Glu Leu Pro Ile Met His Gln Asp Trp Leu Asn
305                 310                 315                 320

Gly Lys Glu Phe Lys Cys Arg Val Asn Ser Ala Ala Phe Pro Ala Pro
                325                 330                 335

Ile Glu Lys Thr Ile Ser Lys Thr Lys Gly Arg Pro Lys Ala Pro Gln
            340                 345                 350

Val Tyr Thr Ile Pro Pro Pro Lys Glu Gln Met Ala Lys Asp Lys Val
        355                 360                 365

Ser Leu Thr Cys Met Ile Thr Asp Phe Phe Pro Glu Asp Ile Thr Val
    370                 375                 380

Glu Trp Gln Trp Asn Gly Gln Pro Ala Glu Asn Tyr Lys Asn Thr Gln
385                 390                 395                 400

Pro Ile Met Asn Thr Asn Gly Ser Tyr Phe Val Tyr Ser Lys Leu Asn
                405                 410                 415

Val Gln Lys Ser Asn Trp Glu Ala Gly Asn Thr Phe Thr Cys Ser Val
            420                 425                 430

Leu His Glu Gly Leu His Asn His His Thr Glu Lys Ser Leu Ser His
        435                 440                 445

Ser Pro Gly Lys
    450

<210> SEQ ID NO 30
<211> LENGTH: 1359
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody

<400> SEQUENCE: 30
atggagactg ggctgcgctg gcttctcctg gtcgctgtgc tcaaaggtgt ccactgtcag     60
tcgctggagg agtccggggg tcgcctggtc acgcctggga caccctgac actcacctgc    120 acagcctctg gattctccct cagtagttat tggatgaact gggtccgcca ggctccaggg    180
gaggggctgg aatggatcgg aaccattgat tctggtggta ggacggacta cgcgagctgg    240
gcaaaaggcc gattcaccat ctccagaacc tcgactacga tggatctgaa aatgaccagt    300
ctgacgaccg gggacacggc ccgttatttc tgtgccagaa attggaactt gtggggccaa    360 ggcacccctcg tcaccgtctc gagcgcttct acaaagggcc atctgtcta tccactggcc    420 cctggatctg ctgcccaaac taactccatg gtgaccctgg gatgcctggt caagggctat    480
ttccctgagc cagtgacagt gacctggaac tctggatccc tgtccagcgg tgtgcacacc    540
ttcccagctg tcctgcagtc tgacctctac actctgagca gctcagtgac tgtcccctcc    600
agcacctggc ccagcgagac cgtcacctgc aacgttgccc accggccag cagcaccaag    660 gtggacaaga aaattgtgcc cagggattgt ggttgtaagc cttgcatatg tacagtccca    720
```

```
gaagtatcat ctgtcttcat cttccccca aagcccaagg atgtgctcac cattactctg      780
actcctaagg tcacgtgtgt tgtggtagac atcagcaagg atgatcccga ggtccagttc      840
agctggtttg tagatgatgt ggaggtgcac acagctcaga cgcaaccccg ggaggagcag      900
ttcaacagca ctttccgctc agtcagtgaa cttcccatca tgcaccagga ctggctcaat      960
ggcaaggagt tcaaatgcag ggtcaacagt gcagctttcc ctgcccccat cgagaaaacc     1020
atctccaaaa ccaaaggcag accgaaggct ccacaggtgt acaccattcc acctcccaag     1080
gagcagatgg ccaaggataa agtcagtctg acctgcatga taacagactt cttccctgaa     1140
gacattactg tggagtggca gtggaatggg cagccagcgg agaactacaa gaacactcag     1200
cccatcatgg acacagatgg ctcttacttc gtctacagca agctcaatgt gcagaagagc     1260
aactgggagg caggaaatac tttcacctgc tctgtgttac atgagggcct gcacaaccac     1320
catactgaga agagcctctc ccactctcct ggtaaatga                            1359
```

```
<210> SEQ ID NO 31
<211> LENGTH: 213
<212> TYPE: PRT
<213> ORGANISM: Mus musculus

<400> SEQUENCE: 31
```

Gln Ile Val Leu Thr Gln Ser Pro Thr Ile Val Ser Ala Ser Pro Gly
1               5                   10                  15

Glu Lys Val Thr Leu Ile Cys Ser Ala Ser Ser Ser Val Ser Phe Val
            20                  25                  30

Asp Trp Phe Gln Gln Lys Pro Gly Thr Ser Pro Lys Arg Trp Ile Tyr
        35                  40                  45

Arg Thr Ser Asn Leu Gly Phe Gly Val Pro Ala Arg Phe Ser Gly Gly
    50                  55                  60

Gly Ser Gly Thr Ser His Ser Leu Thr Ile Ser Arg Met Glu Ala Glu
65                  70                  75                  80

Asp Ala Ala Thr Tyr Tyr Cys Gln Gln Arg Ser Thr Tyr Pro Pro Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

```
<210> SEQ ID NO 32
<211> LENGTH: 642
<212> TYPE: DNA
<213> ORGANISM: Mus musculus

<400> SEQUENCE: 32
```

```
caaattgttc tcacccagtc tccaacaatc gtgtctgcat ctccagggga gaaggtcacc    60
ctaatctgca gtgccagttc aagtgtaagt ttcgtggact ggttccagca gaagccaggc   120
acttctccca aacgctggat ttacagaaca tccaacctgg ttttggagt ccctgctcgc    180 ttcagtggcg gtggatctgg gacctctcac tctctcacaa tcagccgaat ggaggctgaa   240
gatgctgcca cttattactg ccagcaaagg agtacttacc cacccacgtt cggtgctggg   300
accaagctgg aactgaaacg ggctgatgct gcaccaactg tatccatctt cccaccatcc   360
agtgagcagt taacatctgg aggtgcctca gtcgtgtgct tcttgaacaa cttctacccc   420
aaagacatca atgtcaagtg gaagattgat ggcagtgaac gacaaaatgg cgtcctgaac   480
agttggactg atcaggacag caaagacagc acctacagca tgagcagcac cctcacgttg   540
accaaggacg agtatgaacg acataacagc tatacctgtg aggccactca caagacatca   600
acttcaccca ttgtcaagag cttcaacagg aatgagtgtt ag                       642
```

`<210>` SEQ ID NO 33
`<211>` LENGTH: 235
`<212>` TYPE: PRT
`<213>` ORGANISM: Mus musculus

`<400>` SEQUENCE: 33

```
Met His Phe Gln Val Gln Ile Phe Ser Phe Leu Leu Ile Ser Ala Ser
1               5                   10                  15

Val Ile Val Ser Arg Gly Gln Ile Val Leu Thr Gln Ser Pro Thr Ile
            20                  25                  30

Val Ser Ala Ser Pro Gly Glu Lys Val Thr Leu Ile Cys Ser Ala Ser
        35                  40                  45

Ser Ser Val Ser Phe Val Asp Trp Phe Gln Gln Lys Pro Gly Thr Ser
    50                  55                  60

Pro Lys Arg Trp Ile Tyr Arg Thr Ser Asn Leu Gly Phe Gly Val Pro
65                  70                  75                  80

Ala Arg Phe Ser Gly Gly Gly Ser Gly Thr Ser His Ser Leu Thr Ile
                85                  90                  95

Ser Arg Met Glu Ala Glu Asp Ala Ala Thr Tyr Tyr Cys Gln Gln Arg
            100                 105                 110

Ser Thr Tyr Pro Pro Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235
```

`<210>` SEQ ID NO 34
`<211>` LENGTH: 708
`<212>` TYPE: DNA

<213> ORGANISM: Mus musculus

<400> SEQUENCE: 34

```
atgcattttc aagtgcagat tttcagcttc ctgctaatca gtgcctcagt catagtgtcc      60
agagggcaaa ttgttctcac ccagtctcca acaatcgtgt ctgcatctcc aggggagaag     120
gtcaccctaa tctgcagtgc cagttcaagt gtaagtttcg tggactggtt ccagcagaag     180
ccaggcactt ctcccaaacg ctggatttac agaacatcca acctgggttt tggagtccct     240
gctcgcttca gtggcggtgg atctgggacc tctcactctc tcacaatcag ccgaatggag     300
gctgaagatg ctgccactta ttactgccag caaaggagta cttacccacc cacgttcggt     360
gctgggacca gctggaact gaaacgggct gatgctgcac caactgtatc catcttccca     420
ccatccagtg agcagttaac atctggaggt gcctcagtcg tgtgcttctt gaacaacttc     480
taccccaaag acatcaatgt caagtggaag attgatggca gtgaacgaca aaatggcgtc     540
ctgaacagtt ggactgatca ggacagcaaa gacagcacct acagcatgag cagcaccctc     600
acgttgacca aggacgagta tgaacgacat aacagctata cctgtgaggc cactcacaag     660
acatcaactt cacccattgt caagagcttc aacaggaatg agtgttag                 708
```

<210> SEQ ID NO 35
<211> LENGTH: 449
<212> TYPE: PRT
<213> ORGANISM: Mus musculus

<400> SEQUENCE: 35

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg His Pro Ser Gly Lys Asn Leu Glu
        35                  40                  45

Trp Leu Ala His Ile Trp Trp Asp Asp Val Lys Arg Tyr Asn Pro Val
    50                  55                  60

Leu Lys Ser Arg Leu Thr Ile Ser Lys Asp Thr Ser Asn Ser Gln Val
65                  70                  75                  80

Phe Leu Lys Ile Ala Asn Val Asp Thr Ala Asp Thr Ala Thr Tyr Tyr
                85                  90                  95

Cys Ala Arg Ile Glu Asp Phe Asp Tyr Asp Glu Tyr Tyr Ala Met
            100                 105                 110

Asp Tyr Trp Gly Gln Gly Thr Ser Val Ile Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240
```

```
Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
        355                 360                 365

Cys Met Ile Thr Asp Phe Phe Pro Glu Asp Ile Thr Val Glu Trp Gln
    370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Val Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
        435                 440                 445

Lys

<210> SEQ ID NO 36
<211> LENGTH: 1350
<212> TYPE: DNA
<213> ORGANISM: Mus musculus

<400> SEQUENCE: 36
caggttactc tgaaagagtc tggccctggg atattgcagc cctcccagac cctcagtctg      60
acttgttctt tctctgggtt ttcactgagc acttctggta tgggtgtagg ctggattcgt     120
cacccatcag ggaagaatct ggagtggctg gcacacattt ggtgggatga tgtcaagcgc     180
tataacccag tcctgaagag ccgactgact atctccaagg atacctccaa cagccaggta     240
ttcctcaaga tcgccaatgt ggacactgca gatactgcca catactactg tgctcgaata     300
gaggactttg attacgacga ggagtattat gctatggact actggggtca aggaacctca     360
gtcatcgtct cctcagccaa aacgacaccc ccatctgtct atccactggc ccctggatct     420
gctgcccaaa ctaactccat ggtgaccctg ggatgcctgg tcaagggcta tttccctgag     480
ccagtgacag tgacctggaa ctctggatcc ctgtccagcg gtgtgcacac cttcccagct     540
gtcctgcagt ctgacctcta cactctgagc agctcagtga ctgtccgctc agcacctgg      600
cccagcgaga ccgtcacctg caacgttgcc cacccggcca gcagcaccaa ggtggacaag     660
aaaattgtgc cagggattg tggttgtaag ccttgcatat gtacagtccc agaagtatca     720
tctgtcttca tcttccccc aaagcccaag gatgtgctca ccattactct gactcctaag     780
gtcacgtgtg ttgtggtaga catcagcaag gatgatcccg aggtccagtt cagctggttt     840
gtagatgatg tggaggtgca cacagctcag acgcaacccc gggaggagca gttcaacagc     900
```

-continued

```
actttccgct cagtcagtga acttcccatc atgcaccagg actggctcaa tggcaaggag      960
ttcaaatgca gggtcaacag tgcagctttc cctgccccca tcgagaaaac catctccaaa     1020
accaaaggca gaccgaaggc tccacaggtg tacaccattc caccctccca ggagcagatg     1080
gccaaggata aagtcagtct gacctgcatg ataacagact tcttccctga agacattact     1140
gtggagtggc agtggaatgg gcagccagcg gagaactaca agaacactca gcccatcatg     1200
gacacagatg gctcttactt cgtctacagc aagctcaatg tgcagaagag caactgggag     1260
gcaggaaata ctttcacctg ctctgtgtta catgagggcc tgcacaacca ccatactgag     1320
aagagcctct cccactctcc tggtaaatga                                      1350
```

<210> SEQ ID NO 37
<211> LENGTH: 468
<212> TYPE: PRT
<213> ORGANISM: Mus musculus

<400> SEQUENCE: 37

```
Met Gly Arg Leu Thr Ser Ser Phe Leu Leu Ile Val Pro Ala Tyr
1               5                   10                  15

Val Leu Ser Gln Val Thr Leu Lys Glu Ser Gly Pro Gly Ile Leu Gln
                20                  25                  30

Pro Ser Gln Thr Leu Ser Leu Thr Cys Ser Phe Ser Gly Phe Ser Leu
            35                  40                  45

Ser Thr Ser Gly Met Gly Val Gly Trp Ile Arg His Pro Ser Gly Lys
        50                  55                  60

Asn Leu Glu Trp Leu Ala His Ile Trp Trp Asp Asp Val Lys Arg Tyr
65                  70                  75                  80

Asn Pro Val Leu Lys Ser Arg Leu Thr Ile Ser Lys Asp Thr Ser Asn
                85                  90                  95

Ser Gln Val Phe Leu Lys Ile Ala Asn Val Asp Thr Ala Asp Thr Ala
            100                 105                 110

Thr Tyr Tyr Cys Ala Arg Ile Glu Asp Phe Asp Tyr Asp Glu Glu Tyr
        115                 120                 125

Tyr Ala Met Asp Tyr Trp Gly Gln Gly Thr Ser Val Ile Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
    210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Val Glu
    290                 295                 300
```

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
            325                 330                 335

Gly Lys Glu Phe Lys Cys Arg Val Asn Ser Ala Ala Phe Pro Ala Pro
                340                 345                 350

Ile Glu Lys Thr Ile Ser Lys Thr Lys Gly Arg Pro Lys Ala Pro Gln
            355                 360                 365

Val Tyr Thr Ile Pro Pro Pro Lys Glu Gln Met Ala Lys Asp Lys Val
        370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415

Pro Ile Met Asp Thr Asp Gly Ser Tyr Phe Val Tyr Ser Lys Leu Asn
            420                 425                 430

Val Gln Lys Ser Asn Trp Glu Ala Gly Asn Thr Phe Thr Cys Ser Val
        435                 440                 445

Leu His Glu Gly Leu His Asn His His Thr Glu Lys Ser Leu Ser His
    450                 455                 460

Ser Pro Gly Lys
465

<210> SEQ ID NO 38
<211> LENGTH: 1407
<212> TYPE: DNA
<213> ORGANISM: Mus musculus

<400> SEQUENCE: 38
atgggcaggc ttacttcttc attcctgcta ctgattgtcc ctgcatatgt cctgtcccag      60
gttactctga aagagtctgg ccctgggata ttgcagccct cccagaccct cagtctgact     120
tgttctttct ctgggttttc actgagcact tctggtatgg gtgtaggctg gattcgtcac     180
ccatcaggga agaatctgga gtggctggca cacatttggt gggatgatgt caagcgctat     240
aacccagtcc tgaagagccg actgactatc tccaaggata cctccaacag ccaggtattc     300
ctcaagatcg ccaatgtgga cactgcagat actgccacat actactgtgc tcgaatagag     360
gactttgatt acgacgagga gtattatgct atggactact ggggtcaagg aacctcagtc     420
atcgtctcct cagccaaaac gacacccca tctgtctatc cactggcccc tggatctgct     480
gcccaaacta actccatggt gaccctggga tgcctggtca agggctattt ccctgagcca     540
gtgacagtga cctggaactc tggatccctg tccagcggtg tgcacacctt cccagctgtc     600
ctgcagtctg acctctacac tctgagcagc tcagtgactg tcccctccag cacctggccc     660
agcgagaccg tcacctgcaa cgttgcccac ccgccagca gcaccaaggt ggacaagaaa     720
attgtgccca gggattgtgg ttgtaagcct tgcatatgta cagtcccaga agtatcatct     780
gtcttcatct ccccccaaa gcccaaggat gtgctcacca ttactctgac tcctaaggtc     840
acgtgtgttg tggtagacat cagcaaggat gatcccgagg tccagttcag ctggtttgta     900
gatgatgtgg aggtgcacac agctcagacg caacccgggc aggagcagtt caacagcact     960
ttccgctcag tcagtgaact tcccatcatg caccaggact ggctcaatgg caaggagttc    1020
aaatgcaggg tcaacagtgc agctttccct gccccatcg agaaaccat ctccaaaacc    1080 aaaggcagac cgaaggctcc acaggtgtac accattccac ctcccaagga gcagatggcc    1140

```
aaggataaag tcagtctgac ctgcatgata acagacttct tccctgaaga cattactgtg    1200
gagtggcagt ggaatgggca gccagcggag aactacaaga acactcagcc catcatggac    1260
acagatggct cttacttcgt ctacagcaag ctcaatgtgc agaagagcaa ctgggaggca    1320
ggaaatactt tcacctgctc tgtgttacat gagggcctgc acaaccacca tactgagaag    1380
agcctctccc actctcctgg taaatga                                        1407

<210> SEQ ID NO 39
<211> LENGTH: 5
<212> TYPE: PRT
<213> ORGANISM: Mus musculus

<400> SEQUENCE: 39

Asp His Tyr Met Ser
1               5

<210> SEQ ID NO 40
<211> LENGTH: 17
<212> TYPE: PRT
<213> ORGANISM: Mus musculus

<400> SEQUENCE: 40

Asp Ile Asn Pro Tyr Ser Gly Glu Thr Thr Tyr Asn Gln Lys Phe Lys
1               5                   10                  15

Gly

<210> SEQ ID NO 41
<211> LENGTH: 10
<212> TYPE: PRT
<213> ORGANISM: Mus musculus

<400> SEQUENCE: 41

Asp Asp Tyr Asp Ala Ser Pro Phe Ala Tyr
1               5                   10

<210> SEQ ID NO 42
<211> LENGTH: 11
<212> TYPE: PRT
<213> ORGANISM: Mus musculus

<400> SEQUENCE: 42

Gln Ala Ser Gln Gly Thr Ser Ile Asn Leu Asn
1               5                   10

<210> SEQ ID NO 43
<211> LENGTH: 7
<212> TYPE: PRT
<213> ORGANISM: Mus musculus

<400> SEQUENCE: 43

Gly Ser Ser Asn Leu Glu Asp
1               5

<210> SEQ ID NO 44
<211> LENGTH: 9
<212> TYPE: PRT
<213> ORGANISM: Mus musculus

<400> SEQUENCE: 44

Leu Gln His Ser Tyr Leu Pro Tyr Thr
1               5

<210> SEQ ID NO 45
```

```
<211> LENGTH: 5
<212> TYPE: PRT
<213> ORGANISM: Mus musculus

<400> SEQUENCE: 45

Asp Cys Tyr Met Asn
1               5

<210> SEQ ID NO 46
<211> LENGTH: 17
<212> TYPE: PRT
<213> ORGANISM: Mus musculus

<400> SEQUENCE: 46

Asp Ile Asn Pro Phe Asn Gly Gly Thr Thr Tyr Asn Gln Lys Phe Lys
1               5                   10                  15

Gly

<210> SEQ ID NO 47
<211> LENGTH: 16
<212> TYPE: PRT
<213> ORGANISM: Mus musculus

<400> SEQUENCE: 47

Ser His Tyr Tyr Phe Asp Gly Arg Val Pro Trp Asp Ala Met Asp Tyr
1               5                   10                  15

<210> SEQ ID NO 48
<211> LENGTH: 15
<212> TYPE: PRT
<213> ORGANISM: Mus musculus

<400> SEQUENCE: 48

Lys Ala Ser Gln Ser Val Asp Tyr Asp Gly Asp Ser Tyr Met Asn
1               5                   10                  15

<210> SEQ ID NO 49
<211> LENGTH: 7
<212> TYPE: PRT
<213> ORGANISM: Mus musculus

<400> SEQUENCE: 49

Ala Ala Ser Asn Leu Glu Ser
1               5

<210> SEQ ID NO 50
<211> LENGTH: 9
<212> TYPE: PRT
<213> ORGANISM: Mus musculus

<400> SEQUENCE: 50

Gln Gln Ser Asn Glu Asp Pro Trp Thr
1               5

<210> SEQ ID NO 51
<211> LENGTH: 5
<212> TYPE: PRT
<213> ORGANISM: Rabbit-Mouse Chimera

<400> SEQUENCE: 51

Ser Tyr Trp Met Asn
1               5

<210> SEQ ID NO 52
<211> LENGTH: 16
```

```
<212> TYPE: PRT
<213> ORGANISM: Rabbit-Mouse Chimera

<400> SEQUENCE: 52

Thr Ile Asp Ser Gly Gly Arg Thr Asp Tyr Ala Ser Trp Ala Lys Gly
1               5                   10                  15

<210> SEQ ID NO 53
<211> LENGTH: 4
<212> TYPE: PRT
<213> ORGANISM: Rabbit-Mouse Chimera

<400> SEQUENCE: 53

Asn Trp Asn Leu
1

<210> SEQ ID NO 54
<211> LENGTH: 13
<212> TYPE: PRT
<213> ORGANISM: Rabbit-Mouse Chimera

<400> SEQUENCE: 54

Gln Ser Ser Gln Ser Val Tyr Asp Asn Asn Trp Leu Ala
1               5                   10

<210> SEQ ID NO 55
<211> LENGTH: 7
<212> TYPE: PRT
<213> ORGANISM: Rabbit-Mouse Chimera

<400> SEQUENCE: 55

Asp Ala Ser Asp Leu Ala Ser
1               5

<210> SEQ ID NO 56
<211> LENGTH: 10
<212> TYPE: PRT
<213> ORGANISM: Rabbit-Mouse Chimera

<400> SEQUENCE: 56

Gln Gly Ala Tyr Asn Asp Val Ile Tyr Ala
1               5                   10

<210> SEQ ID NO 57
<211> LENGTH: 7
<212> TYPE: PRT
<213> ORGANISM: Mus musculus

<400> SEQUENCE: 57

Thr Ser Gly Met Gly Val Gly
1               5

<210> SEQ ID NO 58
<211> LENGTH: 16
<212> TYPE: PRT
<213> ORGANISM: Mus musculus

<400> SEQUENCE: 58

His Ile Trp Trp Asp Asp Val Lys Arg Tyr Asn Pro Val Leu Lys Ser
1               5                   10                  15

<210> SEQ ID NO 59
<211> LENGTH: 14
<212> TYPE: PRT
<213> ORGANISM: Mus musculus
```

-continued

```
<400> SEQUENCE: 59

Glu Asp Phe Asp Tyr Asp Glu Glu Tyr Tyr Ala Met Asp Tyr
1               5                   10

<210> SEQ ID NO 60
<211> LENGTH: 10
<212> TYPE: PRT
<213> ORGANISM: Mus musculus

<400> SEQUENCE: 60

Ser Ala Ser Ser Ser Val Ser Phe Val Asp
1               5                   10

<210> SEQ ID NO 61
<211> LENGTH: 7
<212> TYPE: PRT
<213> ORGANISM: Mus musculus

<400> SEQUENCE: 61

Arg Thr Ser Asn Leu Gly Phe
1               5

<210> SEQ ID NO 62
<211> LENGTH: 9
<212> TYPE: PRT
<213> ORGANISM: Mus musculus

<400> SEQUENCE: 62

Gln Gln Arg Ser Thr Tyr Pro Pro Thr
1               5

<210> SEQ ID NO 63
<211> LENGTH: 20
<212> TYPE: PRT
<213> ORGANISM: Homo sapiens

<400> SEQUENCE: 63

Cys Gly Pro Ala Arg Leu Leu Pro Asn Ala Ile Gly Arg Gly Lys Trp
1               5                   10                  15

Trp Arg Pro Ser
            20

<210> SEQ ID NO 64
<211> LENGTH: 20
<212> TYPE: PRT
<213> ORGANISM: Homo sapiens

<400> SEQUENCE: 64

Gly Pro Ala Arg Leu Leu Pro Asn Ala Ile Gly Arg Gly Lys Trp Trp
1               5                   10                  15

Arg Pro Ser Gly
            20

<210> SEQ ID NO 65
<211> LENGTH: 20
<212> TYPE: PRT
<213> ORGANISM: Homo sapiens

<400> SEQUENCE: 65

Pro Ala Arg Leu Leu Pro Asn Ala Ile Gly Arg Gly Lys Trp Trp Arg
1               5                   10                  15

Pro Ser Gly Pro
            20
```

<210> SEQ ID NO 66
<211> LENGTH: 20
<212> TYPE: PRT
<213> ORGANISM: Homo sapiens

<400> SEQUENCE: 66

Ala Arg Leu Leu Pro Asn Ala Ile Gly Arg Gly Lys Trp Trp Arg Pro
1               5                   10                  15

Ser Gly Pro Asp
            20

<210> SEQ ID NO 67
<211> LENGTH: 20
<212> TYPE: PRT
<213> ORGANISM: Homo sapiens

<400> SEQUENCE: 67

Arg Leu Leu Pro Asn Ala Ile Gly Arg Gly Lys Trp Trp Arg Pro Ser
1               5                   10                  15

Gly Pro Asp Phe
            20

<210> SEQ ID NO 68
<211> LENGTH: 20
<212> TYPE: PRT
<213> ORGANISM: Homo sapiens

<400> SEQUENCE: 68

Leu Leu Pro Asn Ala Ile Gly Arg Gly Lys Trp Trp Arg Pro Ser Gly
1               5                   10                  15

Pro Asp Phe Arg
            20

<210> SEQ ID NO 69
<211> LENGTH: 20
<212> TYPE: PRT
<213> ORGANISM: Homo sapiens

<400> SEQUENCE: 69

Leu Pro Asn Ala Ile Gly Arg Gly Lys Trp Trp Arg Pro Ser Gly Pro
1               5                   10                  15

Asp Phe Arg Cys
            20

<210> SEQ ID NO 70
<211> LENGTH: 14
<212> TYPE: PRT
<213> ORGANISM: Homo sapiens

<400> SEQUENCE: 70

Ser Ala Lys Pro Val Thr Glu Leu Val Cys Ser Gly Gln Cys
1               5                   10

<210> SEQ ID NO 71
<211> LENGTH: 7
<212> TYPE: PRT
<213> ORGANISM: Homo sapiens

<400> SEQUENCE: 71

Leu Val Ala Ser Cys Lys Cys
1               5

<210> SEQ ID NO 72

<211> LENGTH: 8
<212> TYPE: PRT
<213> ORGANISM: Homo sapiens

<400> SEQUENCE: 72

Cys Arg Glu Leu His Phe Thr Arg
1               5

<210> SEQ ID NO 73
<211> LENGTH: 7
<212> TYPE: PRT
<213> ORGANISM: Homo sapiens

<400> SEQUENCE: 73

Cys Ile Pro Asp Arg Tyr Arg
1               5

<210> SEQ ID NO 74
<211> LENGTH: 399
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 74

```
atggacacga gggccccac tcagctgctg gggctcctgc tgctctggct cccaggtgcc    60
acatttgctc aagttctgac ccagagtcca agcagtctct ccgccagcgt aggcgatcgt   120
gtgactatta cctgtcaatc tagtcagagc gtgtatgata caattggct ggcgtggtac    180
cagcaaaaac cgggcaaagc cccgaagctg ctcatctatg acgcgtccga tctggctagc   240
ggtgtgccaa gccgtttcag tggcagtggc agcggtactg actttaccct cacaatttcg   300
tctctccagc cggaagattt cgccacttac tattgtcaag gtgcttacaa cgatgtgatt   360
tatgccttcg gtcagggcac taaagtagaa atcaaacgt                         399
```

<210> SEQ ID NO 75
<211> LENGTH: 133
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 75

Met Asp Thr Arg Ala Pro Thr Gln Leu Leu Gly Leu Leu Leu Trp
1               5                   10                  15

Leu Pro Gly Ala Thr Phe Ala Gln Val Leu Thr Gln Ser Pro Ser
                20                  25                  30

Leu Ser Ala Ser Val Gly Asp Arg Val Thr Ile Thr Cys Gln Ser Ser
            35                  40                  45

Gln Ser Val Tyr Asp Asn Asn Trp Leu Ala Trp Tyr Gln Gln Lys Pro
        50                  55                  60

Gly Lys Ala Pro Lys Leu Leu Ile Tyr Asp Ala Ser Asp Leu Ala Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gly Ala Tyr Asn Asp Val Ile Tyr Ala Phe Gly Gln Gly Thr Lys
        115                 120                 125

Val Glu Ile Lys Arg
    130

<210> SEQ ID NO 76
<211> LENGTH: 393
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 76
atggagactg ggctgcgctg cttctcctg gtcgctgtgc tcaaaggtgt ccactgtgag      60
gtgcagctgt tggagtctgg aggcgggctt gtccagcctg agggagcct gcgtctctct    120 tgtgcagcaa gcggcttcag cttatcctct tactggatga attgggtgcg gcaggcacct   180
gggaagggcc tggagtgggt gggcaccatt gattccggag ccgtacaga ctacgcgtct    240 tgggcaaagg gccgtttcac catttcccgc gacaactcca aaaataccat gtacctccag   300
atgaactctc tccgcgcaga ggacacagca cgttattact gtgcacgcaa ctggaatctg   360
tggggtcaag gtactcttgt aacagtctcg agc                                 393

<210> SEQ ID NO 77
<211> LENGTH: 131
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 77

Met Glu Thr Gly Leu Arg Trp Leu Leu Leu Val Ala Val Leu Lys Gly
1               5                   10                  15

Val His Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Ser Leu
        35                  40                  45

Ser Ser Tyr Trp Met Asn Trp Val Arg Gln Ala Pro Gly Lys Gly Leu
    50                  55                  60

Glu Trp Val Gly Thr Ile Asp Ser Gly Gly Arg Thr Asp Tyr Ala Ser
65                  70                  75                  80

Trp Ala Lys Gly Arg Phe Thr Ile Ser Arg Asp Asn Ser Lys Asn Thr
                85                  90                  95

Met Tyr Leu Gln Met Asn Ser Leu Arg Ala Glu Asp Thr Ala Arg Tyr
            100                 105                 110

Tyr Cys Ala Arg Asn Trp Asn Leu Trp Gly Gln Gly Thr Leu Val Thr
        115                 120                 125

Val Ser Ser
    130

<210> SEQ ID NO 78
<211> LENGTH: 11
<212> TYPE: PRT
<213> ORGANISM: Mus musculus

```
<400> SEQUENCE: 78

Arg Ala Ser Gln Asp Ile Ser Asn Tyr Leu Asn
1               5                   10

<210> SEQ ID NO 79
<211> LENGTH: 7
<212> TYPE: PRT
<213> ORGANISM: Mus musculus

<400> SEQUENCE: 79

Tyr Thr Ser Arg Leu Leu Ser
1               5

<210> SEQ ID NO 80
<211> LENGTH: 9
<212> TYPE: PRT
<213> ORGANISM: Mus musculus

<400> SEQUENCE: 80

Gln Gln Gly Asp Thr Leu Pro Tyr Thr
1               5

<210> SEQ ID NO 81
<211> LENGTH: 11
<212> TYPE: PRT
<213> ORGANISM: Mus musculus

<400> SEQUENCE: 81

Arg Ala Ser Gln Asp Ile Ser Asn Tyr Leu Asn
1               5                   10

<210> SEQ ID NO 82
<211> LENGTH: 24
<212> TYPE: PRT
<213> ORGANISM: Rattus norvegicus

<400> SEQUENCE: 82

Gln Gly Trp Gln Ala Phe Lys Asn Asp Ala Thr Glu Ile Ile Pro Gly
1               5                   10                  15

Leu Arg Glu Tyr Pro Glu Pro Pro
            20

<210> SEQ ID NO 83
<211> LENGTH: 20
<212> TYPE: PRT
<213> ORGANISM: Rattus norvegicus

<400> SEQUENCE: 83

Thr Glu Ile Ile Pro Gly Leu Arg Glu Tyr Pro Glu Pro Pro Gln Glu
1               5                   10                  15

Leu Glu Asn Asn
            20

<210> SEQ ID NO 84
<211> LENGTH: 20
<212> TYPE: PRT
<213> ORGANISM: Rattus norvegicus

<400> SEQUENCE: 84

Pro Glu Pro Pro Gln Glu Leu Glu Asn Asn Gln Thr Met Asn Arg Ala
1               5                   10                  15

Glu Asn Gly Gly
            20
```

```
<210> SEQ ID NO 85
<211> LENGTH: 20
<212> TYPE: PRT
<213> ORGANISM: Rattus norvegicus

<400> SEQUENCE: 85

Glu Asn Gly Gly Arg Pro Pro His His Pro Tyr Asp Thr Lys Asp Val
1               5                   10                  15

Ser Glu Tyr Ser
            20

<210> SEQ ID NO 86
<211> LENGTH: 14
<212> TYPE: PRT
<213> ORGANISM: Rattus norvegicus

<400> SEQUENCE: 86

Cys Arg Glu Leu His Tyr Thr Arg Phe Val Thr Asp Gly Pro
1               5                   10

<210> SEQ ID NO 87
<211> LENGTH: 25
<212> TYPE: PRT
<213> ORGANISM: Rattus norvegicus

<400> SEQUENCE: 87

Cys Arg Glu Leu His Tyr Thr Arg Phe Val Thr Asp Gly Pro Ser Arg
1               5                   10                  15

Ser Ala Lys Pro Val Thr Glu Leu Val
            20                  25

<210> SEQ ID NO 88
<211> LENGTH: 23
<212> TYPE: PRT
<213> ORGANISM: Rattus norvegicus

<400> SEQUENCE: 88

Cys Arg Ser Ala Lys Pro Val Thr Glu Leu Val Ser Ser Gly Gln Ser
1               5                   10                  15

Gly Pro Arg Ala Arg Leu Leu
            20

<210> SEQ ID NO 89
<211> LENGTH: 25
<212> TYPE: PRT
<213> ORGANISM: Rattus norvegicus

<400> SEQUENCE: 89

Cys Gly Pro Ala Arg Leu Leu Pro Asn Ala Ile Gly Arg Val Lys Trp
1               5                   10                  15

Trp Arg Pro Asn Gly Pro Asp Phe Arg
            20                  25

<210> SEQ ID NO 90
<211> LENGTH: 20
<212> TYPE: PRT
<213> ORGANISM: Rattus norvegicus

<400> SEQUENCE: 90

Arg Ala Gln Arg Val Gln Leu Leu Cys Pro Gly Gly Ala Ala Pro Arg
1               5                   10                  15

Ser Arg Lys Val
            20
```

```
<210> SEQ ID NO 91
<211> LENGTH: 16
<212> TYPE: PRT
<213> ORGANISM: Rattus norvegicus

<400> SEQUENCE: 91

Pro Gly Gly Ala Ala Pro Arg Ser Arg Lys Val Arg Leu Val Ala Ser
1               5                   10                  15

<210> SEQ ID NO 92
<211> LENGTH: 23
<212> TYPE: PRT
<213> ORGANISM: Rattus norvegicus

<400> SEQUENCE: 92

Lys Arg Leu Thr Arg Phe His Asn Gln Ser Glu Leu Lys Asp Phe Gly
1               5                   10                  15

Pro Glu Thr Ala Arg Pro Gln
            20

<210> SEQ ID NO 93
<211> LENGTH: 16
<212> TYPE: PRT
<213> ORGANISM: Rattus norvegicus

<400> SEQUENCE: 93

Ile Pro Asp Arg Tyr Ala Gln Arg Val Gln Leu Leu Ser Pro Gly Gly
1               5                   10                  15

<210> SEQ ID NO 94
<211> LENGTH: 24
<212> TYPE: PRT
<213> ORGANISM: Rattus norvegicus

<400> SEQUENCE: 94

Ser Glu Leu Lys Asp Phe Gly Pro Glu Thr Ala Arg Pro Gln Lys Gly
1               5                   10                  15

Arg Lys Pro Arg Pro Arg Ala Arg
            20

<210> SEQ ID NO 95
<211> LENGTH: 23
<212> TYPE: PRT
<213> ORGANISM: Rattus norvegicus

<400> SEQUENCE: 95

Lys Gly Arg Lys Pro Arg Pro Arg Ala Arg Gly Ala Lys Ala Asn Gln
1               5                   10                  15

Ala Glu Leu Glu Asn Ala Tyr
            20

<210> SEQ ID NO 96
<211> LENGTH: 18
<212> TYPE: PRT
<213> ORGANISM: Rattus norvegicus

<400> SEQUENCE: 96

Pro Asn Ala Ile Gly Arg Val Lys Trp Trp Arg Pro Asn Gly Pro Asp
1               5                   10                  15

Phe Arg

<210> SEQ ID NO 97
```

```
<211> LENGTH: 22
<212> TYPE: PRT
<213> ORGANISM: Rattus norvegicus

<400> SEQUENCE: 97

Lys Trp Trp Arg Pro Asn Gly Pro Asp Phe Arg Cys Ile Pro Asp Arg
1               5                   10                  15

Tyr Arg Ala Gln Arg Val
            20

<210> SEQ ID NO 98
<211> LENGTH: 213
<212> TYPE: PRT
<213> ORGANISM: Rattus norvegicus

<400> SEQUENCE: 98

Met Gln Leu Ser Leu Ala Pro Cys Leu Ala Cys Leu Leu Val His Ala
1               5                   10                  15

Ala Phe Val Ala Val Glu Ser Gln Gly Trp Gln Ala Phe Lys Asn Asp
            20                  25                  30

Ala Thr Glu Ile Ile Pro Gly Leu Arg Glu Tyr Pro Glu Pro Pro Gln
        35                  40                  45

Glu Leu Glu Asn Asn Gln Thr Met Asn Arg Ala Glu Asn Gly Gly Arg
    50                  55                  60

Pro Pro His His Pro Tyr Asp Thr Lys Asp Val Ser Glu Tyr Ser Cys
65                  70                  75                  80

Arg Glu Leu His Tyr Thr Arg Phe Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Val Lys Trp Trp Arg Pro Asn
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Ala Ala Pro Arg Ser Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Pro Glu Thr Ala Arg Pro Gln Lys Gly
            180                 185                 190

Arg Lys Pro Arg Pro Arg Ala Arg Gly Ala Lys Ala Asn Gln Ala Glu
        195                 200                 205

Leu Glu Asn Ala Tyr
    210

<210> SEQ ID NO 99
<211> LENGTH: 7
<212> TYPE: PRT
<213> ORGANISM: Mus musculus

<400> SEQUENCE: 99

Tyr Thr Ser Arg Leu His Ser
1               5

<210> SEQ ID NO 100
<211> LENGTH: 9
<212> TYPE: PRT
<213> ORGANISM: Mus musculus

<400> SEQUENCE: 100
```

```
Gln Gln Gly Asp Thr Leu Pro Tyr Thr
1               5
```

<210> SEQ ID NO 101
<211> LENGTH: 11
<212> TYPE: PRT
<213> ORGANISM: Mus musculus

<400> SEQUENCE: 101

```
Arg Ala Ser Gln Val Ile Thr Asn Tyr Leu Tyr
1               5                   10
```

<210> SEQ ID NO 102
<211> LENGTH: 7
<212> TYPE: PRT
<213> ORGANISM: Mus musculus

<400> SEQUENCE: 102

```
Tyr Thr Ser Arg Leu His Ser
1               5
```

<210> SEQ ID NO 103
<211> LENGTH: 9
<212> TYPE: PRT
<213> ORGANISM: Mus musculus

<400> SEQUENCE: 103

```
Gln Gln Gly Asp Thr Leu Pro Tyr Thr
1               5
```

<210> SEQ ID NO 104
<211> LENGTH: 11
<212> TYPE: PRT
<213> ORGANISM: Mus musculus

<400> SEQUENCE: 104

```
Arg Ala Ser Gln Asp Ile Ser Asn Tyr Leu Asn
1               5                   10
```

<210> SEQ ID NO 105
<211> LENGTH: 7
<212> TYPE: PRT
<213> ORGANISM: Mus musculus

<400> SEQUENCE: 105

```
Tyr Thr Ser Arg Leu Leu Ser
1               5
```

<210> SEQ ID NO 106
<211> LENGTH: 9
<212> TYPE: PRT
<213> ORGANISM: Mus musculus

<400> SEQUENCE: 106

```
Gln Gln Gly Asp Thr Leu Pro Tyr Thr
1               5
```

<210> SEQ ID NO 107
<211> LENGTH: 11
<212> TYPE: PRT
<213> ORGANISM: Mus musculus

<400> SEQUENCE: 107

```
Arg Ala Ser Gln Asp Ile Ser Asn Tyr Leu Asn
1               5                   10
```

```
<210> SEQ ID NO 108
<211> LENGTH: 7
<212> TYPE: PRT
<213> ORGANISM: Mus musculus

<400> SEQUENCE: 108

Tyr Thr Ser Arg Leu Phe Ser
1               5

<210> SEQ ID NO 109
<211> LENGTH: 9
<212> TYPE: PRT
<213> ORGANISM: Mus musculus

<400> SEQUENCE: 109

Gln Gln Gly Asp Thr Leu Pro Tyr Thr
1               5

<210> SEQ ID NO 110
<211> LENGTH: 11
<212> TYPE: PRT
<213> ORGANISM: Mus musculus

<400> SEQUENCE: 110

Arg Ala Ser Gln Asp Ile Ser Asn Tyr Leu Asn
1               5                   10

<210> SEQ ID NO 111
<211> LENGTH: 7
<212> TYPE: PRT
<213> ORGANISM: Mus musculus

<400> SEQUENCE: 111

Tyr Thr Ser Arg Leu Leu Ser
1               5

<210> SEQ ID NO 112
<211> LENGTH: 9
<212> TYPE: PRT
<213> ORGANISM: Mus musculus

<400> SEQUENCE: 112

Gln Gln Gly Asp Thr Leu Pro Tyr Thr
1               5

<210> SEQ ID NO 113
<211> LENGTH: 11
<212> TYPE: PRT
<213> ORGANISM: Mus musculus

<400> SEQUENCE: 113

Arg Ala Ser Gln Asp Ile Ser Asn Tyr Leu Asn
1               5                   10

<210> SEQ ID NO 114
<211> LENGTH: 7
<212> TYPE: PRT
<213> ORGANISM: Mus musculus

<400> SEQUENCE: 114

Tyr Thr Ser Thr Leu Gln Ser
1               5

<210> SEQ ID NO 115
```

```
<211> LENGTH: 9
<212> TYPE: PRT
<213> ORGANISM: Mus musculus

<400> SEQUENCE: 115

Gln Gln Gly Asp Thr Leu Pro Tyr Thr
1               5

<210> SEQ ID NO 116
<211> LENGTH: 12
<212> TYPE: PRT
<213> ORGANISM: Mus musculus

<400> SEQUENCE: 116

Ser Val Ser Ser Ile Ser Ser Ser Asn Leu His
1               5                   10

<210> SEQ ID NO 117
<211> LENGTH: 213
<212> TYPE: PRT
<213> ORGANISM: Mus musculus

<400> SEQUENCE: 117

Gln Ile Val Leu Ser Gln Ser Pro Ala Ile Leu Ser Thr Ser Pro Gly
1               5                   10                  15

Glu Lys Val Thr Met Thr Cys Arg Ala Ser Ser Ser Val Tyr Tyr Met
                20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Thr Arg Val Glu Ala Glu
65                  70                  75                  80

Asp Ala Ala Thr Tyr Tyr Cys Gln Gln Trp Ser Ser Asp Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 118
<211> LENGTH: 642
<212> TYPE: DNA
<213> ORGANISM: Mus musculus

<400> SEQUENCE: 118
caaattgttc tctcccagtc tccagcaatc ctgtctacat ctccagggga gaaggtcaca    60
```

```
atgacttgca gggccagctc aagtgtatat tacatgcact ggtaccagca gaagccagga    120
tcctccccca aaccctggat ttatgccaca tccaacctgg cttctggagt ccctgttcgc    180
ttcagtggca gtgggtctgg gacctcttac tctctcacaa tcaccagagt ggaggctgaa    240
gatgctgcca cttattactg ccagcagtgg agtagtgacc cactcacgtt cggtgctggg    300
accaagctgg agctgaaacg ggctgatgct gcaccaactg tatccatctt cccaccatcc    360
agtgagcagt taacatctgg aggtgcctca gtcgtgtgct tcttgaacaa cttctacccc    420
aaagacatca atgtcaagtg gaagattgat ggcagtgaac gacaaaatgg cgtcctgaac    480
agttggactg atcaggacag caaagacagc acctacagca tgagcagcac cctcacgttg    540
accaaggacg agtatgaacg acataacagc tatacctgtg aggccactca caagacatca    600
acttcaccca ttgtcaagag cttcaacagg aatgagtgtt ag                      642
```

<210> SEQ ID NO 119
<211> LENGTH: 235
<212> TYPE: PRT
<213> ORGANISM: Mus musculus

<400> SEQUENCE: 119

```
Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Thr Ser Pro Gly Glu Lys Val Thr Met Thr Cys Arg Ala Ser
        35                  40                  45

Ser Ser Val Tyr Tyr Met His Trp Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Thr Arg Val Glu Ala Glu Asp Ala Ala Thr Tyr Tyr Cys Gln Gln Trp
            100                 105                 110

Ser Ser Asp Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235
```

<210> SEQ ID NO 120
<211> LENGTH: 708
<212> TYPE: DNA
<213> ORGANISM: Mus musculus

<400> SEQUENCE: 120

-continued

```
atggattttc aagtgcagat tttcagcttc ctgctaatca gtgcttcagt cattatgtcc        60 agggggacaaa ttgttctctc ccagtctcca gcaatcctgt ctacatctcc aggggagaag      120
gtcacaatga cttgcagggc cagctcaagt gtatattaca tgcactggta ccagcagaag      180
ccaggatcct cccccaaacc ctggatttat gccacatcca acctggcttc tggagtccct      240
gttcgcttca gtggcagtgg gtctgggacc tcttactctc tcacaatcac cagagtggag      300
gctgaagatg ctgccactta ttactgccag cagtggagta gtgacccact cacgttcggt      360
gctgggacca agctggagct gaaacgggct gatgctgcac caactgtatc catcttccca      420
ccatccagtg agcagttaac atctggaggt gcctcagtcg tgtgcttctt gaacaacttc      480
taccccaaag acatcaatgt caagtggaag attgatggca gtgaacgaca aaatggcgtc      540
ctgaacagtt ggactgatca ggacagcaaa gacagcacct acagcatgag cagcacctc      600 acgttgacca aggacgagta tgaacgacat aacagctata cctgtgaggc cactcacaag      660
acatcaactt cacccattgt caagagcttc aacaggaatg agtgttag                  708
```

```
<210> SEQ ID NO 121
<211> LENGTH: 445
<212> TYPE: PRT
<213> ORGANISM: Mus musculus

<400> SEQUENCE: 121
```

```
Glu Val Gln Val Gln Gln Ser Gly Pro Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Phe Ile His Trp Val Lys Gln Arg Pro Glu Gln Gly Leu Glu Trp Ile
        35                  40                  45

Gly Arg Leu Asp Pro Glu Asp Gly Glu Ser Asp Tyr Ala Pro Lys Phe
    50                  55                  60

Gln Asp Lys Ala Ile Met Thr Ala Asp Thr Ser Ser Asn Thr Ala Tyr
65                  70                  75                  80

Leu Gln Leu Arg Ser Leu Thr Ser Glu Asp Thr Ala Ile Tyr Tyr Cys
                85                  90                  95

Glu Arg Glu Asp Tyr Asp Gly Thr Tyr Thr Phe Phe Pro Tyr Trp Gly
            100                 105                 110

Gln Gly Thr Leu Val Thr Val Ser Ala Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255
```

```
Val Thr Cys Val Val Asp Ile Ser Lys Asp Asp Pro Glu Val Gln
            260                 265                 270

Phe Ser Trp Phe Val Asp Val Glu Val His Thr Ala Gln Thr Gln
            275                 280                 285

Pro Arg Glu Glu Gln Phe Asn Ser Thr Phe Arg Ser Val Ser Glu Leu
            290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
            355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asp Thr Asp Gly
385                 390                 395                 400

Ser Tyr Phe Ile Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
            435                 440                 445

<210> SEQ ID NO 122
<211> LENGTH: 1338
<212> TYPE: DNA
<213> ORGANISM: Mus musculus

<400> SEQUENCE: 122
gaggttcagg tgcagcagtc tgggccagaa cttgtgaagc caggggcctc agtcaagttg      60
tcctgcacag cttctggctt caacattaaa gactacttta cactgggt gaagcagagg       120
cctgaacagg gcctggagtg gattggaagg cttgatcctg aggatggtga aagtgattat      180
gccccgaagt tccaggacaa ggccattatg acagcagaca catcatccaa cacagcctat      240
cttcagctca gaagcctgac atctgaggac actgccatct attattgtga gagaggac       300
tacgatggta cctacacctt ttttccttac tggggccaag ggactctggt cactgtctct      360
gcagccaaaa cgacaccccc atctgtctat ccactggccc ctggatctgc tgcccaaact      420
aactccatgg tgaccctggg atgcctggtc aagggctatt ccctgagcc agtgacagtg       480
acctggaact ctgatccct gtccagcggt gtgcacacct tcccagctgt cctgcagtct      540
gacctctaca ctctgagcag ctcagtgact gtcccctcca gcacctggcc cagcgagacc      600
gtcacctgca acgttgccca ccggccagc agcaccaagg tggacaagaa aattgtgccc      660
agggattgtg gttgtaagcc ttgcatatgt acagtcccag aagtatcatc tgtcttcatc      720
ttccccccaa agcccaagga tgtgctcacc attactctga ctcctaaggt cacgtgtgtt      780
gtggtagaca tcagcaagga tgatcccgag gtccagttca gctggtttgt agatgatgtg      840
gaggtgcaca cagctcagac gcaacccgg gaggagcagt tcaacagcac tttccgctca      900
gtcagtgaac ttcccatcat gcaccaggac tggctcaatg gcaaggagtt caaatgcagg      960
gtcaacagtg cagctttccc tgcccccatc gagaaaacca tctccaaaac caaaggcaga     1020
ccgaaggctc cacaggtgta caccattcca cctcccaagg agcagatggc caaggataaa     1080
```

-continued

```
gtcagtctga cctgcatgat aacagacttc ttccctgaag acattactgt ggagtggcag    1140
tggaatgggc agccagcgga gaactacaag aacactcagc ccatcatgga cacagatggc    1200
tcttacttca tctacagcaa gctcaatgtg cagaagagca actgggaggc aggaaatact    1260
ttcacctgct ctgtgttaca tgagggcctg cacaaccacc atactgagaa gagcctctcc    1320
cactctcctg gtaaatga                                                  1338
```

<210> SEQ ID NO 123
<211> LENGTH: 464
<212> TYPE: PRT
<213> ORGANISM: Mus musculus

<400> SEQUENCE: 123

```
Met Lys Cys Ser Trp Val Ile Phe Phe Leu Met Ala Val Val Thr Gly
1               5                   10                  15

Val Asn Ser Glu Val Gln Val Gln Gln Ser Gly Pro Glu Leu Val Lys
                20                  25                  30

Pro Gly Ala Ser Val Lys Leu Ser Cys Thr Ala Ser Gly Phe Asn Ile
            35                  40                  45

Lys Asp Tyr Phe Ile His Trp Val Lys Gln Arg Pro Glu Gln Gly Leu
        50                  55                  60

Glu Trp Ile Gly Arg Leu Asp Pro Glu Asp Gly Glu Ser Asp Tyr Ala
65                  70                  75                  80

Pro Lys Phe Gln Asp Lys Ala Ile Met Thr Ala Asp Thr Ser Ser Asn
                85                  90                  95

Thr Ala Tyr Leu Gln Leu Arg Ser Leu Thr Ser Glu Asp Thr Ala Ile
            100                 105                 110

Tyr Tyr Cys Glu Arg Glu Asp Tyr Asp Gly Thr Tyr Thr Phe Phe Pro
        115                 120                 125

Tyr Trp Gly Gln Gly Thr Leu Val Thr Val Ser Ala Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
```

```
                        325                 330                 335
Lys Cys Arg Val Asn Ser Ala Ala Phe Pro Ala Pro Ile Glu Lys Thr
                340                 345                 350

Ile Ser Lys Thr Lys Gly Arg Pro Lys Ala Pro Gln Val Tyr Thr Ile
            355                 360                 365

Pro Pro Pro Lys Glu Gln Met Ala Lys Asp Lys Val Ser Leu Thr Cys
        370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Ile Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460

<210> SEQ ID NO 124
<211> LENGTH: 1395
<212> TYPE: DNA
<213> ORGANISM: Mus musculus

<400> SEQUENCE: 124
atgaaatgca gctgggtcat cttcttcctg atggcagtgg ttacaggggt caattcagag      60
gttcaggtgc agcagtctgg gccagaactt gtgaagccag ggcctcagt caagttgtcc     120 tgcacagctt ctggcttcaa cattaaagac tactttatac actgggtgaa gcagaggcct     180
gaacagggcc tggagtggat tggaaggctt gatcctgagg atggtgaaag tgattatgcc     240
ccgaagttcc aggacaaggc cattatgaca gcagacacat catccaacac agcctatctt     300
cagctcagaa gcctgacatc tgaggacact gccatctatt attgtgagag agaggactac     360
gatggtacct acaccttttt tccttactgg ggccaaggga ctctggtcac tgtctctgca     420
gccaaaacga caccccatc tgtctatcca ctggcccctg gatctgctgc ccaaactaac     480
tccatggtga ccctgggatg cctggtcaag ggctatttcc ctgagccagt gacagtgacc     540
tggaactctg gatccctgtc cagcggtgtg cacaccttcc cagctgtcct gcagtctgac     600
ctctacactc tgagcagctc agtgactgtc ccctccagca cctggcccag cgagaccgtc     660
acctgcaacg ttgcccaccc ggccagcagc accaaggtgg acaagaaaat tgtgcccagg     720
gattgtggtt gtaagccttg catatgtaca gtcccagaag tatcatctgt cttcatcttc     780
cccccaaagc caaggatgt gctcaccatt actctgactc ctaaggtcac gtgtgttgtg     840
gtagacatca gcaaggatga tcccgaggtc cagttcagct ggtttgtaga tgatgtggag     900
gtgcacacag ctcagacgca accccgggag gagcagttca acagcacttt ccgctcagtc     960
agtgaacttc ccatcatgca ccaggactgg ctcaatggca aggagttcaa atgcagggtc    1020
aacagtgcag ctttccctgc ccccatcgag aaaccatct ccaaaaccaa aggcagaccg    1080
aaggctccac aggtgtacac cattccacct cccaaggagc agatggccaa ggataaagtc    1140
agtctgacct gcatgataac agacttcttc cctgaagaca ttactgtgga gtggcagtgg    1200
aatgggcagc cagcggagaa ctacaagaac actcagccca tcatggacac agatggctct    1260
tacttcatct acagcaagct caatgtgcag aagagcaact gggaggcagg aaatactttc    1320
acctgctctg tgttacatga gggcctgcac aaccaccata ctgagaagag cctctcccac    1380
```
tctcctggta aatga                                               1395

<210> SEQ ID NO 125
<211> LENGTH: 215
<212> TYPE: PRT
<213> ORGANISM: Mus musculus

<400> SEQUENCE: 125

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Thr Ile Ser Ser Asn
            20                  25                  30

His Leu His Trp Phe Gln Gln Lys Ser Asp Thr Ser Pro Lys Pro Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Leu Thr Phe Gly Ala Gly Thr Lys Leu Glu Leu Arg Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215

<210> SEQ ID NO 126
<211> LENGTH: 648
<212> TYPE: DNA
<213> ORGANISM: Mus musculus

<400> SEQUENCE: 126
gaaattgtgc tcacccagtc tccagcactc atggctgcat ctccggggga gaaggtcacc    60
atcacctgca gtgtcagttc aactataagt tccaaccact tgcactggtt ccagcagaag   120
tcagacacct cccccaaacc ctggatttat ggcacatcca acctggcttc tggagtccct   180
gttcgcttca gtggcagtgg atctgggacc tcttattctc tcacaatcag cagcatggag   240
gctgaggatg ctgccactta ttactgtcaa cagtggagta gttacccact cacgttcggc   300
gctgggacca agctggagct gagacgggct gatgctgcac caactgtatc catcttccca   360
ccatccagtg agcagttaac atctggaggt gcctcagtcg tgtgcttctt gaacaacttc   420
taccccaaag acatcaatgt caagtggaag attgatggca gtgaacgaca aaatggcgtc   480
ctgaacagtt ggactgatca ggacagcaaa gacagcacct acagcatgag cagcaccctc   540
acgttgacca aggacgagta tgaacgacat aacagctata cctgtgaggc cactcacaag   600
acatcaactt cacccattgt caagagcttc aacaggaatg agtgttag         648

<210> SEQ ID NO 127
<211> LENGTH: 237
<212> TYPE: PRT
<213> ORGANISM: Mus musculus

<400> SEQUENCE: 127

Met Asp Phe His Val Gln Ile Phe Ser Phe Met Leu Ile Ser Val Thr
1               5                   10                  15

Val Ile Leu Ser Ser Gly Glu Ile Val Leu Thr Gln Ser Pro Ala Leu
            20                  25                  30

Met Ala Ala Ser Pro Gly Glu Lys Val Thr Ile Thr Cys Ser Val Ser
        35                  40                  45

Ser Thr Ile Ser Ser Asn His Leu His Trp Phe Gln Gln Lys Ser Asp
    50                  55                  60

Thr Ser Pro Lys Pro Trp Ile Tyr Gly Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys Gln
            100                 105                 110

Gln Trp Ser Ser Tyr Pro Leu Thr Phe Gly Ala Gly Thr Lys Leu Glu
        115                 120                 125

Leu Arg Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235

<210> SEQ ID NO 128
<211> LENGTH: 714
<212> TYPE: DNA
<213> ORGANISM: Mus musculus

<400> SEQUENCE: 128 atggatttc atgtgcagat tttcagcttc atgctaatca gtgtcacagt cattttgtcc      60
agtggagaaa ttgtgctcac ccagtctcca gcactcatgg ctgcatctcc ggggagaag     120 gtcaccatca cctgcagtgt cagttcaact ataagttcca accacttgca ctggttccag    180
cagaagtcag acacctcccc caaaccctgg atttatggca catccaacct ggcttctgga    240
gtccctgttc gcttcagtgg cagtggatct gggacctctt attctctcac aatcagcagc    300
atggaggctg aggatgctgc cacttattac tgtcaacagt ggagtagtta cccactcacg    360
ttcggcgctg ggaccaagct ggagctgaga cgggctgatg ctgcaccaac tgtatccatc    420
ttcccaccat ccagtgagca gttaacatct ggaggtgcct cagtcgtgtg cttcttgaac    480
aacttctacc ccaaagacat caatgtcaag tggaagattg atggcagtga acgacaaaat    540

```
ggcgtcctga acagttggac tgatcaggac agcaaagaca gcacctacag catgagcagc      600
accctcacgt tgaccaagga cgagtatgaa cgacataaca gctatacctg tgaggccact      660
cacaagacat caacttcacc cattgtcaag agcttcaaca ggaatgagtg ttag            714
```

<210> SEQ ID NO 129
<211> LENGTH: 449
<212> TYPE: PRT
<213> ORGANISM: Mus musculus

<400> SEQUENCE: 129

```
Glu Val Gln Leu Gln Gln Ser Gly Ala Glu Leu Val Arg Pro Gly Ala
1               5                   10                  15

Leu Val Lys Leu Ser Cys Thr Ala Ser Asp Phe Asn Ile Lys Asp Phe
            20                  25                  30

Tyr Leu His Trp Met Arg Gln Arg Pro Glu Gln Gly Leu Asp Trp Ile
        35                  40                  45

Gly Arg Ile Asp Pro Glu Asn Gly Asp Thr Leu Tyr Asp Pro Lys Phe
    50                  55                  60

Gln Asp Lys Ala Thr Leu Thr Thr Asp Thr Ser Ser Asn Thr Ala Tyr
65                  70                  75                  80

Leu Gln Leu Ser Gly Leu Thr Ser Glu Thr Thr Ala Val Tyr Tyr Cys
                85                  90                  95

Ser Arg Glu Ala Asp Tyr Phe His Asp Gly Thr Ser Tyr Trp Tyr Phe
            100                 105                 110

Asp Val Trp Gly Ala Gly Thr Thr Ile Thr Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350
```

```
Ile Pro Pro Pro Lys Glu Gln Met Ala Lys Asp Lys Val Ser Leu Thr
        355                 360                 365
Cys Met Ile Thr Asp Phe Phe Pro Glu Asp Ile Thr Val Glu Trp Gln
    370                 375                 380
Trp Asn Gly Gln Pro Ala Glu Asn Tyr Lys Asn Thr Gln Pro Ile Met
385                 390                 395                 400
Asp Thr Asp Gly Ser Tyr Phe Ile Tyr Ser Lys Leu Asn Val Gln Lys
                405                 410                 415
Ser Asn Trp Glu Ala Gly Asn Thr Phe Thr Cys Ser Val Leu His Glu
            420                 425                 430
Gly Leu His Asn His His Thr Glu Lys Ser Leu Ser His Ser Pro Gly
            435                 440                 445
Lys

<210> SEQ ID NO 130
<211> LENGTH: 1350
<212> TYPE: DNA
<213> ORGANISM: Mus musculus

<400> SEQUENCE: 130
gaggttcagc tgcagcagtc tggggctgaa cttgtgaggc caggggcctt agtcaagttg      60
tcctgcacag cttctgactt caacattaaa gacttctatc tacactggat gaggcagcgg     120
cctgaacagg gcctggactg gattggaagg attgatcctg agaatggtga tactttatat     180
gacccgaagt tccaggacaa ggccactctt acaacagaca catcctccaa cacagcctac     240
ctgcagctca gcggcctgac atctgagacc actgccgtct attactgttc tagagaggcg     300
gattatttcc acgatggtac ctcctactgg tacttcgatg tctggggcgc agggaccaca     360
atcaccgtct cctcagccaa aacgacaccc ccatctgtct atccactggc ccctggatct     420
gctgcccaaa ctaactccat ggtgaccctg ggatgcctgg tcaagggcta tttccctgag     480
ccagtgacag tgacctggaa ctctggatcc ctgtccagcg gtgtgcacac cttcccagct     540
gtcctgcagt ctgacctcta cactctgagc agctcagtga ctgtcccctc agcacctgg      600
cccagcgaga ccgtcacctg caacgttgcc cacccggcca gcagcaccaa ggtggacaag     660
aaaattgtgc ccagggattg tggttgtaag ccttgcatat gtacagtccc agaagtatca     720
tctgtcttca tcttcccccc aaagcccaag gatgtgctca ccattactct gactcctaag     780
gtcacgtgtg ttgtggtaga catcagcaag gatgatcccg aggtccagtt cagctggttt     840
gtagatgatg tggaggtgca cacagctcag acgcaacccc gggaggagca gttcaacagc     900
actttccgct cagtcagtga acttcccatc atgcaccagg actggctcaa tggcaaggag     960
ttcaaatgca gggtcaacag tgcagctttc cctgccccca tcgagaaaac catctccaaa    1020
accaaaggca gaccgaaggc tccacaggtg tacaccattc cacctcccaa ggagcagatg    1080
gccaaggata agtcagtctc gacctgcatg ataacagact cttccctga agacattact    1140
gtggagtggc agtggaatgg gcagccagcg gagaactaca agaacactca gcccatcatg    1200
gacacagatg gctcttactt catctacagc aagctcaatg tgcagaagag caactgggag    1260
gcaggaaata ctttcacctg ctctgtgtta catgagggcc tgcacaacca ccatactgag    1320
aagagcctct cccactctcc tggtaaatga                                     1350

<210> SEQ ID NO 131
<211> LENGTH: 468
<212> TYPE: PRT
<213> ORGANISM: Mus musculus
```

<400> SEQUENCE: 131

```
Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Thr Ala Ser Asp Phe Asn Ile
            35                  40                  45

Lys Asp Phe Tyr Leu His Trp Met Arg Gln Arg Pro Glu Gln Gly Leu
50                  55                  60

Asp Trp Ile Gly Arg Ile Asp Pro Glu Asn Gly Asp Thr Leu Tyr Asp
65                  70                  75                  80

Pro Lys Phe Gln Asp Lys Ala Thr Leu Thr Thr Asp Thr Ser Ser Asn
                85                  90                  95

Thr Ala Tyr Leu Gln Leu Ser Gly Leu Thr Ser Glu Thr Thr Ala Val
            100                 105                 110

Tyr Tyr Cys Ser Arg Glu Ala Asp Tyr Phe His Asp Gly Thr Ser Tyr
            115                 120                 125

Trp Tyr Phe Asp Val Trp Gly Ala Gly Thr Thr Ile Thr Val Ser Ser
        130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
        210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Asp Val Glu
        290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro
            340                 345                 350

Ile Glu Lys Thr Ile Ser Lys Thr Lys Gly Arg Pro Lys Ala Pro Gln
        355                 360                 365

Val Tyr Thr Ile Pro Pro Pro Lys Glu Gln Met Ala Lys Asp Lys Val
        370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415
```

Pro Ile Met Asp Thr Asp Gly Ser Tyr Phe Ile Tyr Ser Lys Leu Asn
            420                 425                 430

Val Gln Lys Ser Asn Trp Glu Ala Gly Asn Thr Phe Thr Cys Ser Val
        435                 440                 445

Leu His Glu Gly Leu His Asn His His Thr Glu Lys Ser Leu Ser His
    450                 455                 460

Ser Pro Gly Lys
465

<210> SEQ ID NO 132
<211> LENGTH: 1407
<212> TYPE: DNA
<213> ORGANISM: Mus musculus

<400> SEQUENCE: 132

| | | | | |
|---|---|---|---|---|
| atgaaatgca | gctgggtcat | cttcttcctg | atggcagtgg | ttacaggggt | caattcagag | 60 |
| gttcagctgc | agcagtctgg | ggctgaactt | gtgaggccag | gggccttagt | caagttgtcc | 120 |
| tgcacagctt | ctgacttcaa | cattaaagac | ttctatctac | actggatgag | gcagcggcct | 180 |
| gaacagggcc | tggactggat | tggaaggatt | gatcctgaga | atggtgatac | tttatatgac | 240 |
| ccgaagttcc | aggacaaggc | cactcttaca | acagacacat | cctccaacac | agcctacctg | 300 |
| cagctcagcg | gcctgacatc | tgagaccact | gccgtctatt | actgttctag | agaggcggat | 360 |
| tatttccacg | atggtaccct | ctactggtac | ttcgatgtct | ggggcgcagg | gaccacaatc | 420 |
| accgtctcct | cagccaaaac | gacaccccca | tctgtctatc | cactggcccc | tggatctgct | 480 |
| gcccaaacta | actccatggt | gaccctggga | tgcctggtca | agggctattt | ccctgagcca | 540 |
| gtgacagtga | cctggaactc | tggatccctg | tccagcggtg | tgcacacctt | cccagctgtc | 600 |
| ctgcagtctg | acctctacac | tctgagcagc | tcagtgactg | tcccctccag | cacctggccc | 660 |
| agcgagaccg | tcacctgcaa | cgttgcccac | ccggccagca | gcaccaaggt | ggacaagaaa | 720 |
| attgtgccca | gggattgtgg | ttgtaagcct | tgcatatgta | cagtcccaga | agtatcatct | 780 |
| gtcttcatct | tccccccaaa | gcccaaggat | gtgctcacca | ttactctgac | tcctaaggtc | 840 |
| acgtgtgttg | tggtagacat | cagcaaggat | gatcccgagg | tccagttcag | ctggtttgta | 900 |
| gatgatgtgg | aggtgcacac | agctcagacg | caaccccggg | aggagcagtt | caacagcact | 960 |
| ttccgctcag | tcagtgaact | tcccatcatg | caccaggact | ggctcaatgg | caaggagttc | 1020 |
| aaatgcaggg | tcaacagtgc | agcttttccct | gcccccatcg | agaaaaccat | ctccaaaacc | 1080 |
| aaaggcagac | cgaaggctcc | acaggtgtac | accattccac | ctcccaagga | gcagatggcc | 1140 |
| aaggataaag | tcagtctgac | ctgcatgata | acagacttct | tccctgaaga | cattactgtg | 1200 |
| gagtggcagt | ggaatgggca | gccagcggag | aactacaaga | acactcagcc | catcatggac | 1260 |
| acagatggct | cttacttcat | ctacagcaag | ctcaatgtgc | agaagagcaa | ctgggaggca | 1320 |
| ggaaatactt | tcacctgctc | tgtgttacat | gagggcctgc | acaaccacca | tactgagaag | 1380 |
| agcctctccc | actctcctgg | taaatga | | | | 1407 |

<210> SEQ ID NO 133
<211> LENGTH: 214
<212> TYPE: PRT
<213> ORGANISM: Mus musculus

<400> SEQUENCE: 133

Asp Ile Gln Met Thr Gln Ile Thr Ser Ser Leu Ser Ala Ser Leu Gly
1               5                   10                  15

```
Asp Arg Val Ser Ile Ser Cys Arg Ala Ser Gln Asp Ile Ser Asn Tyr
         20                  25                  30

Leu Asn Trp Tyr Gln Gln Lys Pro Asp Gly Thr Phe Lys Leu Leu Ile
         35                  40                  45

Phe Tyr Thr Ser Arg Leu Leu Ser Gly Val Pro Ser Arg Phe Ser Gly
 50                  55                  60

Ser Gly Ser Gly Thr Asp Tyr Ser Leu Thr Ile Tyr Asn Leu Glu Gln
 65                  70                  75                  80

Glu Asp Phe Ala Thr Tyr Phe Cys Gln Gln Gly Asp Thr Leu Pro Tyr
                 85                  90                  95

Thr Phe Gly Gly Gly Thr Lys Leu Glu Ile Lys Arg Ala Asp Ala Ala
                100                 105                 110

Pro Thr Val Ser Ile Phe Pro Pro Ser Ser Glu Gln Leu Thr Ser Gly
             115                 120                 125

Gly Ala Ser Val Val Cys Phe Leu Asn Asn Phe Tyr Pro Lys Asp Ile
 130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 134
<211> LENGTH: 645
<212> TYPE: DNA
<213> ORGANISM: Mus musculus

<400> SEQUENCE: 134
gatatccaga tgacacagat tacatcctcc ctgtctgcct ctctgggaga cagggtctcc      60
atcagttgca gggcaagtca agacattagc aattatttaa actggtatca gcagaaacca     120
gatggaactt ttaaactcct tatcttctac acatcaagat tactctcagg agtcccatca     180
aggttcagtg gcagtgggtc tggaacagat tattctctca ccatttacaa cctggagcaa     240
gaagattttg ccacttactt ttgccaacag ggagatacgc ttccgtacac tttcggaggg     300
gggaccaagc tggaaataaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag cacccctcacg    540 ttgaccaagg acgagtatga acgacataac agctatacct gtgaggccac tcacaagaca     600
tcaacttcac ccattgtcaa gagcttcaac aggaatgagt gttag                     645

<210> SEQ ID NO 135
<211> LENGTH: 234
<212> TYPE: PRT
<213> ORGANISM: Mus musculus

<400> SEQUENCE: 135

Met Met Ser Ser Ala Gln Phe Leu Gly Leu Leu Leu Leu Cys Phe Gln
1               5                  10                  15
```

```
Gly Thr Arg Cys Asp Ile Gln Met Thr Gln Ile Thr Ser Ser Leu Ser
                 20                  25                  30
Ala Ser Leu Gly Asp Arg Val Ser Ile Ser Cys Arg Ala Ser Gln Asp
             35                  40                  45
Ile Ser Asn Tyr Leu Asn Trp Tyr Gln Gln Lys Pro Asp Gly Thr Phe
 50                  55                  60
Lys Leu Leu Ile Phe Tyr Thr Ser Arg Leu Leu Ser Gly Val Pro Ser
 65                  70                  75                  80
Arg Phe Ser Gly Ser Gly Ser Gly Thr Asp Tyr Ser Leu Thr Ile Tyr
                 85                  90                  95
Asn Leu Glu Gln Glu Asp Phe Ala Thr Tyr Phe Cys Gln Gln Gly Asp
            100                 105                 110
Thr Leu Pro Tyr Thr Phe Gly Gly Gly Thr Lys Leu Glu Ile Lys Arg
        115                 120                 125
Ala Asp Ala Ala Pro Thr Val Ser Ile Phe Pro Pro Ser Ser Glu Gln
130                 135                 140
Leu Thr Ser Gly Gly Ala Ser Val Val Cys Phe Leu Asn Asn Phe Tyr
145                 150                 155                 160
Pro Lys Asp Ile Asn Val Lys Trp Lys Ile Asp Gly Ser Glu Arg Gln
                165                 170                 175
Asn Gly Val Leu Asn Ser Trp Thr Asp Gln Asp Ser Lys Asp Ser Thr
            180                 185                 190
Tyr Ser Met Ser Ser Thr Leu Thr Leu Thr Lys Asp Glu Tyr Glu Arg
        195                 200                 205
His Asn Ser Tyr Thr Cys Glu Ala Thr His Lys Thr Ser Thr Ser Pro
210                 215                 220
Ile Val Lys Ser Phe Asn Arg Asn Glu Cys
225                 230

<210> SEQ ID NO 136
<211> LENGTH: 705
<212> TYPE: DNA
<213> ORGANISM: Mus musculus

<400> SEQUENCE: 136
atgatgtcct ctgctcagtt cctTggtctc ctgttgctct gttttcaagg taccagatgt    60
gatatccaga tgacacagat tacatcctcc ctgtctgcct ctctgggaga cagggtctcc   120
atcagttgca gggcaagtca agacattagc aattatttaa actggtatca gcagaaacca   180
gatggaactt ttaaactcct tatcttctac acatcaagat tactctcagg agtcccatca   240
aggttcagtg gcagtgggtc tggaacagat tattctctca ccatttacaa cctggagcaa   300
gaagattttg ccacttactt ttgccaacag ggagatacgc ttccgtacac tttcggaggg   360
gggaccaagc tggaaataaa acgggctgat gctgcaccaa ctgtatccat cttcccacca   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag cacccTcacg   600
ttgaccaagg acgagtatga acgacataac agctatacct gtgaggccac tcacaagaca   660
tcaacttcac ccattgtcaa gagcttcaac aggaatgagt gttag              705

<210> SEQ ID NO 137
<211> LENGTH: 447
<212> TYPE: PRT
<213> ORGANISM: Mus musculus
```

<400> SEQUENCE: 137

| | | | | | | | | | | | | | | |
|---|---|---|---|---|---|---|---|---|---|---|---|---|---|---|
|Glu|Val|Gln|Leu|Gln|Gln|Ser|Gly|Pro|Glu|Leu|Met|Lys|Pro|Gly|Ala|
|1| | | |5| | | | |10| | | | |15| |
|Ser|Val|Lys|Met|Ser|Cys|Lys|Ala|Ser|Gly|Tyr|Thr|Phe|Thr|Asp|Tyr|
| | | |20| | | | |25| | | | |30| | |
|Asn|Met|His|Trp|Val|Lys|Gln|Asn|Gln|Gly|Lys|Thr|Leu|Glu|Trp|Ile|
| | |35| | | | |40| | | | |45| | | |
|Gly|Glu|Ile|Asn|Pro|Asn|Ser|Gly|Gly|Ala|Gly|Tyr|Asn|Gln|Lys|Phe|
| |50| | | | |55| | | | |60| | | | |
|Lys|Gly|Lys|Ala|Thr|Leu|Thr|Val|Asp|Lys|Ser|Ser|Thr|Thr|Ala|Tyr|
|65| | | | |70| | | | |75| | | | |80|
|Met|Glu|Leu|Arg|Ser|Leu|Thr|Ser|Glu|Asp|Ser|Ala|Val|Tyr|Tyr|Cys|
| | | | |85| | | | |90| | | | |95| |
|Ala|Arg|Leu|Gly|Tyr|Asp|Asp|Ile|Tyr|Asp|Asp|Trp|Tyr|Phe|Asp|Val|
| | | |100| | | | |105| | | | |110| | |
|Trp|Gly|Ala|Gly|Thr|Thr|Val|Thr|Val|Ser|Ser|Ala|Lys|Thr|Thr|Pro|
| | |115| | | | |120| | | | |125| | | |
|Pro|Ser|Val|Tyr|Pro|Leu|Ala|Pro|Gly|Ser|Ala|Ala|Gln|Thr|Asn|Ser|
| |130| | | | |135| | | | |140| | | | |
|Met|Val|Thr|Leu|Gly|Cys|Leu|Val|Lys|Gly|Tyr|Phe|Pro|Glu|Pro|Val|
|145| | | | |150| | | | |155| | | | |160|
|Thr|Val|Thr|Trp|Asn|Ser|Gly|Ser|Leu|Ser|Ser|Gly|Val|His|Thr|Phe|
| | | | |165| | | | |170| | | | |175| |
|Pro|Ala|Val|Leu|Gln|Ser|Asp|Leu|Tyr|Thr|Leu|Ser|Ser|Ser|Val|Thr|
| | | |180| | | | |185| | | | |190| | |
|Val|Pro|Ser|Ser|Thr|Trp|Pro|Ser|Glu|Thr|Val|Thr|Cys|Asn|Val|Ala|
| | |195| | | | |200| | | | |205| | | |
|His|Pro|Ala|Ser|Ser|Thr|Lys|Val|Asp|Lys|Lys|Ile|Val|Pro|Arg|Asp|
| |210| | | | |215| | | | |220| | | | |
|Cys|Gly|Cys|Lys|Pro|Cys|Ile|Cys|Thr|Val|Pro|Glu|Val|Ser|Ser|Val|
|225| | | | |230| | | | |235| | | | |240|
|Phe|Ile|Phe|Pro|Pro|Lys|Pro|Lys|Asp|Val|Leu|Thr|Ile|Thr|Leu|Thr|
| | | | |245| | | | |250| | | | |255| |
|Pro|Lys|Val|Thr|Cys|Val|Val|Val|Asp|Ile|Ser|Lys|Asp|Asp|Pro|Glu|
| | | |260| | | | |265| | | | |270| | |
|Val|Gln|Phe|Ser|Trp|Phe|Val|Asp|Asp|Val|Glu|Val|His|Thr|Ala|Gln|
| | |275| | | | |280| | | | |285| | | |
|Thr|Gln|Pro|Arg|Glu|Gln|Phe|Asn|Ser|Thr|Phe|Arg|Ser|Val|Ser|
| |290| | | | |295| | | | |300| | | | |
|Glu|Leu|Pro|Ile|Met|His|Gln|Asp|Trp|Leu|Asn|Gly|Lys|Glu|Phe|Lys|
|305| | | | |310| | | | |315| | | | |320|
|Cys|Arg|Val|Asn|Ser|Ala|Ala|Phe|Pro|Ala|Pro|Ile|Glu|Lys|Thr|Ile|
| | | | |325| | | | |330| | | | |335| |
|Ser|Lys|Thr|Lys|Gly|Arg|Pro|Lys|Ala|Pro|Gln|Val|Tyr|Thr|Ile|Pro|
| | | |340| | | | |345| | | | |350| | |
|Pro|Pro|Lys|Glu|Gln|Met|Ala|Lys|Asp|Lys|Val|Ser|Leu|Thr|Cys|Met|
| | |355| | | | |360| | | | |365| | | |
|Ile|Thr|Asp|Phe|Phe|Pro|Glu|Asp|Ile|Thr|Val|Glu|Trp|Gln|Trp|Asn|
| |370| | | | |375| | | | |380| | | | |
|Gly|Gln|Pro|Ala|Glu|Asn|Tyr|Lys|Asn|Thr|Gln|Pro|Ile|Met|Asp|Thr|
|385| | | | |390| | | | |395| | | | |400|
|Asp|Gly|Ser|Tyr|Phe|Ile|Tyr|Ser|Lys|Leu|Asn|Val|Gln|Lys|Ser|Asn|
| | | | |405| | | | |410| | | | |415| |

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
            435                 440                 445

<210> SEQ ID NO 138
<211> LENGTH: 1344
<212> TYPE: DNA
<213> ORGANISM: Mus musculus

<400> SEQUENCE: 138
gaggtccaac tgcaacagtc tggacctgaa ctaatgaagc tggggcttc agtgaagatg      60 tcctgcaagg cttctggata cattcact gactacaaca tgcactgggt gaagcagaac     120
caaggaaaga ccctagagtg gataggagaa attaatccta cagtggtgg tgctggctac    180 aaccagaagt tcaagggcaa ggccacattg actgtagaca agtcctccac cacagcctac    240
atggagctcc gcagcctgac atctgaggac tctgcagtct attactgtgc aagattgggc    300
tacgatgata tctacgacga ctggtacttc gatgtctggg gcgcaggac cacggtcacc    360 gtctcctcag ccaaaacgac accccatct gtctatccac tggcccctgg atctgctgcc    420
caaactaact ccatggtgac cctgggatgc ctggtcaagg ctatttccc tgagccagtg    480 acagtgacct ggaactctgg atccctgtcc agcggtgtgc acaccttccc agctgtcctg    540
cagtctgacc tctacactct gagcagctca gtgactgtcc cctccagcac ctggcccagc    600
gagaccgtca cctgcaacgt tgcccacccg gccagcagca ccaaggtgga caagaaaatt    660
gtgcccaggg attgtggttg taagccttgc atatgtacag tcccagaagt atcatctgtc    720
ttcatcttcc ccccaaagcc caaggatgtg ctcaccatta ctctgactcc taaggtcacg    780
tgtgttgtgg tagacatcag caaggatgat cccgaggtcc agttcagctg gtttgtagat    840
gatgtggagg tgcacacagc tcagacgcaa ccccgggagg agcagttcaa cagcactttc    900
cgctcagtca gtgaacttcc catcatgcac caggactggc tcaatggcaa ggagttcaaa    960
tgcagggtca acagtgcagc tttccctgcc cccatcgaga aaccatctc caaaaccaaa   1020 ggcagaccga aggctccaca ggtgtacacc attccacctc ccaaggagca gatggccaag   1080
gataaagtca gtctgacctg catgataaca gacttcttcc ctgaagacat tactgtggag   1140
tggcagtgga atgggcagcc agcggagaac tacaagaaca ctcagcccat catggacaca   1200
gatggctctt acttcatcta cagcaagctc aatgtgcaga gagcaactg ggaggcagga   1260 aatactttca cctgctctgt gttacatgag ggcctgcaca accaccatac tgagaagagc   1320
ctctcccact ctcctggtaa atga                                         1344

<210> SEQ ID NO 139
<211> LENGTH: 466
<212> TYPE: PRT
<213> ORGANISM: Mus musculus

<400> SEQUENCE: 139

Met Gly Trp Ser Trp Thr Phe Leu Phe Leu Leu Ser Gly Thr Ala Gly
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Val Lys Gln Asn Gln Gly Lys Thr Leu
    50                  55                  60

```
Glu Trp Ile Gly Glu Ile Asn Pro Asn Ser Gly Ala Gly Tyr Asn
65                  70                  75                  80

Gln Lys Phe Lys Gly Lys Ala Thr Leu Thr Val Asp Lys Ser Ser Thr
                85                  90                  95

Thr Ala Tyr Met Glu Leu Arg Ser Leu Thr Ser Glu Asp Ser Ala Val
                100                 105                 110

Tyr Tyr Cys Ala Arg Leu Gly Tyr Asp Asp Ile Tyr Asp Asp Trp Tyr
            115                 120                 125

Phe Asp Val Trp Gly Ala Gly Thr Thr Val Thr Val Ser Ser Ala Lys
        130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
                180                 185                 190

His Thr Phe Pro Ala Val Leu Gln Ser Asp Leu Tyr Thr Leu Ser Ser
            195                 200                 205

Ser Val Thr Val Pro Ser Ser Thr Trp Pro Ser Glu Thr Val Thr Cys
210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Asp Ile Ser Lys Asp
        275                 280                 285

Asp Pro Glu Val Gln Phe Ser Trp Phe Val Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465

<210> SEQ ID NO 140
```

```
<211> LENGTH: 1401
<212> TYPE: DNA
<213> ORGANISM: Mus musculus

<400> SEQUENCE: 140
atgggatgga gctggacctt tctcttcctc ctgtcaggaa ctgcaggtgt cctctctgag      60
gtccaactgc aacagtctgg acctgaacta atgaagcctg ggcttcagt gaagatgtcc      120
tgcaaggctt ctggatatac attcactgac tacaacatgc actgggtgaa gcagaaccaa     180
ggaaagaccc tagagtggat aggagaaatt aatcctaaca gtggtggtgc tggctacaac     240
cagaagttca gggcaaggc cacattgact gtagacaagt cctccaccac agcctacatg      300
gagctccgca gcctgacatc tgaggactct gcagtctatt actgtgcaag attgggctac     360
gatgatatct acgacgactg gtacttcgat gtctggggcg cagggaccac ggtcaccgtc     420
tcctcagcca aaacgacacc cccatctgtc tatccactgg cccctggatc tgctgcccaa     480
actaactcca tggtgaccct gggatgcctg gtcaagggc atttccctga ccagtgaca       540
gtgacctgga actctggatc cctgtccagc ggtgtgcaca ccttcccagc tgtcctgcag     600
tctgacctct acactctgag cagctcagtg actgtcccct ccagcacctg gcccagcgag     660
accgtcacct gcaacgttgc ccacccggcc agcagcacca aggtggacaa gaaaattgtg     720
cccagggatt gtggttgtaa gccttgcata tgtacagtcc cagaagtatc atctgtcttc     780
atcttcccc caaagcccaa ggatgtgctc accattactc tgactcctaa ggtcacgtgt     840
gttgtggtag acatcagcaa ggatgatccc gaggtccagt tcagctggtt tgtagatgat     900
gtggaggtgc acacagctca gacgcaaccc cgggaggagc agttcaacag cactttccgc     960
tcagtcagtg aacttcccat catgcaccag gactggctca atggcaagga gttcaaatgc     1020
agggtcaaca gtgcagcttt ccctgccccc atcgagaaaa ccatctccaa accaaaggc     1080
agaccgaagg ctccacaggt gtacaccatt ccacctccca aggagcagat ggccaaggat     1140
aaagtcagtc tgacctgcat gataacagac ttcttccctg aagacattac tgtggagtgg     1200
cagtggaatg gcagccagc ggagaactac aagaacactc agcccatcat ggacacagat     1260
ggctcttact tcatctacag caagctcaat gtgcagaaga caactgggga ggcaggaat     1320
actttcacct gctctgtgtt acatgagggc ctgcacaacc accatactga aagagcctc     1380
tcccactctc ctggtaaatg a                                              1401

<210> SEQ ID NO 141
<211> LENGTH: 214
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
```

```
            65                  70                  75                  80
Glu Asp Phe Ala Thr Tyr Tyr Cys Gln Gln Gly Asp Thr Leu Pro Tyr
                        85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 142
<211> LENGTH: 642
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 142

```
gacatccaga tgacccagtc tccatcctcc ctctccgcat ccgtaggcga ccgcgtaacc    60
ataacatgta gagcatctca agatatttcc aactatttga attggtacca acaaaaaccc   120
ggcaaagcac ctaaactcct catttactat acatcaagac tcctctccgg cgttccatca   180
cgattctcag gctccggctc cggcacagat ttcacactca ctatttcctc cctccaacca   240
gaagattttg caacctatta ctgtcaacaa ggcgatacac tcccatacac attcggcggc   300
ggcacaaaag ttgaaattaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                       642
```

<210> SEQ ID NO 143
<211> LENGTH: 236
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 143

```
Met Asp Met Arg Val Pro Ala Gln Leu Leu Gly Leu Leu Leu Leu Trp
1               5                   10                  15
```

```
Leu Arg Gly Ala Arg Cys Asp Ile Gln Met Thr Gln Ser Pro Ser Ser
         20                  25                  30

Leu Ser Ala Ser Val Gly Asp Arg Val Thr Ile Thr Cys Arg Ala Ser
             35                  40                  45

Gln Asp Ile Ser Asn Tyr Leu Asn Trp Tyr Gln Gln Lys Pro Gly Lys
        50                  55                  60

Ala Pro Lys Leu Leu Ile Tyr Tyr Thr Ser Arg Leu Leu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Gly Asp Thr Leu Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 144
<211> LENGTH: 708
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 144
atggacatga gggtccccgc tcagctcctg gggctcctgc tactctggct ccgaggtgcc      60
agatgtgaca tccagatgac ccagtctcca tcctccctct ccgcatccgt aggcgaccgc     120
gtaaccataa catgtagagc atctcaagat atttccaact atttgaattg gtaccaacaa     180
aaacccggca agcacctaaa ctcctcatt tactatacat caagactcct ctccggcgtt     240
ccatcacgat tctcaggctc cggctccggc acagatttca cactcactat ttcctccctc     300
caaccagaag attttgcaac ctattactgt caacaaggcg atacactccc atacacattc     360
ggcggcggca caaagttga attaaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgt                   708
```

<210> SEQ ID NO 145
<211> LENGTH: 449
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 145

```
Glu Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365
```

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

```
<210> SEQ ID NO 146
<211> LENGTH: 1347
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 146
```

| | | | | | |
|---|---|---|---|---|---|
| gaggtgcagc | tggtgcagag | cggcgccgag | gtaaaaaaac | caggagcaag | cgttaaagtt | 60 |
| tcttgtaaag | caagcggata | tacatttaca | gattacaaca | tgcattgggt | aagacaagcg | 120 |
| ccaggacaag | gattgaatg | gatgggcgaa | attaaccct | atagtggagg | agcaggctac | 180 |
| aatcaaaaat | tcaaaggag | agttacaatg | acaacagaca | caagcacttc | aacagcatat | 240 |
| atggaactgc | gatcacttag | aagcgacgat | acagctgtat | actattgcgc | acgacttggg | 300 |
| tatgatgata | tatatgatga | ctggtatttc | gatgtttggg | gccagggaac | aacagttacc | 360 |
| gtctctagtg | cctccaccaa | gggcccatcg | gtcttcccc  | tggcgccctg | ctccaggagc | 420 |
| acctccgaga | gcacagcggc | cctgggctgc | ctggtcaagg | actacttccc | cgaaccggtg | 480 |
| acggtgtcgt | ggaactcagg | cgctctgacc | agcggcgtgc | acaccttccc | agctgtccta | 540 |
| cagtcctcag | gactctactc | cctcagcagc | gtggtgaccg | tgccctccag | caacttcggc | 600 |
| acccagacct | acacctgcaa | cgtagatcac | aagcccagca | acaccaaggt | ggacaagaca | 660 |
| gttgagcgca | aatgttgtgt | cgagtgccca | ccgtgcccag | caccacctgt | ggcaggaccg | 720 |
| tcagtcttcc | tcttccccc  | aaaacccaag | gacaccctca | tgatctcccg | gacccctgag | 780 |
| gtcacgtgcg | tggtggtgga | cgtgagccac | gaagacccccg | aggtccagtt | caactggtac | 840 |
| gtggacggcg | tggaggtgca | taatgccaag | acaaagccac | gggaggagca | gttcaacagc | 900 |
| acgttccgtg | tggtcagcgt | cctcaccgtt | gtgcaccagg | actggctgaa | cggcaaggag | 960 |
| tacaagtgca | aggtctccaa | caaaggcctc | ccagccccca | tcgagaaaac | catctccaaa | 1020 |
| accaaagggc | agccccgaga | accacaggtg | tacaccctgc | ccccatcccg | ggaggagatg | 1080 |
| accaagaacc | aggtcagcct | gacctgcctg | gtcaaaggct | tctacccag  | cgacatcgcc | 1140 |
| gtggagtggg | agagcaatgg | gcagccggag | aacaactaca | agaccacacc | tcccatgctg | 1200 |
| gactccgacg | gctccttctt | cctctacagc | aagctcaccg | tggacaagag | caggtggcag | 1260 |
| caggggaacg | tcttctcatg | ctccgtgatg | catgaggctc | tgcacaacca | ctacacgcag | 1320 |
| aagagcctct | ccctgtctcc | gggtaaa    |            |            |            | 1347 |

```
<210> SEQ ID NO 147
<211> LENGTH: 468
```

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 147
```

Met Asp Trp Thr Trp Arg Ile Leu Phe Leu Val Ala Ala Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Asn Met His Trp Val Arg Gln Ala Pro Gly Gln Gly Leu
50                  55                  60

Glu Trp Met Gly Glu Ile Asn Pro Asn Ser Gly Ala Gly Tyr Asn
65              70                  75                  80

Gln Lys Phe Lys Gly Arg Val Thr Met Thr Thr Asp Thr Ser Thr Ser
            85                  90                  95

Thr Ala Tyr Met Glu Leu Arg Ser Leu Arg Ser Asp Asp Thr Ala Val
            100                 105                 110

Tyr Tyr Cys Ala Arg Leu Gly Tyr Asp Asp Ile Tyr Asp Asp Trp Tyr
        115                 120                 125

Phe Asp Val Trp Gly Gln Gly Thr Thr Val Thr Val Ser Ser Ala Ser
130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
            165                 170                 175

Glu Pro Val Thr Val Ser Trp Asn Ser Gly Ala Leu Thr Ser Gly Val
        180                 185                 190

His Thr Phe Pro Ala Val Leu Gln Ser Ser Gly Leu Tyr Ser Leu Ser
    195                 200                 205

Ser Val Val Thr Val Pro Ser Ser Asn Phe Gly Thr Gln Thr Tyr Thr
210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
            245                 250                 255

Ala Gly Pro Ser Val Phe Leu Phe Pro Pro Lys Pro Lys Asp Thr Leu
        260                 265                 270

Met Ile Ser Arg Thr Pro Glu Val Thr Cys Val Val Val Asp Val Ser
    275                 280                 285

His Glu Asp Pro Glu Val Gln Phe Asn Trp Tyr Val Asp Gly Val Glu
290                 295                 300

Val His Asn Ala Lys Thr Lys Pro Arg Glu Glu Gln Phe Asn Ser Thr
305                 310                 315                 320

Phe Arg Val Val Ser Val Leu Thr Val His Gln Asp Trp Leu Asn
            325                 330                 335

Gly Lys Glu Tyr Lys Cys Lys Val Ser Asn Lys Gly Leu Pro Ala Pro
        340                 345                 350

Ile Glu Lys Thr Ile Ser Lys Thr Lys Gly Gln Pro Arg Glu Pro Gln
    355                 360                 365

Val Tyr Thr Leu Pro Pro Ser Arg Glu Glu Met Thr Lys Asn Gln Val

```
                370             375             380
Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
                435                 440                 445

Met His Glu Ala Leu His Asn His Tyr Thr Gln Lys Ser Leu Ser Leu
                450                 455                 460

Ser Pro Gly Lys
465

<210> SEQ ID NO 148
<211> LENGTH: 1404
<212> TYPE: DNA
<213> ORGANISM: Mus musculus

<400> SEQUENCE: 148
atggactgga cctggaggat cctcttcttg gtggcagcag ccacaggagc ccactccgag      60
gtgcagctgg tgcagagcgg cgccgaggta aaaaaaccag agcaagcgt taaagtttct     120 tgtaaagcaa gcggatatac atttacagat tacaacatgc attgggtaag acaagcgcca    180
ggacaaggat tggaatggat gggcgaaatt aaccctaata gtggaggagc aggctacaat    240
caaaaattca agggagagt tacaatgaca acagacacaa gcacttcaac agcatatatg    300
gaactgcgat cacttagaag cgacgataca gctgtatact attgcgcacg acttgggtat    360
gatgatatat atgatgactg gtatttcgat gtttggggcc agggaacaac agttaccgtc    420
tctagtgcct ccaccaaggg cccatcggtc ttccccctgg cgccctgctc caggagcacc    480
tccgagagca gcgcggcccct gggctgcctg gtcaaggact acttccccga accggtgacg    540
gtgtcgtgga actcaggcgc tctgaccagc ggcgtgcaca ccttcccagc tgtcctacag    600
tcctcaggac tctactccct cagcagcgtg gtgaccgtgc cctccagcaa cttcggcacc    660
cagacctaca cctgcaacgt agatcacaag cccagcaaca ccaaggtgga caagacagtt    720
gagcgcaaat gttgtgtcga gtgcccaccg tgcccagcac cacctgtggc aggaccgtca    780
gtcttcctct tccccccaaa acccaaggac accctcatga tctcccggac ccctgaggtc    840
acgtgcgtgg tggtggacgt gagccacgaa gaccccgagg tccagttcaa ctggtacgtg    900
gacggcgtgg aggtgcataa tgccaagaca aagccacggg aggagcagtt caacagcacg    960
ttccgtgtgg tcagcgtcct caccgttgtg caccaggact ggctgaacgg caaggagtac   1020
aagtgcaagg tctccaacaa aggcctccca gcccccatcg agaaaaccat ctccaaaacc   1080
aaagggcagc cccgagaacc acaggtgtac accctgcccc catcccggga ggagatgacc   1140
aagaaccagg tcagcctgac ctgcctggtc aaaggcttct accccagcga catcgccgtg   1200
gagtgggaga gcaatgggca gccggagaac aactacaaga ccacacctcc catgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaa                                          1404

<210> SEQ ID NO 149
<211> LENGTH: 214
<212> TYPE: PRT
```

<213> ORGANISM: Mus musculus

<400> SEQUENCE: 149

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Phe Gln Gln Lys Pro Asp Gly Thr Leu Lys Leu Leu Ile
        35                  40                  45

Phe Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Tyr
                85                  90                  95

Thr Phe Gly Gly Gly Thr Lys Leu Glu Ile Arg Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 150
<211> LENGTH: 645
<212> TYPE: DNA
<213> ORGANISM: Mus musculus

<400> SEQUENCE: 150
gatatccaga tgacacagac tacatcctcc ctgtctgcct ctctgggaga cagagtcacc      60
atcagttgca gggcaagtca ggacattagc aattatttaa actggtttca gcagaaacca     120
gatggaactc ttaaactcct gatcttctac acatcaagat tacactcagg agttccatca     180
aggttcagtg gcagtgggtc tggaacagat tattctctca ccattagcaa cctggagcaa     240
gaagatattg ccacttactt ttgccaacag ggtgatacgc ttccgtacac gttcggggg      300
gggaccaagc tggaaataag acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga acgacataac agctatacct gtgaggccac tcacaagaca     600
tcaacttcac ccattgtcaa gagcttcaac aggaatgagt gttag                     645

<210> SEQ ID NO 151
<211> LENGTH: 234
<212> TYPE: PRT

<213> ORGANISM: Mus musculus

<400> SEQUENCE: 151

```
Met Met Ser Ser Ala Gln Phe Leu Gly Leu Leu Leu Cys Phe Gln
1               5                   10                  15

Gly Thr Arg Cys Asp Ile Gln Met Thr Gln Thr Ser Ser Leu Ser
                20                  25                  30

Ala Ser Leu Gly Asp Arg Val Thr Ile Ser Cys Arg Ala Ser Gln Asp
            35                  40                  45

Ile Ser Asn Tyr Leu Asn Trp Phe Gln Gln Lys Pro Asp Gly Thr Leu
        50                  55                  60

Lys Leu Leu Ile Phe Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asp
                100                 105                 110

Thr Leu Pro Tyr Thr Phe Gly Gly Gly Thr Lys Leu Glu Ile Arg Arg
            115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 152
<211> LENGTH: 705
<212> TYPE: DNA
<213> ORGANISM: Mus musculus

<400> SEQUENCE: 152

```
atgatgtcct ctgctcagtt ccttggtctc ctgttgctct gttttcaagg taccagatgt    60
gatatccaga tgacacagac tacatcctcc ctgtctgcct ctctgggaga cagagtcacc   120
atcagttgca gggcaagtca ggacattagc aattatttaa actggtttca gcagaaacca   180
gatggaactc ttaaactcct gatcttctac acatcaagat acactcagg agttccatca   240 aggttcagtg gcagtgggtc tggaacagat tattctctca ccattagcaa cctggagcaa   300
gaagatattg ccacttactt ttgccaacag ggtgatacgc ttccgtacac gttcggggg   360 gggaccaagc tggaaataag acgggctgat gctgcaccaa ctgtatccat cttcccacca   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag caccctcacg   600
ttgaccaagg acgagtatga acgacataac agctatacct gtgaggccac tcacaagaca   660
tcaacttcac ccattgtcaa gagcttcaac aggaatgagt gttag                   705
```

<210> SEQ ID NO 153
<211> LENGTH: 447
<212> TYPE: PRT
<213> ORGANISM: Mus musculus

<400> SEQUENCE: 153

| | | | | | | | | | | | | | | | |
|---|---|---|---|---|---|---|---|---|---|---|---|---|---|---|---|
| Glu | Val | Gln | Leu | Gln | Gln | Ser | Gly | Pro | Glu | Leu | Met | Lys | Pro | Gly | Ala |
| 1 | | | | 5 | | | | | 10 | | | | | 15 | |
| Ser | Val | Lys | Met | Ser | Cys | Lys | Ala | Ser | Gly | Tyr | Thr | Phe | Thr | Asp | Tyr |
| | | | 20 | | | | | 25 | | | | | 30 | | |
| Asn | Met | His | Trp | Val | Lys | Gln | Asn | Gly | Lys | Ser | Leu | Glu | Trp | Ile | |
| | | 35 | | | | | 40 | | | | | 45 | | | |
| Gly | Glu | Ile | Asn | Pro | Asn | Ser | Gly | Ser | Gly | Tyr | Asn | Gln | Lys | Phe | |
| 50 | | | | | 55 | | | | | 60 | | | | | |
| Lys | Gly | Lys | Ala | Thr | Leu | Thr | Val | Asp | Lys | Ser | Ser | Ser | Thr | Ala | Tyr |
| 65 | | | | | 70 | | | | 75 | | | | | | 80 |
| Met | Glu | Leu | Arg | Ser | Leu | Thr | Ser | Glu | Asp | Ser | Ala | Val | Tyr | Tyr | Cys |
| | | | | 85 | | | | | 90 | | | | | 95 | |
| Ala | Arg | Leu | Val | Tyr | Asp | Gly | Ser | Tyr | Glu | Asp | Trp | Tyr | Phe | Asp | Val |
| | | | 100 | | | | | 105 | | | | | 110 | | |
| Trp | Gly | Ala | Gly | Thr | Thr | Val | Thr | Val | Ser | Ser | Ala | Lys | Thr | Thr | Pro |
| | | 115 | | | | | 120 | | | | | 125 | | | |
| Pro | Ser | Val | Tyr | Pro | Leu | Ala | Pro | Gly | Ser | Ala | Ala | Gln | Thr | Asn | Ser |
| 130 | | | | | 135 | | | | | 140 | | | | | |
| Met | Val | Thr | Leu | Gly | Cys | Leu | Val | Lys | Gly | Tyr | Phe | Pro | Glu | Pro | Val |
| 145 | | | | | 150 | | | | | 155 | | | | | 160 |
| Thr | Val | Thr | Trp | Asn | Ser | Gly | Ser | Leu | Ser | Ser | Gly | Val | His | Thr | Phe |
| | | | | 165 | | | | | 170 | | | | | 175 | |
| Pro | Ala | Val | Leu | Gln | Ser | Asp | Leu | Tyr | Thr | Leu | Ser | Ser | Ser | Val | Thr |
| | | | 180 | | | | | 185 | | | | | 190 | | |
| Val | Pro | Ser | Ser | Thr | Trp | Pro | Ser | Glu | Thr | Val | Thr | Cys | Asn | Val | Ala |
| | | 195 | | | | | 200 | | | | | 205 | | | |
| His | Pro | Ala | Ser | Ser | Thr | Lys | Val | Asp | Lys | Lys | Ile | Val | Pro | Arg | Asp |
| 210 | | | | | 215 | | | | | 220 | | | | | |
| Cys | Gly | Cys | Lys | Pro | Cys | Ile | Cys | Thr | Val | Pro | Glu | Val | Ser | Ser | Val |
| 225 | | | | | 230 | | | | | 235 | | | | | 240 |
| Phe | Ile | Phe | Pro | Pro | Lys | Pro | Lys | Asp | Val | Leu | Thr | Ile | Thr | Leu | Thr |
| | | | | 245 | | | | | 250 | | | | | 255 | |
| Pro | Lys | Val | Thr | Cys | Val | Val | Val | Asp | Ile | Ser | Lys | Asp | Asp | Pro | Glu |
| | | | 260 | | | | | 265 | | | | | 270 | | |
| Val | Gln | Phe | Ser | Trp | Phe | Val | Asp | Asp | Val | Glu | Val | His | Thr | Ala | Gln |
| | | | 275 | | | | | 280 | | | | | 285 | | |
| Thr | Gln | Pro | Arg | Glu | Glu | Gln | Phe | Asn | Ser | Thr | Phe | Arg | Ser | Val | Ser |
| | 290 | | | | | 295 | | | | | 300 | | | | |
| Glu | Leu | Pro | Ile | Met | His | Gln | Asp | Trp | Leu | Asn | Gly | Lys | Glu | Phe | Lys |
| 305 | | | | | 310 | | | | | 315 | | | | | 320 |
| Cys | Arg | Val | Asn | Ser | Ala | Ala | Phe | Pro | Ala | Pro | Ile | Glu | Lys | Thr | Ile |
| | | | | 325 | | | | | 330 | | | | | 335 | |
| Ser | Lys | Thr | Lys | Gly | Arg | Pro | Lys | Ala | Pro | Gln | Val | Tyr | Thr | Ile | Pro |
| | | | 340 | | | | | 345 | | | | | 350 | | |
| Pro | Pro | Lys | Glu | Gln | Met | Ala | Lys | Asp | Lys | Val | Ser | Leu | Thr | Cys | Met |
| | | | 355 | | | | | 360 | | | | | 365 | | |
| Ile | Thr | Asp | Phe | Phe | Pro | Glu | Asp | Ile | Thr | Val | Glu | Trp | Gln | Trp | Asn |
| | 370 | | | | | 375 | | | | | 380 | | | | |

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
            405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
            435                 440                 445

<210> SEQ ID NO 154
<211> LENGTH: 1344
<212> TYPE: DNA
<213> ORGANISM: Mus musculus

<400> SEQUENCE: 154

```
gaggtccagc tgcaacagtc tggacctgaa ctaatgaagc ctggggcttc agtgaagatg      60
tcctgcaagg cttctggata cacattcact gactacaaca tgcactgggt gaaacagaac     120
caaggaaaga gcctagagtg gataggagaa attaatccta acagtggtgg tagtggctac     180
aaccaaaagt tcaaaggcaa ggccacattg actgtagaca agtcttccag cacagcctac     240
atggagctcc gcagcctgac atctgaggac tctgcagtct attactgtgc aagattggtc     300
tacgatggca gctacgagga ctggtacttc gatgtctggg gcgcagggac cacggtcacc     360
gtctcctcag ccaaaacgac cccccatctg tctatccac tggcccctgg atctgctgcc     420
caaactaact ccatggtgac cctgggatgc ctggtcaagg gctatttccc tgagccagtg     480
acagtgacct ggaactctgg atccctgtcc agcggtgtgc acaccttccc agctgtcctg     540
cagtctgacc tctacactct gagcagctca gtgactgtcc cctccagcac ctggcccagc     600
gagaccgtca cctgcaacgt tgcccacccg gccagcagca ccaaggtgga caagaaaatt     660
gtgcccaggg attgtggttg taagccttgc atatgtacag tcccagaagt atcatctgtc     720
ttcatcttcc ccccaaagcc caaggatgtg ctcaccatta ctctgactcc taaggtcacg     780
tgtgttgtgg tagacatcag caaggatgat cccgaggtcc agttcagctg gtttgtagat     840
gatgtggagg tgcacacagc tcagacgcaa ccccgggagg agcagttcaa cagcactttc     900
cgctcagtca gtgaacttcc catcatgcac caggactggc tcaatggcaa ggagttcaaa     960
tgcagggtca acagtgcagc tttccctgcc cccatcgaga aaaccatctc caaaaccaaa    1020
ggcagaccga aggctccaca ggtgtacacc attccacctc ccaaggagca gatggccaag    1080
gataaagtca gtctgacctg catgataaca gacttcttcc ctgaagacat tactgtggag    1140
tggcagtgga tgggcagcc agcggagaac tacaagaaca ctcagcccat catggacaca    1200
gatggctctt acttcatcta cagcaagctc aatgtgcaga gagcaactg ggaggcagga    1260
aatactttca cctgctctgt gttacatgag ggcctgcaca accaccatac tgagaagagc    1320
ctctcccact ctcctggtaa atga                                         1344
```

<210> SEQ ID NO 155
<211> LENGTH: 466
<212> TYPE: PRT
<213> ORGANISM: Mus musculus

<400> SEQUENCE: 155

Met Gly Trp Ser Trp Thr Phe Leu Phe Leu Leu Ser Gly Thr Ala Gly
1               5                   10                  15

Val Leu Ser Glu Val Gln Leu Gln Gln Ser Gly Pro Glu Leu Met Lys
            20                  25                  30

```
Pro Gly Ala Ser Val Lys Met Ser Cys Lys Ala Ser Gly Tyr Thr Phe
            35                  40                  45
Thr Asp Tyr Asn Met His Trp Val Lys Gln Asn Gln Gly Lys Ser Leu
 50                  55                  60
Glu Trp Ile Gly Glu Ile Asn Pro Asn Ser Gly Gly Ser Gly Tyr Asn
 65                  70                  75                  80
Gln Lys Phe Lys Gly Lys Ala Thr Leu Thr Val Asp Lys Ser Ser Ser
                 85                  90                  95
Thr Ala Tyr Met Glu Leu Arg Ser Leu Thr Ser Glu Asp Ser Ala Val
            100                 105                 110
Tyr Tyr Cys Ala Arg Leu Val Tyr Asp Gly Ser Tyr Glu Asp Trp Tyr
            115                 120                 125
Phe Asp Val Trp Gly Ala Gly Thr Thr Val Thr Val Ser Ser Ala Lys
    130                 135                 140
Thr Thr Pro Pro Ser Val Tyr Pro Leu Ala Pro Gly Ser Ala Ala Gln
145                 150                 155                 160
Thr Asn Ser Met Val Thr Leu Gly Cys Leu Val Lys Gly Tyr Phe Pro
                165                 170                 175
Glu Pro Val Thr Val Thr Trp Asn Ser Gly Ser Leu Ser Ser Gly Val
            180                 185                 190
His Thr Phe Pro Ala Val Leu Gln Ser Asp Leu Tyr Thr Leu Ser Ser
        195                 200                 205
Ser Val Thr Val Pro Ser Ser Thr Trp Pro Ser Glu Thr Val Thr Cys
    210                 215                 220
Asn Val Ala His Pro Ala Ser Ser Thr Lys Val Asp Lys Lys Ile Val
225                 230                 235                 240
Pro Arg Asp Cys Gly Cys Lys Pro Cys Ile Cys Thr Val Pro Glu Val
                245                 250                 255
Ser Ser Val Phe Ile Phe Pro Pro Lys Pro Lys Asp Val Leu Thr Ile
            260                 265                 270
Thr Leu Thr Pro Lys Val Thr Cys Val Val Val Asp Ile Ser Lys Asp
        275                 280                 285
Asp Pro Glu Val Gln Phe Ser Trp Phe Val Asp Asp Val Glu Val His
    290                 295                 300
Thr Ala Gln Thr Gln Pro Arg Glu Glu Gln Phe Asn Ser Thr Phe Arg
305                 310                 315                 320
Ser Val Ser Glu Leu Pro Ile Met His Gln Asp Trp Leu Asn Gly Lys
                325                 330                 335
Glu Phe Lys Cys Arg Val Asn Ser Ala Ala Phe Pro Ala Pro Ile Glu
            340                 345                 350
Lys Thr Ile Ser Lys Thr Lys Gly Arg Pro Lys Ala Pro Gln Val Tyr
        355                 360                 365
Thr Ile Pro Pro Pro Lys Glu Gln Met Ala Lys Asp Lys Val Ser Leu
    370                 375                 380
Thr Cys Met Ile Thr Asp Phe Phe Pro Glu Asp Ile Thr Val Glu Trp
385                 390                 395                 400
Gln Trp Asn Gly Gln Pro Ala Glu Asn Tyr Lys Asn Thr Gln Pro Ile
                405                 410                 415
Met Asp Thr Asp Gly Ser Tyr Phe Ile Tyr Ser Lys Leu Asn Val Gln
            420                 425                 430
Lys Ser Asn Trp Glu Ala Gly Asn Thr Phe Thr Cys Ser Val Leu His
        435                 440                 445
Glu Gly Leu His Asn His His Thr Glu Lys Ser Leu Ser His Ser Pro
```

```
                450                 455                 460
Gly Lys
465

<210> SEQ ID NO 156
<211> LENGTH: 1401
<212> TYPE: DNA
<213> ORGANISM: Mus musculus

<400> SEQUENCE: 156
atgggatgga gctggacctt tctcttcctc ctgtcaggaa ctgcaggtgt cctctctgag      60
gtccagctgc aacagtctgg acctgaacta atgaagcctg gggcttcagt gaagatgtcc     120
tgcaaggctt ctggatacac attcactgac tacaacatgc actgggtgaa acagaaccaa     180
ggaaagagcc tagagtggat aggagaaatt aatcctaaca gtggtggtag tggctacaac     240
caaaagttca aggcaaggc cacattgact gtagacaagt cttccagcac agcctacatg      300
gagctccgca gcctgacatc tgaggactct gcagtctatt actgtgcaag attggtctac     360
gatggcagct acgaggactg gtacttcgat gtctggggcg cagggaccac ggtcaccgtc     420
tcctcagcca aaacgacacc cccatctgtc tatccactgg ccctggatc tgctgcccaa     480 actaactcca tggtgaccct gggatgcctg gtcaagggct atttccctga gccagtgaca     540
gtgacctgga actctggatc cctgtccagc ggtgtgcaca ccttcccagc tgtcctgcag     600
tctgacctct acactctgag cagctcagtg actgtcccct ccagcacctg gcccagcgag     660
accgtcacct gcaacgttgc ccacccggcc agcagcacca aggtggacaa gaaaattgtg     720
cccagggatt gtggttgtaa gccttgcata tgtacagtcc cagaagtatc atctgtcttc     780
atcttccccc caaagcccaa ggatgtgctc accattactc tgactcctaa ggtcacgtgt     840
gttgtggtag acatcagcaa ggatgatccc gaggtccagt tcagctggtt tgtagatgat     900
gtggaggtgc acacagctca gacgcaaccc cgggaggagc agttcaacag cactttccgc     960
tcagtcagtg aacttcccat catgcaccag gactggctca atggcaagga gttcaaatgc    1020
agggtcaaca gtgcagcttt ccctgccccc atcgagaaaa ccatctccaa aaccaaaggc    1080
agaccgaagg ctccacaggt gtacaccatt ccacctccca aggagcagat ggccaaggat    1140
aaagtcagtc tgacctgcat gataacagac ttcttccctg aagacattac tgtggagtgg    1200
cagtggaatg ggcagccagc ggagaactac aagaacactc agcccatcat ggacacagat    1260
ggctcttact tcatctacag caagctcaat gtgcagaaga gcaactggga ggcaggaaat    1320
actttcacct gctctgtgtt acatgagggc ctgcacaacc accatactga gaagagcctc    1380
tcccactctc ctggtaaatg a                                              1401

<210> SEQ ID NO 157
<211> LENGTH: 214
<212> TYPE: PRT
<213> ORGANISM: Mus musculus

<400> SEQUENCE: 157

Asp Ile Gln Met Thr Gln Thr Thr Ser Ser Leu Ser Ala Ser Leu Gly
1               5                   10                  15

Asp Arg Val Thr Ile Cys Cys Arg Ala Ser Gln Val Ile Thr Asn Tyr
            20                  25                  30

Leu Tyr Trp Tyr Gln Gln Lys Pro Asp Gly Thr Phe Lys Leu Leu Ile
        35                  40                  45

Tyr Tyr Thr Ser Arg Leu His Ser Gly Val Pro Ser Arg Phe Ser Gly
    50                  55                  60
```

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asp Thr Leu Pro Tyr
                 85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 158
<211> LENGTH: 642
<212> TYPE: DNA
<213> ORGANISM: Mus musculus

<400> SEQUENCE: 158
gatatccaga tgacacagac tacatcctcc ctgtctgcct ctctgggaga cagagtcacc      60
atctgttgca gggcaagtca ggtcattacc aattatttat actggtatca gcagaaacca     120
gatggaactt ttaaactcct gatctactac acatcaagat acactcagg agtcccatca      180 aggttcagtg gcagtgggtc tggaacagat tattctctca ccattagcaa cctggaacag     240
gaagatattg ccacttactt ttgccaacag ggtgatacgc ttccgtacac gttcggaggg     300
gggaccaagc tggaaataaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag cacccctcacg    540 ttgaccaagg acgagtatga acgacataac agctatacct gtgaggccac tcacaagaca     600
tcaacttcac ccattgtcaa gagcttcaac aggaatgagt gt                        642

<210> SEQ ID NO 159
<211> LENGTH: 234
<212> TYPE: PRT
<213> ORGANISM: Mus musculus

<400> SEQUENCE: 159

Met Met Ser Ser Ala Gln Phe Leu Gly Leu Leu Leu Leu Cys Phe Gln
  1               5                  10                  15

Gly Thr Arg Cys Asp Ile Gln Met Thr Gln Thr Thr Ser Ser Leu Ser
             20                  25                  30

Ala Ser Leu Gly Asp Arg Val Thr Ile Cys Cys Arg Ala Ser Gln Val
         35                  40                  45

Ile Thr Asn Tyr Leu Tyr Trp Tyr Gln Gln Lys Pro Asp Gly Thr Phe
 50                  55                  60

```
Lys Leu Leu Ile Tyr Tyr Thr Ser Arg Leu His Ser Gly Val Pro Ser
 65                  70                  75                  80

Arg Phe Ser Gly Ser Gly Ser Gly Thr Asp Tyr Ser Leu Thr Ile Ser
                 85                  90                  95

Asn Leu Glu Gln Glu Asp Ile Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
210                 215                 220

Ile Val Lys Ser Phe Asn Arg Asn Glu Cys
225                 230
```

<210> SEQ ID NO 160
<211> LENGTH: 702
<212> TYPE: DNA
<213> ORGANISM: Mus musculus

<400> SEQUENCE: 160

```
atgatgtcct ctgctcagtt cctttggtctc ctgttgctct gttttcaagg taccagatgt    60
gatatccaga tgacacagac tacatcctcc ctgtctgcct ctctgggaga cagagtcacc   120
atctgttgca gggcaagtca ggtcattacc aattatttat actggtatca gcagaaacca   180
gatggaactt ttaaactcct gatctactac acatcaagat acactcagg agtcccatca   240
aggttcagtg gcagtgggtc tggaacagat tattctctca ccattagcaa cctggaacag   300
gaagatattg ccacttactt tgccaacag ggtgatacgc ttccgtacac gttcggaggg   360
gggaccaagc tggaaataaa acgggctgat gctgcaccaa ctgtatccat cttcccacca   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag cacccctcacg   600
ttgaccaagg acgagtatga acgacataac agctatacct gtgaggccac tcacaagaca   660
tcaacttcac ccattgtcaa gagcttcaac aggaatgagt gt                       702
```

<210> SEQ ID NO 161
<211> LENGTH: 447
<212> TYPE: PRT
<213> ORGANISM: Mus musculus

<400> SEQUENCE: 161

```
Glu Val Gln Leu Gln Gln Ser Gly Pro Glu Leu Met Lys Pro Gly Ala
  1               5                  10                  15

Ser Val Lys Met Ser Cys Lys Ala Ser Gly Tyr Thr Phe Thr Asp Tyr
             20                  25                  30
```

Asn Met His Trp Met Lys Gln Asn Gln Gly Lys Ser Leu Glu Trp Ile
         35                  40                  45

Gly Glu Ile Asn Pro Asn Ser Gly Gly Ala Gly Tyr Asn Gln Gln Phe
 50                  55                  60

Lys Gly Lys Ala Thr Leu Thr Val Asp Lys Ser Ser Arg Thr Ala Tyr
 65                  70                  75                  80

Met Glu Leu Arg Ser Leu Thr Ser Glu Asp Ser Ala Val Tyr Tyr Cys
                 85                  90                  95

Ala Arg Leu Gly Tyr Val Gly Asn Tyr Glu Asp Trp Tyr Phe Asp Val
                100                 105                 110

Trp Gly Ala Gly Thr Thr Val Thr Val Ser Ser Ala Lys Thr Thr Pro
                115                 120                 125

Pro Ser Val Tyr Pro Leu Ala Pro Gly Ser Ala Ala Gln Thr Asn Ser
130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
                180                 185                 190

Val Pro Ser Ser Thr Trp Pro Ser Glu Thr Val Thr Cys Asn Val Ala
195                 200                 205

His Pro Ala Ser Ser Thr Lys Val Asp Lys Lys Ile Val Pro Arg Asp
210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
                260                 265                 270

Val Gln Phe Ser Trp Phe Val Asp Asp Val Glu Val His Thr Ala Gln
                275                 280                 285

Thr Gln Pro Arg Glu Glu Gln Phe Asn Ser Thr Phe Arg Ser Val Ser
                290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
                340                 345                 350

Pro Pro Lys Glu Gln Met Ala Lys Asp Lys Val Ser Leu Thr Cys Met
                355                 360                 365

Ile Thr Asp Phe Phe Pro Glu Asp Ile Thr Val Glu Trp Gln Trp Asn
370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
                420                 425                 430

His Asn His His Thr Glu Lys Ser Leu Ser His Ser Pro Gly Lys
                435                 440                 445

<210> SEQ ID NO 162

<211> LENGTH: 1341
<212> TYPE: DNA
<213> ORGANISM: Mus musculus

<400> SEQUENCE: 162

```
gaggtccagc tgcaacagtc tggacctgaa ctaatgaagc tggggcttc agtgaagatg      60
tcctgcaagg cttctggata cacattcact gactacaaca tgcactggat gaagcagaac     120
caaggaaaga gcctagaatg gataggagaa attaatccta acagtggtgg tgctggctac     180
aaccagcagt tcaaaggcaa ggccacattg actgtagaca agtcctccag gacagcctac     240
atggagctcc gcagcctgac atctgaggac tctgcagtct attactgtgc aagattgggc     300
tacgttggta attacgagga ctggtacttc gatgtctggg gcgcagggac cacggtcacc     360
gtctcctcag ccaaaacgac accccatct gtctatccac tggcccctgg atctgctgcc     420
caaactaact ccatggtgac cctgggatgc ctggtcaagg gctatttccc tgagccagtg     480
acagtgacct ggaactctgg atccctgtcc agcggtgtgc acaccttccc agctgtcctg     540
cagtctgacc tctacactct gagcagctca gtgactgtcc cctccagcac ctggcccagc     600
gagaccgtca cctgcaacgt tgcccacccg gccagcagca ccaaggtgga caagaaaatt     660
gtgcccaggg attgtggttg taagccttgc atatgtacag tcccagaagt atcatctgtc     720
ttcatcttcc ccccaaagcc caaggatgtg ctcaccatta ctctgactcc taaggtcacg     780
tgtgttgtgg tagacatcag caaggatgat cccgaggtcc agttcagctg gtttgtagat     840
gatgtggagg tgcacacagc tcagacgcaa ccccgggagg agcagttcaa cagcactttc     900
cgctcagtca gtgaacttcc catcatgcac caggactggc tcaatggcaa ggagttcaaa     960
tgcagggtca acagtgcagc tttccctgcc cccatcgaga aaaccatctc caaaaccaaa    1020
ggcagaccga aggctccaca ggtgtacacc attccacctc ccaaggagca gatggccaag    1080
gataaagtca gtctgacctg catgataaca gacttcttcc ctgaagacat tactgtggag    1140
tggcagtgga atgggcagcc agcggagaac tacaagaaca ctcagcccat catggacaca    1200
gatggctctt acttcatcta cagcaagctc aatgtgcaga gagcaactg ggaggcagga    1260
aatactttca cctgctctgt gttacatgag ggcctgcaca accaccatac tgagaagagc    1320
ctctcccact ctcctggtaa a                                              1341
```

<210> SEQ ID NO 163
<211> LENGTH: 466
<212> TYPE: PRT
<213> ORGANISM: Mus musculus

<400> SEQUENCE: 163

```
Met Gly Trp Ser Trp Thr Phe Leu Phe Leu Leu Ser Gly Thr Ala Gly
  1               5                  10                  15

Val Leu Ser Glu Val Gln Leu Gln Gln Ser Gly Pro Glu Leu Met Lys
             20                  25                  30

Pro Gly Ala Ser Val Lys Met Ser Cys Lys Ala Ser Gly Tyr Thr Phe
         35                  40                  45

Thr Asp Tyr Asn Met His Trp Met Lys Gln Asn Gln Gly Lys Ser Leu
     50                  55                  60

Glu Trp Ile Gly Glu Ile Asn Pro Asn Ser Gly Gly Ala Gly Tyr Asn
 65                  70                  75                  80

Gln Gln Phe Lys Gly Lys Ala Thr Leu Thr Val Asp Lys Ser Ser Arg
                 85                  90                  95

Thr Ala Tyr Met Glu Leu Arg Ser Leu Thr Ser Glu Asp Ser Ala Val
            100                 105                 110
```

Tyr Tyr Cys Ala Arg Leu Gly Tyr Val Gly Asn Tyr Glu Asp Trp Tyr
            115                 120                 125

Phe Asp Val Trp Gly Ala Gly Thr Thr Val Thr Val Ser Ser Ala Lys
        130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465

<210> SEQ ID NO 164
<211> LENGTH: 1398
<212> TYPE: DNA
<213> ORGANISM: Mus musculus

<400> SEQUENCE: 164
atgggatgga gctggaccct tctcttcctc ctgtcaggaa ctgcaggtgt cctctctgag      60

```
gtccagctgc aacagtctgg acctgaacta atgaagcctg ggcttcagt gaagatgtcc    120 tgcaaggctt ctggatacac attcactgac tacaacatgc actggatgaa gcagaaccaa    180
ggaaagagcc tagaatggat aggagaaatt aatcctaaca gtggtggtgc tggctacaac    240
cagcagttca aaggcaaggc cacattgact gtagacaagt cctccaggac agcctacatg    300
gagctccgca gcctgacatc tgaggactct gcagtctatt actgtgcaag attgggctac    360
gttggtaatt acgaggactg gtacttcgat gtctggggcg cagggaccac ggtcaccgtc    420
tcctcagcca aaacgacacc cccatctgtc tatccactgg cccctggatc tgctgcccaa    480
actaactcca tggtgaccct gggatgcctg gtcaagggct atttccctga gccagtgaca    540
gtgacctgga actctggatc cctgtccagc ggtgtgcaca ccttcccagc tgtcctgcag    600
tctgacctct acactctgag cagctcagtg actgtcccct ccagcacctg gcccagcgag    660
accgtcacct gcaacgttgc ccacccggcc agcagcacca aggtggacaa gaaaattgtg    720
cccagggatt gtggttgtaa gccttgcata tgtacagtcc cagaagtatc atctgtcttc    780
atcttccccc caaagcccaa ggatgtgctc accattactc tgactcctaa ggtcacgtgt    840
gttgtggtag acatcagcaa ggatgatccc gaggtccagt tcagctggtt tgtagatgat    900
gtggaggtgc acacagctca gacgcaaccc cgggaggagc agttcaacag cactttccgc    960
tcagtcagtg aacttcccat catgcaccag gactggctca atggcaagga gttcaaatgc    1020
agggtcaaca gtgcagcttt ccctgccccc atcgagaaaa ccatctccaa aaccaaaggc    1080
agaccgaagg ctccacaggt gtacaccatt ccacctccca aggagcagat ggccaaggat    1140
aaagtcagtc tgacctgcat gataacagac ttcttccctg aagacattac tgtggagtgg    1200
cagtggaatg ggcagccagc ggagaactac aagaacactc agcccatcat ggacacagat    1260
ggctcttact tcatctacag caagctcaat gtgcagaaga gcaactggga ggcaggaaat    1320
actttcacct gctctgtgtt acatgagggc ctgcacaacc accatactga aagagcctc    1380 tcccactctc ctggtaaa                                                  1398

<210> SEQ ID NO 165
<211> LENGTH: 214
<212> TYPE: PRT
<213> ORGANISM: Mus musculus

<400> SEQUENCE: 165

Asp Ile Gln Met Thr Gln Thr Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Leu Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140
```

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 166
<211> LENGTH: 645
<212> TYPE: DNA
<213> ORGANISM: Mus musculus

<400> SEQUENCE: 166
gatatccaga tgacacagac tacatcctcc ctgtctgcct ctctgggaga cagggtctcc      60
atcagttgca gggcaagtca agacattagc aattatttaa actggtatca gcagaaacca     120
gatggaactt ttaaactcct tatcttctac acatcaagat tactctcagg agtcccatca     180
aggttcagtg gcagtgggtc tggaacagat tattctctca ccatttacaa cctggagcaa     240
gaagattttg ccacttactt ttgccaacag ggagatacgc ttccgtacac tttcggaggg     300
gggaccaaac tggaaataaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga acgacataac agctatacct gtgaggccac tcacaagaca     600
tcaacttcac ccattgtcaa gagcttcaac aggaatgagt gttag                     645

<210> SEQ ID NO 167
<211> LENGTH: 234
<212> TYPE: PRT
<213> ORGANISM: Mus musculus

<400> SEQUENCE: 167

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Ser Ile Ser Cys Arg Ala Ser Gln Asp
        35                  40                  45

Ile Ser Asn Tyr Leu Asn Trp Tyr Gln Gln Lys Pro Asp Gly Thr Phe
    50                  55                  60

Lys Leu Leu Ile Phe Tyr Thr Ser Arg Leu Leu Ser Gly Val Pro Ser
65                  70                  75                  80

Arg Phe Ser Gly Ser Gly Ser Gly Thr Asp Tyr Ser Leu Thr Ile Tyr
                85                  90                  95

Asn Leu Glu Gln Glu Asp Phe Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
            165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 168
<211> LENGTH: 705
<212> TYPE: DNA
<213> ORGANISM: Mus musculus

<400> SEQUENCE: 168
atgatgtcct ctgctcagtt ccttggtctc ctgttgctct gttttcaagg taccagatgt      60
gatatccaga tgacacagac tacatcctcc ctgtctgcct ctctgggaga cagggtctcc     120
atcagttgca gggcaagtca agacattagc aattatttaa actggtatca gcagaaacca     180
gatggaactt ttaaactcct tatcttctac acatcaagat tactctcagg agtcccatca     240
aggttcagtg gcagtgggtc tggaacagat tattctctca ccatttacaa cctggagcaa     300
gaagattttg ccacttactt ttgccaacag ggagatacgc ttccgtacac tttcggaggg     360
gggaccaaac tggaaataaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag caccctcacg     600
ttgaccaagg acgagtatga acgacataac agctatacct gtgaggccac tcacaagaca     660
tcaacttcac ccattgtcaa gagcttcaac aggaatgagt gttag                     705

<210> SEQ ID NO 169
<211> LENGTH: 447
<212> TYPE: PRT
<213> ORGANISM: Mus musculus

<400> SEQUENCE: 169

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gly Lys Thr Leu Asp Trp Ile
        35                  40                  45

Gly Glu Ile Asn Pro Asn Ser Gly Ala Gly Tyr Asn Gln Lys Phe
    50                  55                  60

Lys Gly Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

```
Trp Gly Ala Gly Thr Thr Val Thr Val Ser Ser Ala Lys Thr Thr Pro
            115                 120                 125
Pro Ser Val Tyr Pro Leu Ala Pro Gly Ser Ala Ala Gln Thr Asn Ser
        130                 135                 140
Met Val Thr Leu Gly Cys Leu Val Lys Gly Tyr Phe Pro Glu Pro Val
145                 150                 155                 160
Thr Val Thr Trp Asn Ser Gly Ser Leu Ser Ser Gly Val His Thr Phe
                165                 170                 175
Pro Ala Val Leu Gln Ser Asp Leu Tyr Thr Leu Ser Ser Ser Val Thr
            180                 185                 190
Val Pro Ser Ser Thr Trp Pro Ser Glu Thr Val Thr Cys Asn Val Ala
        195                 200                 205
His Pro Ala Ser Ser Thr Lys Val Asp Lys Lys Ile Val Pro Arg Asp
210                 215                 220
Cys Gly Cys Lys Pro Cys Ile Cys Thr Val Pro Glu Val Ser Ser Val
225                 230                 235                 240
Phe Ile Phe Pro Pro Lys Pro Lys Asp Val Leu Thr Ile Thr Leu Thr
                245                 250                 255
Pro Lys Val Thr Cys Val Val Asp Ile Ser Lys Asp Asp Pro Glu
            260                 265                 270
Val Gln Phe Ser Trp Phe Val Asp Asp Val Glu Val His Thr Ala Gln
        275                 280                 285
Thr Gln Pro Arg Glu Glu Gln Phe Asn Ser Thr Phe Arg Ser Val Ser
        290                 295                 300
Glu Leu Pro Ile Met His Gln Asp Trp Leu Asn Gly Lys Glu Phe Lys
305                 310                 315                 320
Cys Arg Val Asn Ser Ala Ala Phe Pro Ala Pro Ile Glu Lys Thr Ile
                325                 330                 335
Ser Lys Thr Lys Gly Arg Pro Lys Ala Pro Gln Val Tyr Thr Ile Pro
            340                 345                 350
Pro Pro Lys Glu Gln Met Ala Lys Asp Lys Val Ser Leu Thr Cys Met
        355                 360                 365
Ile Thr Asp Phe Phe Pro Glu Asp Ile Thr Val Glu Trp Gln Trp Asn
370                 375                 380
Gly Gln Pro Ala Glu Asn Tyr Lys Asn Thr Gln Pro Ile Met Asp Thr
385                 390                 395                 400
Asp Gly Ser Tyr Phe Ile Tyr Ser Lys Leu Asn Val Gln Lys Ser Asn
                405                 410                 415
Trp Glu Ala Gly Asn Thr Phe Thr Cys Ser Val Leu His Glu Gly Leu
            420                 425                 430
His Asn His His Thr Glu Lys Ser Leu Ser His Ser Pro Gly Lys
        435                 440                 445

<210> SEQ ID NO 170
<211> LENGTH: 1344
<212> TYPE: DNA
<213> ORGANISM: Mus musculus

<400> SEQUENCE: 170
gaggtccaac tgcaacagtc tggacctgaa ctaatgaagc ctggggcttc agtgaagatg      60
tcctgcaagg cttctggata cattcact gactacaaca tgcactgggt gaagcagaac      120
caaggaaaga ccctagactg gataggagaa attaatccta acagtggtgg tgctggctac      180
aaccagaagt tcaagggcaa ggccacattg actgtagaca gtcctccac cacagcctac      240 atggagctcc gcagcctgac atctgaggac tctgcagtct attactgtgc aagattgggc      300
```

```
tacgatgata tctacgacga ctggtacttc gatgtctggg gcgcaggggac cacggtcacc    360 gtctcctcag ccaaaacgac acccccatct gtctatccac tggcccctgg atctgctgcc    420
caaactaact ccatggtgac cctgggatgc ctggtcaagg gctatttccc tgagccagtg    480
acagtgacct ggaactctgg atccctgtcc agcggtgtgc acaccttccc agctgtcctg    540
cagtctgacc tctacactct gagcagctca gtgactgtcc cctccagcac ctggcccagc    600
gagaccgtca cctgcaacgt tgcccacccg gccagcagca ccaaggtgga caagaaaatt    660
gtgcccaggg attgtggttg taagccttgc atatgtacag tcccagaagt atcatctgtc    720
ttcatcttcc ccccaaagcc caaggatgtg ctcaccatta ctctgactcc taaggtcacg    780
tgtgttgtgg tagacatcag caaggatgat cccgaggtcc agttcagctg gtttgtagat    840
gatgtggagg tgcacacagc tcagacgcaa ccccgggagg agcagttcaa cagcactttc    900
cgctcagtca gtgaacttcc catcatgcac caggactggc tcaatggcaa ggagttcaaa    960
tgcagggtca acagtgcagc tttccctgcc cccatcgaga aaaccatctc caaaaccaaa   1020
ggcagaccga aggctccaca ggtgtacacc attccacctc caaggagcaa gatggccaag   1080
gataaagtca gtctgacctg catgataaca gacttcttcc ctgaagacat tactgtggag   1140
tggcagtgga atgggcagcc agcggagaac tacaagaaca ctcagcccat catggacaca   1200
gatggctctt acttcatcta cagcaagctc aatgtgcaga gagcaactg ggaggcagga   1260 aatactttca cctgctctgt gttacatgag ggcctgcaca accaccatac tgagaagagc   1320 ctctccccact ctcctggtaa atga                                         1344

<210> SEQ ID NO 171
<211> LENGTH: 466
<212> TYPE: PRT
<213> ORGANISM: Mus musculus

<400> SEQUENCE: 171

Met Gly Trp Ser Trp Thr Phe Leu Phe Leu Leu Ser Gly Thr Ala Gly
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Val Lys Gln Asn Gly Lys Thr Leu
    50                  55                  60

Asp Trp Ile Gly Glu Ile Asn Pro Asn Ser Gly Ala Gly Tyr Asn
65                  70                  75                  80

Gln Lys Phe Lys Gly Lys Ala Thr Leu Thr Val Asp Lys Ser Ser Thr
                85                  90                  95

Thr Ala Tyr Met Glu Leu Arg Ser Leu Thr Ser Glu Asp Ser Ala Val
            100                 105                 110

Tyr Tyr Cys Ala Arg Leu Gly Tyr Asp Asp Ile Tyr Asp Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190
```

```
His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
        210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
                260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Val Glu Val His
        290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
                340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
        370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
                420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
        450                 455                 460

Gly Lys
465

<210> SEQ ID NO 172
<211> LENGTH: 1401
<212> TYPE: DNA
<213> ORGANISM: Mus musculus

<400> SEQUENCE: 172
atgggatgga gctggacctt tctcttcctc ctgtcaggaa ctgcaggtgt cctctctgag      60
gtccaactgc aacagtctgg acctgaacta atgaagcctg ggcttcagt gaagatgtcc     120 tgcaaggctt ctggatatac attcactgac tacaacatgc actgggtgaa gcagaaccaa    180
ggaaagaccc tagactggat aggagaaatt aatcctaaca gtggtggtgc tggctacaac    240
cagaagttca gggcaaggc acattgact gtagacaagt cctccaccac agcctacatg      300
gagctccgca gcctgacatc tgaggactct gcagtctatt actgtgcaag attgggctac    360
gatgatatct acgacgactg gtacttcgat gtctggggcg cagggaccac ggtcaccgtc    420
tcctcagcca aaacgacacc cccatctgtc tatccactgg ccctggatc tgctgcccaa    480 actaactcca tggtgaccct gggatgcctg gtcaagggct atttccctga gccagtgaca    540
```

```
gtgacctgga actctggatc cctgtccagc ggtgtgcaca ccttcccagc tgtcctgcag      600
tctgacctct acactctgag cagctcagtg actgtccct ccagcacctg cccagcgag       660
accgtcacct gcaacgttgc ccacccggcc agcagcacca aggtggacaa gaaaattgtg      720
cccagggatt gtggttgtaa gccttgcata tgtacagtcc cagaagtatc atctgtcttc      780
atcttccccc caaagcccaa ggatgtgctc accattactc tgactcctaa ggtcacgtgt      840
gttgtggtag acatcagcaa ggatgatccc gaggtccagt tcagctggtt tgtagatgat      900
gtggaggtgc acacagctca gacgcaaccc cgggaggagc agttcaacag cactttccgc      960
tcagtcagtg aacttcccat catgcaccag gactggctca atggcaagga gttcaaatgc     1020
agggtcaaca gtgcagcttt ccctgccccc atcgagaaaa ccatctccaa aaccaaaggc     1080
agaccgaagg ctccacaggt gtacaccatt ccacctccca aggagcagat ggccaaggat     1140
aaagtcagtc tgacctgcat gataacagac ttcttccctg aagacattac tgtggagtgg     1200
cagtggaatg ggcagccagc ggagaactac aagaacactc agcccatcat ggacacagat     1260
ggctcttact tcatctacag caagctcaat gtgcagaaga caactgggga ggcaggaaat     1320
actttcacct gctctgtgtt acatgagggc ctgcacaacc accatactga aagagcctc     1380
tcccactctc ctggtaaatg a                                               1401

<210> SEQ ID NO 173
<211> LENGTH: 214
<212> TYPE: PRT
<213> ORGANISM: Mus musculus

<400> SEQUENCE: 173

Asp Ile Gln Met Thr Gln Ile Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Phe Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 174
<211> LENGTH: 642
<212> TYPE: DNA
<213> ORGANISM: Mus musculus

<400> SEQUENCE: 174

| | | |
|---|---|---|
| gatatccaga tgacacagat tacatcctcc ctgtctgcct ctctgggaga cagggtctcc | 60 |
| atcagttgca gggcaagtca agacattagc aattatttaa attggtatca gcagaaacca | 120 |
| gatggaactt ttaaactcct tatcttctac acatcaagat tattttcagg agtcccatca | 180 |
| aggttcagtg gcagtgggtc tggaacagat tattctctca ccatttacaa cctggagcaa | 240 |
| gaagattttg ccacttactt ttgccaacag gagatacgc ttccgtacac tttcggaggg | 300 |
| gggaccaagg tggaaataaa acgggctgat gctgcaccaa ctgtatccat cttcccacca | 360 |
| tccagtgagc agttaacatc tggaggtgcc tcagtcgtgt gcttcttgaa caacttctac | 420 |
| cccaaagaca tcaatgtcaa gtggaagatt gatggcagtg aacgacaaaa tggcgtcctg | 480 |
| aacagttgga ctgatcagga cagcaaagac agcacctaca gcatgagcag caccctcacg | 540 |
| ttgaccaagg acgagtatga acgacataac agctatacct gtgaggccac tcacaagaca | 600 |
| tcaacttcac ccattgtcaa gagcttcaac aggaatgagt gt | 642 |

<210> SEQ ID NO 175
<211> LENGTH: 234
<212> TYPE: PRT
<213> ORGANISM: Mus musculus

<400> SEQUENCE: 175

Met Met Ser Ser Ala Gln Phe Leu Gly Leu Leu Leu Leu Cys Phe Gln
1               5                   10                  15

Gly Thr Arg Cys Asp Ile Gln Met Thr Gln Ile Thr Ser Ser Leu Ser
            20                  25                  30

Ala Ser Leu Gly Asp Arg Val Ser Ile Ser Cys Arg Ala Ser Gln Asp
        35                  40                  45

Ile Ser Asn Tyr Leu Asn Trp Tyr Gln Gln Lys Pro Asp Gly Thr Phe
    50                  55                  60

Lys Leu Leu Ile Phe Tyr Thr Ser Arg Leu Phe Ser Gly Val Pro Ser
65                  70                  75                  80

Arg Phe Ser Gly Ser Gly Ser Gly Thr Asp Tyr Ser Leu Thr Ile Tyr
                85                  90                  95

Asn Leu Glu Gln Glu Asp Phe Ala Thr Tyr Phe Cys Gln Gln Gly Asp
            100                 105                 110

Thr Leu Pro Tyr Thr Phe Gly Gly Gly Thr Lys Val Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 176
<211> LENGTH: 702
<212> TYPE: DNA
<213> ORGANISM: Mus musculus

<400> SEQUENCE: 176
atgatgtcct ctgctcagtt ccttggtctc ctgttgctct gttttcaagg taccagatgt    60
gatatccaga tgacacagat tacatcctcc ctgtctgcct ctctgggaga cagggtctcc   120
atcagttgca gggcaagtca agacattagc aattatttaa attggtatca gcagaaacca   180
gatggaactt ttaaactcct tatcttctac acatcaagat tatttcagg agtcccatca    240
aggttcagtg gcagtgggtc tggaacagat tattctctca ccatttacaa cctggagcaa   300
gaagattttg ccacttactt ttgccaacag ggagatacgc ttccgtacac tttcggaggg   360
gggaccaagg tggaaataaa acgggctgat gctgcaccaa ctgtatccat cttcccacca   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag caccctcacg   600
ttgaccaagg acgagtatga acgacataac agctatacct gtgaggccac tcacaagaca   660
tcaacttcac ccattgtcaa gagcttcaac aggaatgagt gt                      702

<210> SEQ ID NO 177
<211> LENGTH: 450
<212> TYPE: PRT
<213> ORGANISM: Mus musculus

<400> SEQUENCE: 177

Glu Val Gln Leu Gln Gln Ser Gly Pro Glu Leu Met Lys Pro Gly Thr
1               5                   10                  15

Ser Val Lys Met Ser Cys Lys Ala Ser Gly Tyr Thr Phe Thr Asp Tyr
            20                  25                  30

Asn Met His Trp Val Lys Gln Thr Gln Gly Lys Thr Leu Glu Trp Ile
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Lys Leu Gly Tyr Asp Asp Ile Tyr Asp Asp Trp Tyr Phe Asp Val
            100                 105                 110

Trp Gly Ala Gly Thr Thr Val Thr Val Ser Ser Ala Lys Thr Thr Ala
        115                 120                 125

Pro Ser Val Tyr Pro Leu Ala Pro Val Cys Gly Asp Thr Thr Gly Ser
    130                 135                 140

Ser Val Thr Leu Gly Cys Leu Val Lys Gly Tyr Phe Pro Glu Pro Val
145                 150                 155                 160

Thr Leu Thr Trp Asn Ser Gly Ser Leu Ser Ser Asp Val His Thr Phe
                165                 170                 175

Pro Ala Leu Leu Gln Ser Gly Leu Tyr Thr Leu Ser Ser Ser Val Thr
            180                 185                 190

```
Val Thr Thr Trp Pro Ser Gln Thr Ile Thr Cys Asn Val Ala His Pro
            195                 200                 205
Ala Ser Ser Thr Lys Val Asp Lys Lys Ile Glu Pro Arg Gly Ser Pro
    210                 215                 220
Thr His Lys Pro Cys Pro Pro Cys Pro Ala Pro Asn Leu Leu Gly Gly
225                 230                 235                 240
Pro Ser Val Phe Ile Phe Pro Pro Lys Ile Lys Asp Val Leu Met Ile
                245                 250                 255
Ser Leu Ser Pro Met Val Thr Cys Val Val Asp Val Ser Glu Asp
                260                 265                 270
Asp Pro Asp Val His Val Ser Trp Phe Val Asn Asn Val Glu Val His
            275                 280                 285
Thr Ala Gln Thr Gln Thr His Arg Glu Asp Tyr Asn Ser Thr Ile Arg
    290                 295                 300
Val Val Ser Ala Leu Pro Ile Gln His Gln Asp Trp Met Ser Gly Lys
305                 310                 315                 320
Glu Phe Lys Cys Lys Val Asn Asn Lys Ala Leu Pro Ala Pro Ile Glu
                325                 330                 335
Arg Thr Ile Ser Lys Pro Lys Gly Pro Val Arg Ala Pro Gln Val Tyr
            340                 345                 350
Val Leu Pro Pro Pro Glu Glu Glu Met Thr Lys Lys Gln Val Thr Leu
    355                 360                 365
Thr Cys Met Ile Thr Asp Phe Met Pro Glu Asp Ile Tyr Val Glu Trp
370                 375                 380
Thr Asn Asn Gly Gln Thr Glu Leu Asn Tyr Lys Asn Thr Glu Pro Val
385                 390                 395                 400
Leu Asp Ser Asp Gly Ser Tyr Phe Met Tyr Ser Lys Leu Arg Val Glu
                405                 410                 415
Lys Lys Asn Trp Val Glu Arg Asn Ser Tyr Ser Cys Ser Val Val His
            420                 425                 430
Glu Gly Leu His Asn His His Thr Thr Lys Ser Phe Ser Arg Thr Pro
    435                 440                 445
Gly Lys
    450

<210> SEQ ID NO 178
<211> LENGTH: 1350
<212> TYPE: DNA
<213> ORGANISM: Mus musculus

<400> SEQUENCE: 178
gaggtccaac tgcaacagtc tggacctgaa ctaatgaagc ctgggacttc agtgaagatg      60
tcctgcaagg cttctggata cattcact gactacaaca tgcactgggt gaagcagacc     120
caaggaaaga ccctagagtg gataggagaa attaatccta acagtggtgg tgctggctac     180
aaccagaagt tcaagggcaa ggccacattg actagaca agtcctccac cacagcctac     240
atggagctcc gcagcctgac atctgaggac tctgcagtct attactgtgc aaaattgggc     300
tacgatgata tctacgacga ctggtatttc gatgtctggg gcgcagggac cacggtcacc     360
gtctcctcag ccaaaacaac agccccatcg gtctatccac tggcccctgt gtgtggagat     420
acaactggct cctcggtgac tctaggatgc ctggtcaagg gttatttccc tgagccagtg     480
accttgacct ggaactctgg atccctgtcc agtgatgtgc acaccttccc agctctcctg     540
cagtctggcc tctacaccct cagcagctca gtgactgtaa ccacctggcc cagccagacc     600
atcacctgca atgtggccca cccggcaagc agcaccaaag tggacaagaa aattgagccc     660
```

-continued

```
agagggtccc caacacataa accctgtcct ccatgcccag ctcctaacct cttgggtgga    720
ccatccgtct tcatcttccc tccaaagatc aaggatgtac tcatgatctc cctgagcccc    780
atggtcacgt gtgtggtggt ggatgtgagc gaggatgacc cagatgtcca tgtcagctgg    840
ttcgtgaaca acgtggaagt acacacagct cagacacaaa cccatagaga ggattacaac    900
agtactatcc gggtggtcag tgccctcccc atccagcacc aggactggat gagtggcaag    960
gagttcaaat gcaaggtcaa caacaaagcc ctcccagcgc ccatcgagag aaccatctca   1020
aaacccaaag gccagtaag agctccacag gtatatgtct tgcctccacc agaagaagag    1080
atgactaaga aacaggtcac tctgacctgc atgatcacag acttcatgcc tgaagacatt   1140
tacgtggagt ggaccaacaa cgggcaaaca gagctaaact acaagaacac tgaaccagtc   1200
ctggactctg atggttctta cttcatgtac agcaagctga gagtggaaaa gaagaactgg   1260
gtggaaagaa atagctactc ctgttcagtg gtccacgagg gtctgcacaa tcaccacacg   1320
actaagagct tctcccggac tccgggtaaa                                    1350
```

<210> SEQ ID NO 179
<211> LENGTH: 469
<212> TYPE: PRT
<213> ORGANISM: Mus musculus

<400> SEQUENCE: 179

```
Met Gly Trp Ser Trp Thr Phe Leu Phe Leu Leu Ser Gly Thr Ala Gly
1               5                   10                  15
Val Leu Ser Glu Val Gln Leu Gln Gln Ser Gly Pro Glu Leu Met Lys
            20                  25                  30
Pro Gly Thr Ser Val Lys Met Ser Cys Lys Ala Ser Gly Tyr Thr Phe
        35                  40                  45
Thr Asp Tyr Asn Met His Trp Val Lys Gln Thr Gln Gly Lys Thr Leu
    50                  55                  60
Glu Trp Ile Gly Glu Ile Asn Pro Asn Ser Gly Gly Ala Gly Tyr Asn
65                  70                  75                  80
Gln Lys Phe Lys Gly Lys Ala Thr Leu Thr Val Asp Lys Ser Ser Thr
                85                  90                  95
Thr Ala Tyr Met Glu Leu Arg Ser Leu Thr Ser Glu Asp Ser Ala Val
            100                 105                 110
Tyr Tyr Cys Ala Lys Leu Gly Tyr Asp Asp Ile Tyr Asp Asp Trp Tyr
        115                 120                 125
Phe Asp Val Trp Gly Ala Gly Thr Thr Val Thr Val Ser Ser Ala Lys
    130                 135                 140
Thr Thr Ala Pro Ser Val Tyr Pro Leu Ala Pro Val Cys Gly Asp Thr
145                 150                 155                 160
Thr Gly Ser Ser Val Thr Leu Gly Cys Leu Val Lys Gly Tyr Phe Pro
                165                 170                 175
Glu Pro Val Thr Leu Thr Trp Asn Ser Gly Ser Leu Ser Ser Asp Val
            180                 185                 190
His Thr Phe Pro Ala Leu Leu Gln Ser Gly Leu Tyr Thr Leu Ser Ser
        195                 200                 205
Ser Val Thr Val Thr Ser Trp Pro Ser Gln Thr Ile Thr Cys Asn Val
    210                 215                 220
Ala His Pro Ala Ser Ser Thr Lys Val Asp Lys Lys Ile Glu Pro Arg
225                 230                 235                 240
Gly Ser Pro Thr His Lys Pro Cys Pro Pro Cys Pro Ala Pro Asn Leu
                245                 250                 255
```

```
Leu Gly Gly Pro Ser Val Phe Ile Phe Pro Lys Ile Lys Asp Val
            260                 265                 270
Leu Met Ile Ser Leu Ser Pro Met Val Thr Cys Val Val Asp Val
        275                 280                 285
Ser Glu Asp Asp Pro Asp Val His Val Ser Trp Phe Val Asn Asn Val
290                 295                 300
Glu Val His Thr Ala Gln Thr Gln Thr His Arg Glu Asp Tyr Asn Ser
305                 310                 315                 320
Thr Ile Arg Val Val Ser Ala Leu Pro Ile Gln His Gln Asp Trp Met
                325                 330                 335
Ser Gly Lys Glu Phe Lys Cys Lys Val Asn Asn Lys Ala Leu Pro Ala
                340                 345                 350
Pro Ile Glu Arg Thr Ile Ser Lys Pro Lys Gly Pro Val Arg Ala Pro
                355                 360                 365
Gln Val Tyr Val Leu Pro Pro Pro Glu Glu Glu Met Thr Lys Lys Gln
        370                 375                 380
Val Thr Leu Thr Cys Met Ile Thr Asp Phe Met Pro Glu Asp Ile Tyr
385                 390                 395                 400
Val Glu Trp Thr Asn Asn Gly Gln Thr Glu Leu Asn Tyr Lys Asn Thr
                405                 410                 415
Glu Pro Val Leu Asp Ser Asp Gly Ser Tyr Phe Met Tyr Ser Lys Leu
            420                 425                 430
Arg Val Glu Lys Lys Asn Trp Val Glu Arg Asn Ser Tyr Ser Cys Ser
                435                 440                 445
Val Val His Glu Gly Leu His Asn His His Thr Thr Lys Ser Phe Ser
        450                 455                 460
Arg Thr Pro Gly Lys
465

<210> SEQ ID NO 180
<211> LENGTH: 1407
<212> TYPE: DNA
<213> ORGANISM: Mus musculus

<400> SEQUENCE: 180
atgggatgga gctggacctt tctcttcctc ctgtcaggaa ctgcaggtgt cctctctgag     60
gtccaactgc aacagtctgg acctgaacta atgaagcctg ggacttcagt gaagatgtcc    120
tgcaaggctt ctggatatac attcactgac tacaacatgc actgggtgaa gcagacccaa    180
ggaaagaccc tagagtggat aggagaaatt aatcctaaca gtggtggtgc tggctacaac    240
cagaagttca gggcaaggc acattgact gtagacaagt cctccaccac agcctacatg      300
gagctccgca gcctgacatc tgaggactct gcagtctatt actgtgcaaa attgggctac    360
gatgatatct acgacgactg gtatttcgat gtctggggcg cagggaccac ggtcaccgtc    420
tcctcagcca aaacaacagc cccatcggtc tatccactgg cccctgtgtg tggagataca    480
actggctcct cggtgactct aggatgcctg gtcaagggtt atttccctga gccagtgacc    540
ttgacctgga actctggatc cctgtccagt gatgtgcaca ccttcccagc tctcctgcag    600
tctggcctct acaccctcag cagctcagtg actgtaacca cctggcccag ccagaccatc    660
acctgcaatg tggcccaccc ggcaagcagc accaaagtgg acaagaaaat tgagcccaga    720
gggtccccaa cacataaacc ctgtcctcca tgcccagctc ctaacctctt gggtggacca    780
tccgtcttca tcttccctcc aaagatcaag gatgtactca tgatctccct gagccccatg    840
gtcacgtgtg tggtggtgga tgtgagcgag gatgacccag atgtccatgt cagctggttc    900
```

-continued

```
gtgaacaacg tggaagtaca cacagctcag acacaaaccc atagagagga ttacaacagt    960
actatccggg tggtcagtgc cctccccatc cagcaccagg actggatgag tgcaaggag    1020 ttcaaatgca aggtcaacaa caaagccctc ccagcgccca tcgagagaac catctcaaaa    1080
cccaaagggc cagtaagagc tccacaggta tatgtcttgc ctccaccaga agaagagatg    1140
actaagaaac aggtcactct gacctgcatg atcacagact tcatgcctga agacatttac    1200
gtggagtgga ccaacaacgg gcaaacagag ctaaactaca gaacactga accagtcctg    1260 gactctgatg gttcttactt catgtacagc aagctgagag tggaaaagaa gaactgggtg    1320
gaaagaaata gctactcctg ttcagtggtc acgagggtc tgcacaatca ccacacgact    1380
aagagcttct cccggactcc gggtaaa                                        1407
```

<210> SEQ ID NO 181
<211> LENGTH: 214
<212> TYPE: PRT
<213> ORGANISM: Mus musculus

<400> SEQUENCE: 181

Asp Ile Gln Met Thr Gln Thr Thr Ser Ser Leu Ser Ala Ser Leu Gly
1               5                   10                  15

Asp Arg Val Ser Ile Ser Cys Arg Ala Ser Gln Asp Ile Ser Asn Tyr
                20                  25                  30

Leu Asn Trp Tyr Gln Gln Lys Pro Asp Gly Thr Phe Lys Leu Leu Ile
            35                  40                  45

Phe Tyr Thr Ser Arg Leu Leu Ser Gly Val Pro Ser Arg Phe Ser Gly
        50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Leu Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 182
<211> LENGTH: 645
<212> TYPE: DNA
<213> ORGANISM: Mus musculus

<400> SEQUENCE: 182

```
gatatccaga tgacacagac tacatcctcc ctgtctgcct ctctgggaga cagggtctcc     60
atcagttgca gggcaagtca agacattagc aattatttaa actggtatca gcagaaacca    120
```

```
gatggaactt ttaaactcct tatcttctac acatcaagat tactctcagg agtcccatca    180
aggttcagtg gcagtgggtc tggaacagat tattctctca ccatttacaa cctggagcaa    240
gaagattttg ccacttactt ttgccaacag ggagatacgc ttccgtacac tttcggaggg    300
gggaccaaac tggaaataaa acgggctgat gctgcaccaa ctgtatccat cttcccacta    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag cacccctcacg   540 ttgaccaagg acgagtatga acgacataac agctatacct gtgaggccac tcacaagaca    600
tcaacttcac ccattgtcaa gagcttcaac aggaatgagt gttag                    645
```

<210> SEQ ID NO 183
<211> LENGTH: 234
<212> TYPE: PRT
<213> ORGANISM: Mus musculus

<400> SEQUENCE: 183

```
Met Met Ser Ser Ala Gln Phe Leu Gly Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Ser Ile Ser Cys Arg Ala Ser Gln Asp
        35                  40                  45

Ile Ser Asn Tyr Leu Asn Trp Tyr Gln Gln Lys Pro Asp Gly Thr Phe
    50                  55                  60

Lys Leu Leu Ile Phe Tyr Thr Ser Arg Leu Leu Ser Gly Val Pro Ser
65                  70                  75                  80

Arg Phe Ser Gly Ser Gly Ser Gly Thr Asp Tyr Ser Leu Thr Ile Tyr
                85                  90                  95

Asn Leu Glu Gln Glu Asp Phe Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125

Ala Asp Ala Ala Pro Thr Val Ser Ile Phe Pro Leu Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 184
<211> LENGTH: 705
<212> TYPE: DNA
<213> ORGANISM: Mus musculus

<400> SEQUENCE: 184

```
atgatgtcct ctgctcagtt ccttggtctc ctgttgctct gttttcaagg taccagatgt    60
gatatccaga tgacacagac tacatcctcc ctgtctgcct ctctgggaga cagggtctcc   120
atcagttgca gggcaagtca agacattagc aattatttaa actggtatca gcagaaacca   180
gatggaactt ttaaactcct tatcttctac acatcaagat actctcagg agtcccatca    240 aggttcagtg gcagtgggtc tggaacagat tattctctca ccatttacaa cctggagcaa   300
gaagattttg ccacttactt ttgccaacag gagatacgc ttccgtacac tttcggaggg    360
gggaccaaac tggaaataaa acgggctgat gctgcaccaa ctgtatccat cttcccacta   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag caccctcacg   600
ttgaccaagg acgagtatga acgacataac agctatacct gtgaggccac tcacaagaca   660
tcaacttcac ccattgtcaa gagcttcaac aggaatgagt gttag                   705

<210> SEQ ID NO 185
<211> LENGTH: 447
<212> TYPE: PRT
<213> ORGANISM: Mus musculus

<400> SEQUENCE: 185

Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gly Lys Thr Leu Glu Trp Ile
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255
```

-continued

```
Pro Lys Val Thr Cys Val Val Asp Ile Ser Lys Asp Asp Pro Glu
            260                 265                 270
Val Gln Phe Ser Trp Phe Val Asp Val Glu Val His Thr Ala Gln
        275                 280                 285
Thr Gln Pro Arg Glu Glu Gln Phe Asn Ser Thr Phe Arg Ser Val Ser
    290                 295                 300
Glu Leu Pro Ile Met His Gln Asp Trp Leu Asn Gly Lys Glu Phe Lys
305                 310                 315                 320
Cys Arg Val Asn Ser Ala Ala Phe Pro Ala Pro Ile Glu Lys Thr Ile
                325                 330                 335
Ser Lys Thr Lys Gly Arg Pro Lys Ala Pro Gln Val Tyr Thr Ile Pro
            340                 345                 350
Pro Pro Lys Glu Gln Met Ala Lys Asp Lys Val Ser Leu Thr Cys Met
        355                 360                 365
Ile Thr Asp Phe Phe Pro Glu Asp Ile Thr Val Glu Trp Gln Trp Asn
    370                 375                 380
Gly Gln Pro Ala Glu Asn Tyr Lys Asn Thr Gln Pro Ile Met Asp Thr
385                 390                 395                 400
Asp Gly Ser Tyr Phe Ile Tyr Ser Lys Leu Asn Val Gln Lys Ser Asn
                405                 410                 415
Trp Glu Ala Gly Asn Thr Phe Thr Cys Ser Val Leu His Glu Gly Leu
            420                 425                 430
His Asn His His Thr Glu Lys Ser Leu Ser His Ser Pro Gly Lys
        435                 440                 445
```

<210> SEQ ID NO 186
<211> LENGTH: 1344
<212> TYPE: DNA
<213> ORGANISM: Mus musculus

<400> SEQUENCE: 186

```
gaggtccaac tgcaacagtc tggacctgaa ctaatgaagc ctggggcttc agtgaagatg     60
tcctgcaagg cttctggata cattcact gactacaaca tgcactgggt gaagcagaac    120
caaggaaaga ccctagaatg gataggagaa attaatccta cagtggtgg tgctggctac    180
aaccagaagt tcaagggcaa ggccacattg actgtagaca gtcctccac cacagcctac    240
atggagctcc gcagcctgac atctgaggac tctgcagtct attactgtgc aagattgggc    300
tacgatgata tctacgacga ctggtacttc gatgtctggg gcgcaggga cacggtcacc    360
gtctcctcag ccaaaacgac accccatct gtctatccac tggcccctgg atctgctgcc    420
caaactaact ccatggtgac cctgggatgc ctggtcaagg ctatttccc tgagccagtg    480
acagtgacct ggaactctgg atccctgtcc agcggtgtgc acaccttccc agctgtcctg    540
cagtctgacc tctacactct gagcagctca gtgactgtcc cctccagcac ctggcccagc    600
gagaccgtca cctgcaacgt tgcccacccg gccagcagca ccaaggtgga caagaaaatt    660
gtgcccaggg attgtggttg taagccttgc atatgtacag tcccagaagt atcatctgtc    720
ttcatcttcc ccccaaagcc caaggatgtg ctcaccatta ctctgactcc taaggtcacg    780
tgtgttgtgg tagacatcag caaggatgat cccgaggtcc agttcagctg gtttgtagat    840
gatgtggagg tgcacacagc tcagacgcaa ccccgggagg agcagttcaa cagcactttc    900
cgctcagtca gtgaacttcc catcatgcac caggactggc tcaatggcaa ggagttcaaa    960
tgcagggtca acagtgcagc tttccctgcc cccatcgaga aaaccatctc caaaaccaaa   1020
ggcagaccga aggctccaca ggtgtacacc attccacctc ccaaggagca gatggccaag   1080
```

```
gataaagtca gtctgacctg catgataaca gacttcttcc ctgaagacat tactgtggag   1140
tggcagtgga atgggcagcc agcggagaac tacaagaaca ctcagcccat catggacaca   1200
gatggctctt acttcatcta cagcaagctc aatgtgcaga agagcaactg ggaggcagga   1260
aatactttca cctgctctgt gttacatgag ggcctgcaca accaccatac tgagaagagc   1320
ctctcccact ctcctggtaa atga                                           1344
```

<210> SEQ ID NO 187
<211> LENGTH: 466
<212> TYPE: PRT
<213> ORGANISM: Mus musculus

<400> SEQUENCE: 187

```
Met Gly Trp Ser Trp Thr Phe Leu Phe Leu Leu Ser Gly Thr Ala Gly
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Val Lys Gln Asn Gln Gly Lys Thr Leu
    50                  55                  60

Glu Trp Ile Gly Glu Ile Asn Pro Asn Ser Gly Gly Ala Gly Tyr Asn
65                  70                  75                  80

Gln Lys Phe Lys Gly Lys Ala Thr Leu Thr Val Asp Lys Ser Ser Thr
                85                  90                  95

Thr Ala Tyr Met Glu Leu Arg Ser Leu Thr Ser Glu Asp Ser Ala Val
            100                 105                 110

Tyr Tyr Cys Ala Arg Leu Gly Tyr Asp Asp Ile Tyr Asp Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335
```

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
            405                 410                 415

Met Asp Thr Asp Gly Ser Tyr Phe Ile Tyr Ser Lys Leu Asn Val Gln
        420                 425                 430

Lys Ser Asn Trp Glu Ala Gly Asn Thr Phe Thr Cys Ser Val Leu His
    435                 440                 445

Glu Gly Leu His Asn His His Thr Glu Lys Ser Leu Ser His Ser Pro
450                 455                 460

Gly Lys
465

<210> SEQ ID NO 188
<211> LENGTH: 1401
<212> TYPE: DNA
<213> ORGANISM: Mus musculus

<400> SEQUENCE: 188

```
atgggatgga gctggacctt tctcttcctc ctgtcaggaa ctgcaggtgt cctctctgag      60
gtccaactgc aacagtctgg acctgaacta atgaagcctg gggcttcagt gaagatgtcc     120
tgcaaggctt ctggatatac attcactgac tacaacatgc actgggtgaa gcagaaccaa     180
ggaaagaccc tagaatggat aggagaaatt aatcctaaca gtggtggtgc tggctacaac     240
cagaagttca agggcaaggc cacattgact gtagacaagt cctccaccac agcctacatg     300
gagctccgca gcctgacatc tgaggactct gcagtctatt actgtgcaag attgggctac     360
gatgatatct acgacgactg gtacttcgat gtctggggcg cagggaccac ggtcaccgtc     420
tcctcagcca aaacgacacc cccatctgtc tatccactgg ccctggatc tgctgcccaa     480 actaactcca tggtgaccct gggatgcctg gtcaagggct atttccctga gccagtgaca     540
gtgacctgga actctggatc cctgtccagc ggtgtgcaca ccttcccagc tgtcctgcag     600
tctgacctct acactctgag cagctcagtg actgtcccct ccagcacctg cccagcgag     660 accgtcacct gcaacgttgc cacccggcc agcagcacca aggtggacaa gaaaattgtg     720
cccagggatt gtggttgtaa gccttgcata tgtacagtcc cagaagtatc atctgtcttc     780
atcttccccc caaagcccaa ggatgtgctc accattactc tgactcctaa ggtcacgtgt     840
gttgtggtag acatcagcaa ggatgatccc gaggtccagt tcagctggtt tgtagatgat     900
gtggaggtgc acacagctca gacgcaaccc cgggaggagc agttcaacag cactttccgc     960
tcagtcagtg aacttcccat catgcaccag actggctca atggcaagga gttcaaatgc    1020
agggtcaaca gtgcagcttt ccctgccccc atcgagaaaa ccatctccaa aaccaaaggc    1080
agaccgaagg ctccacaggt gtacaccatt ccacctccca aggagcagat ggccaaggat    1140
aaagtcagtc tgacctgcat gataacagac ttcttccctg aagacattac tgtggagtgg    1200
cagtggaatg gcagccagc ggagaactac aagaacactc agcccatcat ggacacagat    1260
ggctcttact tcatctacag caagctcaat gtgcagaaga caactggga ggcaggaaat    1320
```

```
actttcacct gctctgtgtt acatgagggc ctgcacaacc accatactga gaagagcctc    1380
tcccactctc ctggtaaatg a                                              1401
```

<210> SEQ ID NO 189
<211> LENGTH: 213
<212> TYPE: PRT
<213> ORGANISM: Mus musculus

<400> SEQUENCE: 189

```
Gln Ile Val Leu Ser Gln Ser Pro Ala Phe Leu Ser Val Ser Pro Gly
 1               5                  10                  15

Asp Lys Val Thr Met Thr Cys Arg Ala Ser Ser Ser Ile Ser Tyr Ile
            20                  25                  30

His Trp Phe Gln Gln Lys Pro Gly Ser Ser Pro Arg Ser Trp Ile Tyr
        35                  40                  45

Ala Thr Ser Asn Leu Ala Ser Gly Val Pro Gly Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asp Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

<210> SEQ ID NO 190
<211> LENGTH: 642
<212> TYPE: DNA
<213> ORGANISM: Mus musculus

<400> SEQUENCE: 190

```
caaattgttc tctcccagtc tccagcattc ctgtctgtat ctccagggga taaggtcaca     60
atgacttgca gggccagctc aagtataagt tacatacact ggtttcagca gaagccagga   120
tcctccccca gatcctggat ttatgccaca tccaacctgg cttctggagt ccctggtcgc   180
ttcagtggca gtgggtctgg gacctcttac tctctcacaa tcagcagagt ggaggctgag   240
gatgctgcca cttattactg ccagcagtgg agtagtgacc cactcacgtt cggtgctggg   300
accaagctgg agctgaaacg ggctgatgct gcaccaactg tatccatctt cccaccatcc   360
agtgagcagt taacatctgg aggtgcctca gtcgtgtgct tcttgaacaa cttctacccc   420
aaagacatca atgtcaagtg gaagattgat ggcagtgaac gacaaaatgg cgtcctgaac   480
agttggactg atcaggacag caaagacagc acctacagca tgagcagcac cctcacgttg   540
```

```
accaaggacg agtatgaacg acataacagc tatacctgtg aggccactca caagacatca      600
acttcaccca ttgtcaagag cttcaacagg aatgagtgtt ag                         642
```

<210> SEQ ID NO 191
<211> LENGTH: 235
<212> TYPE: PRT
<213> ORGANISM: Mus musculus

<400> SEQUENCE: 191

```
Met Asp Phe Gln Val Gln Ile Phe Ser Phe Leu Leu Ile Ser Ala Ser
1               5                   10                  15
Val Ile Met Ser Arg Gly Gln Ile Val Leu Ser Gln Ser Pro Ala Phe
            20                  25                  30
Leu Ser Val Ser Pro Gly Asp Lys Val Thr Met Thr Cys Arg Ala Ser
        35                  40                  45
Ser Ser Ile Ser Tyr Ile His Trp Phe Gln Gln Lys Pro Gly Ser Ser
    50                  55                  60
Pro Arg Ser Trp Ile Tyr Ala Thr Ser Asn Leu Ala Ser Gly Val Pro
65                  70                  75                  80
Gly Arg Phe Ser Gly Ser Gly Ser Gly Thr Ser Tyr Ser Leu Thr Ile
                85                  90                  95
Ser Arg Val Glu Ala Glu Asp Ala Ala Thr Tyr Tyr Cys Gln Gln Trp
            100                 105                 110
Ser Ser Asp Pro Leu Thr Phe Gly Ala Gly Thr Lys Leu Glu Leu Lys
        115                 120                 125
Arg Ala Asp Ala Ala Pro Thr Val Ser Ile Phe Pro Pro Ser Ser Glu
    130                 135                 140
Gln Leu Thr Ser Gly Gly Ala Ser Val Val Cys Phe Leu Asn Asn Phe
145                 150                 155                 160
Tyr Pro Lys Asp Ile Asn Val Lys Trp Lys Ile Asp Gly Ser Glu Arg
                165                 170                 175
Gln Asn Gly Val Leu Asn Ser Trp Thr Asp Gln Asp Ser Lys Asp Ser
            180                 185                 190
Thr Tyr Ser Met Ser Ser Thr Leu Thr Leu Thr Lys Asp Glu Tyr Glu
        195                 200                 205
Arg His Asn Ser Tyr Thr Cys Glu Ala Thr His Lys Thr Ser Thr Ser
    210                 215                 220
Pro Ile Val Lys Ser Phe Asn Arg Asn Glu Cys
225                 230                 235
```

<210> SEQ ID NO 192
<211> LENGTH: 708
<212> TYPE: DNA
<213> ORGANISM: Mus musculus

<400> SEQUENCE: 192

```
atggattttc aagtgcagat tttcagcttc ctgctaatca gtgcttcagt cataatgtcc      60
agaggacaaa ttgttctctc ccagtctcca gcattcctgt ctgtatctcc aggggataag     120
gtcacaatga cttgcagggc cagctcaagt ataagttaca tacactggtt tcagcagaag     180
ccaggatcct cccccagatc ctggatttat gccacatcca acctggcttc tggagtccct     240
ggtcgcttca gtggcagtgg gtctgggacc tcttactctc tcacaatcag cagagtggag     300
gctgaggatg ctgccactta ttactgccag cagtggagta gtgacccact cacgttcggt     360
gctgggacca agctggagct gaaacgggct gatgctgcac caactgtatc catcttccca     420
ccatccagtg agcagttaac atctggaggt gcctcagtcg tgtgcttctt gaacaacttc     480
```

```
tacccaaag acatcaatgt caagtggaag attgatggca gtgaacgaca aaatggcgtc    540
ctgaacagtt ggactgatca ggacagcaaa gacagcacct acagcatgag cagcaccctc    600
acgttgacca aggacgagta tgaacgacat aacagctata cctgtgaggc cactcacaag    660
acatcaactt cacccattgt caagagcttc aacaggaatg agtgttag                708
```

<210> SEQ ID NO 193
<211> LENGTH: 445
<212> TYPE: PRT
<213> ORGANISM: Mus musculus

<400> SEQUENCE: 193

| | | | | | | | | | | | | | | |
|---|---|---|---|---|---|---|---|---|---|---|---|---|---|---|
| Glu | Val | Gln | Leu | Gln | Gln | Ser | Gly | Ala | Asp | Leu | Val | Gln | Pro | Gly | Ala |
| 1 | | | | 5 | | | | | 10 | | | | | 15 | |

Ser Val Lys Val Ser Cys Thr Ala Ser Gly Phe Asp Ile Lys Asp Tyr
            20                  25                  30

Tyr Ile His Trp Met Lys Gln Arg Pro Asp Gln Gly Leu Glu Trp Ile
        35                  40                  45

Gly Arg Val Asp Pro Asp Asn Gly Glu Thr Glu Phe Ala Pro Lys Phe
    50                  55                  60

Pro Gly Lys Ala Thr Phe Thr Thr Asp Thr Ser Ser Asn Thr Ala Tyr
65                  70                  75                  80

Leu Gln Leu Arg Gly Leu Thr Ser Glu Asp Thr Ala Ile Tyr Tyr Cys
                85                  90                  95

Gly Arg Glu Asp Tyr Asp Gly Thr Tyr Thr Trp Phe Pro Tyr Trp Gly
            100                 105                 110

Gln Gly Thr Leu Val Thr Val Ser Ala Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

```
            Thr Lys Gly Arg Pro Lys Ala Pro Gln Val Tyr Thr Ile Pro Pro Pro
                        340                 345                 350

Lys Glu Gln Met Ala Lys Asp Lys Val Ser Leu Thr Cys Met Ile Thr
            355                 360                 365

Asp Phe Phe Pro Glu Asp Ile Thr Val Glu Trp Gln Trp Asn Gly Gln
                370                 375                 380

Pro Ala Glu Asn Tyr Lys Asn Thr Gln Pro Ile Met Asp Thr Asp Gly
            385                 390                 395                 400

Ser Tyr Phe Ile Tyr Ser Lys Leu Asn Val Gln Lys Ser Asn Trp Glu
                            405                 410                 415

Ala Gly Asn Thr Phe Thr Cys Ser Val Leu His Glu Gly Leu His Asn
                        420                 425                 430

His His Thr Glu Lys Ser Leu Ser His Ser Pro Gly Lys
                        435                 440                 445

<210> SEQ ID NO 194
<211> LENGTH: 1338
<212> TYPE: DNA
<213> ORGANISM: Mus musculus

<400> SEQUENCE: 194
gaagttcagc tgcaacagtc tggggcagac cttgtgcagc caggggcctc agtcaaggtg      60
tcctgcacag cttctggctt cgacattaag gactactata tacactggat gaaacagagg     120
cctgaccagg gcctggagtg gattggaagg gttgatcctg acaatggtga gactgaattt    180
gccccgaagt tccgggcaa ggccacttt acaacagaca catcctccaa cacagcctac      240
ctacaactca gaggcctgac atctgaggac actgccatct attactgtgg gagagaagac    300
tacgatggta cctacacctg gtttccttat ggggccaag ggactctggt cactgtctct     360
gcagccaaaa cgacaccccc atctgtctat ccactggccc ctggatctgc tgcccaaact    420
aactccatgg tgaccctggg atgcctggtc aagggctatt ccctgagcc agtgacagtg    480 acctggaact ctggatccct gtccagcggt gtgcacacct cccagctgt cctgcagtct    540 gacctctaca ctctgagcag ctcagtgact gtcccctcca gcacctggcc cagcgagacc   600
gtcacctgca acgttgccca cccggccagc agcaccaagg tggacaagaa aattgtgccc   660
agggattgtg gttgtaagcc ttgcatatgt acagtcccag aagtatcatc tgtcttcatc   720
ttccccccaa agcccaagga tgtgctcacc attactctga ctcctaaggt cacgtgtgtt    780
gtggtagaca tcagcaagga tgatcccgag gtccagttca gctggtttgt agatgatgtg    840
gaggtgcaca cagctcagac gcaaccccgg gaggagcagt tcaacagcac tttccgctca    900
gtcagtgaac ttcccatcat gcaccaggac tggctcaatg gcaaggagtt caatgcagg    960 gtcaacagtg cagctttccc tgcccccatc gagaaaacca tctccaaaac caaaggcaga  1020
ccgaaggctc cacaggtgta caccattcca cctcccaagg agcagatggc caaggataaa  1080
gtcagtctga cctgcatgat aacagacttc ttccctgaag acattactgt ggagtggcag  1140
tggaatgggc agccagcgga gaactacaag aacactcagc ccatcatgga cacagatggc  1200
tcttacttca tctacagcaa gctcaatgtg cagaagagca ctgggaggc aggaaatact  1260 ttcacctgct ctgtgttaca tgagggcctg cacaaccacc atactgagaa gagcctctcc  1320
cactctcctg gtaaatga                                                 1338

<210> SEQ ID NO 195
<211> LENGTH: 464
<212> TYPE: PRT
<213> ORGANISM: Mus musculus
```

<400> SEQUENCE: 195

```
Met Lys Cys Ser Trp Val Ile Phe Phe Leu Met Ala Val Val Thr Gly
1               5                   10                  15

Val Asn Ser Glu Val Gln Leu Gln Gln Ser Gly Ala Asp Leu Val Gln
            20                  25                  30

Pro Gly Ala Ser Val Lys Val Ser Cys Thr Ala Ser Gly Phe Asp Ile
        35                  40                  45

Lys Asp Tyr Tyr Ile His Trp Met Lys Gln Arg Pro Asp Gln Gly Leu
    50                  55                  60

Glu Trp Ile Gly Arg Val Asp Pro Asp Asn Gly Glu Thr Glu Phe Ala
65                  70                  75                  80

Pro Lys Phe Pro Gly Lys Ala Thr Phe Thr Thr Asp Thr Ser Ser Asn
                85                  90                  95

Thr Ala Tyr Leu Gln Leu Arg Gly Leu Thr Ser Glu Asp Thr Ala Ile
            100                 105                 110

Tyr Tyr Cys Gly Arg Glu Asp Tyr Asp Gly Thr Tyr Thr Trp Phe Pro
        115                 120                 125

Tyr Trp Gly Gln Gly Thr Leu Val Thr Val Ser Ala Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415
```

Thr Asp Gly Ser Tyr Phe Ile Tyr Ser Lys Leu Asn Val Gln Lys Ser
         420                 425                 430

Asn Trp Glu Ala Gly Asn Thr Phe Thr Cys Ser Val Leu His Glu Gly
     435                 440                 445

Leu His Asn His His Thr Glu Lys Ser Leu Ser His Ser Pro Gly Lys
     450                 455                 460

<210> SEQ ID NO 196
<211> LENGTH: 1395
<212> TYPE: DNA
<213> ORGANISM: Mus musculus

<400> SEQUENCE: 196
atgaaatgca gctgggtcat cttcttcctg atggcagtgg ttacaggggt caattcagaa      60
gttcagctgc aacagtctgg ggcagacctt gtgcagccag ggcctcagt caaggtgtcc      120
tgcacagctt ctggcttcga cattaaggac tactatatac actggatgaa acagaggcct      180
gaccagggcc tggagtggat tggaaggggtt gatcctgaca atggtgagac tgaatttgcc      240
ccgaagttcc cggcaaggc actttttaca acagacacat cctccaacac agcctaccta      300
caactcagag gcctgacatc tgaggacact gccatctatt actgtgggag agaagactac      360
gatggtacct acacctggtt tccttattgg ggccaaggga ctctggtcac tgtctctgca      420
gccaaaacga cacccccatc tgtctatcca ctggcccctg gatctgctgc ccaaactaac      480
tccatggtga ccctgggatg cctggtcaag ggctatttcc ctgagccagt gacagtgacc      540
tggaactctg gatccctgtc cagcggtgtg cacaccttcc cagctgtcct gcagtctgac      600
ctctacactc tgagcagctc agtgactgtc cctccagca cctggcccag cgagaccgtc      660
acctgcaacg ttgcccaccc ggccagcagc accaaggtgg acaagaaaat tgtgcccagg      720
gattgtggtt gtaagccttg catatgtaca gtcccagaag tatcatctgt cttcatcttc      780
cccccaaagc ccaaggatgt gctcaccatt actctgactc ctaaggtcac gtgtgttgtg      840
gtagacatca gcaaggatga tcccgaggtc cagttcagct ggtttgtaga tgatgtggag      900
gtgcacacag ctcagacgca accccgggag gagcagttca acagcacttt ccgctcagtc      960
agtgaacttc ccatcatgca ccaggactgg ctcaatggca aggagttcaa atgcagggtc     1020
aacagtgcag cttcccctgc ccccatcgag aaaaccatct ccaaaaccaa aggcagaccg     1080
aaggctccac aggtgtacac cattccacct cccaaggagc agatggccaa ggataaagtc     1140
agtctgacct gcatgataac agacttcttc cctgaagaca ttactgtgga gtggcagtgg     1200
aatgggcagc cagcggagaa ctacaagaac actcagccca tcatggacac agatggctct     1260
tacttcatct acagcaagct caatgtgcag aagagcaact gggaggcagg aaatactttc     1320
acctgctctg tgttacatga gggcctgcac aaccaccata ctgagaagag cctctcccac     1380
tctcctggta aatga                                                    1395

<210> SEQ ID NO 197
<211> LENGTH: 214
<212> TYPE: PRT
<213> ORGANISM: Mus musculus

<400> SEQUENCE: 197

Asp Leu Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
            35                  40                  45

Phe Tyr Thr Ser Thr Leu Gln Ser Gly Val Pro Ser Arg Phe Ser Gly
    50                  55                  60

Ser Gly Ser Gly Thr Asn Tyr Ser Leu Thr Ile Thr Asn Leu Glu Gln
65                  70                  75                  80

Asp Asp Ala Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
            210

<210> SEQ ID NO 198
<211> LENGTH: 645
<212> TYPE: DNA
<213> ORGANISM: Mus musculus

<400> SEQUENCE: 198
gatctccaga tgacacagac tacttcctcc ctgtctgcct ctctgggaga cagagtcacc      60
atcagttgca gggcaagtca ggacattagc aattatttaa actggtatca gcagaaacca     120
gatggaactg ttaagctcct gatcttctac acatcaacat tacagtcagg agtcccatcg     180
aggttcagtg gcagtgggtc tggaacaaat tattctctca ccattaccaa cctggagcaa     240
gatgatgctg ccacttactt ttgccaacag ggtgatacgc ttccgtacac gttcggaggg     300
gggaccaagc tggaaataaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag cacccTCACG     540
ttgaccaagg acgagtatga acgacataac agctatacct gtgaggccac tcacaagaca     600
tcaacttcac ccattgtcaa gagcttcaac aggaatgagt gttag                     645

<210> SEQ ID NO 199
<211> LENGTH: 234
<212> TYPE: PRT
<213> ORGANISM: Mus musculus

<400> SEQUENCE: 199

Met Met Ser Ser Ala Gln Phe Leu Gly Leu Leu Leu Leu Cys Phe Gln
1               5                   10                  15

Gly Ser Arg Cys Asp Leu Gln Met Thr Gln Thr Thr Ser Ser Leu Ser
            20                  25                  30

Ala Ser Leu Gly Asp Arg Val Thr Ile Ser Cys Arg Ala Ser Gln Asp
         35                  40                  45
Ile Ser Asn Tyr Leu Asn Trp Tyr Gln Gln Lys Pro Asp Gly Thr Val
 50                  55                  60
Lys Leu Leu Ile Phe Tyr Thr Ser Thr Leu Gln Ser Gly Val Pro Ser
 65                  70                  75                  80
Arg Phe Ser Gly Ser Gly Ser Gly Thr Asn Tyr Ser Leu Thr Ile Thr
                 85                  90                  95
Asn Leu Glu Gln Asp Asp Ala Ala Thr Tyr Phe Cys Gln Gln Gly Asp
            100                 105                 110
Thr Leu Pro Tyr Thr Phe Gly Gly Gly Thr Lys Leu Glu Ile Lys Arg
        115                 120                 125
Ala Asp Ala Ala Pro Thr Val Ser Ile Phe Pro Pro Ser Ser Glu Gln
130                 135                 140
Leu Thr Ser Gly Gly Ala Ser Val Val Cys Phe Leu Asn Asn Phe Tyr
145                 150                 155                 160
Pro Lys Asp Ile Asn Val Lys Trp Lys Ile Asp Gly Ser Glu Arg Gln
                165                 170                 175
Asn Gly Val Leu Asn Ser Trp Thr Asp Gln Asp Ser Lys Asp Ser Thr
            180                 185                 190
Tyr Ser Met Ser Ser Thr Leu Thr Leu Thr Lys Asp Glu Tyr Glu Arg
        195                 200                 205
His Asn Ser Tyr Thr Cys Glu Ala Thr His Lys Thr Ser Thr Ser Pro
210                 215                 220
Ile Val Lys Ser Phe Asn Arg Asn Glu Cys
225                 230

<210> SEQ ID NO 200
<211> LENGTH: 705
<212> TYPE: DNA
<213> ORGANISM: Mus musculus

<400> SEQUENCE: 200
atgatgtcct ctgctcagtt ccttggtctc ctgttgctct gttttcaagg ttccagatgt      60
gatctccaga tgacacagac tacttcctcc ctgtctgcct ctctgggaga cagagtcacc     120
atcagttgca gggcaagtca ggacattagc aattatttaa actggtatca gcagaaacca     180
gatggaactg ttaagctcct gatcttctac acatcaacat tacagtcagg agtcccatcg     240
aggttcagtg gcagtgggtc tggaacaaat tattctctca ccattaccaa cctggagcaa     300
gatgatgctg ccacttactt ttgccaacag ggtgatacgc ttccgtacac gttcggaggg     360
gggaccaagc tggaaataaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag caccctcacg     600
ttgaccaagg acgagtatga acgacataac agctatacct gtgaggccac tcacaagaca     660
tcaacttcac ccattgtcaa gagcttcaac aggaatgagt gttag                    705

<210> SEQ ID NO 201
<211> LENGTH: 447
<212> TYPE: PRT
<213> ORGANISM: Mus musculus

<400> SEQUENCE: 201

Glu Val Gln Leu Gln Gln Ser Gly Pro Glu Leu Met Lys Pro Gly Ala

-continued

```
1               5                   10                  15
Ser Val Lys Met Ser Cys Lys Ala Ser Gly Tyr Thr Phe Thr Asp Tyr
            20                  25                  30

Asn Met His Trp Met Lys Gln Asn Gln Gly Lys Ser Leu Glu Trp Ile
            35                  40                  45

Gly Glu Ile Asn Pro Asn Ser Gly Ser Gly Tyr Asn Gln Lys Phe
            50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Tyr Gly Asn Tyr Glu Asp Trp Tyr Phe Asp Val
                100                 105                 110

Trp Gly Ala Gly Thr Thr Val Thr Val Ser Ser Ala Lys Thr Thr Pro
            115                 120                 125

Pro Ser Val Tyr Pro Leu Ala Pro Gly Ser Ala Ala Gln Thr Asn Ser
            130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
            195                 200                 205

His Pro Ala Ser Ser Thr Lys Val Asp Lys Lys Ile Val Pro Arg Asp
            210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
            275                 280                 285

Thr Gln Pro Arg Glu Glu Gln Phe Asn Ser Thr Phe Arg Ser Val Ser
            290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
            355                 360                 365

Ile Thr Asp Phe Phe Pro Glu Asp Ile Thr Val Glu Trp Gln Trp Asn
            370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430
```

```
His Asn His His Thr Glu Lys Ser Leu Ser His Ser Pro Gly Lys
            435                 440                 445
```

<210> SEQ ID NO 202
<211> LENGTH: 1344
<212> TYPE: DNA
<213> ORGANISM: Mus musculus

<400> SEQUENCE: 202

```
gaggtccagt tgcaacagtc tggacctgaa ctaatgaagc ctggggcttc agtgaagatg      60
tcctgcaagg cttctggata cacattcact gactacaaca tgcactggat gaagcagaac     120
caaggaaaga gcctagagtg gataggagag attaatccta cagtggtgg ttctggttac      180
aaccagaagt tcaaaggcaa ggccacattg actgtagaca gtcctccag cacagcctac      240
atggagctcc gcagcctgac atctgaggac tctgcagtct attactgtgc aagattgggc     300
tactatggta actacgagga ctggtatttc gatgtctggg gcgcaggac acggtcacc       360
gtctcctctg ccaaaacgac accccatct gtctatccac tggcccctgg atctgctgcc     420
caaactaact ccatggtgac cctgggatgc ctggtcaagg ctatttccc tgagccagtg     480
acagtgacct ggaactctgg atccctgtcc agcggtgtgc acaccttccc agctgtcctg     540
cagtctgacc tctacactct gagcagctca gtgactgtcc cctccagcac tggcccagc     600
gagaccgtca cctgcaacgt tgcccacccg gccagcagca ccaaggtgga caagaaaatt     660
gtgcccaggg attgtggttg taagccttgc atatgtacag tcccagaagt atcatctgtc     720
ttcatcttcc ccccaaagcc caaggatgtg ctcaccatta ctctgactcc taaggtcacg     780
tgtgttgtgg tagacatcag caaggatgat cccgaggtcc agttcagctg gtttgtagat     840
gatgtggagt gcacacagc tcagacgcaa ccccgggagg agcagttcaa cagcactttc     900
cgctcagtca gtgaacttcc catcatgcac caggactggc tcaatggcaa ggagttcaaa     960
tgcagggtca acagtgcagc tttcctgcc cccatcgaga aaaccatctc caaaaccaaa     1020
ggcagaccga aggctccaca ggtgtacacc attccacctc ccaaggagca gatggccaag     1080
gataaagtca gtctgacctg catgataaca gacttcttcc ctgaagacat tactgtggag     1140
tggcagtgga atgggcagcc agcggagaac tacaagaaca ctcagcccat catggacaca     1200
gatggctctt acttcatcta cagcaagctc aatgtgcaga gagcaactg ggaggcagga      1260
aatactttca cctgctctgt gttacatgag ggcctgcaca ccaccatac tgagaagagc     1320
ctctccccact ctcctggtaa atga                                           1344
```

<210> SEQ ID NO 203
<211> LENGTH: 466
<212> TYPE: PRT
<213> ORGANISM: Mus musculus

<400> SEQUENCE: 203

```
Met Gly Trp Ser Trp Thr Phe Leu Phe Leu Leu Ser Gly Thr Ser Gly
1               5                   10                  15

Val Leu Ser Glu Val Gln Leu Gln Gln Ser Gly Pro Glu Leu Met Lys
            20                  25                  30

Pro Gly Ala Ser Val Lys Met Ser Cys Lys Ala Ser Gly Tyr Thr Phe
        35                  40                  45

Thr Asp Tyr Asn Met His Trp Met Lys Gln Asn Gln Gly Lys Ser Leu
    50                  55                  60

Glu Trp Ile Gly Glu Ile Asn Pro Asn Ser Gly Gly Ser Gly Tyr Asn
65                  70                  75                  80
```

```
Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Leu Gly Tyr Gly Asn Tyr Glu Asp Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145             150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225             230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Val Glu Val His
    290                 295                 300

Thr Ala Gln Thr Gln Pro Arg Glu Glu Gln Phe Asn Ser Thr Phe Arg
305             310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385             390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Ile Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His Thr Glu Lys Ser Leu Ser His Ser Pro
    450                 455                 460

Gly Lys
465

<210> SEQ ID NO 204
<211> LENGTH: 1401
<212> TYPE: DNA
<213> ORGANISM: Mus musculus
```

<400> SEQUENCE: 204

```
atgggatgga gctggacctt tctcttcctc ctgtcaggaa cttcgggtgt cctctctgag      60
gtccagttgc aacagtctgg acctgaacta atgaagcctg gggcttcagt gaagatgtcc     120
tgcaaggctt ctggatacac attcactgac tacaacatgc actggatgaa gcagaaccaa     180
ggaaagagcc tagagtggat aggagagatt aatcctaaca gtggtggttc tggttacaac     240
cagaagttca aggcaaggc cacattgact gtagacaagt cctccagcac agcctacatg     300
gagctccgca gcctgacatc tgaggactct gcagtctatt actgtgcaag attgggctac     360
tatggtaact acgaggactg gtatttcgat gtctggggcg cagggaccac ggtcaccgtc     420
tcctctgcca aaacgacacc cccatctgtc tatccactgg cccctggatc tgctgcccaa     480
actaactcca tggtgaccct gggatgcctg gtcaagggct atttccctga gccagtgaca     540
gtgacctgga actctggatc cctgtccagc ggtgtgcaca ccttcccagc tgtcctgcag     600
tctgacctct acactctgag cagctcagtg actgtcccct ccagcacctg gcccagcgag     660
accgtcacct gcaacgttgc cacccggcc agcagcacca aggtggacaa gaaaattgtg     720
cccagggatt gtggttgtaa gccttgcata tgtacagtcc agaagtatc atctgtcttc     780
atcttccccc caaagcccaa ggatgtgctc accattactc tgactcctaa ggtcacgtgt     840
gttgtggtag acatcagcaa ggatgatccc gaggtccagt tcagctggtt tgtagatgat     900
gtggaggtgc acacagctca gacgcaaccc cgggaggagc agttcaacag cactttccgc     960
tcagtcagtg aacttcccat catgcaccag gactggctca atggcaagga gttcaaatgc    1020
agggtcaaca gtgcagcttt ccctgccccc atcgagaaaa ccatctccaa aaccaaaggc    1080
agaccgaagg ctccacaggt gtacaccatt ccacctccca aggagcagat ggccaaggat    1140
aaagtcagtc tgacctgcat gataacagac ttcttccctg aagacattac tgtggagtgg    1200
cagtggaatg ggcagccagc ggagaactac aagaacactc agcccatcat ggacacagat    1260
ggctcttact tcatctacag caagctcaat gtgcagaaga gcaactggga ggcaggaaat    1320
actttcacct gctctgtgtt acatgagggc ctgcacaacc accatactga gaagagcctc    1380
tcccactctc ctggtaaatg a                                               1401
```

<210> SEQ ID NO 205
<211> LENGTH: 215
<212> TYPE: PRT
<213> ORGANISM: Mus musculus

<400> SEQUENCE: 205

```
Gln Ile Val Leu Thr Gln Ser Pro Ala Ile Met Ser Ala Ser Pro Gly
1               5                  10                  15

Glu Lys Val Thr Met Thr Cys Arg Ala Ser Ser Ser Val Thr Ser Ser
            20                  25                  30

Tyr Leu Asn Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Asp Phe Phe Pro
                85                  90                  95

Ser Thr Phe Gly Gly Gly Thr Lys Leu Glu Ile Lys Arg Ala Asp Ala
            100                 105                 110
```

```
Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
                180                 185                 190

Tyr Thr Cys Glu Ala Thr His Lys Thr Ser Thr Ser Pro Ile Val Lys
                195                 200                 205

Ser Phe Asn Arg Asn Glu Cys
        210                 215

<210> SEQ ID NO 206
<211> LENGTH: 645
<212> TYPE: DNA
<213> ORGANISM: Mus musculus

<400> SEQUENCE: 206
cagattgttc tcacccagtc tccagcaatc atgtctgcat ctccagggga gaaggtcacc    60
atgacctgca gggccagctc aagtgtaact tccagttact tgaactggta ccagcagaag   120
ccaggatctt cccccaaact ctggatttat agcacatcca acctggcttc aggagtccca   180
gctcgcttca gtggcagtgg gtctgggacc tcttactctc tcacaatcag cagtgtggag   240
gctgaggatg ctgccactta ttactgccag cagtatgatt ttttcccatc gacgttcggt   300
ggaggcacca agctggaaat caagcgggct gatgctgcac caactgtatc catcttccca   360
ccatccagtg agcagttaac atctggaggt gcctcagtcg tgtgcttctt gaacaacttc   420
taccccaaag acatcaatgt caagtggaag attgatggca gtgaacgaca aaatggcgtc   480
ctgaacagtt ggactgatca ggacagcaaa gacagcacct acagcatgag cagcaccctc   540
acgttgacca aggacgagta tgaacgacat aacagctata cctgtgaggc cactcacaag   600
acatcaactt cacccatcgt caagagcttc aacaggaatg agtgt                    645

<210> SEQ ID NO 207
<211> LENGTH: 237
<212> TYPE: PRT
<213> ORGANISM: Mus musculus

<400> SEQUENCE: 207

Met Asp Ser Gln Val Gln Ile Phe Ser Phe Leu Leu Ile Ser Ala Leu
1               5                  10                  15

Val Lys Met Ser Arg Gly Gln Ile Val Leu Thr Gln Ser Pro Ala Ile
            20                  25                  30

Met Ser Ala Ser Pro Gly Glu Lys Val Thr Met Thr Cys Arg Ala Ser
        35                  40                  45

Ser Ser Val Thr Ser Ser Tyr Leu Asn Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Val Glu Ala Glu Asp Ala Ala Thr Tyr Tyr Cys Gln
            100                 105                 110
```

```
Gln Tyr Asp Phe Phe Pro Ser Thr Phe Gly Gly Gly Thr Lys Leu Glu
            115                 120                 125
Ile Lys Arg Ala Asp Ala Ala Pro Thr Val Ser Ile Phe Pro Pro Ser
    130                 135                 140
Ser Glu Gln Leu Thr Ser Gly Gly Ala Ser Val Val Cys Phe Leu Asn
145                 150                 155                 160
Asn Phe Tyr Pro Lys Asp Ile Asn Val Lys Trp Lys Ile Asp Gly Ser
                165                 170                 175
Glu Arg Gln Asn Gly Val Leu Asn Ser Trp Thr Asp Gln Asp Ser Lys
            180                 185                 190
Asp Ser Thr Tyr Ser Met Ser Ser Thr Leu Thr Leu Thr Lys Asp Glu
        195                 200                 205
Tyr Glu Arg His Asn Ser Tyr Thr Cys Glu Ala Thr His Lys Thr Ser
210                 215                 220
Thr Ser Pro Ile Val Lys Ser Phe Asn Arg Asn Glu Cys
225                 230                 235

<210> SEQ ID NO 208
<211> LENGTH: 711
<212> TYPE: DNA
<213> ORGANISM: Mus musculus

<400> SEQUENCE: 208
atggattctc aagtgcagat tttcagcttc cttctaatca gtgccttagt caaaatgtcc     60
agaggacaga ttgttctcac ccagtctcca gcaatcatgt ctgcatctcc aggggagaag    120
gtcaccatga cctgcagggc cagctcaagt gtaacttcca gttacttgaa ctggtaccag    180
cagaagccag gatcttcccc caaactctgg atttatagca catccaacct ggcttcagga    240
gtcccagctc gcttcagtgg cagtgggtct gggacctctt actctctcac aatcagcagt    300
gtggaggctg aggatgctgc cacttattac tgccagcagt atgatttttt cccatcgacg    360
ttcggtggag gcaccaagct ggaaatcaag cgggctgatg ctgcaccaac tgtatccatc    420
ttcccaccat ccagtgagca gttaacatct ggaggtgcct cagtcgtgtg cttcttgaac    480
aacttctacc ccaaagacat caatgtcaag tggaagattg atggcagtga acgacaaaat    540
ggcgtcctga cagttggac tgatcaggac agcaaagaca gcacctacag catgagcagc    600
accctcacgt tgaccaagga cgagtatgaa cgacataaca gctatacctg tgaggccact    660
cacaagacat caacttcacc catcgtcaag agcttcaaca ggaatgagtg t             711

<210> SEQ ID NO 209
<211> LENGTH: 445
<212> TYPE: PRT
<213> ORGANISM: Mus musculus

<400> SEQUENCE: 209

Glu Val Gln Leu Gln Gln Ser Gly Pro Glu Leu Val Lys Pro Gly Ala
1               5                   10                  15
Ser Val Lys Met Ser Cys Lys Ala Ser Gly Tyr Thr Phe Thr Asp Tyr
            20                  25                  30
Tyr Met Asn Trp Val Lys Gln Ser His Gly Glu Ser Leu Glu Trp Ile
        35                  40                  45
Gly Asp Ile Asn Pro Tyr Asn Asp Asp Thr Thr Tyr Asn His Lys Phe
    50                  55                  60
Lys Gly Lys Ala Thr Leu Thr Val Asp Lys Ser Ser Asn Thr Ala Tyr
65                  70                  75                  80
Met Gln Leu Asn Ser Leu Thr Ser Glu Asp Ser Ala Val Tyr Tyr Cys
```

```
                     85                  90                  95
Ala Arg Glu Thr Ala Val Ile Thr Thr Asn Ala Met Asp Tyr Trp Gly
                100                 105                 110
Gln Gly Thr Ser Val Thr Val Ser Ser Ala Lys Thr Thr Pro Pro Ser
            115                 120                 125
Val Tyr Pro Leu Ala Pro Gly Ser Ala Ala Gln Thr Asn Ser Met Val
        130                 135                 140
Thr Leu Gly Cys Leu Val Lys Gly Tyr Phe Pro Glu Pro Val Thr Val
145                 150                 155                 160
Thr Trp Asn Ser Gly Ser Leu Ser Ser Gly Val His Thr Phe Pro Ala
                165                 170                 175
Val Leu Gln Ser Asp Leu Tyr Thr Leu Ser Ser Ser Val Thr Val Pro
                180                 185                 190
Ser Ser Thr Trp Pro Ser Glu Thr Val Thr Cys Asn Val Ala His Pro
            195                 200                 205
Ala Ser Ser Thr Lys Val Asp Lys Lys Ile Val Pro Arg Asp Cys Gly
        210                 215                 220
Cys Lys Pro Cys Ile Cys Thr Val Pro Glu Val Ser Ser Val Phe Ile
225                 230                 235                 240
Phe Pro Pro Lys Pro Lys Asp Val Leu Thr Ile Thr Leu Thr Pro Lys
                245                 250                 255
Val Thr Cys Val Val Val Asp Ile Ser Lys Asp Asp Pro Glu Val Gln
                260                 265                 270
Phe Ser Trp Phe Val Asp Asp Val Glu Val His Thr Ala Gln Thr Gln
            275                 280                 285
Pro Arg Glu Glu Gln Phe Asn Ser Thr Phe Arg Ser Val Ser Glu Leu
        290                 295                 300
Pro Ile Met His Gln Asp Trp Leu Asn Gly Lys Glu Phe Lys Cys Arg
305                 310                 315                 320
Val Asn Ser Ala Ala Phe Pro Ala Pro Ile Glu Lys Thr Ile Ser Lys
                325                 330                 335
Thr Lys Gly Arg Pro Lys Ala Pro Gln Val Tyr Thr Ile Pro Pro Pro
                340                 345                 350
Lys Glu Gln Met Ala Lys Asp Lys Val Ser Leu Thr Cys Met Ile Thr
            355                 360                 365
Asp Phe Phe Pro Glu Asp Ile Thr Val Glu Trp Gln Trp Asn Gly Gln
        370                 375                 380
Pro Ala Glu Asn Tyr Lys Asn Thr Gln Pro Ile Met Asp Thr Asp Gly
385                 390                 395                 400
Ser Tyr Phe Ile Tyr Ser Lys Leu Asn Val Gln Lys Ser Asn Trp Glu
                405                 410                 415
Ala Gly Asn Thr Phe Thr Cys Ser Val Leu His Glu Gly Leu His Asn
                420                 425                 430
His His Thr Glu Lys Ser Leu Ser His Ser Pro Gly Lys
            435                 440                 445

<210> SEQ ID NO 210
<211> LENGTH: 1335
<212> TYPE: DNA
<213> ORGANISM: Mus musculus

<400> SEQUENCE: 210
gaggtccagc tgcaacaatc tggacctgag ctggtgaagc ctggggcttc agtgaagatg    60
tcctgtaagg cttctggata cacattcact gactactaca tgaactgggt gaagcagagc   120
```

```
catggagaga gccttgagtg gattggagat attaatcctt acaacgatga tactacctac    180
aaccacaagt tcaagggcaa ggccacattg actgtagaca atcctccaa cacagcctac     240 atgcagctca cagcctgac atctgaggac tctgcagtct attactgtgc aagagagacg     300
gccgttatta ctacgaatgc tatggactac tggggtcaag aacctcagt caccgtctcc     360 tcagccaaaa cgacaccccc atctgtctat ccactggccc ctggatctgc tgcccaaact    420
aactccatgg tgaccctggg atgcctggtc aagggctatt ccctgagcc agtgacagtg     480 acctggaact ctggatccct gtccagcggt gtgcacacct cccagctgt cctgcagtct     540 gacctctaca ctctgagcag ctcagtgact gtccectcca gcacctggcc cagcgagacc    600
gtcacctgca acgttgccca cccggccagc agcaccaagg tggacaagaa aattgtgccc    660
agggattgtg ttgtaagcc ttgcatatgt acagtcccag aagtatcatc tgtcttcatc     720
ttccccccaa agcccaagga tgtgctcacc attactctga ctcctaaggt cacgtgtgtt    780
gtggtagaca tcagcaagga tgatcccgag gtccagttca gctggtttgt agatgatgtg    840
gaggtgcaca cagctcagac gcaaccccgg gaggagcagt tcaacagcac tttccgctca    900
gtcagtgaac ttcccatcat gcaccaggac tggctcaatg gcaaggagtt caatgcagg     960 gtcaacagtg cagctttccc tgcccccatc gagaaaacca tctccaaaac caaaggcaga    1020
ccgaaggctc cacaggtgta caccattcca cctcccaagg agcagatggc caaggataaa    1080
gtcagtctga cctgcatgat aacagacttc ttccctgaag acattactgt ggagtggcag    1140
tggaatgggc agccagcgga gaactacaag aacactcagc ccatcatgga cacagatggc    1200
tcttacttca tctacagcaa gctcaatgtg cagaagagca ctgggaggc aggaaatact     1260 ttcacctgct ctgtgttaca tgagggcctg cacaaccacc atactgagaa gagcctctcc    1320
cactctcctg gtaaa                                                    1335
```

<210> SEQ ID NO 211
<211> LENGTH: 464
<212> TYPE: PRT
<213> ORGANISM: Mus musculus

<400> SEQUENCE: 211

```
Met Gly Trp Asn Trp Ile Phe Leu Phe Leu Leu Ser Gly Thr Ala Gly
1               5                   10                  15

Val Tyr Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Asn Trp Val Lys Gln Ser His Gly Glu Ser Leu
    50                  55                  60

Glu Trp Ile Gly Asp Ile Asn Pro Tyr Asn Asp Asp Thr Thr Tyr Asn
65                  70                  75                  80

His Lys Phe Lys Gly Lys Ala Thr Leu Thr Val Asp Lys Ser Ser Asn
                85                  90                  95

Thr Ala Tyr Met Gln Leu Asn Ser Leu Thr Ser Glu Asp Ser Ala Val
            100                 105                 110

Tyr Tyr Cys Ala Arg Glu Thr Ala Val Ile Thr Thr Asn Ala Met Asp
        115                 120                 125

Tyr Trp Gly Gln Gly Thr Ser Val Thr Val Ser Ala Lys Thr Thr
    130                 135                 140

Pro Pro Ser Val Tyr Pro Leu Ala Pro Gly Ser Ala Ala Gln Thr Asn
145                 150                 155                 160
```

```
Ser Met Val Thr Leu Gly Cys Leu Val Lys Gly Tyr Phe Pro Glu Pro
            165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
            195                 200                 205

Thr Val Pro Ser Ser Thr Trp Pro Ser Glu Thr Val Thr Cys Asn Val
            210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Asp Ile Ser Lys Asp Asp Pro
            275                 280                 285

Glu Val Gln Phe Ser Trp Phe Val Asp Asp Val Glu Val His Thr Ala
            290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
            355                 360                 365

Pro Pro Pro Lys Glu Gln Met Ala Lys Asp Lys Val Ser Leu Thr Cys
            370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Ile Tyr Ser Lys Leu Asn Val Gln Lys Ser
            420                 425                 430

Asn Trp Glu Ala Gly Asn Thr Phe Thr Cys Ser Val Leu His Glu Gly
            435                 440                 445

Leu His Asn His His Thr Glu Lys Ser Leu Ser His Ser Pro Gly Lys
450                 455                 460

<210> SEQ ID NO 212
<211> LENGTH: 1392
<212> TYPE: DNA
<213> ORGANISM: Mus musculus

<400> SEQUENCE: 212
atgggatgga actggatctt tctcttcctc ttgtcaggaa ctgcaggtgt ctactctgag      60
gtccagctgc aacaatctgg acctgagctg gtgaagcctg ggcttcagt gaagatgtcc     120 tgtaaggctt ctggatacac attcactgac tactacatga actgggtgaa gcagagccat     180
ggagagagcc ttagtggat tggagatatt aatccttaca cgatgatac tacctacaac     240 cacaagttca gggcaaggc acattgact gtagacaaat cctccaacac agcctacatg     300
cagctcaaca gcctgacatc tgaggactct gcagtctatt actgtgcaag agagacggcc     360
gttattacta cgaatgctat ggactactgg ggtcaaggaa cctcagtcac cgtctcctca     420
gccaaaacga caccccatc tgtctatcca ctggcccctg gatctgctgc ccaaactaac     480
```

```
tccatggtga ccctgggatg cctggtcaag ggctatttcc ctgagccagt gacagtgacc    540
tggaactctg gatccctgtc cagcggtgtg cacaccttcc cagctgtcct gcagtctgac    600
ctctacactc tgagcagctc agtgactgtc ccctccagca cctggcccag cgagaccgtc    660
acctgcaacg ttgcccaccc ggccagcagc accaaggtgg acaagaaaat tgtgcccagg    720
gattgtggtt gtaagccttg catatgtaca gtcccagaag tatcatctgt cttcatcttc    780
cccccaaagc ccaaggatgt gctcaccatt actctgactc ctaaggtcac gtgtgttgtg    840
gtagacatca gcaaggatga tcccgaggtc cagttcagct ggtttgtaga tgatgtggag    900
gtgcacacag ctcagacgca accccgggag gagcagttca cagcacttt ccgctcagtc     960 agtgaacttc ccatcatgca ccaggactgg ctcaatggca aggagttcaa atgcagggtc   1020
aacagtgcag ctttccctgc ccccatcgag aaaaccatct ccaaaaccaa aggcagaccg   1080
aaggctccac aggtgtacac cattccacct cccaaggagc agatggccaa ggataaagtc   1140
agtctgacct gcatgataac agacttcttc cctgaagaca ttactgtgga gtggcagtgg   1200
aatgggcagc cagcggagaa ctacaagaac actcagccca tcatggacac agatggctct   1260
tacttcatct acagcaagct caatgtgcag aagagcaact gggaggcagg aaatactttc   1320
acctgctctg tgttacatga gggcctgcac aaccaccata ctgagaagag cctctcccac   1380
tctcctggta aa                                                       1392
```

<210> SEQ ID NO 213
<211> LENGTH: 215
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 213

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Thr Ser Ser
            20                  25                  30

Tyr Leu Asn Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Tyr Asp Phe Phe Pro
                85                  90                  95

Ser Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
```

180                 185                 190
Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 214
<211> LENGTH: 645
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 214
gacatccagc tgacccagag ccccagcttc ctttccgcat ccgttggtga ccgagtaaca      60
atcacatgcc gcgcctcatc ttcagttaca tcttcttatc ttaattggta tcaacaaaaa     120
ccaggaaaag cacctaaact tcttatatac tctacatcta atctcgcatc aggagttccc     180
tctcgatttt caggatctgg atcaggcaca gaatttacac ttactatatc atcactccaa     240
ccagaagact tcgccactta ttactgccaa caatacgatt ttttccaag cacattcgga      300 ggaggtacaa agtagaaat caagcgtacg gtggctgcac catctgtctt catcttcccg      360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcacccTG     540
acgctgagca agcagacta cgagaaacac aaagtctacg cctgcgaagt cacccatcag     600
ggcctgagct cgcccgtcac aaagagcttc aacaggggag agtgt                    645

<210> SEQ ID NO 215
<211> LENGTH: 237
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 215

Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Phe
            20                  25                  30

Leu Ser Ala Ser Val Gly Asp Arg Val Thr Ile Thr Cys Arg Ala Ser
        35                  40                  45

Ser Ser Val Thr Ser Ser Tyr Leu Asn Trp Tyr Gln Gln Lys Pro Gly
    50                  55                  60

Lys Ala Pro Lys Leu Leu Ile Tyr Ser Thr Ser Asn Leu Ala Ser Gly
65                  70                  75                  80

Val Pro Ser Arg Phe Ser Gly Ser Gly Ser Gly Thr Glu Phe Thr Leu
                85                  90                  95

Thr Ile Ser Ser Leu Gln Pro Glu Asp Phe Ala Thr Tyr Tyr Cys Gln
            100                 105                 110

Gln Tyr Asp Phe Phe Pro Ser Thr Phe Gly Gly Gly Thr Lys Val Glu
        115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 216
<211> LENGTH: 711
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 216
atggacatga gggtccccgc tcagctcctg gggctcctgc tactctggct cccaggtgcc      60
agatgtgaca tccagctgac ccagagcccc agcttccttt ccgcatccgt tggtgaccga     120
gtaacaatca catgccgcgc ctcatcttca gttacatctt cttatcttaa ttggtatcaa     180
caaaaaccag gaaaagcacc taaacttctt atatactcta catctaatct cgcatcagga     240
gttccctctc gattttcagg atctggatca ggcacagaat ttacacttac tatatcatca     300
ctccaaccag aagacttcgc cacttattac tgccaacaat acgatttttt tccaagcaca     360
ttcggaggag gtacaaaagt agaaatcaag cgtacggtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg t              711

<210> SEQ ID NO 217
<211> LENGTH: 447
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 217

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Arg Leu Glu Trp Met
        35                  40                  45

```
Gly Asp Ile Asn Pro Tyr Asn Asp Asp Thr Thr Tyr Asn His Lys Phe
 50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Thr Ala Val Ile Thr Thr Asn Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 218
<211> LENGTH: 1341
<212> TYPE: DNA
<213> ORGANISM: Artificial Sequence
```

```
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 218
gaggtgcagc tggtgcagag cggcgccgag gtcaagaaac ctggagcaag cgtaaaggtt      60
agttgcaaag catctggata cacatttacc gactactaca tgaattgggt acgacaagcc     120
cctggacaaa gacttgaatg gatgggagac attaacc ctt ataacgacga cactacatac     180
aatcataaat ttaaaggaag agttacaatt acaagagata catccgcatc aaccgcctat     240
atggaacttt cctcattgag atctgaagac actgctgttt attactgtgc aagagaaact     300
gccgttatta ctactaacgc tatggattac tggggtcaag gaaccactgt taccgtctct     360
agtgcctcca ccaagggccc atcggtcttc cccctggcgc cctgctccag gagcacctcc     420
gagagcacag cggccctggg ctgcctggtc aaggactact cccccgaacc ggtgacggtg     480
tcgtggaact caggcgctct gaccagcggc gtgcacacct cccagctgt cctacagtcc     540
tcaggactct actccctcag cagcgtggtg accgtgccct ccagcaactt cggcacccag     600
acctacacct gcaacgtaga tcacaagccc agcaacacca aggtggacaa gacagttgag     660
cgcaaatgtt gtgtcgagtg cccaccgtgc ccagcaccac ctgtggcagg accgtcagtc     720
ttcctcttcc cccccaaaacc caaggacacc ctcatgatct cccggacccc tgaggtcacg     780
tgcgtggtgg tggacgtgag ccacgaagac cccgaggtcc agttcaactg gtacgtggac     840
ggcgtggagg tgcataatgc caagacaaag ccacgggagg agcagttcaa cagcacgttc     900
cgtgtggtca gcgtcctcac cgttgtgcac caggactggc tgaacggcaa ggagtacaag     960
tgcaaggtct ccaacaaagg cctcccagcc cccatcgaga aaaccatctc caaaaccaaa    1020
gggcagcccc gagaaccaca ggtgtacacc ctgcccccat cccgggagga gatgaccaag    1080
aaccaggtca gcctgacctg cctggtcaaa ggcttctacc ccagcgacat cgccgtggag    1140
tgggagagca atgggcagcc ggagaacaac tacaagacca cacctcccat gctggactcc    1200
gacggctcct tcttcctcta cagcaagctc accgtggaca gagcaggtg gcagcagggg    1260
aacgtcttct catgctccgt gatgcatgag gctctgcaca accactacac gcagaagagc    1320
ctctcccctgt ctccgggtaa a                                              1341

<210> SEQ ID NO 219
<211> LENGTH: 466
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 219

Met Asp Trp Thr Trp Arg Ile Leu Phe Leu Val Ala Ala Ala Thr Gly
1               5                   10                  15

Ala His Ser Glu Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asp Tyr Tyr Met Asn Trp Val Arg Gln Ala Pro Gly Gln Arg Leu
        50                  55                  60

Glu Trp Met Gly Asp Ile Asn Pro Tyr Asn Asp Asp Thr Thr Tyr Asn
```

```
                65                  70                  75                  80
            His Lys Phe Lys Gly Arg Val Thr Ile Thr Arg Asp Thr Ser Ala Ser
                            85                  90                  95

Thr Ala Tyr Met Glu Leu Ser Ser Leu Arg Ser Glu Asp Thr Ala Val
                        100                 105                 110

Tyr Tyr Cys Ala Arg Glu Thr Ala Val Ile Thr Thr Asn Ala Met Asp
                        115                 120                 125

Tyr Trp Gly Gln Gly Thr Thr Val Thr Val Ser Ala Ser Thr Lys
                130                 135                 140

Gly Pro Ser Val Phe Pro Leu Ala Pro Cys Ser Arg Ser Thr Ser Glu
            145                 150                 155                 160

Ser Thr Ala Ala Leu Gly Cys Leu Val Lys Asp Tyr Phe Pro Glu Pro
                            165                 170                 175

Val Thr Val Ser Trp Asn Ser Gly Ala Leu Thr Ser Gly Val His Thr
                        180                 185                 190

Phe Pro Ala Val Leu Gln Ser Ser Gly Leu Tyr Ser Leu Ser Ser Val
                        195                 200                 205

Val Thr Val Pro Ser Ser Asn Phe Gly Thr Gln Thr Tyr Thr Cys Asn
            210                 215                 220

Val Asp His Lys Pro Ser Asn Thr Lys Val Asp Lys Thr Val Glu Arg
            225                 230                 235                 240

Lys Cys Cys Val Glu Cys Pro Pro Cys Pro Ala Pro Val Ala Gly
                            245                 250                 255

Pro Ser Val Phe Leu Phe Pro Pro Lys Pro Lys Asp Thr Leu Met Ile
                        260                 265                 270

Ser Arg Thr Pro Glu Val Thr Cys Val Val Val Asp Val Ser His Glu
                        275                 280                 285

Asp Pro Glu Val Gln Phe Asn Trp Tyr Val Asp Gly Val Glu Val His
                290                 295                 300

Asn Ala Lys Thr Lys Pro Arg Glu Glu Gln Phe Asn Ser Thr Phe Arg
            305                 310                 315                 320

Val Val Ser Val Leu Thr Val Val His Gln Asp Trp Leu Asn Gly Lys
                            325                 330                 335

Glu Tyr Lys Cys Lys Val Ser Asn Lys Gly Leu Pro Ala Pro Ile Glu
                        340                 345                 350

Lys Thr Ile Ser Lys Thr Lys Gly Gln Pro Arg Glu Pro Gln Val Tyr
                        355                 360                 365

Thr Leu Pro Pro Ser Arg Glu Glu Met Thr Lys Asn Gln Val Ser Leu
                    370                 375                 380

Thr Cys Leu Val Lys Gly Phe Tyr Pro Ser Asp Ile Ala Val Glu Trp
            385                 390                 395                 400

Glu Ser Asn Gly Gln Pro Glu Asn Asn Tyr Lys Thr Thr Pro Pro Met
                            405                 410                 415

Leu Asp Ser Asp Gly Ser Phe Phe Leu Tyr Ser Lys Leu Thr Val Asp
                        420                 425                 430

Lys Ser Arg Trp Gln Gln Gly Asn Val Phe Ser Cys Ser Val Met His
                        435                 440                 445

Glu Ala Leu His Asn His Tyr Thr Gln Lys Ser Leu Ser Leu Ser Pro
                450                 455                 460

Gly Lys
            465

<210> SEQ ID NO 220
<211> LENGTH: 1398
```

<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 220

```
atggactgga cctggaggat cctcttcttg gtggcagcag ccacaggagc ccactccgag    60
gtgcagctgg tgcagagcgg cgccgaggtc aagaaacctg agcaagcgt aaaggttagt   120
tgcaaagcat ctggatacac atttaccgac tactacatga attgggtacg acaagccct   180
ggacaaagac ttgaatggat gggagacatt aacccttata cgacgacac tacatacaat   240
cataaattta aggaagagt acaattaca agagatacat ccgcatcaac cgcctatatg   300
gaactttcct cattgagatc tgaagacact gctgtttatt actgtgcaag agaaactgcc   360
gttattacta ctaacgctat ggattactgg ggtcaaggaa ccactgttac cgtctctagt   420
gcctccacca agggcccatc ggtcttcccc ctggcgccct gctccaggag cacctccgag   480
agcacagcgg ccctgggctg cctggtcaag gactacttcc ccgaaccggt gacggtgtcg   540
tggaactcag gcgctctgac cagcggcgtg cacaccttcc cagctgtcct acagtcctca   600
ggactctact ccctcagcag cgtggtgacc gtgccctcca gcaacttcgg cacccagacc   660
tacacctgca acgtagatca caagcccagc aacaccaagg tggacaagac agttgagcgc   720
aaatgttgtg tcgagtgccc accgtgccca gcaccacctg tggcaggacc gtcagtcttc   780
ctcttccccc caaaacccaa ggacaccctc atgatctccc ggacccctga ggtcacgtgc   840
gtggtggtgg acgtgagcca cgaagacccc gaggtccagt tcaactggta cgtggacggc   900
gtggaggtgc ataatgccaa gacaaagcca cgggaggagc agttcaacag cacgttccgt   960
gtggtcagcg tcctcaccgt tgtgcaccag gactggctga acggcaagga gtacaagtgc  1020
aaggtctcca acaaaggcct cccagccccc atcgagaaaa ccatctccaa aaccaaaggg  1080
cagccccgag aaccacaggt gtacaccctg cccccatccc gggaggagat gaccaagaac  1140
caggtcagc tgacctgcct ggtcaaaggc ttctacccca gcgacatcgc cgtggagtgg  1200
gagagcaatg ggcagccgga gaacaactac aagaccacac ctcccatgct ggactccgac  1260
ggctccttct cctctacag caagctcacc gtggacaaga gcaggtggca gcagggaac   1320
gtcttctcat gctccgtgat gcatgaggct ctgcacaacc actacacgca gaagagcctc  1380
tccctgtctc cgggtaaa                                               1398
```

<210> SEQ ID NO 221
<211> LENGTH: 215
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 221

```
Asp Ile Gln Met Thr Gln Ser Pro Ser Ser Leu Ser Ala Ser Val Gly
1               5                   10                  15

Asp Arg Val Thr Ile Thr Cys Ser Val Ser Ser Thr Ile Ser Ser Asn
            20                  25                  30

His Leu His Trp Phe Gln Gln Lys Pro Gly Lys Ala Pro Lys Ser Leu
        35                  40                  45
```

```
Ile Tyr Gly Thr Ser Asn Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Trp Ser Ser Tyr Pro
                 85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 222
<211> LENGTH: 645
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 222
gacatccaga tgacccagtc tccatcctcc ctctcagcat ccgtaggcga tagagttaca    60
ataacatgca gcgtatcatc aactatatca tcaaatcatc ttcattggtt ccaacagaaa   120
cccggcaaag cacctaaatc acttatatac ggcacatcaa atctcgcatc aggcgttcct   180
tcaagatttt caggctctgg ctcaggcacc gactttactc ttacaatatc ctccctccaa   240
cccgaagact tcgcaaccta ttactgtcaa caatggtcct catatccact cacatttggc   300
ggcggcacaa aagtagaaat taaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgt              645

<210> SEQ ID NO 223
<211> LENGTH: 237
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 223
```

```
Met Asp Met Arg Val Pro Ala Gln Leu Leu Gly Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Ser Val Ser
        35                  40                  45

Ser Thr Ile Ser Ser Asn His Leu His Trp Phe Gln Gln Lys Pro Gly
    50                  55                  60

Lys Ala Pro Lys Ser Leu Ile Tyr Gly Thr Ser Asn Leu Ala Ser Gly
65              70                  75                  80

Val Pro Ser Arg Phe Ser Gly Ser Gly Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln Trp Ser Ser Tyr Pro Leu Thr Phe Gly Gly Gly Thr Lys Val Glu
        115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
210                 215                 220

Ser Ser Pro Val Thr Lys Ser Phe Asn Arg Gly Glu Cys
225                 230                 235
```

<210> SEQ ID NO 224
<211> LENGTH: 711
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 224
atggacatga gggtccccgc tcagctcctg gggctcctgc tactctggct ccgaggtgcc      60
agatgtgaca tccagatgac ccagtctcca tcctccctct cagcatccgt aggcgataga     120
gttacaataa catgcagcgt atcatcaact atatcatcaa atcatcttca ttggttccaa     180
cagaaacccg gcaaagcacc taatcacttt atatacggca tcaaatctcg catcaggc      240 gttccttcaa gattttcagg ctctggctca ggcaccgact ttactcttac aatatcctcc     300
ctccaacccg aagacttcgc aacctattac tgtcaacaat ggtcctcata tccactcaca     360
tttggcggcg gcacaaaagt agaaattaaa cgtacggtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660

```
catcagggcc tgagctcgcc cgtcacaaag agcttcaaca ggggagagtg t        711
```

<210> SEQ ID NO 225
<211> LENGTH: 451
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 225

```
Glu Val Gln Leu Val Gln Ser Gly Ala Glu Val Lys Lys Pro Gly Ala
1               5                   10                  15

Ser Val Lys Val Ser Cys Lys Ala Ser Asp Phe Asn Ile Lys Asp Phe
            20                  25                  30

Tyr Leu His Trp Val Arg Gln Ala Pro Gly Gln Gly Leu Glu Trp Ile
        35                  40                  45

Gly Arg Ile Asp Pro Glu Asn Gly Asp Thr Leu Tyr Asp Pro Lys Phe
    50                  55                  60

Gln Asp Lys Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Asp Tyr Phe His Asp Gly Thr Ser Tyr Trp Tyr Phe
            100                 105                 110

Asp Val Trp Gly Arg Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
```

```
                340             345             350
Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450

<210> SEQ ID NO 226
<211> LENGTH: 1353
<212> TYPE: DNA
<213> ORGANISM: Artificial Sequence
<220> FEATURE:
<223> OTHER INFORMATION: Synthetic Polynucleotide

<400> SEQUENCE: 226
gaggtgcagc tggtgcagtc tggggctgag gtgaagaagc ctggggcctc agtgaaggtc      60
tcctgcaagg cttctgactt caacattaaa gacttctatc tacactgggt gcgacaggcc     120
cctggacaag gcttgagtg gattggaagg attgatcctg agaatggtga tactttatat     180
gacccgaagt tccaggacaa ggtcaccatg accacagaca cgtccaccag cacagcctac     240
atggagctga ggagcctgag atctgacgac acggccgtgt attactgtgc gagagaggcg     300
gattatttcc acgatggtac ctcctactgg tacttcgatg tctggggccg tggcaccctg     360
gtcaccgtct ctagtgcctc caccaagggc ccatcggtct tccccctggc gccctgctcc     420
aggagcacct ccgagagcac agcggccctg ggctgcctgg tcaaggacta cttccccgaa     480
ccggtgacgg tgtcgtggaa ctcaggcgct ctgaccagcg gcgtgcacac cttcccagct     540
gtcctacagt cctcaggact ctactccctc agcagcgtgg tgaccgtgcc ctccagcaac     600
ttcggcaccc agacctacac ctgcaacgta gatcacaagc ccagcaacac caaggtggac     660
aagacagttg agcgcaaatg ttgtgtcgag tgcccaccgt gcccagcacc acctgtggca     720
ggaccgtcag tcttcctctt cccccaaaa cccaaggaca cctcatgat ctcccggacc      780
cctgaggtca cgtgcgtggt ggtggacgtg agccacgaag accccgaggt ccagttcaac     840
tggtacgtgg acggcgtgga ggtgcataat gccaagacaa agccacggga ggagcagttc     900
aacagcacgt tccgtgtggt cagcgtcctc accgttgtgc accaggactg gctgaacggc     960
aaggagtaca agtgcaaggt ctccaacaaa ggcctcccag cccccatcga gaaaaccatc    1020
tccaaaacca agggcagcc cgagaacca caggtgtaca ccctgcccc atcccgggag      1080
gagatgacca gaaccaggt cagcctgacc tgcctggtca aaggcttcta ccccagcgac    1140
atcgccgtgg agtgggagag caatgggcag ccggagaaca actacaagac cacacctccc    1200
atgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                 1353
```

<210> SEQ ID NO 227
<211> LENGTH: 470
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 227

```
Met Asp Trp Thr Trp Arg Ile Leu Phe Leu Val Ala Ala Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Asp Phe Asn Ile
        35                  40                  45

Lys Asp Phe Tyr Leu His Trp Val Arg Gln Ala Pro Gly Gln Gly Leu
    50                  55                  60

Glu Trp Ile Gly Arg Ile Asp Pro Glu Asn Gly Asp Thr Leu Tyr Asp
65                  70                  75                  80

Pro Lys Phe Gln Asp Lys Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Glu Ala Asp Tyr Phe His Asp Gly Thr Ser Tyr
        115                 120                 125

Trp Tyr Phe Asp Val Trp Gly Arg Gly Thr Leu Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365
```

```
Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 228
<211> LENGTH: 1410
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 228
```

| | | |
|---|---|---|
| atggactgga cctggaggat cctcttcttg gtggcagcag ccacaggagc ccactccgag | 60 |
| gtgcagctgg tgcagtctgg ggctgaggtg aagaagcctg ggcctcagt gaaggtctcc | 120 |
| tgcaaggctt ctgacttcaa cattaaagac ttctatctac actgggtgcg acaggcccct | 180 |
| ggacaaggc ttgagtggat tggaaggatt gatcctgaga atggtgatac tttatatgac | 240 |
| ccgaagttcc aggacaaggt caccatgacc acagacacgt ccaccagcac agcctacatg | 300 |
| gagctgagga gcctgagatc tgacgacacg gccgtgtatt actgtgcgag agaggcggat | 360 |
| tatttccacg atggtaccct ctactggtac ttcgatgtct ggggccgtgg caccctggtc | 420 |
| accgtctcta gtgcctccac caagggccca tcggtcttcc cctggcgcc ctgctccagg | 480 |
| agcacctccg agagcacagc ggccctgggc tgcctggtca aggactactt ccccgaaccg | 540 |
| gtgacggtgt cgtggaactc aggcgctctg accagcggcg tgcacacctt cccagctgtc | 600 |
| ctacagtcct caggactcta ctccctcagc agcgtggtga ccgtgccctc agcaacttc | 660 |
| ggcacccaga cctacacctg caacgtagat cacaagccca gcaacaccaa ggtggacaag | 720 |
| acagttgagc gcaaatgttg tgtcgagtgc ccaccgtgcc cagcaccacc tgtggcagga | 780 |
| ccgtcagtct tcctcttccc cccaaaaccc aaggacaccc tcatgatctc ccggaccct | 840 |
| gaggtcacgt gcgtggtggt ggacgtgagc cacgaagacc ccgaggtcca gttcaactgg | 900 |
| tacgtggacg gcgtggaggt gcataatgcc aagacaaagc cacgggagga gcagttcaac | 960 |
| agcacgttcc gtgtggtcag cgtcctcacc gttgtgcacc aggactggct gaacggcaag | 1020 |
| gagtacaagt gcaaggtctc caacaaaggc ctcccagccc ccatcgagaa aaccatctcc | 1080 |
| aaaaccaaag gcagccccg agaaccacag gtgtacaccc tgcccccatc ccgggaggag | 1140 |
| atgaccaaga accaggtcag cctgacctgc ctggtcaaag gcttctaccc cagcgacatc | 1200 |
| gccgtggagt gggagagcaa tgggcagccg gagaacaact acaagaccac acctcccatg | 1260 |
| ctggactccg acggctcctt cttcctctac agcaagctca ccgtggacaa gagcaggtgg | 1320 |
| cagcagggga acgtcttctc atgctccgtg atgcatgagg ctctgcacaa ccactacacg | 1380 |

```
cagaagagcc tctccctgtc tccgggtaaa                                    1410
```

<210> SEQ ID NO 229
<211> LENGTH: 213
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 229

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Ile Ser Tyr Ile
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asp Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 230
<211> LENGTH: 639
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 230

```
gacatccagt tgacccagtc tccatccttc ctgtctgcat ctgtaggaga cagagtcacc      60
atcacttgca gggccagctc aagtataagt tacatacact ggtatcagca aaaaccaggg     120
aaagccccta agctcctgat ctatgccaca tccaacctgg cttctggggt cccatcaagg     180
ttcagcggca gtggatctgg gacagaattc actctcacaa tcagcagcct gcagcctgaa     240
gattttgcaa cttattactg tcagcagtgg agtagtgacc cactcacgtt cggcggaggg     300
```

```
accaaggtgg agatcaaacg tacggtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag     480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgt                           639
```

<210> SEQ ID NO 231
<211> LENGTH: 235
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 231

```
Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Phe
            20                  25                  30

Leu Ser Ala Ser Val Gly Asp Arg Val Thr Ile Thr Cys Arg Ala Ser
        35                  40                  45

Ser Ser Ile Ser Tyr Ile His Trp Tyr Gln Gln Lys Pro Gly Lys Ala
    50                  55                  60

Pro Lys Leu Leu Ile Tyr Ala Thr Ser Asn Leu Ala Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Glu Asp Phe Ala Thr Tyr Tyr Cys Gln Gln Trp
            100                 105                 110

Ser Ser Asp Pro Leu Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 232
<211> LENGTH: 705
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 232

```
atggacatga gggtccccgc tcagctcctg gggctcctgc tgctctggct cccaggtgcc      60
agatgtgaca tccagttgac ccagtctcca tccttcctgt ctgcatctgt aggagacaga     120
gtcaccatca cttgcagggc cagctcaagt ataagttaca tacactggta tcagcaaaaa     180
ccagggaaag cccctaagct cctgatctat gccacatcca acctggcttc tggggtccca     240
tcaaggttca gcggcagtgg atctgggaca gaattcactc tcacaatcag cagcctgcag     300
cctgaagatt ttgcaactta ttactgtcag cagtggagta gtgacccact cacgttcggc     360
ggagggacca aggtggagat caaacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
ggcctgagct cgcccgtcac aaagagcttc aacaggggag agtgt                     705
```

<210> SEQ ID NO 233
<211> LENGTH: 447
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 233

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Lys Asp Tyr
            20                  25                  30

Tyr Ile His Trp Val Arg Gln Ala Pro Gly Gln Gly Leu Glu Trp Ile
        35                  40                  45

Gly Arg Val Asp Pro Asp Asn Gly Glu Thr Glu Phe Ala Pro Lys Phe
    50                  55                  60

Pro Gly Lys Val Thr Met Thr Thr Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Asp Tyr Asp Gly Thr Tyr Thr Trp Phe Pro Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

```
Lys Pro Ser Asn Thr Lys Val Asp Lys Thr Val Glu Arg Lys Cys Cys
    210                 215                 220

Val Glu Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
    435                 440                 445

<210> SEQ ID NO 234
<211> LENGTH: 1341
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 234
gaggtgcagc tggtgcagtc tggggctgag gtgaagaagc ctggggcctc agtgaaggtc      60
tcctgcaagg cttctggatt cgacattaag gactactata tacactgggt gcgacaggcc     120
cctggacaag ggcttgagtg gatcggaagg gttgatcctg acaatggtga gactgaattt     180
gccccgaagt tccgggcaa ggtcaccatg accacagaca cgtccatcag cacagcctac     240
atggagctga gcaggctgag atctgacgac acggccgtgt attactgtgc gagagaagac     300
tacgatggta cctacacctg gtttccttat tggggccaag ggactctggt caccgtctct     360
agtgcctcca ccaagggccc atcggtcttc cccctggcgc cctgctccag gagcacctcc     420
gagagcacag cggccctggg ctgcctggtc aaggactact tccccgaacc ggtgacggtg     480
tcgtggaact caggcgctct gaccagcggc gtgcacacct tcccagctgt cctacagtcc     540
tcaggactct actccctcag cagcgtggtg accgtgccct ccagcaactt cggcacccag     600
acctacacct gcaacgtaga tcacaagccc agcaacacca aggtggacaa gacagttgag     660
```

```
cgcaaatgtt gtgtcgagtg cccaccgtgc ccagcaccac ctgtggcagg accgtcagtc      720
ttcctcttcc ccccaaaacc caaggacacc ctcatgatct cccggacccc tgaggtcacg      780
tgcgtggtgg tggacgtgag ccacgaagac cccgaggtcc agttcaactg gtacgtggac      840
ggcgtggagg tgcataatgc caagacaaag ccacgggagg agcagttcaa cagcacgttc      900
cgtgtggtca gcgtcctcac cgttgtgcac caggactggc tgaacggcaa ggagtacaag      960
tgcaaggtct ccaacaaagg cctcccagcc cccatcgaga aaaccatctc caaaaccaaa     1020
gggcagcccc gagaaccaca ggtgtacacc ctgcccccat cccgggagga tgaccaag       1080 aaccaggtca gcctgacctg cctggtcaaa ggcttctacc ccagcgacat cgccgtggag     1140
tgggagagca atgggcagcc ggagaacaac tacaagacca cacctcccat gctggactcc     1200
gacggctcct tcttcctcta cagcaagctc accgtggaca gagcaggtg gcagcagggg     1260 aacgtcttct catgctccgt gatgcatgag gctctgcaca accactacac gcagaagagc     1320 ctctcccctgt ctccgggtaa a                                              1341
```

<210> SEQ ID NO 235
<211> LENGTH: 466
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 235

```
Met Asp Trp Thr Trp Arg Ile Leu Phe Leu Val Ala Ala Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Phe Asp Ile
        35                  40                  45

Lys Asp Tyr Tyr Ile His Trp Val Arg Gln Ala Pro Gly Gln Gly Leu
    50                  55                  60

Glu Trp Ile Gly Arg Val Asp Pro Asp Asn Gly Glu Thr Glu Phe Ala
65                  70                  75                  80

Pro Lys Phe Pro Gly Lys Val Thr Met Thr Thr Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Glu Asp Tyr Asp Gly Thr Tyr Thr Trp Phe Pro
        115                 120                 125

Tyr Trp Gly Gln Gly Thr Leu Val Thr Val Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
```

```
                225                 230                 235                 240
Lys Cys Cys Val Glu Cys Pro Pro Cys Pro Ala Pro Val Ala Gly
                245                 250                 255
Pro Ser Val Phe Leu Phe Pro Pro Lys Pro Lys Asp Thr Leu Met Ile
                260                 265                 270
Ser Arg Thr Pro Glu Val Thr Cys Val Val Val Asp Val Ser His Glu
                275                 280                 285
Asp Pro Glu Val Gln Phe Asn Trp Tyr Val Asp Gly Val Glu Val His
                290                 295                 300
Asn Ala Lys Thr Lys Pro Arg Glu Glu Gln Phe Asn Ser Thr Phe Arg
305                 310                 315                 320
Val Val Ser Val Leu Thr Val Val His Gln Asp Trp Leu Asn Gly Lys
                325                 330                 335
Glu Tyr Lys Cys Lys Val Ser Asn Lys Gly Leu Pro Ala Pro Ile Glu
                340                 345                 350
Lys Thr Ile Ser Lys Thr Lys Gly Gln Pro Arg Glu Pro Gln Val Tyr
                355                 360                 365
Thr Leu Pro Pro Ser Arg Glu Glu Met Thr Lys Asn Gln Val Ser Leu
                370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Met
                405                 410                 415
Leu Asp Ser Asp Gly Ser Phe Phe Leu Tyr Ser Lys Leu Thr Val Asp
                420                 425                 430
Lys Ser Arg Trp Gln Gln Gly Asn Val Phe Ser Cys Ser Val Met His
                435                 440                 445
Glu Ala Leu His Asn His Tyr Thr Gln Lys Ser Leu Ser Leu Ser Pro
                450                 455                 460
Gly Lys
465

<210> SEQ ID NO 236
<211> LENGTH: 1398
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 236
atggactgga cctggaggat cctcttcttg gtggcagcag ccacaggagc ccactccgag      60
gtgcagctgg tgcagtctgg ggctgaggtg aagaagcctg gggcctcagt gaaggtctcc     120
tgcaaggctt ctggattcga cattaaggac tactatatac actgggtgcg acaggcccct     180
ggacaagggc ttgagtggat cggaaggggtt gatcctgaca atggtgagac tgaatttgcc    240
ccgaagttcc cgggcaaggt caccatgacc acagacacgt ccatcagcac agcctacatg     300
gagctgagca ggctgagatc tgacgacacg gccgtgtatt actgtgcgag agaagactac     360
gatggtacct acacctggtt tccttattgg ggccaaggga ctctggtcac cgtctctagt     420
gcctccacca agggcccatc ggtcttcccc ctggcgccct gctccaggag cacctccgag     480
agcacagcgg ccctgggctg cctggtcaag gactacttcc ccgaaccggt gacggtgtcg     540
tggaactcag gcgctctgac cagcggcgtg cacaccttcc cagctgtcct acagtcctca     600
```

```
ggactctact ccctcagcag cgtggtgacc gtgccctcca gcaacttcgg cacccagacc    660
tacacctgca acgtagatca caagcccagc aacaccaagg tggacaagac agttgagcgc    720
aaatgttgtg tcgagtgccc accgtgccca gcaccacctg tggcaggacc gtcagtcttc    780
ctcttccccc caaaacccaa ggacaccctc atgatctccc ggacccctga ggtcacgtgc    840
gtggtggtgg acgtgagcca cgaagacccc gaggtccagt tcaactggta cgtggacggc    900
gtggaggtgc ataatgccaa gacaaagcca cgggaggagc agttcaacag cacgttccgt    960
gtggtcagcg tcctcaccgt tgtgcaccag gactggctga acggcaagga gtacaagtgc   1020
aaggtctcca acaaaggcct cccagccccc atcgagaaaa ccatctccaa aaccaaaggg   1080
cagccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
gagagcaatg ggcagccgga gaacaactac aagaccacac ctcccatgct ggactccgac   1260
ggctccttct cctctacag  caagctcacc gtggacaaga gcaggtggca gcaggggaac   1320
gtcttctcat gctccgtgat gcatgaggct ctgcacaacc actacacgca gaagagcctc   1380
tccctgtctc cgggtaaa                                                 1398
```

<210> SEQ ID NO 237
<211> LENGTH: 7
<212> TYPE: PRT
<213> ORGANISM: Mus musculus

<400> SEQUENCE: 237

Gly Thr Ser Asn Leu Ala Ser
1               5

<210> SEQ ID NO 238
<211> LENGTH: 8
<212> TYPE: PRT
<213> ORGANISM: Mus musculus

<400> SEQUENCE: 238

Gln Gln Trp Thr Thr Thr Tyr Thr
1               5

<210> SEQ ID NO 239
<211> LENGTH: 11
<212> TYPE: PRT
<213> ORGANISM: Mus musculus

<400> SEQUENCE: 239

Arg Ala Ser Gln Asp Ile Ser Ser Tyr Leu Asn
1               5                   10

<210> SEQ ID NO 240
<211> LENGTH: 7
<212> TYPE: PRT
<213> ORGANISM: Mus musculus

<400> SEQUENCE: 240

Ser Thr Ser Arg Leu Asn Ser
1               5

<210> SEQ ID NO 241
<211> LENGTH: 8
<212> TYPE: PRT
<213> ORGANISM: Mus musculus

<400> SEQUENCE: 241

Gln Gln Asp Ile Lys His Pro Thr
1               5

<210> SEQ ID NO 242
<211> LENGTH: 11
<212> TYPE: PRT
<213> ORGANISM: Mus musculus

<400> SEQUENCE: 242

Lys Ala Ser Gln Asp Val Phe Thr Ala Val Ala
1               5                   10

<210> SEQ ID NO 243
<211> LENGTH: 7
<212> TYPE: PRT
<213> ORGANISM: Mus musculus

<400> SEQUENCE: 243

Trp Ala Ser Thr Arg His Thr
1               5

<210> SEQ ID NO 244
<211> LENGTH: 9
<212> TYPE: PRT
<213> ORGANISM: Mus musculus

<400> SEQUENCE: 244

Gln Gln Tyr Ser Ser Tyr Pro Leu Thr
1               5

<210> SEQ ID NO 245
<211> LENGTH: 5
<212> TYPE: PRT
<213> ORGANISM: Mus musculus

<400> SEQUENCE: 245

Asp Tyr Asn Met His
1               5

<210> SEQ ID NO 246
<211> LENGTH: 17
<212> TYPE: PRT
<213> ORGANISM: Mus musculus

<400> SEQUENCE: 246

Glu Ile Asn Pro Asn Ser Gly Gly Ala Gly Tyr Asn Gln Lys Phe Lys
1               5                   10                  15

Gly

<210> SEQ ID NO 247
<211> LENGTH: 14
<212> TYPE: PRT
<213> ORGANISM: Mus musculus

<400> SEQUENCE: 247

Leu Gly Tyr Asp Asp Ile Tyr Asp Asp Trp Tyr Phe Asp Val
1               5                   10

<210> SEQ ID NO 248
<211> LENGTH: 5
<212> TYPE: PRT
<213> ORGANISM: Mus musculus

<400> SEQUENCE: 248

Asp Tyr Asn Met His

<210> SEQ ID NO 249
<211> LENGTH: 17
<212> TYPE: PRT
<213> ORGANISM: Mus musculus

<400> SEQUENCE: 249

Glu Ile Asn Pro Asn Ser Gly Gly Ser Gly Tyr Asn Gln Lys Phe Lys
1               5                   10                  15

Gly

<210> SEQ ID NO 250
<211> LENGTH: 14
<212> TYPE: PRT
<213> ORGANISM: Mus musculus

<400> SEQUENCE: 250

Leu Val Tyr Asp Gly Ser Tyr Glu Asp Trp Tyr Phe Asp Val
1               5                   10

<210> SEQ ID NO 251
<211> LENGTH: 5
<212> TYPE: PRT
<213> ORGANISM: Mus musculus

<400> SEQUENCE: 251

Asp Tyr Asn Met His
1               5

<210> SEQ ID NO 252
<211> LENGTH: 17
<212> TYPE: PRT
<213> ORGANISM: Mus musculus

<400> SEQUENCE: 252

Glu Ile Asn Pro Asn Ser Gly Gly Ala Gly Tyr Asn Gln Gln Phe Lys
1               5                   10                  15

Gly

<210> SEQ ID NO 253
<211> LENGTH: 14
<212> TYPE: PRT
<213> ORGANISM: Mus musculus

<400> SEQUENCE: 253

Leu Gly Tyr Val Gly Asn Tyr Glu Asp Trp Tyr Phe Asp Val
1               5                   10

<210> SEQ ID NO 254
<211> LENGTH: 5
<212> TYPE: PRT
<213> ORGANISM: Mus musculus

<400> SEQUENCE: 254

Asp Tyr Asn Met His
1               5

<210> SEQ ID NO 255
<211> LENGTH: 17
<212> TYPE: PRT
<213> ORGANISM: Mus musculus

<400> SEQUENCE: 255

```
Glu Ile Asn Pro Asn Ser Gly Gly Ala Gly Tyr Asn Gln Lys Phe Lys
1               5                   10                  15

Gly

<210> SEQ ID NO 256
<211> LENGTH: 14
<212> TYPE: PRT
<213> ORGANISM: Mus musculus

<400> SEQUENCE: 256

Leu Gly Tyr Asp Asp Ile Tyr Asp Asp Trp Tyr Phe Asp Val
1               5                   10

<210> SEQ ID NO 257
<211> LENGTH: 5
<212> TYPE: PRT
<213> ORGANISM: Mus musculus

<400> SEQUENCE: 257

Asp Tyr Asn Met His
1               5

<210> SEQ ID NO 258
<211> LENGTH: 17
<212> TYPE: PRT
<213> ORGANISM: Mus musculus

<400> SEQUENCE: 258

Glu Ile Asn Pro Asn Ser Gly Gly Ala Gly Tyr Asn Gln Lys Phe Lys
1               5                   10                  15

Gly

<210> SEQ ID NO 259
<211> LENGTH: 14
<212> TYPE: PRT
<213> ORGANISM: Mus musculus

<400> SEQUENCE: 259

Leu Gly Tyr Asp Asp Ile Tyr Asp Asp Trp Tyr Phe Asp Val
1               5                   10

<210> SEQ ID NO 260
<211> LENGTH: 5
<212> TYPE: PRT
<213> ORGANISM: Mus musculus

<400> SEQUENCE: 260

Asp Tyr Asn Met His
1               5

<210> SEQ ID NO 261
<211> LENGTH: 17
<212> TYPE: PRT
<213> ORGANISM: Mus musculus

<400> SEQUENCE: 261

Glu Ile Asn Pro Asn Ser Gly Gly Ala Gly Tyr Asn Gln Lys Phe Lys
1               5                   10                  15

Gly

<210> SEQ ID NO 262
<211> LENGTH: 14
<212> TYPE: PRT
<213> ORGANISM: Mus musculus
```

<400> SEQUENCE: 262

Leu Gly Tyr Asp Asp Ile Tyr Asp Asp Trp Tyr Phe Asp Val
1               5                   10

<210> SEQ ID NO 263
<211> LENGTH: 5
<212> TYPE: PRT
<213> ORGANISM: Mus musculus

<400> SEQUENCE: 263

Asp Tyr Asn Met His
1               5

<210> SEQ ID NO 264
<211> LENGTH: 17
<212> TYPE: PRT
<213> ORGANISM: Mus musculus

<400> SEQUENCE: 264

Glu Ile Asn Pro Asn Ser Gly Gly Ser Gly Tyr Asn Gln Lys Phe Lys
1               5                   10                  15

Gly

<210> SEQ ID NO 265
<211> LENGTH: 14
<212> TYPE: PRT
<213> ORGANISM: Mus musculus

<400> SEQUENCE: 265

Leu Gly Tyr Tyr Gly Asn Tyr Glu Asp Trp Tyr Phe Asp Val
1               5                   10

<210> SEQ ID NO 266
<211> LENGTH: 5
<212> TYPE: PRT
<213> ORGANISM: Mus musculus

<400> SEQUENCE: 266

Asp Tyr Tyr Ile His
1               5

<210> SEQ ID NO 267
<211> LENGTH: 17
<212> TYPE: PRT
<213> ORGANISM: Mus musculus

<400> SEQUENCE: 267

Arg Ile Asp Pro Asp Asn Gly Glu Ser Thr Tyr Val Pro Lys Phe Gln
1               5                   10                  15

Gly

<210> SEQ ID NO 268
<211> LENGTH: 13
<212> TYPE: PRT
<213> ORGANISM: Mus musculus

<400> SEQUENCE: 268

Glu Gly Leu Asp Tyr Gly Asp Tyr Tyr Ala Val Asp Tyr
1               5                   10

<210> SEQ ID NO 269
<211> LENGTH: 5
<212> TYPE: PRT

```
<213> ORGANISM: Mus musculus

<400> SEQUENCE: 269

Asp Tyr Ile Met His
1               5

<210> SEQ ID NO 270
<211> LENGTH: 17
<212> TYPE: PRT
<213> ORGANISM: Mus musculus

<400> SEQUENCE: 270

Tyr Ile Asn Pro Tyr Asn Asp Asp Thr Glu Tyr Asn Glu Lys Phe Lys
1               5                   10                  15

Gly

<210> SEQ ID NO 271
<211> LENGTH: 11
<212> TYPE: PRT
<213> ORGANISM: Mus musculus

<400> SEQUENCE: 271

Ser Ile Tyr Tyr Tyr Asp Ala Pro Phe Ala Tyr
1               5                   10

<210> SEQ ID NO 272
<211> LENGTH: 5
<212> TYPE: PRT
<213> ORGANISM: Mus musculus

<400> SEQUENCE: 272

Asp Tyr Tyr Met His
1               5

<210> SEQ ID NO 273
<211> LENGTH: 17
<212> TYPE: PRT
<213> ORGANISM: Mus musculus

<400> SEQUENCE: 273

Arg Ile Asp Pro Glu Asn Gly Asp Ile Ile Tyr Asp Pro Lys Phe Gln
1               5                   10                  15

Gly

<210> SEQ ID NO 274
<211> LENGTH: 10
<212> TYPE: PRT
<213> ORGANISM: Mus musculus

<400> SEQUENCE: 274

Asp Ala Gly Asp Pro Ala Trp Phe Thr Tyr
1               5                   10

<210> SEQ ID NO 275
<211> LENGTH: 10
<212> TYPE: PRT
<213> ORGANISM: Mus musculus

<400> SEQUENCE: 275

Arg Ala Ser Ser Ser Val Tyr Tyr Met His
1               5                   10

<210> SEQ ID NO 276
<211> LENGTH: 7
```

```
<212> TYPE: PRT
<213> ORGANISM: Mus musculus

<400> SEQUENCE: 276

Ala Thr Ser Asn Leu Ala Ser
1               5

<210> SEQ ID NO 277
<211> LENGTH: 9
<212> TYPE: PRT
<213> ORGANISM: Mus musculus

<400> SEQUENCE: 277

Gln Gln Trp Ser Ser Asp Pro Leu Thr
1               5

<210> SEQ ID NO 278
<211> LENGTH: 12
<212> TYPE: PRT
<213> ORGANISM: Mus musculus

<400> SEQUENCE: 278

Ser Val Ser Ser Thr Ile Ser Ser Asn His Leu His
1               5                   10

<210> SEQ ID NO 279
<211> LENGTH: 7
<212> TYPE: PRT
<213> ORGANISM: Mus musculus

<400> SEQUENCE: 279

Gly Thr Ser Asn Leu Ala Ser
1               5

<210> SEQ ID NO 280
<211> LENGTH: 9
<212> TYPE: PRT
<213> ORGANISM: Mus musculus

<400> SEQUENCE: 280

Gln Gln Trp Ser Ser Tyr Pro Leu Thr
1               5

<210> SEQ ID NO 281
<211> LENGTH: 10
<212> TYPE: PRT
<213> ORGANISM: Mus musculus

<400> SEQUENCE: 281

Arg Ala Ser Ser Ser Ile Ser Tyr Ile His
1               5                   10

<210> SEQ ID NO 282
<211> LENGTH: 7
<212> TYPE: PRT
<213> ORGANISM: Mus musculus

<400> SEQUENCE: 282

Ala Thr Ser Asn Leu Ala Ser
1               5

<210> SEQ ID NO 283
<211> LENGTH: 9
<212> TYPE: PRT
<213> ORGANISM: Mus musculus
```

<400> SEQUENCE: 283

Gln Gln Trp Ser Ser Asp Pro Leu Thr
1               5

<210> SEQ ID NO 284
<211> LENGTH: 12
<212> TYPE: PRT
<213> ORGANISM: Mus musculus

<400> SEQUENCE: 284

Arg Ala Ser Ser Ser Val Thr Ser Ser Tyr Leu Asn
1               5                   10

<210> SEQ ID NO 285
<211> LENGTH: 7
<212> TYPE: PRT
<213> ORGANISM: Mus musculus

<400> SEQUENCE: 285

Ser Thr Ser Asn Leu Ala Ser
1               5

<210> SEQ ID NO 286
<211> LENGTH: 9
<212> TYPE: PRT
<213> ORGANISM: Mus musculus

<400> SEQUENCE: 286

Gln Gln Tyr Asp Phe Phe Pro Ser Thr
1               5

<210> SEQ ID NO 287
<211> LENGTH: 5
<212> TYPE: PRT
<213> ORGANISM: Mus musculus

<400> SEQUENCE: 287

Asp Tyr Phe Ile His
1               5

<210> SEQ ID NO 288
<211> LENGTH: 17
<212> TYPE: PRT
<213> ORGANISM: Mus musculus

<400> SEQUENCE: 288

Arg Leu Asp Pro Glu Asp Gly Glu Ser Asp Tyr Ala Pro Lys Phe Gln
1               5                   10                  15

Asp

<210> SEQ ID NO 289
<211> LENGTH: 12
<212> TYPE: PRT
<213> ORGANISM: Mus musculus

<400> SEQUENCE: 289

Glu Asp Tyr Asp Gly Thr Tyr Thr Phe Phe Pro Tyr
1               5                   10

<210> SEQ ID NO 290
<211> LENGTH: 5
<212> TYPE: PRT
<213> ORGANISM: Mus musculus

<400> SEQUENCE: 290

```
Asp Phe Tyr Leu His
1               5

<210> SEQ ID NO 291
<211> LENGTH: 17
<212> TYPE: PRT
<213> ORGANISM: Mus musculus

<400> SEQUENCE: 291

Arg Ile Asp Pro Glu Asn Gly Asp Thr Leu Tyr Asp Pro Lys Phe Gln
1               5                   10                  15

Asp

<210> SEQ ID NO 292
<211> LENGTH: 16
<212> TYPE: PRT
<213> ORGANISM: Mus musculus

<400> SEQUENCE: 292

Glu Ala Asp Tyr Phe His Asp Gly Thr Ser Tyr Trp Tyr Phe Asp Val
1               5                   10                  15

<210> SEQ ID NO 293
<211> LENGTH: 5
<212> TYPE: PRT
<213> ORGANISM: Mus musculus

<400> SEQUENCE: 293

Asp Tyr Tyr Ile His
1               5

<210> SEQ ID NO 294
<211> LENGTH: 17
<212> TYPE: PRT
<213> ORGANISM: Mus musculus

<400> SEQUENCE: 294

Arg Val Asp Pro Asp Asn Gly Glu Thr Glu Phe Ala Pro Lys Phe Pro
1               5                   10                  15

Gly

<210> SEQ ID NO 295
<211> LENGTH: 12
<212> TYPE: PRT
<213> ORGANISM: Mus musculus

<400> SEQUENCE: 295

Glu Asp Tyr Asp Gly Thr Tyr Thr Trp Phe Pro Tyr
1               5                   10

<210> SEQ ID NO 296
<211> LENGTH: 5
<212> TYPE: PRT
<213> ORGANISM: Mus musculus

<400> SEQUENCE: 296

Asp Tyr Tyr Met Asn
1               5

<210> SEQ ID NO 297
<211> LENGTH: 17
<212> TYPE: PRT
<213> ORGANISM: Mus musculus
```

<400> SEQUENCE: 297

Asp Ile Asn Pro Tyr Asn Asp Asp Thr Thr Tyr Asn His Lys Phe Lys
1               5                   10                  15

Gly

<210> SEQ ID NO 298
<211> LENGTH: 11
<212> TYPE: PRT
<213> ORGANISM: Mus musculus

<400> SEQUENCE: 298

Glu Thr Ala Val Ile Thr Thr Asn Ala Met Asp
1               5                   10

<210> SEQ ID NO 299
<211> LENGTH: 130
<212> TYPE: PRT
<213> ORGANISM: Mus musculus

<400> SEQUENCE: 299

Met Asp Phe Gln Val Gln Ile Phe Ser Phe Met Leu Ile Ser Val Thr
1               5                   10                  15

Val Ile Leu Ser Ser Gly Glu Ile Val Leu Thr Gln Ser Pro Ala Leu
            20                  25                  30

Met Ala Ala Ser Pro Gly Glu Lys Val Thr Ile Thr Cys Ser Val Ser
        35                  40                  45

Ser Ser Ile Ser Ser Asn Leu His Trp Ser Gln Gln Lys Ser Gly
    50                  55                  60

Thr Ser Pro Lys Leu Trp Ile Tyr Gly Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys Gln
            100                 105                 110

Gln Trp Thr Thr Thr Tyr Thr Phe Gly Ser Gly Thr Lys Leu Glu Leu
        115                 120                 125

Lys Arg
    130

<210> SEQ ID NO 300
<211> LENGTH: 390
<212> TYPE: DNA
<213> ORGANISM: Mus musculus

<400> SEQUENCE: 300
atggattttc aggtgcagat tttcagcttc atgctaatca gtgtcacagt catattgtcc      60
agtggagaaa ttgtgctcac ccagtctcca gcactcatgg ctgcatctcc aggggagaag    120
gtcaccatca cctgcagtgt cagctcgagt ataagttcca acttaca ctggtcccag        180 cagaagtcag gaacctcccc caaactctgg atttatggca catccaacct tgcttctgga    240
gtccctgttc gcttcagtgg cagtggatct gggacctctt attctctcac aatcagcagc    300
atggaggctg aagatgctgc cacttattac tgtcaacagt ggactactac gtatacgttc    360
ggatcgggga ccaagctgga gctgaaacgt                                     390

<210> SEQ ID NO 301
<211> LENGTH: 141
<212> TYPE: PRT
<213> ORGANISM: Mus musculus

<400> SEQUENCE: 301

Met Gly Trp Asn Trp Ile Ile Phe Phe Leu Met Ala Val Val Thr Gly
1               5                   10                  15

Val Asn Ser Glu Val Gln Leu Arg Gln Ser Gly Ala Asp Leu Val Lys
            20                  25                  30

Pro Gly Ala Ser Val Lys Leu Ser Cys Thr Ala Ser Gly Phe Asn Ile
        35                  40                  45

Lys Asp Tyr Tyr Ile His Trp Val Lys Gln Arg Pro Glu Gln Gly Leu
    50                  55                  60

Glu Trp Ile Gly Arg Ile Asp Pro Asp Asn Gly Glu Thr Tyr Tyr Val
65                  70                  75                  80

Pro Lys Phe Gln Gly Lys Ala Thr Ile Thr Ala Asp Thr Ser Ser Asn
                85                  90                  95

Thr Ala Tyr Leu Gln Leu Arg Ser Leu Thr Ser Glu Asp Thr Ala Ile
            100                 105                 110

Tyr Tyr Cys Gly Arg Glu Gly Leu Asp Tyr Gly Asp Tyr Tyr Ala Val
        115                 120                 125

Asp Tyr Trp Gly Gln Gly Thr Ser Val Thr Val Ser Ser
    130                 135                 140

<210> SEQ ID NO 302
<211> LENGTH: 423
<212> TYPE: DNA
<213> ORGANISM: Mus musculus

<400> SEQUENCE: 302
atgggatgga actgatcat cttcttcctg atggcagtgg ttacagggt caattcagag      60
gtgcagttgc ggcagtctgg ggcagaccctt gtgaagccag gggcctcagt caagttgtcc    120
tgcacagctt ctggcttcaa cattaaagac tactatatac actgggtgaa gcagaggcct    180
gaacagggcc tggagtggat tggaaggatt gatcctgata atggtgaaag tacatatgtc    240
ccgaagttcc agggcaaggc cactataaca gcagacacat catccaacac agcctaccta    300
caactcagaa gcctgacatc tgaggacact gccatctatt attgtgggag agaggggctc    360
gactatggtg actactatgc tgtggactac tggggtcaag gaacctcggt cacagtctcg    420
agc                                                                  423

<210> SEQ ID NO 303
<211> LENGTH: 130
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 303

Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Phe
            20                  25                  30

Leu Ser Ala Ser Val Gly Asp Arg Val Thr Ile Thr Cys Ser Val Ser
        35                  40                  45

Ser Ser Ile Ser Ser Ser Asn Leu His Trp Tyr Gln Gln Lys Pro Gly
    50                  55                  60

Lys Ala Pro Lys Leu Leu Ile Tyr Gly Thr Ser Asn Leu Ala Ser Gly

```
                65                  70                  75                  80
Val Pro Ser Arg Phe Ser Gly Ser Gly Ser Gly Thr Glu Phe Thr Leu
                    85                  90                  95

Thr Ile Ser Ser Leu Gln Pro Glu Asp Phe Ala Thr Tyr Tyr Cys Gln
                    100                 105                 110

Gln Trp Thr Thr Thr Tyr Thr Phe Gly Gln Gly Thr Lys Leu Glu Ile
                    115                 120                 125

Lys Arg
    130

<210> SEQ ID NO 304
<211> LENGTH: 390
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 304
atggatatgc gcgtgccggc gcagctgctg ggcctgctgc tgctgtggct gccgggcgcg      60
cgctgcgata ttcagctgac ccagagcccg agctttctga gcgcgagcgt gggcgatcgc     120
gtgaccatta cctgcagcgt gagcagcagc attagcagca gcaacctgca ttggtatcag     180
cagaaaccgg gcaaagcgcc gaaactgctg atttatggca ccagcaacct ggcgagcggc     240
gtgccgagcc gctttagcgg cagcggcagc ggcaccgaat ttaccctgac cattagcagc     300
ctgcagccgg aagatttttgc gacctattat tgccagcagt ggaccaccac ctataccttt     360
ggccagggca ccaaactgga aattaaacgt                                       390

<210> SEQ ID NO 305
<211> LENGTH: 141
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 305

Met Asp Trp Thr Trp Ser Ile Leu Phe Leu Val Ala Ala Pro Thr Gly
1               5                   10                  15

Ala His Ser Glu Val Gln Leu Val Gln Ser Gly Ala Glu Val Lys Lys
                20                  25                  30

Pro Gly Ala Ser Val Lys Val Ser Cys Lys Ala Ser Gly Phe Asn Ile
            35                  40                  45

Lys Asp Tyr Tyr Ile His Trp Val Arg Gln Ala Pro Gly Gln Gly Leu
        50                  55                  60

Glu Trp Met Gly Arg Ile Asp Pro Asp Asn Gly Glu Ser Thr Tyr Val
65                  70                  75                  80

Pro Lys Phe Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
                100                 105                 110

Tyr Tyr Cys Ala Arg Glu Gly Leu Asp Tyr Gly Asp Tyr Tyr Ala Val
            115                 120                 125

Asp Tyr Trp Gly Gln Gly Thr Leu Val Thr Val Ser Ser
        130                 135                 140
```

<210> SEQ ID NO 306
<211> LENGTH: 423
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 306

```
atggattgga cctggagcat tctgtttctg gtggcggcgc cgaccggcgc gcatagcgaa    60
gtgcagctgg tgcagagcgg cgcggaagtg aaaaaaccgg gcgcgagcgt gaaagtgagc   120
tgcaaagcga gcggctttaa cattaaagat tattatattc attgggtgcg ccaggcgccg   180
ggccagggcc tggaatggat gggccgcatt gatccggata acggcgaaag caccctatgtg   240
ccgaaatttc agggccgcgt gaccatgacc accgatacca gcaccagcac cgcgtatatg   300
gaactgcgca gcctgcgcag cgatgatacc gcggtgtatt attgcgcgcg cgaaggcctg   360
gattatggcg attattatgc ggtggattat tggggccagg gcaccctggt gaccgtctcg   420
agc                                                                 423
```

<210> SEQ ID NO 307
<211> LENGTH: 127
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 307

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Asn Ile Ser Cys Arg Ala Ser Gln Asp
        35                  40                  45

Ile Ser Ser Tyr Leu Asn Trp Tyr Gln Gln Lys Pro Asp Gly Thr Val
    50                  55                  60

Lys Leu Leu Ile Tyr Ser Thr Ser Arg Leu Asn Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Ala Gln Glu Asp Ile Ala Thr Tyr Phe Cys Gln Gln Asp Ile
            100                 105                 110

Lys His Pro Thr Phe Gly Gly Gly Thr Lys Leu Glu Leu Lys Arg
        115                 120                 125
```

<210> SEQ ID NO 308
<211> LENGTH: 381
<212> TYPE: DNA
<213> ORGANISM: Mus musculus

<400> SEQUENCE: 308

```
atgatgtcct ctgctcagtt cctttggtctc ctgttgctct gttttcaagg taccagatgt    60
gatatccaga tgacacagac tacatcctcc ctgtctgcct ctctgggaga cagagtcaac   120
atcagctgca gggcaagtca ggacattagc agttatttaa actggtatca gcagaaacca   180
```

```
gatggaactg ttaaactcct gatctactcc acatcaagat taaactcagg agtcccatca    240
aggttcagtg gcagtgggtc tgggacagat tattctctca ctattagcaa cctggcacaa    300
gaagatattg ccacttactt ttgccaacag gatattaagc atccgacgtt cggtggaggc    360
accaagttgg agctgaaacg t                                              381
```

<210> SEQ ID NO 309
<211> LENGTH: 139
<212> TYPE: PRT
<213> ORGANISM: Mus musculus

<400> SEQUENCE: 309

```
Met Glu Trp Ile Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Phe Thr Phe
        35                  40                  45

Thr Asp Tyr Ile Met His Trp Val Lys Gln Lys Pro Gly Gln Gly Leu
    50                  55                  60

Glu Trp Ile Gly Tyr Ile Asn Pro Tyr Asn Asp Asp Thr Glu Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Asp Leu Ser Ser Leu Thr Ser Glu Gly Ser Ala Val
            100                 105                 110

Tyr Tyr Cys Ala Arg Ser Ile Tyr Tyr Tyr Asp Ala Pro Phe Ala Tyr
        115                 120                 125

Trp Gly Gln Gly Thr Leu Val Thr Val Ser Ser
    130                 135
```

<210> SEQ ID NO 310
<211> LENGTH: 417
<212> TYPE: DNA
<213> ORGANISM: Mus musculus

<400> SEQUENCE: 310

```
atggaatgga tctggatatt tctcttcctc ctgtcaggaa ctgcaggtgt ccactctgag    60
gtccagctgc agcagtctgg acctgagctg gtaaagcctg ggcttcagt gaagatgtcc     120 tgcaaggctt ctgggttcac attcactgac tacattatgc actgggtgaa gcagaagcct    180
gggcagggcc ttgagtggat tggatatatt aatccttaca atgatgatac tgaatacaat    240
gagaagttca aggcaaggc cacactgact tcagacaaat cctccagcac agcctacatg    300
gatctcagca gtctgacctc tgagggctct gcggtctatt actgtgcaag atcgatttat    360
tactacgatg ccccgtttgc ttactggggc caagggactc tggtcacagt ctcgagc      417
```

<210> SEQ ID NO 311
<211> LENGTH: 127
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 311

```
Met Met Ser Ser Ala Gln Phe Leu Gly Leu Leu Leu Leu Cys Phe Gln
```

```
                1               5                  10                 15
Gly Thr Arg Cys Asp Ile Gln Met Thr Gln Ser Pro Ser Ser Leu Ser
                    20                  25                 30

Ala Ser Val Gly Asp Arg Val Thr Ile Thr Cys Arg Ala Ser Gln Asp
                    35                  40                 45

Ile Ser Ser Tyr Leu Asn Trp Tyr Gln Gln Lys Pro Gly Lys Ala Pro
                50                  55                 60

Lys Leu Leu Ile Tyr Ser Thr Ser Arg Leu Asn Ser Gly Val Pro Ser
65                  70                  75                 80

Arg Phe Ser Gly Ser Gly Ser Gly Thr Asp Phe Thr Leu Thr Ile Ser
                    85                  90                 95

Ser Leu Gln Pro Glu Asp Phe Ala Thr Tyr Tyr Cys Gln Gln Asp Ile
                    100                 105                110

Lys His Pro Thr Phe Gly Gln Gly Thr Lys Val Glu Ile Lys Arg
                    115                 120                125

<210> SEQ ID NO 312
<211> LENGTH: 381
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 312
atgatgtcct ctgctcagtt ccttggtctc ctgttgctct gttttcaagg taccagatgt    60
gatatccaga tgacccagtc tccatcctcc ctgtctgcat ctgtaggtga ccgtgtcacc   120
atcacttgcc gcgcaagtca ggatattagc agctatttaa attggtatca gcagaaacca   180
gggaaagccc ctaagctcct gatctattct acttcccgtt tgaatagtgg ggtcccatca   240
cgcttcagtg gcagtggctc tgggacagat ttcactctca ccatcagcag tctgcaacct   300
gaagattttg caacttacta ctgtcaacag gatattaaac accctacgtt cggtcaaggc   360
accaaggtgg agatcaaacg t                                             381

<210> SEQ ID NO 313
<211> LENGTH: 139
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 313

Met Glu Trp Ile Trp Ile Phe Leu Phe Leu Leu Ser Gly Thr Ala Gly
1               5                   10                 15

Val His Ser Glu Val Gln Leu Val Gln Ser Gly Ala Glu Val Lys Lys
                    20                  25                 30

Pro Gly Ser Ser Val Lys Val Ser Cys Lys Ala Ser Gly Phe Thr Phe
                    35                  40                 45

Thr Asp Tyr Ile Met His Trp Val Arg Gln Ala Pro Gly Gln Gly Leu
                50                  55                 60

Glu Trp Met Gly Tyr Ile Asn Pro Tyr Asn Asp Asp Thr Glu Tyr Asn
65                  70                  75                 80

Glu Lys Phe Lys Gly Arg Val Thr Ile Thr Ala Asp Lys Ser Thr Ser
                    85                  90                 95
```

```
Thr Ala Tyr Met Glu Leu Ser Ser Leu Arg Ser Glu Asp Thr Ala Val
            100                 105                 110

Tyr Tyr Cys Ala Arg Ser Ile Tyr Tyr Tyr Asp Ala Pro Phe Ala Tyr
        115                 120                 125

Trp Gly Gln Gly Thr Leu Val Thr Val Ser Ser
    130                 135

<210> SEQ ID NO 314
<211> LENGTH: 107
<212> TYPE: PRT
<213> ORGANISM: Mus musculus

<400> SEQUENCE: 314

Asp Ile Gln Met Thr Gln Thr Thr Ser Ser Leu Ser Ala Ser Leu Gly
1               5                   10                  15

Asp Arg Val Asn Ile Ser Cys Arg Ala Ser Gln Asp Ile Ser Ser Tyr
            20                  25                  30

Leu Asn Trp Tyr Gln Gln Lys Pro Asp Gly Thr Val Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Tyr Ser Leu Thr Ile Ser Asn Leu Ala Gln
65                  70                  75                  80

Glu Asp Ile Ala Thr Tyr Phe Cys Gln Gln Asp Ile Lys His Pro Thr
                85                  90                  95

Phe Gly Gly Gly Thr Lys Leu Glu Leu Lys Arg
            100                 105

<210> SEQ ID NO 315
<211> LENGTH: 128
<212> TYPE: PRT
<213> ORGANISM: Mus musculus

<400> SEQUENCE: 315

Met Lys Ser Gln Thr Gln Val Phe Val Tyr Met Leu Leu Trp Leu Ser
1               5                   10                  15

Gly Val Glu Gly Asp Ile Val Met Thr Gln Ser His Lys Phe Met Ser
            20                  25                  30

Thr Ser Val Gly Asp Arg Val Thr Ile Thr Cys Lys Ala Ser Gln Asp
        35                  40                  45

Val Phe Thr Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
                100                 105                 110

Ser Tyr Pro Leu Thr Phe Gly Ala Gly Thr Lys Leu Glu Leu Lys Arg
        115                 120                 125

<210> SEQ ID NO 316
<211> LENGTH: 381
<212> TYPE: DNA
<213> ORGANISM: Mus musculus

<400> SEQUENCE: 316
atgaagtcac agacccaggt ctttgtatac atgttgctgt ggttgtctgg tgttgaagga    60
```

```
gacattgtga tgacccagtc tcacaaattc atgtccacgt cagtaggaga cagggtcacc    120
atcacctgca aggccagtca ggatgtcttt actgctgtag cctggtatca acagaaacca    180
ggacaatctc ctaaactact gatttactgg gcatccaccc ggcacactgg agtccctgat    240
cgcttcacag gcagtggatc tgggacagat ttcactctca ccattagcaa tgtgcagtct    300
gaagacttgg cagattattt ctgtcaacaa tatagcagct atcctctcac gttcggtgct    360
gggaccaagt tggagctgaa a                                              381
```

<210> SEQ ID NO 317
<211> LENGTH: 138
<212> TYPE: PRT
<213> ORGANISM: Mus musculus

<400> SEQUENCE: 317

```
Met Gly Trp Asn Trp Ile Ile Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Lys Ala Ser Gly Phe Asn Ile
        35                  40                  45

Lys Asp Tyr Tyr Met His Trp Val Lys Gln Arg Pro Glu Gln Gly Leu
    50                  55                  60

Glu Trp Ile Gly Arg Ile Asp Pro Glu Asn Gly Asp Ile Ile Tyr Asp
65                  70                  75                  80

Pro Lys Phe Gln Gly Lys Ala Ser Ile Thr Thr Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Tyr Asp Ala Gly Asp Pro Ala Trp Phe Thr Tyr Trp
        115                 120                 125

Gly Gln Gly Thr Leu Val Thr Val Ser Ser
    130                 135
```

<210> SEQ ID NO 318
<211> LENGTH: 411
<212> TYPE: DNA
<213> ORGANISM: Mus musculus

<400> SEQUENCE: 318

```
atgggatgga actggatcat cttcttcctg atggcagtgg ttacaggggt caattcagag    60
gttcagctgc agcagtctgg ggctgagctt gtgaggccag ggccttagt caagttgtcc     120 tgcaaagctt ctggcttcaa tattaaagac tactatatgc actgggtgaa gcagaggcct    180
gaacagggcc tggagtggat tggaaggatt gatcctgaga atggtgatat tatatatgac    240
ccgaagttcc agggcaaggc cagtataaca acagacacat cctccaacac agcctacctg    300
cagctcagca gcctgacgtc tgaggacact gccgtctatt actgtgctta cgatgctggt    360
gaccccgcct ggtttactta ctggggccaa gggactctgg tcaccgtctc g             411
```

<210> SEQ ID NO 319
<211> LENGTH: 130
<212> TYPE: PRT
<213> ORGANISM: Mus musculus

<400> SEQUENCE: 319

```
Met Asp Met Arg Val Pro Ala Gln Leu Leu Gly Leu Leu Leu Leu Trp
1               5                   10                  15
```

```
Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
            35                  40                  45

Gln Asp Val Phe Thr Ala Val Ala Trp Tyr Gln Lys Pro Gly Lys
    50                  55                  60

Ala Pro Lys Leu Leu Ile Tyr Trp Ala Ser Thr Arg His Thr Gly Val
 65              70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
                100                 105                 110

Tyr Ser Ser Tyr Pro Leu Thr Phe Gly Gly Gly Thr Lys Val Glu Ile
            115                 120                 125

Lys Arg
    130

<210> SEQ ID NO 320
<211> LENGTH: 390
<212> TYPE: DNA
<213> ORGANISM: Mus musculus

<400> SEQUENCE: 320
atggatatgc gcgtgccggc gcagctgctg ggcctgctgc tgctgtggct gcgcggcgcg      60
cgctgcgata tccagatgac ccagagcccg agcagcctga gcgcgagcgt gggcgatcgc     120
gtgaccatta cctgcaaagc gagccaggat gtgtttaccg cggtggcgtg gtatcagcag     180
aaaccgggca agcgccgaaa actgctgatt tattgggcga gcacccgcca taccggcgtg     240
ccgagtcgct ttagcggcag cggcagcggc accgatttta ccctgaccat tagcagcctg     300
cagccggaag attttgcgac ctattattgc cagcagtata gcagctatcc gctgaccttt     360
ggcggcggca ccaaagtgga aattaaacgt                                       390

<210> SEQ ID NO 321
<211> LENGTH: 138
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 321

Met Asp Trp Thr Trp Ser Ile Leu Phe Leu Val Ala Ala Pro Thr Gly
 1               5                  10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Phe Asn Ile
            35                  40                  45

Lys Asp Tyr Tyr Met His Trp Val Arg Gln Ala Pro Gly Gln Gly Leu
    50                  55                  60

Glu Trp Ile Gly Arg Ile Asp Pro Glu Asn Gly Asp Ile Ile Tyr Asp
 65              70                  75                  80

Pro Lys Phe Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
                100                 105                 110
```

```
Tyr Tyr Cys Ala Tyr Asp Ala Gly Asp Pro Ala Trp Phe Thr Tyr Trp
        115                 120                 125

Gly Gln Gly Thr Leu Val Thr Val Ser Ser
    130                 135

<210> SEQ ID NO 322
<211> LENGTH: 414
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: Humanized Antibody Sequence

<400> SEQUENCE: 322
atggattgga cctggagcat tctgtttctg gtggcggcgc cgaccggcgc gcatagcgaa      60
gtgcagctgg tgcagagcgg cgcggaagtg aaaaaaccgg gcgcgagcgt gaaagtgagc     120
tgcaaagcga gcggctttaa cattaaagat tattatatgc attgggtgcg ccaggcgccg     180
ggccagggcc tggaatggat cggccgcatt gatccggaaa acggcgatat tatttatgat     240
ccgaaatttc agggccgcgt gaccatgacc accgatacca gcaccagcac cgcgtatatg     300
gaactgcgca gcctgcgcag cgatgatacc gcggtgtatt attgcgcgta tgatgcgggc     360
gatccggcgt ggtttaccta ttggggccag ggcaccctgg tgaccgtctc gagc           414

<210> SEQ ID NO 323
<211> LENGTH: 106
<212> TYPE: PRT
<213> ORGANISM: Mus musculus

<400> SEQUENCE: 323

Thr Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105

<210> SEQ ID NO 324
<211> LENGTH: 320
<212> TYPE: PRT
<213> ORGANISM: Mus musculus

<400> SEQUENCE: 324

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45
```

```
Gly Val His Thr Phe Pro Ala Val Leu Gln Ser Asp Leu Tyr Thr Leu
 50                  55                  60

Ser Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                 85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Asp Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

<210> SEQ ID NO 325
<211> LENGTH: 106
<212> TYPE: PRT
<213> ORGANISM: Homo sapiens

<400> SEQUENCE: 325

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 326
<211> LENGTH: 327
<212> TYPE: PRT
<213> ORGANISM: Homo sapiens

<400> SEQUENCE: 326

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 327
<211> LENGTH: 120
<212> TYPE: PRT
<213> ORGANISM: Mus musculus

<400> SEQUENCE: 327

Glu Val Gln Leu Gln Gln Ser Gly Pro Glu Leu Val Lys Pro Gly Ala

```
                       1               5                  10                 15
              Ser Val Lys Met Ser Cys Lys Ala Ser Gly Phe Thr Phe Thr Asp Tyr
                              20                  25                 30

Ile Met His Trp Val Lys Gln Lys Pro Gly Gln Gly Leu Glu Trp Ile
                              35                  40                 45

Gly Tyr Ile Asn Pro Tyr Asn Asp Asp Thr Glu Tyr Asn Glu Lys Phe
                              50                  55                 60

Lys Gly Lys Ala Thr Leu Thr Ser Asp Lys Ser Ser Ser Thr Ala Tyr
               65                  70                  75                  80

Met Asp Leu Ser Ser Leu Thr Ser Glu Gly Ser Ala Val Tyr Tyr Cys
                                  85                  90                 95

Ala Arg Ser Ile Tyr Tyr Tyr Asp Ala Pro Phe Ala Tyr Trp Gly Gln
                                  100                 105                110

Gly Thr Leu Val Thr Val Ser Ser
                              115                 120

<210> SEQ ID NO 328
<211> LENGTH: 120
<212> TYPE: PRT
<213> ORGANISM: Mus musculus

<400> SEQUENCE: 328

Glu Val Gln Leu Gln Gln Ser Gly Pro Glu Leu Val Lys Pro Gly Ala
               1               5                   10                  15

Ser Val Lys Met Ser Cys Lys Ala Ser Gly Phe Thr Phe Thr Asp Tyr
                              20                  25                 30

Ile Met His Trp Val Lys Gln Lys Pro Gly Gln Gly Leu Glu Trp Ile
                              35                  40                 45

Gly Tyr Ile Asn Pro Tyr Asn Asp Asp Thr Glu Tyr Asn Glu Lys Phe
                              50                  55                 60

Lys Gly Lys Ala Thr Leu Thr Ser Asp Lys Ser Ser Ser Thr Ala Tyr
               65                  70                  75                  80

Met Asp Leu Ser Ser Leu Thr Ser Glu Gly Ser Ala Val Tyr Tyr Cys
                                  85                  90                 95

Ala Arg Ser Ile Tyr Tyr Tyr Asp Ala Pro Phe Ala Tyr Trp Gly Gln
                                  100                 105                110

Gly Thr Leu Val Thr Val Ser Ser
                              115                 120

<210> SEQ ID NO 329
<211> LENGTH: 120
<212> TYPE: PRT
<213> ORGANISM: Mus musculus

<400> SEQUENCE: 329

Glu Val Gln Leu Val Gln Ser Gly Ala Glu Val Lys Lys Pro Gly Ser
               1               5                   10                  15

Ser Val Lys Val Ser Cys Lys Ala Ser Gly Phe Thr Phe Thr Asp Tyr
                              20                  25                 30

Ile Met His Trp Val Arg Gln Ala Pro Gly Gln Gly Leu Glu Trp Met
                              35                  40                 45

Gly Tyr Ile Asn Pro Tyr Asn Asp Asp Thr Glu Tyr Asn Glu Lys Phe
                              50                  55                 60

Lys Gly Arg Val Thr Ile Thr Ala Asp Lys Ser Thr Ser Thr Ala Tyr
               65                  70                  75                  80

Met Glu Leu Ser Ser Leu Arg Ser Glu Asp Thr Ala Val Tyr Tyr Cys
                                  85                  90                 95
```

```
Ala Arg Ser Ile Tyr Tyr Tyr Asp Ala Pro Phe Ala Tyr Trp Gly Gln
            100                 105                 110

Gly Thr Leu Val Thr Val Ser Ser
            115                 120

<210> SEQ ID NO 330
<211> LENGTH: 226
<212> TYPE: PRT
<213> ORGANISM: Mus musculus

<400> SEQUENCE: 330

Glu Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Tyr
            20                  25                  30

Ile Met His Trp Val Lys Gln Lys Pro Gly Gln Gly Leu Glu Trp Ile
            35                  40                  45

Gly Tyr Ile Asn Pro Tyr Asn Asp Asp Thr Glu Tyr Asn Glu Lys Phe
    50                  55                  60

Lys Gly Lys Ala Thr Leu Thr Ser Asp Lys Ser Ser Thr Ala Tyr
65                  70                  75                  80

Met Asp Leu Ser Ser Leu Thr Ser Glu Gly Ser Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser Thr Val Ala Ala Pro Ser Val Phe
            115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
            195                 200                 205

Thr His Gln Gly Leu Ser Ser Pro Val Thr Lys Ser Phe Asn Arg Gly
    210                 215                 220

Glu Cys
225

<210> SEQ ID NO 331
<211> LENGTH: 447
<212> TYPE: PRT
<213> ORGANISM: Mus musculus

<400> SEQUENCE: 331

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
            35                  40                  45

Gly Tyr Ile Asn Pro Tyr Asn Asp Asp Thr Glu Tyr Asn Glu Lys Phe
    50                  55                  60
```

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Asp Ala Pro Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 332
<211> LENGTH: 107
<212> TYPE: PRT
<213> ORGANISM: Mus musculus

<400> SEQUENCE: 332

Asp Ile Gln Met Thr Gln Ile Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Leu Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys
            100                 105

<210> SEQ ID NO 333
<211> LENGTH: 324
<212> TYPE: PRT
<213> ORGANISM: Mus musculus

<400> SEQUENCE: 333

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

```
Pro Ile Met Asp Thr Asp Gly Ser Tyr Phe Ile Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His Thr Glu Lys Ser Leu Ser His
305                 310                 315                 320

Ser Pro Gly Lys

<210> SEQ ID NO 334
<211> LENGTH: 213
<212> TYPE: PRT
<213> ORGANISM: Mus musculus

<400> SEQUENCE: 334

Asp Ile Gln Met Thr Gln Thr Thr Ser Ser Leu Ser Ala Ser Leu Gly
1               5                   10                  15

Asp Arg Val Asn Ile Ser Cys Arg Ala Ser Gln Asp Ile Ser Ser Tyr
            20                  25                  30

Leu Asn Trp Tyr Gln Gln Lys Pro Asp Gly Thr Val Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Tyr Ser Leu Thr Ile Ser Asn Leu Ala Gln
65                  70                  75                  80

Glu Asp Ile Ala Thr Tyr Phe Cys Gln Gln Asp Ile Lys His Pro Thr
                85                  90                  95

Phe Gly Gly Gly Thr Lys Leu Glu Leu Lys Arg Thr Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 335
<211> LENGTH: 444
<212> TYPE: PRT
<213> ORGANISM: Mus musculus

<400> SEQUENCE: 335

Glu Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Tyr
            20                  25                  30

Ile Met His Trp Val Lys Gln Lys Pro Gly Gln Gly Leu Glu Trp Ile
        35                  40                  45

Gly Tyr Ile Asn Pro Tyr Asn Asp Asp Thr Glu Tyr Asn Glu Lys Phe
    50                  55                  60
```

```
Lys Gly Lys Ala Thr Leu Thr Ser Asp Lys Ser Ser Ser Thr Ala Tyr
 65                  70                  75                  80

Met Asp Leu Ser Ser Leu Thr Ser Glu Gly Ser Ala Val Tyr Tyr Cys
                 85                  90                  95

Ala Arg Ser Ile Tyr Tyr Asp Ala Pro Phe Ala Tyr Trp Gly Gln
            100                 105                 110

Gly Thr Leu Val Thr Val Ser Ala Lys Thr Thr Pro Pro Ser Val
        115                 120                 125

Tyr Pro Leu Ala Pro Gly Ser Ala Ala Gln Thr Asn Ser Met Val Thr
        130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Val Thr Val Pro Ser
                180                 185                 190

Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Cys Gly Cys
        210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
                260                 265                 270

Ser Trp Phe Val Asp Asp Val Glu Val His Thr Ala Gln Thr Gln Pro
            275                 280                 285

Arg Glu Glu Gln Phe Asn Ser Thr Phe Arg Ser Val Ser Glu Leu Pro
290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
            355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Lys
            435                 440

<210> SEQ ID NO 336
<211> LENGTH: 108
<212> TYPE: PRT
<213> ORGANISM: Mus musculus

<400> SEQUENCE: 336
```

-continued

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Phe Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Ser Ser Tyr Pro Leu
                85                  90                  95

Thr Phe Gly Gly Gly Thr Lys Val Glu Ile Lys Arg
            100                 105

<210> SEQ ID NO 337
<211> LENGTH: 324
<212> TYPE: DNA
<213> ORGANISM: Mus musculus

<400> SEQUENCE: 337
gatatccaga tgacccagag cccgagcagc ctgagcgcga gcgtgggcga tcgcgtgacc      60
attacctgca aagcgagcca ggatgtgttt accgcggtgg cgtggtatca gcagaaaccg     120
ggcaaagcgc cgaaactgct gatttattgg gcgagcaccc gccataccgg cgtgccgagt     180
cgctttagcg gcagcggcag cggcaccgat tttaccctga ccattagcag cctgcagccg     240
gaagattttg cgacctatta ttgccagcag tatagcagct atccgctgac ctttggcggc     300
ggcaccaaag tggaaattaa acgt                                           324

<210> SEQ ID NO 338
<211> LENGTH: 119
<212> TYPE: PRT
<213> ORGANISM: Mus musculus

<400> SEQUENCE: 338

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Ile
        35                  40                  45

Gly Arg Ile Asp Pro Glu Asn Gly Asp Ile Ile Tyr Asp Pro Lys Phe
    50                  55                  60

Gln Gly Arg Val Thr Met Thr Thr Asp Thr Ser Thr Ser Thr Ala Tyr
65              70                  75                  80

Met Glu Leu Arg Ser Leu Arg Ser Asp Asp Thr Ala Val Tyr Tyr Cys
                85                  90                  95

Ala Tyr Asp Ala Gly Asp Pro Ala Trp Phe Thr Tyr Trp Gly Gln Gly
            100                 105                 110

Thr Leu Val Thr Val Ser Ser
        115

<210> SEQ ID NO 339
<211> LENGTH: 357
<212> TYPE: DNA
<213> ORGANISM: Mus musculus

<400> SEQUENCE: 339

```
gaagtgcagc tggtgcagag cggcgcggaa gtgaaaaaac cgggcgcgag cgtgaaagtg    60
agctgcaaag cgagcggctt taacattaaa gattattata tgcattgggt gcgccaggcg   120
ccgggccagg gcctggaatg gatcggccgc attgatccgg aaaacggcga tattatttat   180
gatccgaaat ttcagggccg cgtgaccatg accaccgata ccagcaccag caccgcgtat   240
atggaactgc gcagcctgcg cagcgatgat accgcggtgt attattgcgc gtatgatgcg   300
ggcgatccgg cgtggtttac ctattggggc cagggcaccc tggtgaccgt ctcgagc     357
```

<210> SEQ ID NO 340
<211> LENGTH: 1395
<212> TYPE: DNA
<213> ORGANISM: Mus musculus

<400> SEQUENCE: 340

```
atggactgga cctggaggat cctcttcttg gtggcagcag ccacaggagc ccactccgag    60
gtgcagctgg tgcagtctgg ggctgaggtg aagaagcctg gtcctcggt gaaggtctcc   120
tgcaaggctt ctggttttac cttcaccgac tatattatgc actgggtgcg tcaggccccct  180
ggtcaagggc ttgagtggat gggctatatc aaccttata atgatgacac cgaatacaac   240
gagaagttca agggccgtgt cacgattacc gcggacaaat ccacgagcac agcctacatg   300
gagctgagca gcctgcgctc tgaggacacg gccgtgtatt actgtgcgcg ttcgatttat   360
tactacgatg ccccgtttgc ttactggggc caagggactc tggtcaccgt ctctagtgcc   420
tccaccaagg gcccatcggt cttccccctg gcgccctgct ccaggagcac ctccgagagc   480
acagcggccc tgggctgcct ggtcaaggac tacttcccg aaccggtgac ggtgtcgtgg   540
aactcaggcg ctctgaccag cggcgtgcac accttcccag ctgtcctaca gtcctcagga   600
ctctactccc tcagcagcgt ggtgaccgtg ccctccagca acttcggcac ccagacctac   660
acctgcaacg tagatcacaa gcccagcaac accaaggtgg acaagacagt tgagcgcaaa   720
tgttgtgtcg agtgcccacc gtgcccagca ccacctgtgg caggaccgtc agtcttcctc   780
ttccccccaa aacccaagga caccctcatg atctcccgga ccctgaggt cacgtgcgtg   840
gtggtggacg tgagccacga agaccccgag gtccagttca actggtacgt ggacggcgtg   900
gaggtgcata atgccaagac aaagccacgg gaggagcagt tcaacagcac gttccgtgtg   960
gtcagcgtcc tcaccgttgt gcaccaggac tggctgaacg gcaaggagta caagtgcaag  1020
gtctccaaca aaggcctccc agcccccatc gagaaaacca tctccaaaac caagggcag  1080
ccccgagaac cacaggtgta caccctgccc ccatcccggg aggagatgac caagaaccag  1140
gtcagcctga cctgcctggt caaaggcttc taccccagcg acatcgccgt ggagtgggag  1200
agcaatgggc agccggagaa caactacaag accacacctc ccatgctgga ctccgacggc  1260
tccttcttcc tctacagcaa gctcaccgtg gacaagagca ggtggcagca ggggaacgtc  1320
ttctcatgct ccgtgatgca tgaggctctg cacaaccact acacgcagaa gagcctctcc  1380
ctgtctccgg gtaaa                                                   1395
```

<210> SEQ ID NO 341
<211> LENGTH: 213
<212> TYPE: PRT
<213> ORGANISM: Mus musculus

<400> SEQUENCE: 341

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
         35                  40                  45

Tyr Ser Thr Ser Arg Leu Asn Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ile Lys His Pro Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 342
<211> LENGTH: 639
<212> TYPE: DNA
<213> ORGANISM: Mus musculus

<400> SEQUENCE: 342
gacatccaga tgacccagtc tccatcctcc ctgtctgcat ctgtaggtga ccgtgtcacc     60
atcacttgcc gcgcaagtca ggatattagc agctatttaa attggtatca gcagaaacca    120
gggaaagccc ctaagctcct gatctattct acttcccgtt tgaatagtgg ggtcccatca    180
cgcttcagtg gcagtggctc tgggacagat ttcactctca ccatcagcag tctgcaacct    240
gaagattttg caacttacta ctgtcaacag gatattaaac accctacgtt cggtcaaggc    300
accaaggtgg agatcaaacg tacggtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgt                           639

<210> SEQ ID NO 343
<211> LENGTH: 235
<212> TYPE: PRT
<213> ORGANISM: Mus musculus

<400> SEQUENCE: 343

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
         20                  25                  30

Leu Ser Ala Ser Val Gly Asp Arg Val Thr Ile Thr Cys Arg Ala Ser
             35                  40                  45

Gln Asp Ile Ser Ser Tyr Leu Asn Trp Tyr Gln Gln Lys Pro Gly Lys
 50                  55                  60

Ala Pro Lys Leu Leu Ile Tyr Ser Thr Ser Arg Leu Asn Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
                100                 105                 110

Asp Ile Lys His Pro Thr Phe Gly Gln Gly Thr Lys Val Glu Ile Lys
                115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
                195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 344
<211> LENGTH: 705
<212> TYPE: DNA
<213> ORGANISM: Mus musculus

<400> SEQUENCE: 344
atggacatga gggtgcccgc tcagctcctg gggctcctgc tgctgtggct gagaggtgcc      60
agatgtgaca tccagatgac ccagtctcca tcctccctgt ctgcatctgt aggtgaccgt     120
gtcaccatca cttgccgcgc aagtcaggat attagcagct atttaaattg gtatcagcag     180
aaaccaggga agcccctaa gctcctgatc tattctactt cccgttttga atagtggggtc     240
ccatcacgct tcagtggcag tggctctggg acagatttca ctctcaccat cagcagtctg     300
caacctgaag attttgcaac ttactactgt caacaggata ttaaacaccc tacgttcggt     360
caaggcacca aggtggagat caaacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
ggcctgagct cgcccgtcac aaagagcttc aacaggggag agtgt                     705

<210> SEQ ID NO 345
<211> LENGTH: 446
<212> TYPE: PRT
<213> ORGANISM: Mus musculus

<400> SEQUENCE: 345

```
Glu Val Gln Leu Val Gln Ser Gly Ala Glu Val Lys Lys Pro Gly Ser
1               5                   10                  15
Ser Val Lys Val Ser Cys Lys Ala Ser Gly Phe Thr Phe Thr Asp Tyr
            20                  25                  30
Ile Met His Trp Val Arg Gln Ala Pro Gly Gln Gly Leu Glu Trp Met
        35                  40                  45
Gly Tyr Ile Asn Pro Tyr Asn Asp Asp Thr Glu Tyr Asn Glu Lys Phe
    50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Ile Tyr Tyr Tyr Asp Ala Pro Phe Ala Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Asn Phe Gly Thr Gln Thr Tyr Thr Cys Asn Val Asp His Lys
        195                 200                 205
Pro Ser Asn Thr Lys Val Asp Lys Thr Val Glu Arg Lys Cys Cys Val
    210                 215                 220
Glu Cys Pro Pro Cys Pro Ala Pro Pro Val Ala Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Phe Arg Val Val Ser Val
    290                 295                 300
Leu Thr Val Val His Gln Asp Trp Leu Asn Gly Lys Glu Tyr Lys Cys
305                 310                 315                 320
Lys Val Ser Asn Lys Gly Leu Pro Ala Pro Ile Glu Lys Thr Ile Ser
                325                 330                 335
Lys Thr Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Met Leu Asp Ser Asp
385                 390                 395                 400
Gly Ser Phe Phe Leu Tyr Ser Lys Leu Thr Val Asp Lys Ser Arg Trp
                405                 410                 415
```

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 346
<211> LENGTH: 1338
<212> TYPE: DNA
<213> ORGANISM: Mus musculus

<400> SEQUENCE: 346
gaggtgcagc tggtgcagtc tggggctgag gtgaagaagc ctgggtcctc ggtgaaggtc      60
tcctgcaagg cttctggttt taccttcacc gactatatta tgcactgggt gcgtcaggcc     120
cctggtcaag ggcttgagtg gatgggctat atcaacccct ataatgatga caccgaatac     180
aacgagaagt tcaagggccg tgtcacgatt accgcggaca atccacgag cacagcctac      240 atggagctga gcagcctgcg ctctgaggac acggccgtgt attactgtgc gcgttcgatt     300
tattactacg atgccccgtt tgcttactgg ggccaaggga ctctggtcac cgtctctagt     360
gcctccacca agggcccatc ggtcttcccc ctggcgccct gctccaggag cacctccgag     420
agcacagcgg ccctgggctg cctggtcaag gactacttcc ccgaaccggt gacggtgtcg     480
tggaactcag cgctctgac cagcggcgtg cacaccttcc cagctgtcct acagtcctca      540
ggactctact ccctcagcag cgtggtgacc gtgccctcca gcaacttcgg cacccagacc     600
tacacctgca acgtagatca caagcccagc aacaccaagg tggacaagac agttgagcgc     660
aaatgttgtg tcgagtgccc accgtgccca gcaccacctg tggcaggacc gtcagtcttc     720
ctcttccccc caaaacccaa ggacaccctc atgatctccc ggacccctga ggtcacgtgc     780
gtggtggtgg acgtgagcca cgaagacccc gaggtccagt tcaactggta cgtggacggc     840
gtggaggtgc ataatgccaa gacaaagcca cgggaggagc agttcaacag cacgttccgt     900
gtggtcagcg tcctcaccgt tgtgcaccag gactggctga acggcaagga gtacaagtgc     960
aaggtctcca acaaaggcct cccagccccc atcgagaaaa ccatctccaa aaccaaaggg    1020
cagccccgag aaccacaggt gtacaccctg cccccatccc gggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacac tcccatgct ggactccgac     1200 ggctccttct cctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaa                                                  1338

<210> SEQ ID NO 347
<211> LENGTH: 465
<212> TYPE: PRT
<213> ORGANISM: Mus musculus

<400> SEQUENCE: 347

Met Asp Trp Thr Trp Arg Ile Leu Phe Leu Val Ala Ala Ala Thr Gly
1               5                   10                  15

Ala His Ser Glu Val Gln Leu Val Gln Ser Gly Ala Glu Val Lys Lys
            20                  25                  30

Pro Gly Ser Ser Val Lys Val Ser Cys Lys Ala Ser Gly Phe Thr Phe
        35                  40                  45

Thr Asp Tyr Ile Met His Trp Val Arg Gln Ala Pro Gly Gln Gly Leu
    50                  55                  60

-continued

Glu Trp Met Gly Tyr Ile Asn Pro Tyr Asn Asp Asp Thr Glu Tyr Asn
 65                  70                  75                  80

Glu Lys Phe Lys Gly Arg Val Thr Ile Thr Ala Asp Lys Ser Thr Ser
             85                  90                  95

Thr Ala Tyr Met Glu Leu Ser Ser Leu Arg Ser Glu Asp Thr Ala Val
            100                 105                 110

Tyr Tyr Cys Ala Arg Ser Ile Tyr Tyr Asp Ala Pro Phe Ala Tyr
        115                 120                 125

Trp Gly Gln Gly Thr Leu Val Thr Val Ser Ser Ala Ser Thr Lys Gly
        130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Asn Phe Gly Thr Gln Thr Tyr Thr Cys Asn Val
210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
            355                 360                 365

Leu Pro Pro Ser Arg Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
        450                 455                 460

Lys
465

<210> SEQ ID NO 348
<211> LENGTH: 1395
<212> TYPE: DNA
<213> ORGANISM: Mus musculus

<400> SEQUENCE: 348

| atggactgga | cctggaggat | cctcttcttg | gtggcagcag | ccacaggagc | ccactccgag | 60 |
| gtgcagctgg | tgcagtctgg | ggctgaggtg | aagaagcctg | gtcctcggt | gaaggtctcc | 120 |
| tgcaaggctt | ctggttttac | cttcaccgac | tatattatgc | actgggtgcg | tcaggcccct | 180 |
| ggtcaagggc | ttgagtggat | gggctatatc | aaccctata | atgatgacac | cgaatacaac | 240 |
| gagaagttca | agggccgtgt | cacgattacc | gcggacaaat | ccacgagcac | agcctacatg | 300 |
| gagctgagca | gcctgcgctc | tgaggacacg | gccgtgtatt | actgtgcgcg | ttcgatttat | 360 |
| tactacgatg | ccccgtttgc | ttactggggc | caagggactc | tggtcaccgt | ctctagtgcc | 420 |
| tccaccaagg | gcccatcggt | cttccccctg | gcgccctgct | ccaggagcac | ctccgagagc | 480 |
| acagcggccc | tgggctgcct | ggtcaaggac | tacttccccg | aaccggtgac | ggtgtcgtgg | 540 |
| aactcaggcg | ctctgaccag | cggcgtgcac | accttcccag | ctgtcctaca | gtcctcagga | 600 |
| ctctactccc | tcagcagcgt | ggtgaccgtg | ccctccagca | acttcggcac | ccagacctac | 660 |
| acctgcaacg | tagatcacaa | gcccagcaac | accaaggtgg | acaagacagt | tgagcgcaaa | 720 |
| tgttgtgtcg | agtgcccacc | gtgcccagca | ccacctgtgg | caggaccgtc | agtcttcctc | 780 |
| ttccccccaa | aacccaagga | caccctcatg | atctcccgga | cccctgaggt | cacgtgcgtg | 840 |
| gtggtggacg | tgagccacga | agaccccgag | gtccagttca | actggtacgt | ggacggcgtg | 900 |
| gaggtgcata | atgccaagac | aaagccacgg | gaggagcagt | tcaacagcac | gttccgtgtg | 960 |
| gtcagcgtcc | tcaccgttgt | gcaccaggac | tggctgaacg | gcaaggagta | caagtgcaag | 1020 |
| gtctccaaca | aaggcctccc | agcccccatc | gagaaaacca | tctccaaaac | caaagggcag | 1080 |
| ccccgagaac | cacaggtgta | caccctgccc | ccatcccggg | aggagatgac | caagaaccag | 1140 |
| gtcagcctga | cctgcctggt | caaaggcttc | taccccagcg | acatcgccgt | ggagtgggag | 1200 |
| agcaatgggc | agccggagaa | caactacaag | accacacctc | ccatgctgga | ctccgacggc | 1260 |
| tccttcttcc | tctacagcaa | gctcaccgtg | gacaagagca | ggtggcagca | ggggaacgtc | 1320 |
| ttctcatgct | ccgtgatgca | tgaggctctg | cacaaccact | acacgcagaa | gagcctctcc | 1380 |
| ctgtctccgg | gtaaa | | | | | 1395 |

<210> SEQ ID NO 349
<211> LENGTH: 417
<212> TYPE: DNA
<213> ORGANISM: Mus musculus

<400> SEQUENCE: 349

| atggaatgga | tctggatatt | tctcttcctc | ctgtcaggaa | ctgcaggtgt | ccactctgag | 60 |
| gtgcagctgg | tgcagtctgg | ggctgaggtg | aagaagcctg | gtcctcggt | gaaggtctcc | 120 |
| tgcaaggctt | ctggttttac | cttcaccgac | tatattatgc | actgggtgcg | tcaggcccct | 180 |
| ggtcaagggc | ttgagtggat | gggctatatc | aaccctata | atgatgacac | cgaatacaac | 240 |
| gagaagttca | agggccgtgt | cacgattacc | gcggacaaat | ccacgagcac | agcctacatg | 300 |
| gagctgagca | gcctgcgctc | tgaggacacg | gccgtgtatt | actgtgcgcg | ttcgatttat | 360 |
| tactacgatg | ccccgtttgc | ttactggggc | caagggactc | tggtcacagt | ctcgagc | 417 |

<210> SEQ ID NO 350
<211> LENGTH: 218

```
<212> TYPE: PRT
<213> ORGANISM: Mus musculus

<400> SEQUENCE: 350

Asp Ile Val Leu Thr Gln Ser Pro Ala Ser Leu Ala Val Ser Leu Gly
1               5                   10                  15

Gln Arg Ala Thr Ile Ala Cys Lys Ala Ser Gln Ser Val Asp Tyr Asp
            20                  25                  30

Gly Thr Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Glu Ile Pro Ala
    50                  55                  60

Arg Phe Ser Gly Thr Gly Ser Gly Thr Asp Phe Thr Leu Asn Ile His
65                  70                  75                  80

Pro Val Glu Glu Glu Asp Ile Thr Thr Tyr Tyr Cys Gln Gln Ser Asn
                85                  90                  95

Glu Asp Pro Phe Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 351
<211> LENGTH: 15
<212> TYPE: PRT
<213> ORGANISM: Mus musculus

<400> SEQUENCE: 351

Lys Ala Ser Gln Ser Val Asp Tyr Asp Gly Thr Ser Tyr Met Asn
1               5                   10                  15

<210> SEQ ID NO 352
<211> LENGTH: 7
<212> TYPE: PRT
<213> ORGANISM: Mus musculus

<400> SEQUENCE: 352

Ala Ala Ser Asn Leu Glu Ser
1               5

<210> SEQ ID NO 353
<211> LENGTH: 9
<212> TYPE: PRT
<213> ORGANISM: Mus musculus

<400> SEQUENCE: 353

Gln Gln Ser Asn Glu Asp Pro Phe Thr
1               5
```

<210> SEQ ID NO 354
<211> LENGTH: 657
<212> TYPE: DNA
<213> ORGANISM: Mus musculus

<400> SEQUENCE: 354

```
gacattgtgt tgacccagtc tccagcttct ttggctgtgt ctctagggca gagggccacc      60
atcgcctgca aggccagcca aagtgttgat tatgatggta ctagttatat gaattggtac     120
caacagaaac caggacagcc acccaaactc ctcatctatg ctgcatccaa tctagaatct     180
gagatcccag ccaggtttag tggcactggg tctgggacag acttcaccct caacatccat     240
cctgtggagg aggaggatat acaaacctat tactgtcagc aaagtaatga ggatccgttc     300
acgttcggag gggggaccaa gttggaaata aaacgggctg atgctgcacc aactgtatcc     360
atcttcccac catccagtga gcagttaaca tctggaggtg cctcagtcgt gtgcttcttg     420
aacaacttct accccaaaga catcaatgtc aagtggaaga ttgatggcag tgaacgacaa     480
aatggcgtcc tgaacagttg gactgatcag gacagcaaag acagcaccta cagcatgagc     540
agcaccctca cgttgaccaa ggacgagtat gaacgacata cagctatac ctgtgaggcc      600
actcacaaga catcaacttc acccattgtc aagagcttca acaggaatga gtgttag       657
```

<210> SEQ ID NO 355
<211> LENGTH: 238
<212> TYPE: PRT
<213> ORGANISM: Mus musculus

<400> SEQUENCE: 355

Met Glu Thr Asp Thr Ile Leu Leu Trp Val Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ala Cys Lys Ala Ser Gln Ser
        35                  40                  45

Val Asp Tyr Asp Gly Thr Ser Tyr Met Asn Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Glu Ile Pro Ala Arg Phe Ser Gly Thr Gly Ser Gly Thr Asp Phe Thr
                85                  90                  95

Leu Asn Ile His Pro Val Glu Glu Asp Ile Thr Thr Tyr Tyr Cys
            100                 105                 110

Gln Gln Ser Asn Glu Asp Pro Phe Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

```
Ser Thr Ser Pro Ile Val Lys Ser Phe Asn Arg Asn Glu Cys
225                 230                 235
```

<210> SEQ ID NO 356
<211> LENGTH: 717
<212> TYPE: DNA
<213> ORGANISM: Mus musculus

<400> SEQUENCE: 356

```
atggagacag acacaatcct gctatgggtg ctgctgctct gggttccagg ctccactggt    60
gacattgtgt tgacccagtc tccagcttct ttggctgtgt ctctagggca gagggccacc   120
atcgcctgca aggccagcca agtgttgat tatgatggta ctagttatat gaattggtac    180
caacagaaac caggacagcc acccaaactc ctcatctatg ctgcatccaa tctagaatct   240
gagatcccag ccaggtttag tggcactggg tctgggacag acttcaccct caacatccat   300
cctgtggagg aggaggatat cacaacctat tactgtcagc aaagtaatga ggatccgttc   360
acgttcggag gggggaccaa gttggaaata aaacggctg atgctgcacc aactgtatcc    420
atcttcccac catccagtga gcagttaaca tctggaggtg cctcagtcgt gtgcttcttg    480
aacaacttct accccaaaga catcaatgtc aagtggaaga ttgatggcag tgaacgacaa    540
aatggcgtcc tgaacagttg gactgatcag gacagcaaag acagcaccta cagcatgagc   600
agcaccctca cgttgaccaa ggacgagtat gaacgacata cagctatac ctgtgaggcc     660
actcacaaga catcaacttc acccattgtc aagagcttca caggaatga gtgttag       717
```

<210> SEQ ID NO 357
<211> LENGTH: 442
<212> TYPE: PRT
<213> ORGANISM: Mus musculus

<400> SEQUENCE: 357

```
Gln Val Gln Leu Gln Gln Pro Gly Thr Glu Leu Val Arg Pro Gly Thr
1               5                   10                  15

Ser Val Lys Leu Ser Cys Lys Ala Ser Gly Tyr Ile Phe Thr Thr Tyr
                20                  25                  30

Trp Met Asn Trp Val Lys Gln Arg Pro Gly Gln Gly Leu Glu Trp Ile
            35                  40                  45

Gly Met Ile His Pro Ser Ala Ser Glu Ile Arg Leu Asp Gln Lys Phe
        50                  55                  60

Lys Asp Lys Ala Thr Leu Thr Leu Asp Lys Ser Ser Ser Thr Ala Tyr
65                  70                  75                  80

Met His Leu Ser Gly Pro Thr Ser Val Asp Ser Ala Val Tyr Tyr Cys
                85                  90                  95

Ala Arg Ser Gly Glu Trp Gly Ser Met Asp Tyr Trp Gly Gln Gly Thr
            100                 105                 110

Ser Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
```

```
                195                 200                 205
Thr Lys Val Asp Lys Lys Ile Val Pro Arg Asp Cys Gly Cys Lys Pro
210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
                260                 265                 270

Phe Val Asp Asp Val Glu Val His Thr Ala Gln Thr Gln Pro Arg Glu
                275                 280                 285

Glu Gln Phe Asn Ser Thr Phe Arg Ser Val Ser Glu Leu Pro Ile Met
290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
                340                 345                 350

Met Ala Lys Asp Lys Val Ser Leu Thr Cys Met Ile Thr Asp Phe Phe
                355                 360                 365

Pro Glu Asp Ile Thr Val Glu Trp Gln Trp Asn Gly Gln Pro Ala Glu
370                 375                 380

Asn Tyr Lys Asn Thr Gln Pro Ile Met Asp Thr Asp Gly Ser Tyr Phe
385                 390                 395                 400

Ile Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
                420                 425                 430

Glu Lys Ser Leu Ser His Ser Pro Gly Lys
                435                 440

<210> SEQ ID NO 358
<211> LENGTH: 5
<212> TYPE: PRT
<213> ORGANISM: Mus musculus

<400> SEQUENCE: 358

Thr Tyr Trp Met Asn
1               5

<210> SEQ ID NO 359
<211> LENGTH: 17
<212> TYPE: PRT
<213> ORGANISM: Mus musculus

<400> SEQUENCE: 359

Met Ile His Pro Ser Ala Ser Glu Ile Arg Leu Asp Gln Lys Phe Lys
1               5                   10                  15

Asp

<210> SEQ ID NO 360
<211> LENGTH: 9
<212> TYPE: PRT
<213> ORGANISM: Mus musculus

<400> SEQUENCE: 360

Ser Gly Glu Trp Gly Ser Met Asp Tyr
```

<210> SEQ ID NO 361
<211> LENGTH: 1329
<212> TYPE: DNA
<213> ORGANISM: Mus musculus

<400> SEQUENCE: 361

```
caggtccaac tacagcagcc tgggactgag ctggtgaggc ctggaacttc agtgaagttg    60
tcctgtaagg cttctggcta catcttcacc acctactgga tgaactgggt gaaacagagg   120
cctggacaag gccttgagtg gattggcatg attcatcctt ccgcaagtga aattaggttg   180
gatcagaaat tcaaggacaa ggccacattg actcttgaca atcctccag cacagcctat    240
atgcacctca gcggcccgac atctgtggat tctgcggtct attactgtgc aagatcaggg   300
gaatggggt ctatggacta ctggggtcaa ggaacctcag tcaccgtctc ctcagccaaa    360
acgacacccc catctgtcta tccactggcc cctggatctg ctgcccaaac taactccatg   420
gtgaccctgg atgcctggt caagggctat ttccctgagc cagtgacagt gacctggaac    480
tctggatccc tgtccagcgg tgtgcacacc ttcccagctg tcctgcagtc tgacctctac   540
actctgagca gctcagtgac tgtcccctcc agcacctggc ccagcgagac cgtcacctgc   600
aacgttgccc accggccag cagcaccaag gtggacaaga aaattgtgcc cagggattgt    660
ggttgtaagc cttgcatatg tacagtccca gaagtatcat ctgtcttcat cttccccca    720
aagcccaagg atgtgctcac cattactctg actcctaagg tcacgtgtgt tgtggtagac   780
atcagcaagg atgatcccga ggtccagttc agctggtttg tagatgatgt ggaggtgcac   840
acagctcaga cgcaaccccg ggaggagcag ttcaacagca cttttccgctc agtcagtgaa   900
cttcccatca tgcaccagga ctggctcaat ggcaaggagt tcaaatgcag ggtcaacagt   960
gcagctttcc ctgcccccat cgagaaaacc atctccaaaa ccaaaggcag accgaaggct  1020
ccacaggtgt acaccattcc acctcccaag gagcagatgg ccaaggataa agtcagtctg  1080
acctgcatga taacagactt cttccctgaa gacattactg tggagtggca gtggaatggg  1140
cagccagcgg agaactacaa gaacactcag cccatcatgg acacagatgg ctcttacttc  1200
atctacagca agctcaatgt gcagaagagc aactgggagg caggaaatac tttcacctgc  1260
tctgtgttac atgagggcct gcacaaccac catactgaga agagcctctc ccactctcct  1320
ggtaaatga                                                          1329
```

<210> SEQ ID NO 362
<211> LENGTH: 461
<212> TYPE: PRT
<213> ORGANISM: Mus musculus

<400> SEQUENCE: 362

Met Gly Trp Ser Ser Ile Ile Leu Phe Leu Val Ala Thr Ala Thr Gly
1               5                   10                  15

Val His Ser Gln Val Gln Leu Gln Gln Pro Gly Thr Glu Leu Val Arg
            20                  25                  30

Pro Gly Thr Ser Val Lys Leu Ser Cys Lys Ala Ser Gly Tyr Ile Phe
        35                  40                  45

Thr Thr Tyr Trp Met Asn Trp Val Lys Gln Arg Pro Gly Gln Gly Leu
    50                  55                  60

Glu Trp Ile Gly Met Ile His Pro Ser Ala Ser Glu Ile Arg Leu Asp
65                  70                  75                  80

Gln Lys Phe Lys Asp Lys Ala Thr Leu Thr Leu Asp Lys Ser Ser Ser

|     |     |     |     | 85  |     |     |     |     | 90  |     |     |     |     | 95  |
| --- | --- | --- | --- | --- | --- | --- | --- | --- | --- | --- | --- | --- | --- | --- |
| Thr | Ala | Tyr | Met | His | Leu | Ser | Gly | Pro | Thr | Ser | Val | Asp | Ser | Ala | Val |

Thr Ala Tyr Met His Leu Ser Gly Pro Thr Ser Val Asp Ser Ala Val
                                100                 105                 110

Tyr Tyr Cys Ala Arg Ser Gly Glu Trp Gly Ser Met Asp Tyr Trp Gly
            115                 120                 125

Gln Gly Thr Ser Val Thr Val Ser Ala Lys Thr Thr Pro Pro Ser
        130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
                180                 185                 190

Val Leu Gln Ser Asp Leu Tyr Thr Leu Ser Ser Ser Val Thr Val Pro
            195                 200                 205

Ser Ser Thr Trp Pro Ser Glu Thr Val Thr Cys Asn Val Ala His Pro
        210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
                260                 265                 270

Val Thr Cys Val Val Val Asp Ile Ser Lys Asp Asp Pro Glu Val Gln
            275                 280                 285

Phe Ser Trp Phe Val Asp Asp Val Glu Val His Thr Ala Gln Thr Gln
        290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
                340                 345                 350

Thr Lys Gly Arg Pro Lys Ala Pro Gln Val Tyr Thr Ile Pro Pro Pro
            355                 360                 365

Lys Glu Gln Met Ala Lys Asp Lys Val Ser Leu Thr Cys Met Ile Thr
        370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Ile Tyr Ser Lys Leu Asn Val Gln Lys Ser Asn Trp Glu
                420                 425                 430

Ala Gly Asn Thr Phe Thr Cys Ser Val Leu His Glu Gly Leu His Asn
            435                 440                 445

His His Thr Glu Lys Ser Leu Ser His Ser Pro Gly Lys
        450                 455                 460

<210> SEQ ID NO 363
<211> LENGTH: 1386
<212> TYPE: DNA
<213> ORGANISM: Mus musculus

<400> SEQUENCE: 363
atgggatgga gctctatcat cctcttcttg gtagcaacag ctacaggtgt ccactcccag    60

```
gtccaactac agcagcctgg gactgagctg gtgaggcctg gaacttcagt gaagttgtcc    120
tgtaaggctt ctggctacat cttcaccacc tactggatga actgggtgaa acagaggcct    180
ggacaaggcc ttgagtggat tggcatgatt catccttccg caagtgaaat taggttggat    240
cagaaattca aggacaaggc cacattgact cttgacaaat cctccagcac agcctatatg    300
cacctcagcg cccgacatc tgtggattct gcggtctatt actgtgcaag atcaggggaa    360
tgggggtcta tggactactg gggtcaagga acctcagtca ccgtctcctc agccaaaacg    420
acacccccat ctgtctatcc actggcccct ggatctgctg cccaaactaa ctccatggtg    480
accctgggat gcctggtcaa gggctatttc cctgagccag tgacagtgac ctggaactct    540
ggatccctgt ccagcggtgt gcacaccttc ccagctgtcc tgcagtctga cctctacact    600
ctgagcagct cagtgactgt cccctccagc acctggccca cgagaccgt cacctgcaac    660 gttgcccacc cggccagcag caccaaggtg gacaagaaaa ttgtgcccag ggattgtggt    720
tgtaagcctt gcatatgtac agtcccagaa gtatcatctg tcttcatctt ccccccaaag    780
cccaaggatg tgctcaccat tactctgact cctaaggtca cgtgtgttgt ggtagacatc    840
agcaaggatg atcccgaggt ccagttcagc tggtttgtag atgatgtgga ggtgcacaca    900
gctcagacgc aaccccggga ggagcagttc aacagcactt tccgctcagt cagtgaactt    960
cccatcatgc accaggactg gctcaatggc aaggagttca aatgcagggt caacagtgca   1020
gctttccctg cccccatcga gaaaaccatc tccaaaacca aggcagacc gaaggctcca   1080 caggtgtaca ccattccacc tcccaaggag cagatggcca aggataaagt cagtctgacc   1140
tgcatgataa cagacttctt ccctgaagac attactgtgg agtggcagtg gaatgggcag   1200
ccagcggaga actacaagaa cactcagccc atcatggaca cagatggctc ttacttcatc   1260
tacagcaagc tcaatgtgca gaagagcaac tgggaggcag gaaatacttt cacctgctct   1320
gtgttacatg agggcctgca caaccaccat actgagaaga gcctctccca ctctcctggt   1380
aaatga                                                              1386
```

<210> SEQ ID NO 364
<211> LENGTH: 106
<212> TYPE: PRT
<213> ORGANISM: Mus musculus

<400> SEQUENCE: 364

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ile Lys His Pro Thr
                85                  90                  95

Phe Gly Gln Gly Thr Lys Val Glu Ile Lys
            100                 105
```

<210> SEQ ID NO 365
<211> LENGTH: 318
<212> TYPE: DNA

<213> ORGANISM: Mus musculus

<400> SEQUENCE: 365

```
gacatccaga tgacccagtc tccatcctcc ctgtctgcat ctgtaggtga ccgtgtcacc    60
atcacttgcc gcgcaagtca ggatattagc agctatttaa attggtatca gcagaaacca   120
gggaaagccc ctaagctcct gatctattct acttcccgtt tgaatagtgg ggtcccatca   180
cgcttcagtg gcagtggctc tgggacagat ttcactctca ccatcagcag tctgcaacct   240
gaagattttg caacttacta ctgtcaacag gatattaaac ccctacgttt cggtcaaggc   300
accaaggtgg agatcaaa                                                 318
```

<210> SEQ ID NO 366
<211> LENGTH: 120
<212> TYPE: PRT
<213> ORGANISM: Mus musculus

<400> SEQUENCE: 366

```
Glu Val Gln Leu Val Gln Ser Gly Ala Glu Val Lys Lys Pro Gly Ser
 1               5                  10                  15

Ser Val Lys Val Ser Cys Lys Ala Ser Gly Phe Thr Phe Thr Asp Tyr
             20                  25                  30

Ile Met His Trp Val Arg Gln Ala Pro Gly Gln Gly Leu Glu Trp Met
         35                  40                  45

Gly Tyr Ile Asn Pro Tyr Asn Asp Asp Thr Glu Tyr Asn Glu Lys Phe
     50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser
        115                 120
```

<210> SEQ ID NO 367
<211> LENGTH: 360
<212> TYPE: DNA
<213> ORGANISM: Mus musculus

<400> SEQUENCE: 367

```
gaggtgcagc tggtgcagtc tggggctgag gtgaagaagc ctgggtcctc ggtgaaggtc    60
tcctgcaagg cttctggttt taccttcacc gactatatta tgcactgggt gcgtcaggcc   120
cctggtcaag gcttgagtg gatgggctat atcaaccctt ataatgatga caccgaatac   180
aacgagaagt tcaagggccg tgtcacgatt accgcggaca aatccacgag cacagcctac   240
atggagctga gcagcctgcg ctctgaggac acggccgtgt attactgtgc gcgttcgatt   300
tattactacg atgccccgtt tgcttactgg ggccaaggga ctctggtcac cgtctctagt   360
```

<210> SEQ ID NO 368
<211> LENGTH: 108
<212> TYPE: PRT
<213> ORGANISM: Mus musculus

<400> SEQUENCE: 368

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Phe Thr Ala
```

```
                20                  25                  30
Val Ala Trp Tyr Gln Gln Lys Pro Gly Lys Ala Pro Lys Leu Leu Ile
            35                  40                  45

Tyr Trp Ala Ser Thr Arg His Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gly Gly Thr Lys Val Glu Ile Lys Arg
            100                 105

<210> SEQ ID NO 369
<211> LENGTH: 324
<212> TYPE: DNA
<213> ORGANISM: Mus musculus

<400> SEQUENCE: 369
gatatccaga tgacccagag cccgagcagc ctgagcgcga gcgtgggcga tcgcgtgacc      60
attacctgca aagcgagcca ggatgtgttt accgcggtgg cgtggtatca gcagaaaccg     120
ggcaaagcgc cgaaactgct gatttattgg gcgagcaccc gccataccgg cgtgccgagt     180
cgctttagcg gcagcggcag cggcaccgat tttaccctga ccattagcag cctgcagccg     240
gaagattttg cgacctatta ttgccagcag tatagcagct atccgctgac ctttggcggc     300
ggcaccaaag tggaaattaa acgt                                             324

<210> SEQ ID NO 370
<211> LENGTH: 119
<212> TYPE: PRT
<213> ORGANISM: Mus musculus

<400> SEQUENCE: 370

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Ile
        35                  40                  45

Gly Arg Ile Asp Pro Glu Asn Gly Asp Ile Ile Tyr Asp Pro Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Tyr Asp Ala Gly Asp Pro Ala Trp Phe Thr Tyr Trp Gly Gln Gly
            100                 105                 110

Thr Leu Val Thr Val Ser Ser
        115

<210> SEQ ID NO 371
<211> LENGTH: 357
<212> TYPE: DNA
<213> ORGANISM: Mus musculus

<400> SEQUENCE: 371
gaagtgcagc tggtgcagag cggcgcggaa gtgaaaaaac cgggcgcgag cgtgaaagtg      60
agctgcaaag cgagcggctt taacattaaa gattattata tgcattgggt gcgccaggcg     120
```

```
ccgggccagg gcctggaatg gatcggccgc attgatccgg aaaacggcga tattatttat    180
gatccgaaat ttcagggccg cgtgaccatg accaccgata ccagcaccag caccgcgtat    240
atggaactgc gcagcctgcg cagcgatgat accgcggtgt attattgcgc gtatgatgcg    300
ggcgatccgg cgtggtttac ctattgggc cagggcaccc tggtgaccgt ctcgagc        357
```

<210> SEQ ID NO 372
<211> LENGTH: 108
<212> TYPE: PRT
<213> ORGANISM: Mus musculus

<400> SEQUENCE: 372

```
Asp Ile Gln Leu Thr Gln Ser Pro Ser Phe Leu Ser Ala Ser Val Gly
1               5                   10                  15

Asp Arg Val Thr Ile Thr Cys Ser Val Ser Ser Ile Ser Ser Ser
            20                  25                  30

Asn Leu His Trp Tyr Gln Gln Lys Pro Gly Lys Ala Pro Lys Leu Leu
        35                  40                  45

Ile Tyr Gly Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Trp Thr Thr Thr Tyr
                85                  90                  95

Thr Phe Gly Gln Gly Thr Lys Leu Glu Ile Lys Arg
            100                 105
```

<210> SEQ ID NO 373
<211> LENGTH: 324
<212> TYPE: DNA
<213> ORGANISM: Mus musculus

<400> SEQUENCE: 373

```
gatattcagc tgacccagag cccgagcttt ctgagcgcga gcgtgggcga tcgcgtgacc    60
attacctgca gcgtgagcag cagcattagc agcagcaacc tgcattggta tcagcagaaa    120
ccgggcaaag cgccgaaact gctgatttat ggcaccagca acctggcgag cggcgtgccg    180
agccgcttta gcggcagcgg cagcggcacc gaatttaccc tgaccattag cagcctgcag    240
ccggaagatt ttgcgaccta ttattgccag cagtggacca ccacctatac ctttggccag    300
ggcaccaaac tggaaattaa acgt                                           324
```

<210> SEQ ID NO 374
<211> LENGTH: 122
<212> TYPE: PRT
<213> ORGANISM: Mus musculus

<400> SEQUENCE: 374

```
Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Ile His Trp Val Arg Gln Ala Pro Gly Gln Gly Leu Glu Trp Met
        35                  40                  45

Gly Arg Ile Asp Pro Asp Asn Gly Glu Ser Thr Tyr Val Pro Lys Phe
    50                  55                  60

Gln Gly Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85                  90                  95
Ala Arg Glu Gly Leu Asp Tyr Gly Asp Tyr Tyr Ala Val Asp Tyr Trp
            100                 105                 110
Gly Gln Gly Thr Leu Val Thr Val Ser Ser
        115                 120

<210> SEQ ID NO 375
<211> LENGTH: 366
<212> TYPE: DNA
<213> ORGANISM: Mus musculus

<400> SEQUENCE: 375
gaagtgcagc tggtgcagag cggcgcggaa gtgaaaaaac cgggcgcgag cgtgaaagtg      60
agctgcaaag cgagcggctt taacattaaa gattattata ttcattgggt gcgccaggcg     120
ccgggccagg gcctggaatg gatgggccgc attgatccgg ataacggcga aagcacctat     180
gtgccgaaat ttcagggccg cgtgaccatg accaccgata ccagcaccag caccgcgtat     240
atggaactgc gcagcctgcg cagcgatgat accgcggtgt attattgcgc gcgcgaaggc     300
ctggattatg gcgattatta tgcggtggat tattggggcc agggcaccct ggtgaccgtc     360
tcgagc                                                                366

<210> SEQ ID NO 376
<211> LENGTH: 107
<212> TYPE: PRT
<213> ORGANISM: Mus musculus

<400> SEQUENCE: 376

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Asn Tyr
            20                  25                  30
Leu Asn Trp Tyr Gln Gln Lys Pro Gly Lys Ala Pro Lys Leu Leu Ile
        35                  40                  45
Tyr Tyr Thr Ser Arg Leu Leu Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Asp Thr Leu Pro Tyr
                85                  90                  95
Thr Phe Gly Gly Gly Thr Lys Val Glu Ile Lys
            100                 105

<210> SEQ ID NO 377
<211> LENGTH: 321
<212> TYPE: DNA
<213> ORGANISM: Mus musculus

<400> SEQUENCE: 377
gacatccaga tgacccagtc tccatcctcc ctctccgcat ccgtaggcga ccgcgtaacc      60
ataacatgta gagcatctca agatatttcc aactatttga attggtacca acaaaaaccc     120
ggcaaagcac ctaaactcct catttactat acatcaagac tcctctccgg cgttccatca     180
cgattctcag gctccggctc cggcacagat ttcacactca ctatttcctc cctccaacca     240
gaagattttg caacctatta ctgtcaacaa ggcgatacac tcccatacac attcggcggc     300
ggcacaaaag ttgaaattaa a                                               321
```

<210> SEQ ID NO 378
<211> LENGTH: 123
<212> TYPE: PRT
<213> ORGANISM: Mus musculus

<400> SEQUENCE: 378

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Gln Gly Thr Thr Val Thr Val Ser Ser
        115                 120
```

<210> SEQ ID NO 379
<211> LENGTH: 369
<212> TYPE: DNA
<213> ORGANISM: Mus musculus

<400> SEQUENCE: 379

```
gaggtgcagc tggtgcagag cggcgccgag gtaaaaaaac caggagcaag cgttaaagtt      60
tcttgtaaag caagcggata tacatttaca gattacaaca tgcattgggt aagacaagcg     120
ccaggacaag gattggaatg gatgggcgaa attaacccta atagtggagg agcaggctac     180
aatcaaaaat tcaaagggag agttacaatg acaacagaca caagcacttc aacagcatat     240
atggaactgc gatcacttag aagcgacgat acagctgtat actattgcgc acgacttggg     300
tatgatgata tatatgatga ctggtatttc gatgtttggg gccagggaac aacagttacc     360
gtctctagt                                                             369
```

<210> SEQ ID NO 380
<211> LENGTH: 108
<212> TYPE: PRT
<213> ORGANISM: Mus musculus

<400> SEQUENCE: 380

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Thr Ser Ser
            20                  25                  30

Tyr Leu Asn Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Tyr Asp Phe Phe Pro
                85                  90                  95
```

```
Ser Thr Phe Gly Gly Gly Thr Lys Val Glu Ile Lys
            100                 105
```

<210> SEQ ID NO 381
<211> LENGTH: 324
<212> TYPE: DNA
<213> ORGANISM: Mus musculus

<400> SEQUENCE: 381

```
gacatccagc tgacccagag ccccagcttc ctttccgcat ccgttggtga ccgagtaaca    60
atcacatgcc gcgcctcatc ttcagttaca tcttcttatc ttaattggta tcaacaaaaa   120
ccaggaaaag cacctaaact tcttatatac tctacatcta atctcgcatc aggagttccc   180
tctcgatttt caggatctgg atcaggcaca gaatttacac ttactatatc atcactccaa   240
ccagaagact tcgccactta ttactgccaa caatacgatt ttttttccaag cacattcgga   300
ggaggtacaa aagtagaaat caag                                          324
```

<210> SEQ ID NO 382
<211> LENGTH: 121
<212> TYPE: PRT
<213> ORGANISM: Mus musculus

<400> SEQUENCE: 382

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Tyr Met Asn Trp Val Arg Gln Ala Pro Gly Gln Arg Leu Glu Trp Met
        35                  40                  45
Gly Asp Ile Asn Pro Tyr Asn Asp Asp Thr Thr Tyr Asn His Lys Phe
    50                  55                  60
Lys Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Thr Ala Val Ile Thr Thr Asn Ala Met Asp Tyr Trp Gly
            100                 105                 110
Gln Gly Thr Thr Val Thr Val Ser Ser
        115                 120
```

<210> SEQ ID NO 383
<211> LENGTH: 363
<212> TYPE: DNA
<213> ORGANISM: Mus musculus

<400> SEQUENCE: 383

```
gaggtgcagc tggtgcagag cggcgccgag gtcaagaaac ctggagcaag cgtaaaggtt    60
agttgcaaag catctggata cacatttacc gactactaca tgaattgggt acgacaagcc   120
cctggacaaa gacttgaatg gatgggagac attaaccctt ataacgacga cactacatac   180
aatcataaat ttaaaggaag agttacaatt acaagagata catccgcatc aaccgcctat   240
atggaacttt cctcattgag atctgaagac actgctgttt attactgtgc aagagaaact   300
gccgttatta ctactaacgc tatggattac tggggtcaag aaccactgt taccgtctct   360
agt                                                                 363
```

<210> SEQ ID NO 384

```
<211> LENGTH: 108
<212> TYPE: PRT
<213> ORGANISM: Mus musculus

<400> SEQUENCE: 384

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Thr Ile Ser Ser Asn
            20                  25                  30

His Leu His Trp Phe Gln Gln Lys Pro Gly Lys Ala Pro Lys Ser Leu
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Ser Tyr Pro
                85                  90                  95

Leu Thr Phe Gly Gly Gly Thr Lys Val Glu Ile Lys
            100                 105

<210> SEQ ID NO 385
<211> LENGTH: 324
<212> TYPE: DNA
<213> ORGANISM: Mus musculus

<400> SEQUENCE: 385
gacatccaga tgacccagtc tccatcctcc ctctcagcat ccgtaggcga tagagttaca      60
ataacatgca gcgtatcatc aactatatca tcaaatcatc ttcattggtt ccaacagaaa     120
cccggcaaag cacctaaatc acttatatac ggcacatcaa atctcgcatc aggcgttcct     180
tcaagatttt caggctctgg ctcaggcacc gactttactc ttacaatatc ctccctccaa     240
cccgaagact tcgcaaccta ttactgtcaa caatggtcct catatccact cacatttggc     300
ggcggcacaa agtagaaat taaa                                             324

<210> SEQ ID NO 386
<211> LENGTH: 125
<212> TYPE: PRT
<213> ORGANISM: Mus musculus

<400> SEQUENCE: 386

Glu Val Gln Leu Val Gln Ser Gly Ala Glu Val Lys Lys Pro Gly Ala
1               5                   10                  15

Ser Val Lys Val Ser Cys Lys Ala Ser Asp Phe Asn Ile Lys Asp Phe
            20                  25                  30

Tyr Leu His Trp Val Arg Gln Ala Pro Gly Gln Gly Leu Glu Trp Ile
        35                  40                  45

Gly Arg Ile Asp Pro Glu Asn Gly Asp Thr Leu Tyr Asp Pro Lys Phe
    50                  55                  60

Gln Asp Lys Val Thr Met Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Asp Tyr Phe His Asp Gly Thr Ser Tyr Trp Tyr Phe
            100                 105                 110

Asp Val Trp Gly Arg Gly Thr Leu Val Thr Val Ser Ser
        115                 120                 125
```

<210> SEQ ID NO 387
<211> LENGTH: 375
<212> TYPE: DNA
<213> ORGANISM: Mus musculus

<400> SEQUENCE: 387

```
gaggtgcagc tggtgcagtc tggggctgag gtgaagaagc tggggcctc agtgaaggtc        60 tcctgcaagg cttctgactt caacattaaa gacttctatc tacactgggt gcgacaggcc      120
cctggacaag ggcttgagtg gattggaagg attgatcctg agaatggtga tactttatat      180
gacccgaagt tccaggacaa ggtcaccatg accacagaca cgtccaccag cacagcctac      240
atggagctga ggagcctgag atctgacgac acggccgtgt attactgtgc gagagaggcg      300
gattatttcc acgatggtac ctcctactgg tacttcgatg tctggggccg tggcaccctg      360
gtcaccgtct ctagt                                                        375
```

<210> SEQ ID NO 388
<211> LENGTH: 106
<212> TYPE: PRT
<213> ORGANISM: Mus musculus

<400> SEQUENCE: 388

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Ile Ser Tyr Ile
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asp Pro Leu Thr
                85                  90                  95

Phe Gly Gly Gly Thr Lys Val Glu Ile Lys
            100                 105
```

<210> SEQ ID NO 389
<211> LENGTH: 318
<212> TYPE: DNA
<213> ORGANISM: Mus musculus

<400> SEQUENCE: 389

```
gacatccagt tgacccagtc tccatccttc ctgtctgcat ctgtaggaga cagagtcacc        60
atcacttgca gggccagctc aagtataagt tacatacact ggtatcagca aaaaccaggg      120
aaagccccta agctcctgat ctatgccaca tccaacctgg cttctggggt cccatcaagg      180
ttcagcggca gtggatctgg gacagaattc actctcacaa tcagcagcct gcagcctgaa      240
gattttgcaa cttattactg tcagcagtgg agtagtgacc cactcacgtt cggcggaggg      300
accaaggtgg agatcaaa                                                     318
```

<210> SEQ ID NO 390
<211> LENGTH: 121
<212> TYPE: PRT
<213> ORGANISM: Mus musculus

<400> SEQUENCE: 390

```
Glu Val Gln Leu Val Gln Ser Gly Ala Glu Val Lys Lys Pro Gly Ala
1               5                   10                  15
```

Ser Val Lys Val Ser Cys Lys Ala Ser Gly Phe Asp Ile Lys Asp Tyr
            20                  25                  30

Tyr Ile His Trp Val Arg Gln Ala Pro Gly Gln Gly Leu Glu Trp Ile
        35                  40                  45

Gly Arg Val Asp Pro Asp Asn Gly Glu Thr Glu Phe Ala Pro Lys Phe
    50                  55                  60

Pro Gly Lys Val Thr Met Thr Thr Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Asp Tyr Asp Gly Thr Tyr Thr Trp Phe Pro Tyr Trp Gly
                100                 105                 110

Gln Gly Thr Leu Val Thr Val Ser Ser
            115                 120

<210> SEQ ID NO 391
<211> LENGTH: 363
<212> TYPE: DNA
<213> ORGANISM: Mus musculus

<400> SEQUENCE: 391
gaggtgcagc tggtgcagtc tggggctgag gtgaagaagc ctggggcctc agtgaaggtc     60
tcctgcaagg cttctggatt cgacattaag gactactata tacactgggt gcgacaggcc    120
cctggacaag gcttgagtg gatcggaagg gttgatcctg acaatggtga gactgaattt    180
gccccgaagt tcccgggcaa ggtcaccatg accacagaca cgtccatcag cacagcctac    240
atggagctga gcaggctgag atctgacgac acggccgtgt attactgtgc gagagaagac    300
tacgatggta cctacacctg gtttccttat tggggccaag ggactctggt caccgtctct    360
agt                                                                   363

<210> SEQ ID NO 392
<211> LENGTH: 448
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 392

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Ser Gly Gly Ala Gly Tyr Asn Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Tyr Asp Asp Ile Tyr Asp Asp Trp Tyr Phe Asp Val
                100                 105                 110

Trp Gly Gln Gly Thr Thr Val Thr Val Ser Ser Ala Ser Thr Lys Gly
            115                 120                 125

```
Pro Ser Val Phe Pro Leu Ala Pro Cys Ser Arg Ser Thr Ser Glu Ser
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 393
<211> LENGTH: 446
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 393

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30
```

```
Tyr Met Asn Trp Val Arg Gln Ala Pro Gly Gln Arg Leu Glu Trp Met
     35                  40                  45
Gly Asp Ile Asn Pro Tyr Asn Asp Thr Thr Tyr Asn His Lys Phe
 50                  55                  60
Lys Gly Arg Val Thr Ile Thr Arg Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Glu Thr Ala Val Ile Thr Thr Asn Ala Met Asp Tyr Trp Gly
            100                 105                 110
Gln Gly Thr Thr Val Thr Val Ser Ser Ala Ser Thr Lys Gly Pro Ser
            115                 120                 125
Val Phe Pro Leu Ala Pro Cys Ser Arg Ser Thr Ser Glu Ser Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Asn Phe Gly Thr Gln Thr Tyr Thr Cys Asn Val Asp His
        195                 200                 205
Lys Pro Ser Asn Thr Lys Val Asp Lys Thr Val Glu Arg Lys Cys Cys
210                 215                 220
Val Glu Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Phe Arg Val Val Ser
290                 295                 300
Val Leu Thr Val Val His Gln Asp Trp Leu Asn Gly Lys Glu Tyr Lys
305                 310                 315                 320
Cys Lys Val Ser Asn Lys Gly Leu Pro Ala Pro Ile Glu Lys Thr Ile
                325                 330                 335
Ser Lys Thr Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Met Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly
        435                 440                 445

<210> SEQ ID NO 394
```

```
<211> LENGTH: 450
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 394
```

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Asp | Phe | Asn | Ile | Lys | Asp | Phe |
| | | 20 | | | | | 25 | | | | | 30 | | | |
| Tyr | Leu | His | Trp | Val | Arg | Gln | Ala | Pro | Gly | Gln | Gly | Leu | Glu | Trp | Ile |
| | | 35 | | | | | 40 | | | | | 45 | | | |
| Gly | Arg | Ile | Asp | Pro | Glu | Asn | Gly | Asp | Thr | Leu | Tyr | Asp | Pro | Lys | Phe |
| | 50 | | | | | 55 | | | | | 60 | | | | |
| Gln | Asp | Lys | Val | Thr | Met | Thr | Thr | Asp | Thr | Ser | Thr | Ser | Thr | Ala | Tyr |
| 65 | | | | | 70 | | | | | 75 | | | | | 80 |
| Met | Glu | Leu | Arg | Ser | Leu | Arg | Ser | Asp | Asp | Thr | Ala | Val | Tyr | Tyr | Cys |
| | | | | 85 | | | | | 90 | | | | | 95 | |
| Ala | Arg | Glu | Ala | Asp | Tyr | Phe | His | Asp | Gly | Thr | Ser | Tyr | Trp | Tyr | Phe |
| | | | 100 | | | | | 105 | | | | | 110 | | |
| Asp | Val | Trp | Gly | Arg | Gly | Thr | Leu | Val | Thr | Val | Ser | Ser | Ala | Ser | Thr |
| | | 115 | | | | | 120 | | | | | 125 | | | |
| Lys | Gly | Pro | Ser | Val | Phe | Pro | Leu | Ala | Pro | Cys | Ser | Arg | Ser | Thr | Ser |
| | 130 | | | | | 135 | | | | | 140 | | | | |
| Glu | Ser | Thr | Ala | Ala | Leu | Gly | Cys | Leu | Val | Lys | Asp | Tyr | Phe | Pro | Glu |
| 145 | | | | | 150 | | | | | 155 | | | | | 160 |
| Pro | Val | Thr | Val | Ser | Trp | Asn | Ser | Gly | Ala | Leu | Thr | Ser | Gly | Val | His |
| | | | | 165 | | | | | 170 | | | | | 175 | |
| Thr | Phe | Pro | Ala | Val | Leu | Gln | Ser | Ser | Gly | Leu | Tyr | Ser | Leu | Ser | Ser |
| | | | 180 | | | | | 185 | | | | | 190 | | |
| Val | Val | Thr | Val | Pro | Ser | Ser | Asn | Phe | Gly | Thr | Gln | Thr | Tyr | Thr | Cys |
| | | 195 | | | | | 200 | | | | | 205 | | | |
| Asn | Val | Asp | His | Lys | Pro | Ser | Asn | Thr | Lys | Val | Asp | Lys | Thr | Val | Glu |
| | 210 | | | | | 215 | | | | | 220 | | | | |
| Arg | Lys | Cys | Cys | Val | Glu | Cys | Pro | Pro | Cys | Pro | Ala | Pro | Pro | Val | Ala |
| 225 | | | | | 230 | | | | | 235 | | | | | 240 |
| Gly | Pro | Ser | Val | Phe | Leu | Phe | Pro | Pro | Lys | Pro | Lys | Asp | Thr | Leu | Met |
| | | | | 245 | | | | | 250 | | | | | 255 | |
| Ile | Ser | Arg | Thr | Pro | Glu | Val | Thr | Cys | Val | Val | Val | Asp | Val | Ser | His |
| | | | 260 | | | | | 265 | | | | | 270 | | |
| Glu | Asp | Pro | Glu | Val | Gln | Phe | Asn | Trp | Tyr | Val | Asp | Gly | Val | Glu | Val |
| | | 275 | | | | | 280 | | | | | 285 | | | |
| His | Asn | Ala | Lys | Thr | Lys | Pro | Arg | Glu | Glu | Gln | Phe | Asn | Ser | Thr | Phe |
| | 290 | | | | | 295 | | | | | 300 | | | | |
| Arg | Val | Val | Ser | Val | Leu | Thr | Val | Val | His | Gln | Asp | Trp | Leu | Asn | Gly |
| 305 | | | | | 310 | | | | | 315 | | | | | 320 |
| Lys | Glu | Tyr | Lys | Cys | Lys | Val | Ser | Asn | Lys | Gly | Leu | Pro | Ala | Pro | Ile |
| | | | | 325 | | | | | 330 | | | | | 335 | |
| Glu | Lys | Thr | Ile | Ser | Lys | Thr | Lys | Gly | Gln | Pro | Arg | Glu | Pro | Gln | Val |
| | | | 340 | | | | | 345 | | | | | 350 | | |
| Tyr | Thr | Leu | Pro | Pro | Ser | Arg | Glu | Glu | Met | Thr | Lys | Asn | Gln | Val | Ser |
| | | 355 | | | | | 360 | | | | | 365 | | | |

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 395
<211> LENGTH: 446
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 395

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Lys Asp Tyr
            20                  25                  30

Tyr Ile His Trp Val Arg Gln Ala Pro Gly Gln Gly Leu Glu Trp Ile
        35                  40                  45

Gly Arg Val Asp Pro Asp Asn Gly Glu Thr Glu Phe Ala Pro Lys Phe
    50                  55                  60

Pro Gly Lys Val Thr Met Thr Thr Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Glu Asp Tyr Asp Gly Thr Tyr Thr Trp Phe Pro Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu

```
                  260                 265                 270
Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
        290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 396
<211> LENGTH: 445
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 396

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Asp Thr Glu Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Asp Ala Pro Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                     230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
        290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445
```